US009643986B2

(12) United States Patent
Wiles et al.

(10) Patent No.: US 9,643,986 B2
(45) Date of Patent: May 9, 2017

(54) FACTOR D INHIBITORS USEFUL FOR TREATING INFLAMMATORY DISORDERS

(71) Applicant: Achillion Pharmaceuticals, Inc., New Haven, CT (US)

(72) Inventors: Jason Allan Wiles, Madison, CT (US); Milind Deshpande, Madison, CT (US)

(73) Assignee: ACHILLION PHARMACEUTICALS, INC., New Haven, CT (US)

( * ) Notice: Subject to any disclaimer, the term of this patent is extended or adjusted under 35 U.S.C. 154(b) by 0 days.

(21) Appl. No.: 14/630,959

(22) Filed: Feb. 25, 2015

(65) Prior Publication Data

US 2015/0239837 A1 Aug. 27, 2015

Related U.S. Application Data

(60) Provisional application No. 61/944,189, filed on Feb. 25, 2014, provisional application No. 62/022,916,
(Continued)

(51) Int. Cl.
| | |
|---|---|
| *C07D 403/06* | (2006.01) |
| *C07F 9/572* | (2006.01) |
| *C07D 209/42* | (2006.01) |
| *C07D 403/12* | (2006.01) |
| *C07D 403/14* | (2006.01) |
| *C07D 401/14* | (2006.01) |
| *C07D 471/04* | (2006.01) |
| *C07D 417/06* | (2006.01) |
| *C07D 417/14* | (2006.01) |
| *C07F 7/08* | (2006.01) |
| *C07D 413/14* | (2006.01) |
| *C07D 487/04* | (2006.01) |
| *C07D 405/14* | (2006.01) |
| *C07D 403/08* | (2006.01) |
| *C07D 413/06* | (2006.01) |
| *C07F 5/02* | (2006.01) |
| *C07F 9/6561* | (2006.01) |
| *C07F 9/6558* | (2006.01) |
| *A61K 31/404* | (2006.01) |

(Continued)

(52) U.S. Cl.
CPC .......... *C07F 9/5728* (2013.01); *A61K 31/404* (2013.01); *A61K 31/407* (2013.01); *A61K 31/4162* (2013.01); *A61K 31/4178* (2013.01); *A61K 31/4184* (2013.01); *A61K 31/4188* (2013.01); *A61K 31/4192* (2013.01); *A61K 31/437* (2013.01); *A61K 31/4439* (2013.01); *A61K 31/4709* (2013.01); *A61K 31/496* (2013.01); *A61K 31/506* (2013.01); *A61K 31/549* (2013.01); *A61K 31/55* (2013.01); *A61K 31/675* (2013.01); *A61K 31/683* (2013.01); *C07B 59/002* (2013.01); *C07D 209/14* (2013.01); *C07D 209/40* (2013.01); *C07D 209/42* (2013.01); *C07D 401/14* (2013.01); *C07D 403/06* (2013.01); *C07D 403/08* (2013.01); *C07D 403/12* (2013.01); *C07D 403/14* (2013.01); *C07D 405/12* (2013.01); *C07D 405/14* (2013.01); *C07D 413/06* (2013.01); *C07D 413/14* (2013.01); *C07D 417/06* (2013.01); *C07D 417/12* (2013.01); *C07D 417/14* (2013.01); *C07D 471/04* (2013.01); *C07D 487/04* (2013.01); *C07D 487/14* (2013.01); *C07D 491/113* (2013.01); *C07D 495/04* (2013.01); *C07D 513/04* (2013.01); *C07F 5/025* (2013.01); *C07F 5/027* (2013.01); *C07F 7/0812* (2013.01); *C07F 9/6561* (2013.01); *C07F 9/65583* (2013.01); *C07F 9/65616* (2013.01); *C07B 2200/05* (2013.01)

(58) Field of Classification Search
CPC .................................................. C07D 403/06
See application file for complete search history.

(56) References Cited

U.S. PATENT DOCUMENTS

| | | |
|---|---|---|
| 6,653,340 B1 | 11/2003 | Babu et al. |
| 2010/0041628 A1 | 2/2010 | Enomoto et al. |

(Continued)

FOREIGN PATENT DOCUMENTS

| | | |
|---|---|---|
| WO | WO 93/20099 A2 | 10/1993 |
| WO | WO 95/29697 A1 | 11/1995 |

(Continued)

OTHER PUBLICATIONS

Airey et al. "A Convenient Preparation of Thieno[3,2-c]pyrazole" Synthesis, 2014; 46: 96-100. Barraclough et al. "Synthesis of (2S,3R)- and (2S,3S)-[3-$^2$H$_1$]-proline via highly selective hydrolysis of a silyl enol ether" Tetrahedron Letters, 2005; 46: 4653-4655.
Barraclough et al. "Two separate and distinct syntheses of stereospecifically deuteriated samples of (2S)-proline" Organic & Biomolecular Chemistry, 2006; 4: 1483-1491.
Cole et al. "Structure of 3,4-Dichloroisocoumarin-Inhibited Factor D" Acta Crystallographica, 1998; D54: 711-717.

(Continued)

Primary Examiner — Shawquia Jackson
(74) Attorney, Agent, or Firm — Knowles IP Strategies, LLC

(57) ABSTRACT

Compounds, methods of use, and processes for making inhibitors of complement factor D comprising Formula I, or a pharmaceutically acceptable salt or composition thereof are provided. The inhibitors described herein target factor D and inhibit or regulate the complement cascade at an early and essential point in the alternative complement pathway, and reduce factor D's ability to modulate the classical and lectin complement pathways. The inhibitors of factor D described herein are capable of reducing the excessive activation of complement, which has been linked to certain autoimmune, inflammatory, and neurodegenerative diseases, as well as ischemia-reperfusion injury and cancer.

24 Claims, No Drawings

Related U.S. Application Data filed on Jul. 10, 2014, provisional application No. 62/046,783, filed on Sep. 5, 2014.

(51) Int. Cl.

| | | |
|---|---|---|
| *A61K 31/407* | (2006.01) | |
| *A61K 31/4162* | (2006.01) | |
| *A61K 31/4178* | (2006.01) | |
| *A61K 31/4184* | (2006.01) | |
| *A61K 31/4188* | (2006.01) | |
| *A61K 31/4192* | (2006.01) | |
| *A61K 31/437* | (2006.01) | |
| *A61K 31/4439* | (2006.01) | |
| *A61K 31/4709* | (2006.01) | |
| *A61K 31/496* | (2006.01) | |
| *A61K 31/506* | (2006.01) | |
| *A61K 31/549* | (2006.01) | |
| *A61K 31/55* | (2006.01) | |
| *A61K 31/675* | (2006.01) | |
| *A61K 31/683* | (2006.01) | |
| *C07B 59/00* | (2006.01) | |
| *C07D 209/14* | (2006.01) | |
| *C07D 209/40* | (2006.01) | |
| *C07D 405/12* | (2006.01) | |
| *C07D 417/12* | (2006.01) | |
| *C07D 487/14* | (2006.01) | |
| *C07D 491/113* | (2006.01) | |
| *C07D 495/04* | (2006.01) | |
| *C07D 513/04* | (2006.01) | |

(56) References Cited

U.S. PATENT DOCUMENTS

| | | |
|---|---|---|
| 2011/0280808 A1 | 11/2011 | Kroth et al. |
| 2012/0295884 A1 | 11/2012 | Altmann et al. |
| 2013/0296377 A1 | 11/2013 | Adams et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |

FOREIGN PATENT DOCUMENTS

| | | |
|---|---|---|
| WO | WO 99/48492 A1 | 9/1999 |
| WO | WO 2004/007501 A1 | 1/2004 |
| WO | WO 2004/045518 A2 | 6/2004 |
| WO | WO 2004/111041 A1 | 12/2004 |
| WO | WO 2008/047831 A1 | 4/2008 |
| WO | WO 2012/093101 A1 | 7/2012 |
| WO | WO 2012/177782 A1 | 12/2012 |
| WO | WO 2013/166436 A1 | 11/2013 |
| WO | WO 2014/002051 A2 | 1/2014 |
| WO | WO 2014/002052 A1 | 1/2014 |
| WO | WO 2014/002053 A1 | 1/2014 |
| WO | WO 2014/002054 A1 | 1/2014 |
| WO | WO 2014/002057 A1 | 1/2014 |
| WO | WO 2014/002058 A2 | 1/2014 |
| WO | WO 2014/002059 A1 | 1/2014 |
| WO | WO 2014/005150 A1 | 1/2014 |
| WO | WO 2014/009833 A2 | 1/2014 |
| WO | WO 2014/037480 A1 | 3/2014 |
| WO | WO 2015/130784 A1 | 9/2015 |
| WO | WO 2015/130795 A1 | 9/2015 |
| WO | WO 2015/130806 A1 | 9/2015 |
| WO | WO 2015/130830 A1 | 9/2015 |
| WO | WO 2015/130838 A1 | 9/2015 |
| WO | WO 2015/130842 A2 | 9/2015 |
| WO | WO 2015/130845 A1 | 9/2015 |
| WO | WO 2015/130854 A1 | 9/2015 |

OTHER PUBLICATIONS

De Luca et al. "HIV-1 integrase strand-transfer inhibitors: Design, synthesis and molecular modeling investigation" European Journal of Medicinal Chemistry, 2011; 46: 756-764.

Donthiri et al. "Copper-Catalyzed C—H Functionalization of Pyridines and Isoquinolines with Vinyl Azides: Synthesis of Imidazo Heterocycles" Journal of Organic Chemistry, 2014; 79: 11277-11284.

Dormoy et al. "Synthesis of N-t-Butoxycarbonyl-4,4-dideuterio-L-proline" Synthesis, 1986; 1: 81-82.

Hecker et al. "Liver-Targeted Prodrugs of 2'-C-Methyladenosine for Therapy of Hepatitis C Virus Infection" Journal of Medicinal Chemistry, 2007; 50(16): 3891-3896.

Hruby et al. "Carbon-13 NMR studies of the Peptide hormones oxytocin, arginine vasopressin, isotocin, mesotocin, glumitocin, aspartocin, related analogs, and diastereoisomers. Use of specifically deuterated hormone derivatives for assignments and effects of structural changes on carbon-13 NMR chemical shifts in peptides" Journal of the American Chemical Society, 1979; 101(1): 202-212.

Kobayashi et al. "Carboxylation of alkynylsilanes with carbon dioxide mediated by cesium fluoride in DMSO" Organic & Biomolecular Chemistry, 2013; 11: 3773-3775.

Kuang et al. "Synthesis of (Z)-1-bromo-1-alkenes and terminal alkynes from anti-2,3-dibromoalkanoic acids by microwave-induced reaction" Tetrahedron, 2006; 61(16): 4043-4052.

Mackay et al. "Rapid Synthesis of the N-Methylwelwitindolinone Skeleton" Organic Letters, 2005; 7: 3421-3424.

Okutani et al. "Conversion of Bromoalkenes into Alkynes by Wet Tetra-n-butylammonium Fluoride" Journal of Organic Chemistry, 2009; 74: 442-444.

Quesada et al. "One-pot conversion of activated alcohols into terminal alkynes using manganese dioxide in combination with the Bestmann-Ohira reagent" Tetrahedron Letters, 2005; 46: 6473-6476.

Roth et al. "Further Improvements of the Synthesis of Alkynes from Aldehydes" Synthesis, 2004; 1: 59-62.

Ruiz-Gomez et al. "Structure-Activity Relationships for Substrate-Based Inhibitors of Human Complement Factor B" Journal of Medicinal Chemistry, 2009; 52: 6042-6052.

Tandon et al. "Substrate specificity of human prolyl-4-hydroxylase" Bioorganic and Medicinal Chemistry Letters, 1998; 8(10): 1139-1144.

Tang et al. "Palladium-Catalyzed Carbonylative Sonogashira Coupling of Aryl Bromides via tert-Butyl Isocyanide Insertion" Journal of Organic Chemistry, 2013; 78(7): 3170-3175.

International Search Report and Written Opinion for PCT/US2015/017523 mailed May 14, 2015.

International Search Report and Written Opinion for PCT/US2015/017538 mailed May 14, 2015.

International Search Report and Written Opinion for PCT/US2015/017554 mailed May 14, 2015.

International Search Report and Written Opinion for PCT/US2015/017583 mailed May 27, 2015.

International Search Report and Written Opinion for PCT/US2015/017593 mailed Jun. 16, 2015.

International Search Report and Written Opinion for PCT/US2015/017597 mailed Jan. 29, 2016.

International Search Report and Written Opinion for PCT/US2015/17600 mailed May 27, 2015.

International Search Report and Written Opinion for PCT/US2015/017609 mailed May 29, 2015.

FACTOR D INHIBITORS USEFUL FOR TREATING INFLAMMATORY DISORDERS

CROSS-REFERENCE TO RELATED APPLICATIONS

This application claims the benefit of provisional U.S. Application No. 61/944,189 filed Feb. 25, 2014, provisional U.S. Application No. 62/022,916 filed Jul. 10, 2014, and provisional U.S. Application 62/046,783 filed Sep. 5, 2014. The entirety of each of these applications is hereby incorporated by reference for all purposes.

BACKGROUND

Complement Factor D is part of the alternative pathway of the complement cascade and plays an early and central role in activating the pathway. Complement Factor C3b is generated from complement component C3 by the C3 convertase enzyme, distinct forms of which are produced following activation of the alternative pathway and the classical and lectin pathways. Activation of the alternative complement pathway is initiated by spontaneous hydrolysis of a thioester bond within C3 to produce $C3(H_2O)$, which associates with factor B to form the $C3(H_2O)B$ complex. Complement Factor D acts to cleave factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with factor B to form C3bB, which factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

In some instances it is desirable to decrease the response of the alternative pathway. Activation of the alternative pathway of the complement cascade contributes to the production of C3a and C5a, both potent anaphylatoxins, which have roles in a number of inflammatory disorders. C3a and C5a are also formed by the classical pathway of the complement cascade. Regulation of the complement cascade is necessary to prevent damage to non-infected host cells. The balance between complement activation and inhibition is mediated by a series of complement regulatory factors, such as complement factor H and complement factor I.

Age-related macular degeneration (AMD) is a leading cause of vision loss in industrialized countries. There is evidence of the link between the complement cascade and macular degeneration. Individuals with mutations in the gene encoding complement factor H have a fivefold increased risk of macular degeneration and individuals with mutations in other complement factor genes also have an increased risk of AMD. Individuals with mutant factor H also have increased levels of C-reactive protein, a marker of inflammation. Without adequate functioning factor H the alternative pathway of the complement cascade is overly activated leading to cellular damage. Inhibition of the alternative pathway is thus desired.

Factor D is an attractive target for inhibition or regulation of the complement cascade due to its early and essential role in the alternative complement pathway, and its potential role in signal amplification within the classical and lectin complement pathways. Inhibition of Factor D effectively interrupts the pathway and attenuates the formation of the membrane attack complex. Compounds which act as Factor D inhibitors are needed for disruption of the complement cascade alternative pathway and treatment of disorders associated with defects in the complement cascade.

SUMMARY

The disclosure provides compounds of Formula I

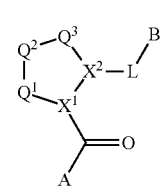

(I)

and the pharmaceutically acceptable salts thereof. Within Formula I the variables, e.g, A, B, L, $X^1$, $X^2$, $Q^1$, $Q^2$, and $Q^3$ carry the following values.

$Q^1$ is $N(R^1)$ or $C(R^1R^{1'})$.

$Q^2$ is $C(R^2R^{2'})$, $C(R^2R^{2'})$—$C(R^2R^{2'})$, or $C(R^2R^{2'})O$.

$Q^3$ is $N(R^3)$, S, or $C(R^3R^{3'})$.

(a) $X^1$ and $X^2$ are independently N or CH, or (b) $X^1$ and $X^2$ together are C=C.

$R^1$, $R^{1'}$, $R^2$, $R^{2'}$, $R^3$, and $R^{3'}$ are independently chosen at each occurrence from (c) and (d):

(c) hydrogen, halogen, hydroxyl, nitro, cyano, amino, $C_1$-$C_6$alkyl, $C_2$-$C_6$alkenyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl$NR^9R^{10}$, —C(O)$OR^9$, —OC(O)$R^9$, —$NR^9$C(O)$R^{10}$, —C(O)$NR^9R^{10}$, —OC(O)$NR^9R^{10}$, —$NR^9$C(O)$OR^{1'}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, and ($C_3$-$C_7$cycloalkyl)$C_0$-$C_4$alkyl;

(d) —$C_0$-$C_4$alkyl ($C_3$-$C_7$cycloalkyl) and —O—$C_0$-$C_4$alkyl($C_3$-$C_7$cycloalkyl).

Additionally any one of the following rings (e), (f), (g), (h), (i), or (j) may be present:

(e) $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S;

(f) $R^2$ and $R^{2'}$ may be taken together to form a 3- to 6-membered carbocyclic spiro ring, (g) $R^2$ and $R^{2'}$ may be taken together to form a 3- to 6-membered heterocyclic spiro ring, each of which spiro rings (e), (f), and (g) is unsubstituted or substituted with one or more halogen or methyl substituents;

(h) $R^1$ and $R^2$ may be taken together to form a 3-membered carbocyclic ring;

(i) $R^1$ and $R^2$ may be taken together to form a 4- to 6-membered carbocyclic ring or a 4- to 6-membered heterocyclic ring containing 1 or 2 heteroatoms independently chosen from N, O, and S.

(j) $R^2$ and $R^3$, if bound to adjacent carbon atoms, may be taken together to form a 3- to 6-membered carbocyclic ring or a 3- to 6-membered heterocyclic ring; each of which ring (g), (h), and (i) may be unsubstituted or substituted with 1 or more substituents independently chosen from halogen, hydroxyl, cyano, —COOH, $C_1$-$C_4$alkyl, $C_2$-$C_4$alkenyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

A is a heterocyclic group chosen from (k) and (l) where (k) is

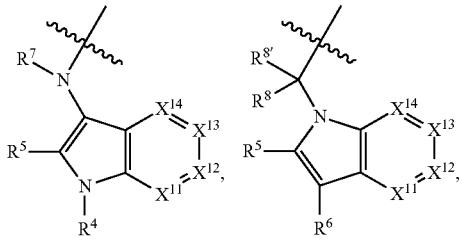

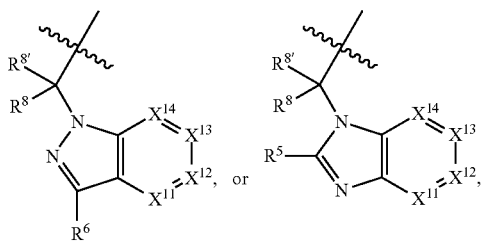

and (l) is

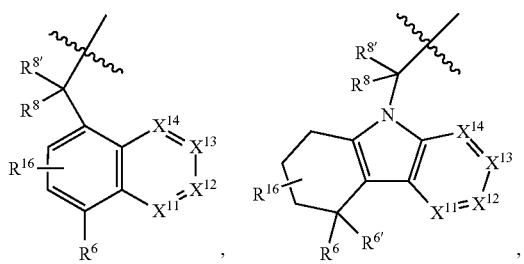

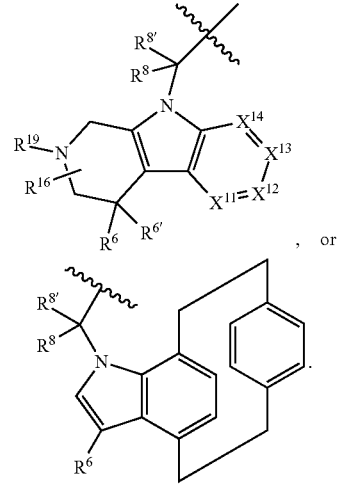

$X^4$ is B(OH) and Y is $CHR^9$; or $X^4$ is $CHR^9$ and Y is B(OH).

$R^4$ is (m) or (n):
  (m) —CHO, —$CONH_2$, or $C_2$-$C_6$alkanoyl;
  (n) hydrogen, —$SO_2NH_2$, —$C(CH_2)F$, —$CH(CF_3)NH_2$, $C_1$-$C_6$alkyl, —$C_0$-$C_4$alkyl($C_3$-$C_7$cycloalkyl), —$C(O)C_0$-$C_2$alkyl($C_3$-$C_7$cycloalkyl),

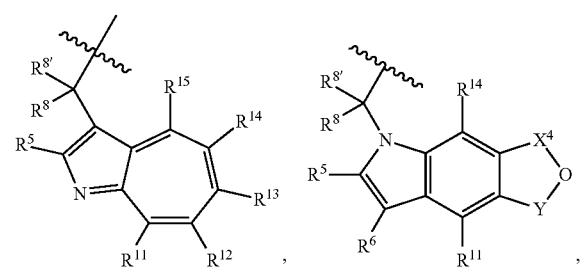

each of which $R^4$ other than hydrogen, —CHO, and —$CONH_2$, is unsubstituted or substituted with one or more of amino, imino, halogen, hydroxyl, cyano, cyanoimino, $C_1$-$C_2$alkyl, $C_1$-$C_2$alkoxy, —$C_0$-$C_2$alkyl(mono- and di-$C_1$-$C_4$alkylamino), $C_1$-$C_2$haloalkyl, and $C_1$-$C_2$haloalkoxy.

$R^5$ and $R^6$ are independently chosen from (o) and (p):
  (o) —CHO, —$C(O)NH_2$, —$C(O)NH(CH_3)$, or $C_2$-$C_6$alkanoyl;
  (p) hydrogen, hydroxyl, halogen, cyano, nitro, —COOH, —$SO_2NH_2$, vinyl, $C_1$-$C_6$alkyl, $C_2$-$C_6$alkenyl, $C_1$-$C_6$alkoxy, —$C_0$-$C_4$alkyl($C_3$-$C_7$cycloalkyl), —$C(O)C_0$-$C_4$alkyl($C_3$-$C_7$cycloalkyl), —$P(O)(OR^9)_2$, —$OC(O)R^9$, —$C(O)OR^9$, —$C(O)N(CH_2CH_2R^9)(R^{10}$, —$NR^9C(O)R^{10}$, phenyl, or 5- to 6-membered heteroaryl.

Each $R^5$ and $R^6$ other than hydrogen, hydroxyl, cyano, and —COOH is unsubstituted or substituted with one or more substituents independently chosen from halogen, hydroxyl, amino, imino, cyano, cyanoimino, $C_1$-$C_2$alkyl, $C_1$-$C_4$alkoxy, —$C_0$-$C_2$alkyl(mono- and di-$C_1$-$C_4$alkylamino), $C_1$-$C_2$haloalkyl, and $C_1$-$C_2$haloalkoxy.

$R^{6'}$ is hydrogen, halogen, hydroxyl, $C_1$-$C_4$alkyl, or $C_1$-$C_4$alkoxy; or $R^6$ and $R^{6'}$ may be taken together to form an oxo, vinyl, or imino group.

$R^7$ is hydrogen, $C_1$-$C_6$alkyl, or —$C_0$-$C_4$alkyl($C_3$-$C_7$cycloalkyl.

$R^8$ and $R^{8'}$ are independently chosen from hydrogen, halogen, hydroxyl, $C_1$-$C_6$alkyl, $C_1$-$C_6$alkoxy, and ($C_1$-$C_4$alkylamino)$C_0$-$C_2$alkyl, or $R^8$ and $R^{8'}$ are taken together to form an oxo group.

$R^{16}$ is 0 or 1 or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, —$C_0$-$C_4$alkyl (mono- and di-$C_1$-$C_6$alkylamino), —$C_0$-$C_4$alkyl($C_3$-$C_7$cycloalkyl), $C_1$-$C_2$haloalkyl, and $C_1$-$C_2$haloalkoxy.

$R^{19}$ is hydrogen, $C_1$-$C_6$alkyl, $C_2$-$C_6$alkenyl, $C_2$-$C_6$alkanoyl, —$SO_2C_1$-$C_6$alkyl, (mono- and di-$C_1$-$C_6$alkylamino)$C_1$-$C_4$alkyl, —$C_0$-$C_4$alkyl($C_3$-$C_7$cycloalkyl), each of which $R^{19}$ other than hydrogen is substituted with 0 or 1 or more substituents independently chosen from halogen, hydroxyl, amino, —COOH, and —C(O)O$C_1$-$C_4$alkyl.

$X^{11}$ is N or $CR^{11}$.
$X^{12}$ is N or $CR^{12}$.
$X^{13}$ is N or $CR^{13}$.
$X^{14}$ is N or $CR^{14}$.
$X^{15}$ is N or $CR^{15}$.

No more than 2 of $X^{11}$, $X^{12}$, $X^{13}$, $X^{14}$, and $X^{15}$ are N.

$R^{11}$, $R^{14}$, and $R^{15}$ are independently chosen at each occurrence from hydrogen, halogen, hydroxyl, nitro, cyano, —O(PO)(O$R^9$)$_2$, —(PO)(O$R^9$)$_2$, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl (mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy.

$R^{12}$ and $R^{13}$ are independently chosen from (q), (r), and (s):

(q) hydrogen, halogen, hydroxyl, nitro, cyano, amino, —COOH, $C_1$-$C_2$haloalkyl, and $C_1$-$C_2$haloalkoxy, (r) $C_1$-$C_6$alkyl, $C_2$-$C_6$alkenyl, $C_2$-$C_6$alkanoyl, $C_1$-$C_6$alkoxy, $C_2$-$C_6$alkenyloxy, —C(O)O$R^9$, $C_1$-$C_6$thioalkyl, —$C_0$-$C_4$alkylN$R^9R^{10}$, —C(O)N$R^9R^{10}$, —$SO_2R^9R^{10}$, —$SO_2NR^9R^{10}$, —OC(O)$R^9$, and —C(N$R^9$)N$R^9R^{10}$, each of which (r) is unsubstituted or substituted with one or more substituents independently selected from halogen, hydroxyl, nitro, cyano, amino, —COOH, —CONH$_2$$C_1$-$C_2$haloalkyl, and $C_1$-$C_2$haloalkoxy, and each of which (r) is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

(s) —$C_2$-$C_6$alkynyl, —$C_2$-$C_6$alkynyl$R^{23}$, $C_2$-$C_6$alkanoyl, -J$C_3$-$C_7$cycloalkyl, —B(OH)$_2$, -JC(O)N$R^9R^{23}$, -JOS$O_2OR^{21}$, —C(O)(CH$_2$)$_{1-4}$S(O)$R^{21}$, —O(CH$_2$)$_{1-4}$S(O)N$R^{21}NR^{22}$, -JOP(O)(O$R^{21}$)(O$R^{22}$), -JP(O)(O$R^{21}$)(O$R^{22}$), -JOP(O)(O$R^{21}$)$R^{22}$, -JP(O)(O$R^{21}$)$R^{22}$, -JOP(O)$R^{21}R^{22}$, -JP(O)$R^{21}R^{22}$, -JSP(O)(O$R^{21}$)(O$R^{22}$), -JSP(O)(O$R^{21}$)($R^{22}$), -JSP(O)($R^{21}$)($R^{22}$), -JN$R^9$P(O)(NH$R^{21}$)(NH$R^{22}$), -JN$R^9$P(O)(O$R^{21}$)(NH$R^{22}$), -JN$R^9$P(O)(O$R^{21}$)(O$R^{22}$), -JC(S)$R^{21}$, -JN$R^{21}SO_2R^{22}$, -JN$R^9$S(O)N$R^{10}R^{22}$, -JN$R^9SO_2NR^{10}R^{22}$, -JS$O_2NR^9COR^{22}$, —O(CH$_2$)$_{1-4}SO_2NR^{21}R^{22}$, -JS$O_2NR^9CONR^{21}R^{22}$, -JN$R^{21}SO_2R^{22}$, - JC(NH$_2$)N$R^{21}R^{22}$, -JC(NH$_2$)NS(O)$_2R^{22}$, -JOC(O)N$R^{21}R^{22}$, -JOC(O)N$R^{24}R^{25}$, -JN$R^9$C(O)O$R^{10}$, -JN$R^9$C(O)O$R^{23}$, -JN$R^{21}$OC(O)$R^{22}$, —(CH$_2$)$_{1-4}$C(O)N$R^{21}R^{22}$, -JC(O)N$R^{24}R^{25}$, -JN$R^9$C(O)$R^{21}$, -JC(O)$R^{21}$, -JN$R^9$C(O)N$R^9R^{10}$, -JN$R^9$C(O)N$R^{10}R^{23}$, -JN$R^9$C(O)N$R^{24}R^{25}$, —CC$R^{21}$, —(CH$_2$)$_{1-4}$OC(O)$R^{21}$, -JC(O)O$R^{23}$, —$C_2$-$C_4$alkyl$R^{23}$, —$C_2$-$C_4$alkenyl$R^{23}$, —$C_2$-$C_4$alkynyl$R^{23}$, and -Jparacyclophane.

J is independently chosen at each occurrence from a covalent bond, $C_1$-$C_4$alkylene, —O$C_1$-$C_4$alkylene, $C_2$-$C_4$alkenylene, and $C_2$-$C_4$alkynylene.

$R^{21}$ and $R^{22}$ are independently chosen at each occurrence from hydrogen, hydroxyl, cyano, amino, $C_1$-$C_6$alkyl, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S.

$R^{23}$ is independently chosen at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S.

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings.

Each of which (s) may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

L is either (t), (u), or (v):
(t) is a group of the formula

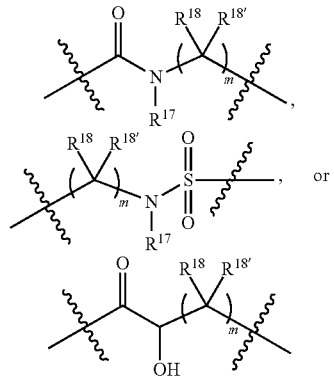

where $R^{17}$ is hydrogen or $C_1$-$C_6$alkyl and $R^{18}$ and $R^{18'}$ are independently chosen from hydrogen, halogen, and methyl; and m is 0, 1, 2, or 3; and (u) is a bond,
(v) or a group of the formula

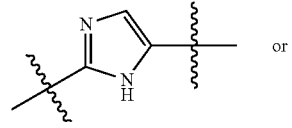

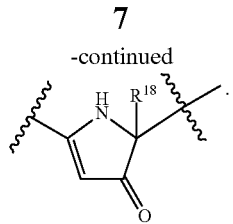

B is a monocyclic or bicyclic carbocyclic or carbocyclic-oxy group or a monocyclic, bicyclic, or tricyclic heterocyclic group having 1, 2, 3, or 4 heteroatoms independently selected from N, O, and S and from 4 to 7 ring atoms per ring, or B is a $C_2$-$C_6$alkenyl or $C_2$-$C_6$alkynyl group.

Each of which B is unsubstituted or substituted with one or more substituents independently chosen from (w) and (x) and 0 or 1 substituents chosen from (y) and (z):

(w) halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

(x) nitro, $C_2$-$C_6$alkenyl, $C_2$-$C_6$alkynyl, $C_1$-$C_6$thioalkyl, -JC$_3$-C$_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^1$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NS(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)R$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which (x) may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl (mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

(y) naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which (y) is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, $C_1$-$C_2$haloalkyl, and $C_1$-$C_2$haloalkoxy; and (z) tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which (z) is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl ($C_3$-$C_7$cycloalkyl), —SO$_2$R$^9$, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy.

Either $X^2$ is nitrogen or at least one of (d), (e), (g), (i), (l), (n), (p), (s), (v), (x), and (y) is present. Pharmaceutical composition comprising a compound or salt of Formula I together with a pharmaceutically acceptable carrier are also disclosed.

Methods of treating or preventing disorders mediated by complement cascade Factor D, such as age-related macular degeneration and retinal degeneration, comprising administering a therapeutically effective amount of a compound or salt of Formula I to a patient in need of such treatment are also disclosed.

DETAILED DESCRIPTION

Terminology

Compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as all pharmaceutically acceptable salts of the compound.

The term "Formula I" encompasses all compounds that satisfy Formula I, including any enantiomers, racemates and stereoisomers, as well as all pharmaceutically acceptable salts of such compounds. "Formula I" includes all subgeneric groups of Formula I, such as Formula IA and Formula IB and also includes pharmaceutically acceptable salts of a compound of Formula I, unless clearly contraindicated by the context in which this phrase is used.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Compounds of Formula I include all compounds of Formula I having isotopic substitutions at any position. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C. While the compounds of Formula I require a moderate or high level of deuteration (substitution of a hydrogen with deuterium) at identified positions, Formula I includes embodiments in which other positions are isotopically enriched.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C=O)NH$_2$ is attached through carbon of the keto (C=O) group.

"Alkyl" is a branched or straight chain saturated aliphatic hydrocarbon group, having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more carbon-carbon double bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more double carbon-carbon triple bonds that may occur at any stable point along the chain, having the specified number of carbon atoms.

"Alkylene" is a bivalent saturated hydrocarbon. Alkylenes include groups having 1 to 8 carbon atoms, 1 to 6 carbon atoms, or the indicated number of carbon atoms, for example $C_1$-$C_4$alkylene.

"Alkenylene" is a bivalent hydrocarbon having at least one carbon-carbon double bond. Alkenylenes include groups having 2 to 8 carbon atoms, 2 to 6 carbon atoms, or the indicated number of carbon atoms, for example $C_2$-$C_4$alkenylene.

"Alkynylene" is a bivalent hydrocarbon having at least one carbon-carbon triple bond. Alkynylenes include groups having 2 to 8 carbon atoms, 2 to 6 carbon atoms, or the indicated number of carbon atoms, for example $C_2$-$C_4$alkenylene.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "Alkylthio" or a "thioalkyl" group is an alkyl group as defined above with the indicated number of carbon atoms covalently bound to the group it substitutes by a sulfur bridge (—S—).

"Alkenyloxy" is an alkenyl group as defined above with the indicated number of carbon atoms covalently bound to the group it substitutes by an oxygen bridge (—O—).

"Alkanoyl" is an alkyl group as defined above with the indicated number of carbon atoms covalently bound to the group is substitutes through a carbonyl (C=O) bridge. The carbonyl carbon is included in the number of carbons, that is $C_2$alkanoyl is a $CH_3$(C=O)— group.

"Alkylester" is an alkyl group as defined herein covalently bound to the group it substitutes by an ester linkage. The ester linkage may be in either orientation, e.g., a group of the formula —O(C=O)alkyl or a group of the formula —(C=O)Oalkyl.

"Carbocyclic group" is a saturated, unsaturated, or partially unsaturated (e.g. aromatic) group containing all carbon ring atoms. A carbocyclic group typically contains 1 ring of 3 to 7 carbon atoms or 2 fused rings each containing 3 to 7 carbon atoms.

"Carbocyclic ring" is a saturated, unsaturated, or partially unsaturated (e.g. aromatic) ring containing all carbon ring atoms. A carbocyclic ring typically contains 1 ring of 3 to 7 carbon atoms or a "carbocyclic group" may contain 1 carbocyclic ring or 2 fused carbocyclic rings each containing 3 to 7 carbon atoms. Examples of carbocyclic rings include phenyl, cyclohexenyl, cyclohexyl, and cyclopropyl rings.

"Carbocyclic-oxy group" is a monocyclic carbocyclic ring or a mono- or bi-cyclic carbocyclic group as defined above attached to the group it substitutes via an oxygen, —O—, linker.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl subisitutuent.

"Aminoalkyl" is an alkyl group as previously described, substituted with at least one amino subisitutuent. "Halo" or "halogen" indicates any of fluoro, chloro, bromo, and iodo.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

A "Heterocyclic ring" is a saturated, unsaturated, or partially unsaturated (e.g. aromatic) ring containing 1 to 4 ring heteroatoms independently chosen from N, O, and S, or if indicated, N, O, S, and B, with remaining ring atoms being carbon. A "heterocyclic group" may contain 1 heterocyclic ring 1 ring of 3 to 7 ring atoms or 2 fused rings each containing 3 to 7 ring atoms with at least one ring being a heterocyclic ring.

"Heterocyclicoxy group" is a monocyclic heterocyclic ring or a bicyclic heterocyclic group as described previously linked to the group it substitutes via an oxygen, —O—, linker.

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl. "Heteroaryloxy" is a heteroaryl group as described bound to the group it substituted via an oxygen bridge.

"Heterocycloalkyl" is a saturated ring group, having 1, 2, 3, or 4 heteroatoms independently chosen from N, S, and O, with remaining ring atoms being carbon. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion.

Suitable groups that may be present on a "substituted" or "optionally substituted" position include, but are not limited to, e.g., halogen; cyano; hydroxyl; nitro; azido; alkanoyl (such as a $C_2$-$C_6$ alkanoyl group); carboxamide; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —CONH$_2$, $C_1$-$C_6$alkyl, $C_2$-$C_6$alkenyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, and $C_1$-$C_2$haloalkoxy.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions optional contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as hepatitis C.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)$n-COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. In certain embodiments the compound of Formula I and the additional active agent need not be prescribed for a patient by the same medical care worker. In certain embodiments the additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment," as used herein includes providing a compound of Formula I, either as the only active agent or together with at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in macular degeneration that can result in the context of factor D activation); (b) inhibiting the disease, i.e. arresting its development; and (c) relieving the disease, i.e., causing regression of the disease. "Treating" and "treatment" also means providing a therapeutically effective amount of a compound of Formula I, as the only active agent or together with at least one additional active agent to a patient having or susceptible to a condition mediated by complement factor D.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a macular degeneration. A therapeutically effective amount is also an amount sufficient to prevent a significant increase or significantly reduce the detectable level of complement Factor D in the patient's blood, serum, or tissues.

Chemical Description

In addition to compounds of Formula I shown in the SUMMARY section the disclosure also include compounds in which the variables, e.g., A, B, L, $R^1$-$R^{3'}$, and L carry the following definitions. The disclosure includes all combinations of these definitions so long as a stable compound results.

For example the disclosure includes compounds and salts of Formula II, III, IV, V, VI, VII, VIII, IX, X, XI, XII, XIII, XIV, XV, XVI, XVII, XVIII, XIX, XX, XXI, and XXII which are with in the scope of Formula I. The variables shown in Formula II-XXIV carry the definitions set forth in the SUMMARY section for Formula I or any of the definitions set forth in this disclosure.

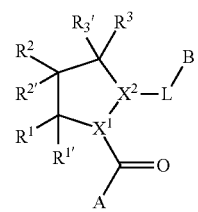

Formula II

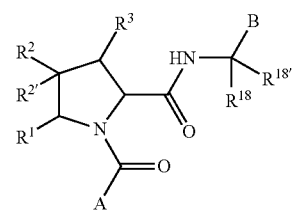

Formula III

-continued
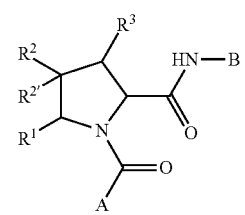
Formula IV
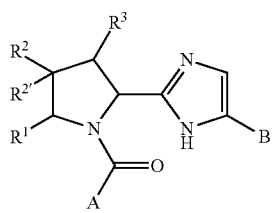
Formula V
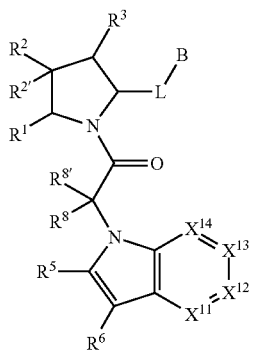
Formula VI
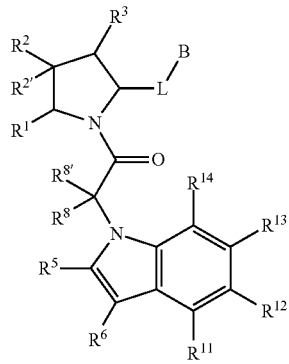
Formula VII
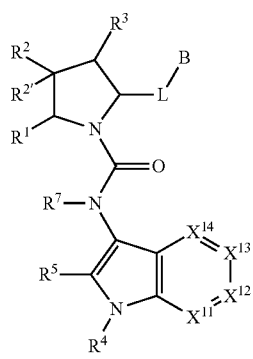
Formula VIII
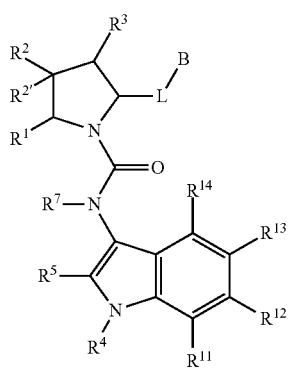
Formula IX
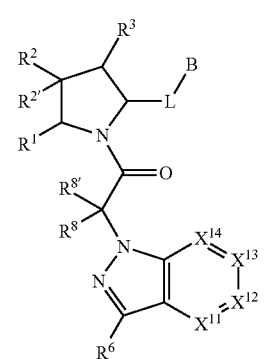
Formula X
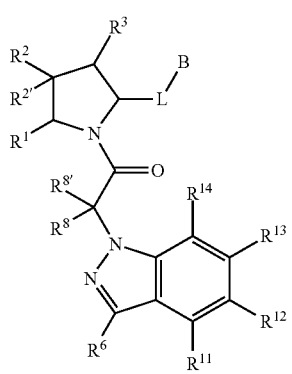
Formula XI
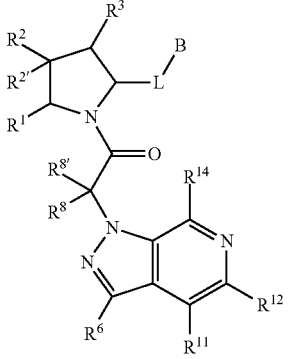
Formula XII Formula XIII
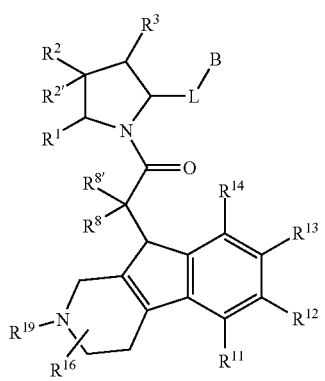
Formula XIV
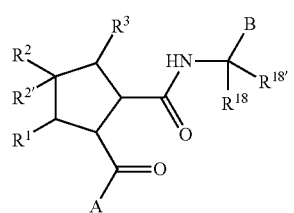
Formula XV
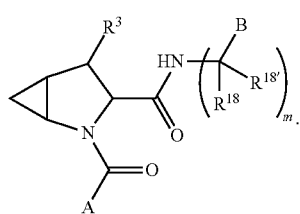
m is 0 or 1
Formula XVI
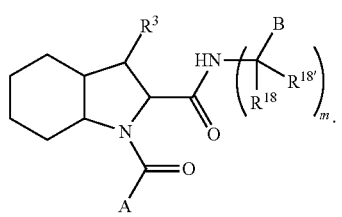
m is 0 or 1
Formula XVII
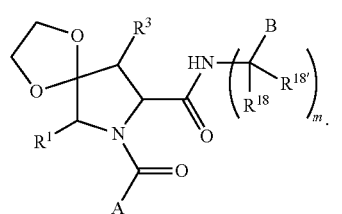
m is 0 or 1
Formula XVIII
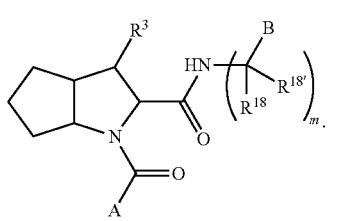
m is 0 or 1
Formula XIX
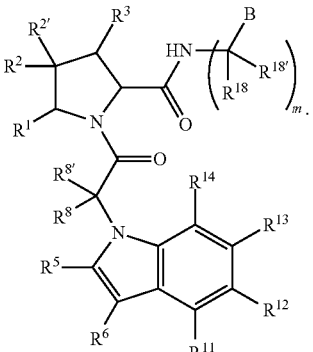
m is 0 or 1
Formula XX
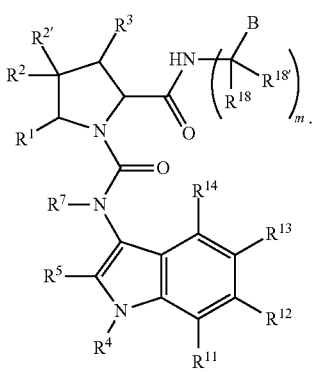
m is 0 or 1
Formula XXI
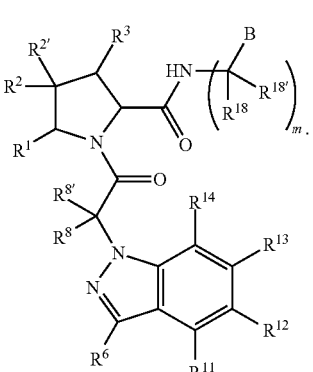
m is 0 or 1
Formula XXII
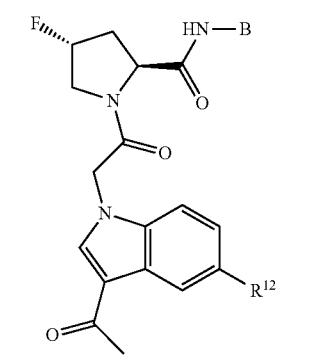

-continued

Formula XXIII

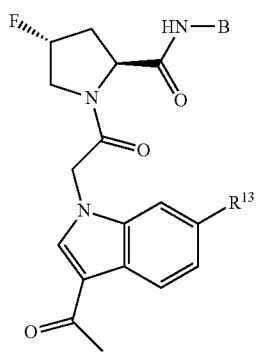

Formula XXIV

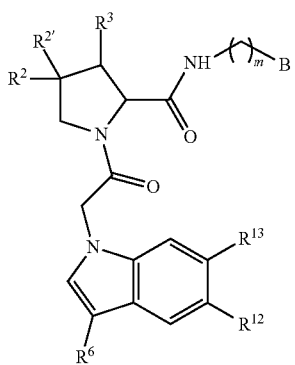

Additionally, the disclosure includes compounds and salts of Formula I and any of its subformulae (II-XXIV) in which at least one of the following conditions is met.

$R^1$, $R^{1'}$, $R^{2'}$, $R^3$, and $R^{3'}$, if present, are all hydrogen; and $R^2$ is fluoro.

$R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).

$R^1$ and $R^2$ are taken together to form a 3- to 6-membered cycloalkyl group, and $R^{1'}$, $R^{2'}$, $R^3$, and $R^{3'}$, where present, are all hydrogen.

$R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

-L-B— is

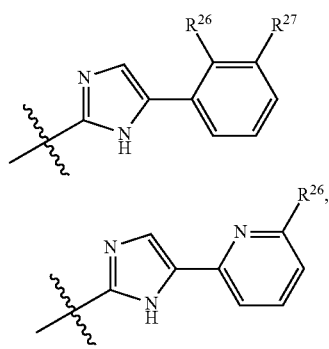

where $R^{26}$ and $R^{27}$ are independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl (mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, $C_1$-$C_2$haloalkoxy, and $C_1$-$C_2$haloalkylthio.

(f) -L-B— is

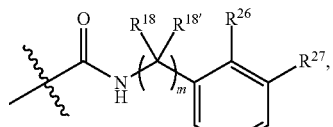

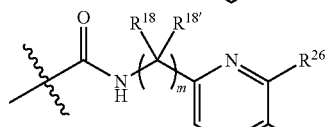

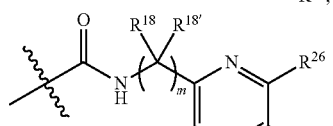

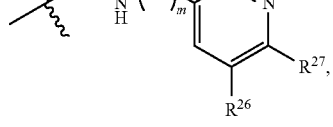

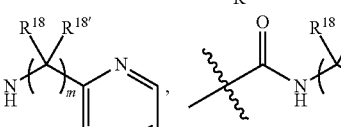

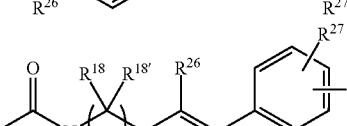

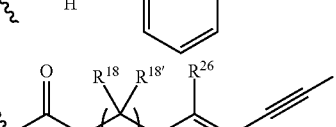

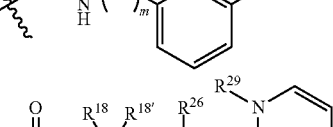

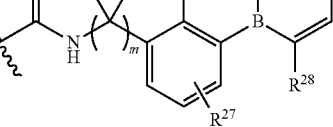

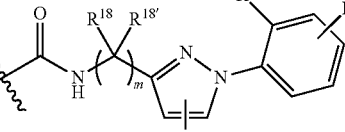

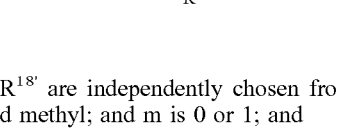

wherein $R^{18}$ and $R^{18'}$ are independently chosen from hydrogen, halogen, and methyl; and m is 0 or 1; and $R^{26}$, $R^{27}$, and $R^{28}$ are independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-

$C_7$cycloalkyl)$C_0$-$C_4$alkyl, and —$C_0$-$C_4$alkoxy($C_3$-$C_7$cycloalkyl); each of which $R^{26}$, $R^{27}$, and $R^{28}$ other than hydrogen, halogen, hydroxyl, nitro, cyano, is unsubstituted or substituted with one or more substituents independently chosen from halogen, hydroxyl, amino, $C_1$-$C_2$alkoxy, $C_1$-$C_2$haloalkyl, and $C_1$-$C_2$haloalkoxy; and $R^{29}$ is hydrogen, $C_1$-$C_2$alkyl, $C_1C_2$haloalkyl or —Si$(CH_3)_2$ $C(CH_3)_3$.

(g) R8 and R8' are independently hydrogen or methyl.
(h) R8 and R8' are hydrogen.
(i) R7 is hydrogen or methyl.
(j) R7 is hydrogen.
(k) One of $R^{12}$ and $R^{13}$ is chosen from hydrogen, halogen, hydroxyl, amino, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl (mono- and di-$C_1$-$C_6$alkylamino), —$C_0$-$C_4$alkyl($C_3$-$C_7$cycloalkyl), —O$C_0$-$C_4$alkyl($C_3$-$C_7$cycloalkyl), $C_1$-$C_2$haloalkyl, and $C_1$-$C_2$haloalkoxy.

(l) $R^1$, $R^{1'}$, $R^2$, and $R^{3'}$ are all hydrogen;
$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);
$R^5$ is hydrogen, halogen, or $C_1$-$C_2$alkyl;
$R^{11}$, $R^{13}$ $R^{14}$, and $R^{15}$, if present, are independently chosen at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_2$alkylamino), trifluoromethyl, and trifluoromethoxy;
$X^{12}$ is $CR^{12}$; and
$R^{12}$ is -JN$R^9$C(O)O$R^{10}$, -JN$R^9$C(O)O$R^{23}$, -JOC(O)N$R^{21}R^{22}$, -JOC(O)N$R^{24}R^{25}$, -JN$R^9$C(O)N$R^{10}R^{23}$, or -JN$R^9$C(O)N$R^{24}R^{25}$.

(m) J is a bond.
(n) One of $R^{12}$ and $R^{13}$ is selected from

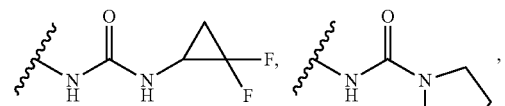

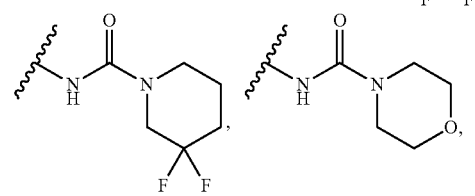

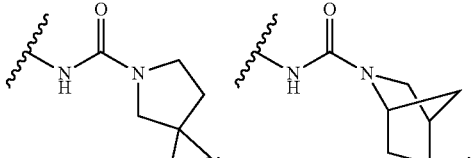

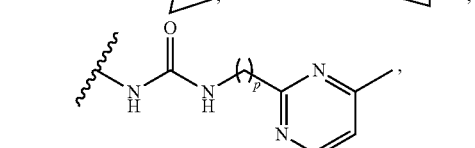

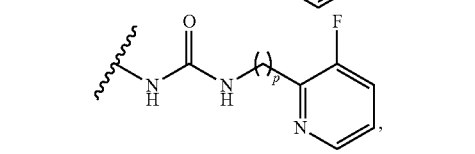

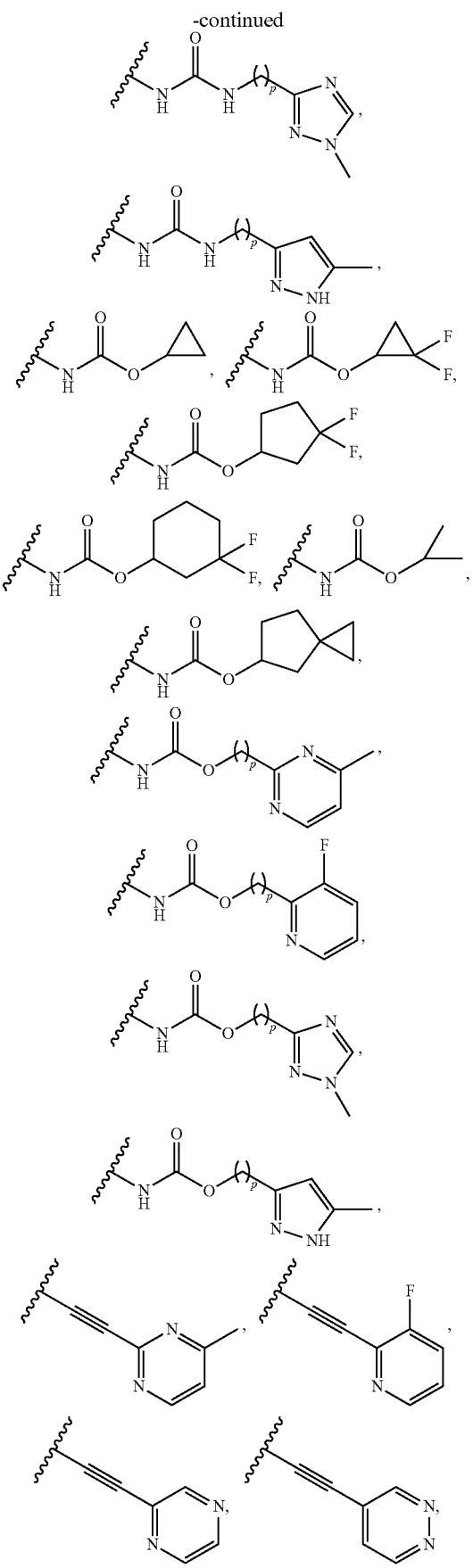

-continued

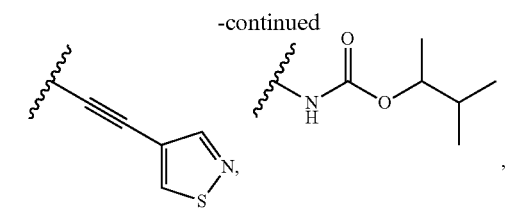

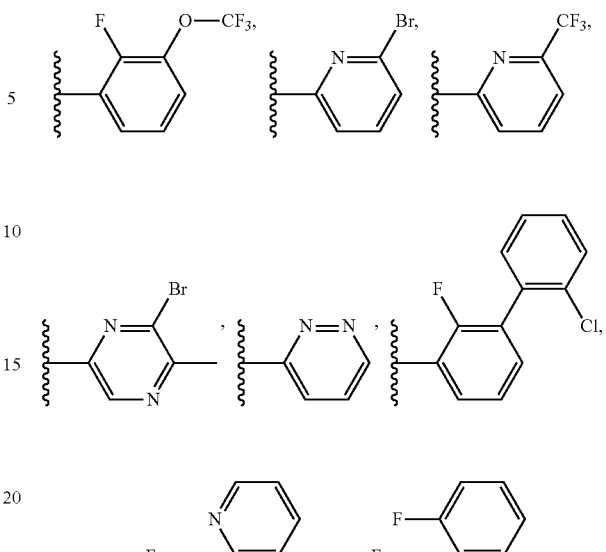

where p is 0, 1, 2, 3, or 4.

(o) The disclosure includes compounds and salts for Formula VII

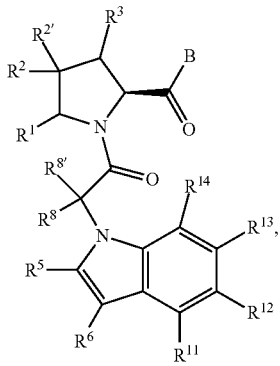

(VII)

wherein:

R$^1$, R$^2$, R$^{2'}$, and R$^3$ are independently chosen from hydrogen, halogen, C$_1$-C$_4$alkyl, C$_1$-C$_4$alkoxy, —C$_0$-C$_2$alkylNR$^9$R$^{10}$, —C$_0$-C$_4$alkyl(C$_3$-C$_7$cycloalkyl), —O—C$_0$-C$_4$alkyl(C$_3$-C$_7$cycloalkyl), C$_1$-C$_2$haloalkyl, and C$_1$-C$_2$haloalkoxy;

R$^8$ and R$^{8'}$ are independently chosen from hydrogen, halogen, and methyl;

R$^5$ is hydrogen, hydroxyl, cyano, —COOH, C$_1$-C$_6$alkyl, C$_1$-C$_6$alkoxy, C$_2$-C$_6$alkanoyl —C$_0$-C$_4$alkyl(C$_3$-C$_7$cycloalkyl), —C(O)C$_0$-C$_4$alkyl(C$_3$-C$_7$cycloalkyl), C$_1$-C$_2$haloalkyl, or C$_1$-C$_2$haloalkoxy;

R$^6$ is —C(O)CH$_3$, —C(O)NH$_2$, —C(O)CF$_3$, —C(O)(cyclopropyl), or -ethyl(cyanoimino); and R$^{11}$ and R$^{14}$ are independently chosen from hydrogen, halogen, hydroxyl, amino, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, —C$_0$-C$_4$alkyl(mono- and di-C$_1$-C$_6$alkylamino), —C$_0$-C$_4$alkyl(C$_3$-C$_7$cycloalkyl), —OC$_0$-C$_4$alkyl(C$_3$-C$_7$cycloalkyl), C$_1$-C$_2$haloalkyl, and C$_1$-C$_2$haloalkoxy.

(p) B is selected from

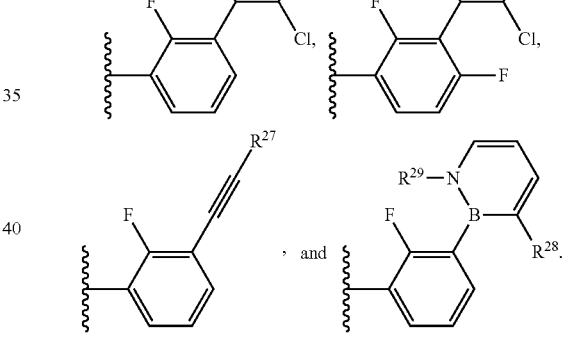

where R$^{27}$ is hydrogen, methyl, or trifluoromethyl; R$^{28}$ is hydrogen or halogen; and R$^{29}$ is hydrogen, methyl, trifluoromethyl, or —Si(CH$_3$)$_2$C(CH$_3$)$_3$.

(q) B is phenyl, pyridyl, or indanyl each of which is unsubstituted or substituted with one or more substituents independently chosen from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, (mono- and di-C$_1$-C$_6$alkylamino)C$_0$-C$_4$alkyl, (C$_3$-C$_7$cycloalkyl)C$_0$-C$_4$alkyl, —C$_0$-C$_4$alkoxy(C$_3$-C$_7$cycloalkyl), (phenyl)C$_0$-C$_2$alkyl, (pyridyl)C$_0$-C$_2$alkyl; each of which substituents other than hydrogen, halogen, hydroxyl, nitro, cyano, is unsubstituted or substituted with one or more substituents independently chosen from halogen, hydroxyl, amino, C$_1$-C$_2$alkyl, C$_1$-C$_2$alkoxy, —OSi(CH$_3$)$_2$C(CH$_3$)$_3$, —Si(CH$_3$)$_2$C(CH$_3$)$_3$, C$_1$-C$_2$haloalkyl, and C$_1$-C$_2$haloalkoxy.

(r) B is phenyl or pyridyl substituted with 1, 2, or 3 substituents chosen from chloro, bromo, hydroxyl, —SCF$_3$, C$_1$-C$_2$alkyl, C$_1$-C$_2$alkoxy, trifluoromethyl, and trifluoromethoxy.

(s) A is a group of the formula

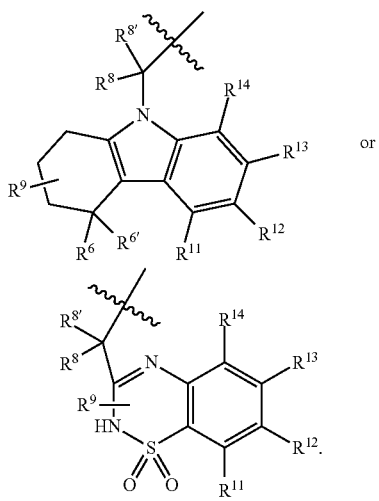

or (t) -L-B is a bond and indanyl group of the formula

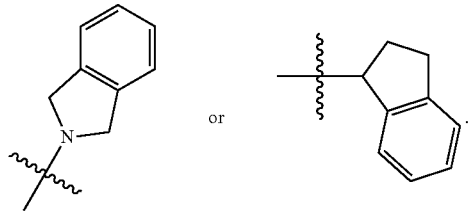 [SMILES: *N1Cc2ccccc2C1 ; *C1CCc2ccccc21]

This disclosure further includes embodiments in which m is 0 or 1;

$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl;

$R^6$ is —C(O)$C_1$-$C_4$alkyl, —C(O)NH$_2$, —C(O)CF$_3$, —C(O)($C_3$-$C_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ a is chosen from (s), where (s) is $C_2$-$C_6$alkynyl, —$C_2$-$C_6$alkynyl$R^{23}$, $C_2$-$C_6$alkanoyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$NR$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{21}$R$^{22}$, JNR$^9$SO$_2$NR$^{10}$R$^{22}$, -JSO$_2$NR$^9$COR$^{22}$, —O(CH$_2$)$_{1-4}$SO$_2$NR$^{21}$R$^{22}$, -JSO$_2$NR$^9$CONR$^{21}$R$^{22}$, -JNR$^{21}$SO$_2$R$^{22}$-JC(O)NR$^{21}$SO$_2$R$^{22}$, -JC(NH$_2$)NCN, -JC(NH$_2$)NR$^{22}$, -JC(NH$_2$)NS(O)$_2$R$^{22}$, -JOC(O)NR$^{21}$R$^{22}$, -JOC(O)NR$^{24}$R$^{25}$, -JNR$^9$C(O)OR$^1$, -JNR$^9$C(O)OR$^{23}$, -JNR$^{21}$OC(O)R$^{22}$, —(CH$_2$)$_{1-4}$C(O)NR$^{21}$R$^{22}$, -JNR$^9$C(O)R$^{21}$, -JC(O)R$^{21}$, -JNR$^9$C(O)NR$^9$R$^{10}$, -JNR$^9$C(O)NR$^{10}$R$^{23}$, -JNR$^9$C(O)NR$^{24}$R$^{25}$, —CCR$^{21}$, —(CH$_2$)$_{1-4}$OC(O)R$^{21}$, -JC(O)OR$^{23}$, —$C_2$-$C_4$alkylR$^{23}$, and -Jparacyclophane; where J is independently chosen at each occurrence and is a covalent bond, $C_1$-$C_4$alkylene, $C_2$-$C_4$alkenylene, or $C_2$-$C_4$alkynylene;

$R^{21}$ and $R^{22}$ are independently chosen at each occurrence from hydrogen, hydroxyl, cyano, amino, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)$C_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycloalkyl)$C_0$-$C_4$alkyl having 1, 2, or 3 heteroatoms independently chosen from N, O, and S;

$R^{23}$ is independently chosen at each occurrence from ($C_3$-$C_7$-cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

$R^{24}$ and $R^{25}$ are taken together with the nitrogen to which they are attached to form a 4- to 7-membered monocyclic heterocycloalkyl group, or a 6- to 10-membered bicyclic heterocycloalkyl group having fused, spiro, or bridged rings; each of which (s) may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$hydroxyalkyl, $C_1$-$C_2$haloalkyl, and $C_1$-$C_2$haloalkoxy.

(r) This disclosure includes compounds and salts in which one of $R^{12}$ and $R^{13}$ is hydrogen, hydroxyl, halogen, methyl, or methoxy; and the other of $R^{12}$ and $R^{13}$ is independently is chosen from (s), where (s) is $C_2$-$C_6$alkynyl, —$C_2$-$C_6$alkynyl$R^{23}$, $C_2$-$C_6$alkanoyl, -J$C_3$-$C_7$cycloalkyl, -JC(O)NR$^9$R$^{23}$, —C(O)(CH$_2$)$_{1-4}$S(O)R$^{21}$, -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JNR$^{21}$SO$_2$R$^{22}$, -JNR$^{21}$SO$_2$R$^{22}$, -JC(O)NR$^{21}$SO$_2$R$^{22}$, -JC(NH$_2$)NCN, -JC(NH$_2$)NR$^{22}$, -JC(NH$_2$)NS(O)$_2$R$^{22}$, -JOC(O)NR$^{21}$R$^{22}$, -JOC(O)NR$^{24}$R$^{25}$, -JNR$^9$C(O)OR$^1$, -JNR$^9$C(O)OR$^{23}$, -JNR$^{21}$OC(O)R$^{22}$, -JC(O)R$^{21}$, -JNR$^9$C(O)NR$^9$R$^{10}$, -JNR$^9$C(O)NR$^{10}$R$^{23}$, -JNR$^9$C(O)NR$^{24}$R$^{25}$, and -Jparacyclophane; where J is independently chosen at each occurrence and is a covalent bond, $C_1$-$C_4$alkylene, $C_2$-$C_4$alkenylene, or $C_2$-$C_4$alkynylene;

$R^{21}$ and $R^{22}$ are independently chosen at each occurrence from hydrogen, hydroxyl, cyano, amino, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)$C_1$-$C_6$alkyl, —$C_1$-$C_4$alkylC(O)OC$_1$-$C_6$alkyl, (pyrrolidinyl)$C_0$-$C_4$alkyl, ((morpholinyl)$C_0$-$C_4$alkyl, (thiomorpholinyl)$C_0$-$C_4$alkyl, (piperidinyl)$C_0$-$C_4$alkyl, (piperazinyl)$C_0$-$C_4$alkyl, (tetrahydrofuranyl)$C_0$-$C_4$alkyl, pyrazolyl)$C_0$-$C_4$alkyl, (thiazolyl)$C_0$-$C_4$alkyl, (triazolyl)$C_0$-$C_4$alkyl, (tetrazolyl)$C_0$-$C_4$alkyl, (imidazolyl)$C_0$-$C_4$alkyl, (oxazolyl)$C_0$-$C_4$alkyl, (furanyl)$C_0$-$C_4$alkyl, (pyridinyl)$C_0$-$C_4$alkyl, (pyrimidinyl)$C_0$-$C_4$alkyl, (pyrazinyl)$C_0$-$C_4$alkyl, (pyridizinyl)$C_0$-$C_4$alkyl, and (tetrahydropyridinyl)$C_0$-$C_4$alkyl;

$R^{23}$ is independently chosen at each occurrence from ($C_3$-$C_7$cycloalkyl)$C_0$-$C_4$alkyl, (phenyl)$C_0$-$C_4$alkyl, (pyrrolidinyl)$C_0$-$C_4$alkyl, (morpholinyl)$C_0$-$C_4$alkyl, (thiomorpholinyl)$C_0$-$C_4$alkyl, (piperidinyl)$C_0$-$C_4$alkyl, (piperazinyl)$C_0$-$C_4$alkyl, (tetrahydrofuranyl)$C_0$-$C_4$alkyl, (pyrazolyl)$C_0$-$C_4$alkyl, (thiazolyl)$C_0$-$C_4$alkyl, (triazolyl)$C_0$-$C_4$alkyl, (tetrazolyl)$C_0$-$C_4$alkyl, (imidazolyl)$C_0$-$C_4$alkyl, (oxazolyl)$C_0$-$C_4$alkyl, (furanyl)$C_0$-$C_4$alkyl, (pyridinyl)$C_0$-$C_4$alkyl, (pyrimidinyl)$C_0$-$C_4$alkyl, (pyrazinyl)$C_0$-$C_4$alkyl, (pyridizinyl)$C_0$-$C_4$alkyl, and (tetrahydropyridinyl)$C_0$-$C_4$alkyl;

$R^{24}$ and $R^{25}$ are taken together with the nitrogen to which they are attached to form a pyrrolidinyl, piperazinyl, piperidinyl, or morpholinyl group, each of which is optionally bridged with a methylene or ethylene group or spiro to a $C_3$-$C_5$cycloalkyl group;

each of which (s) may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

This disclosure includes compounds and salts in which one of $R^{12}$ and $R^{13}$ is hydrogen, hydroxyl, halogen, methyl, or methoxy; and the other of $R^{12}$ and $R^{13}$ is chosen from (s), where (s) is -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, or -JP(O)R$^{21}$R$^{22}$;

where J is independently chosen at each occurrence and is a covalent bond, $C_1$-$C_4$alkylene, $C_2$-$C_4$alkenylene, or $C_2$-$C_4$alkynylene;

$R^{21}$ and $R^{22}$ are independently chosen at each occurrence from hydrogen, hydroxyl, cyano, amino, $C_1$-$C_6$alkyl, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, and —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl;

each of which (s) may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

This disclosure includes compounds and salts in which one of $R^{12}$ and $R^{13}$ is hydrogen, hydroxyl, halogen, methyl, or methoxy; and the other of $R^{12}$ and $R^{13}$ is —$C_2$-$C_6$alkynylR$^{23}$; where $R^{23}$ is from ($C_3$-$C_7$cycloalkyl)$C_0$-$C_4$alkyl, (phenyl)$C_0$-$C_4$alkyl, (pyrrolidinyl)$C_0$-$C_4$alkyl, (morpholinyl)$C_0$-$C_4$alkyl, (thiomorpholinyl)$C_0$-$C_4$alkyl, (piperidinyl)$C_0$-$C_4$alkyl, (piperazinyl)$C_0$-$C_4$alkyl, (tetrahydrofuranyl)$C_0$-$C_4$alkyl, (pyrazolyl)$C_0$-$C_4$alkyl, (thiazolyl)$C_0$-$C_4$alkyl, (triazolyl)$C_0$-$C_4$alkyl, (tetrazolyl)$C_0$-$C_4$alkyl, (imidazolyl)$C_0$-$C_4$alkyl, (oxazolyl)$C_0$-$C_4$alkyl, (furanyl)$C_0$-$C_4$alkyl, (pyridinyl)$C_0$-$C_4$alkyl, (pyrimidinyl)$C_0$-$C_4$alkyl, (pyrazinyl)$C_0$-$C_4$alkyl, (pyridizinyl)$C_0$-$C_4$alkyl, and (tetrahydropyridinyl)$C_0$-$C_4$alkyl; which may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

This disclosure includes compounds and salts in which one of $R^{12}$ and $R^{13}$ is hydrogen, hydroxyl, halogen, methyl, or methoxy; the other of $R^{12}$ and $R^{13}$ is chosen from (s) where (s) is chosen from -JNR$^9$C(O)OR$^{10}$, -JNR$^9$C(O)OR$^{23}$, -JOC(O)NR$^{21}$R$^{22}$, -JOC(O)NR$^{24}$R$^{25}$, -JNR$^9$C(O)NR$^{10}$R$^{23}$, and -JNR$^9$C(O)NR$^{24}$R$^{25}$;

$R^{21}$ and $R^{22}$ are independently chosen at each occurrence from hydrogen, hydroxyl, cyano, amino, $C_1$-$C_6$alkyl, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (pyrrolidinyl)$C_0$-$C_4$alkyl, ((morpholinyl)$C_0$-$C_4$alkyl, (thiomorpholinyl)$C_0$-$C_4$alkyl, (piperidinyl)$C_0$-$C_4$alkyl, (piperazinyl)$C_0$-$C_4$alkyl, (tetrahydrofuranyl)$C_0$-$C_4$alkyl, pyrazolyl)$C_0$-$C_4$alkyl, (thiazolyl)$C_0$-$C_4$alkyl, (triazolyl)$C_0$-$C_4$alkyl, (tetrazolyl)$C_0$-$C_4$alkyl, (imidazolyl)$C_0$-$C_4$alkyl, (oxazolyl)$C_0$-$C_4$alkyl, (furanyl)$C_0$-$C_4$alkyl, (pyridinyl)$C_0$-$C_4$alkyl, (pyrimidinyl)$C_0$-$C_4$alkyl, (pyrazinyl)$C_0$-$C_4$alkyl, (pyridizinyl)$C_0$-$C_4$alkyl, and (tetrahydropyridinyl)$C_0$-$C_4$alkyl;

$R^{23}$ is independently chosen at each occurrence from ($C_3$-$C_7$cycloalkyl)$C_0$-$C_4$alkyl, (phenyl)$C_0$-$C_4$alkyl, (pyrrolidinyl)$C_0$-$C_4$alkyl, (morpholinyl)$C_0$-$C_4$alkyl, (thiomorpholinyl)$C_0$-$C_4$alkyl, (piperidinyl)$C_0$-$C_4$alkyl, (piperazinyl)$C_0$-$C_4$alkyl, (tetrahydrofuranyl)$C_0$-$C_4$alkyl, (pyrazolyl)$C_0$-$C_4$alkyl, (thiazolyl)$C_0$-$C_4$alkyl, (triazolyl)$C_0$-$C_4$alkyl, (tetrazolyl)$C_0$-$C_4$alkyl, (imidazolyl)$C_0$-$C_4$alkyl, (oxazolyl)$C_0$-$C_4$alkyl, (furanyl)$C_0$-$C_4$alkyl, (pyridinyl)$C_0$-$C_4$alkyl, (pyrimidinyl)$C_0$-$C_4$alkyl, (pyrazinyl)$C_0$-$C_4$alkyl, (pyridizinyl)$C_0$-$C_4$alkyl, and (tetrahydropyridinyl)$C_0$-$C_4$alkyl;

$R^{24}$ and $R^{25}$ are taken together with the nitrogen to which they are attached to form a pyrrolidinyl, piperazinyl, piperidinyl, or morpholinyl group, each of which is optionally bridged with a methylene or ethylene group or spiro to a $C_3$-$C_5$cycloalkyl group; each of which (s) may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

This disclosure includes compounds and salts of Formula IA:

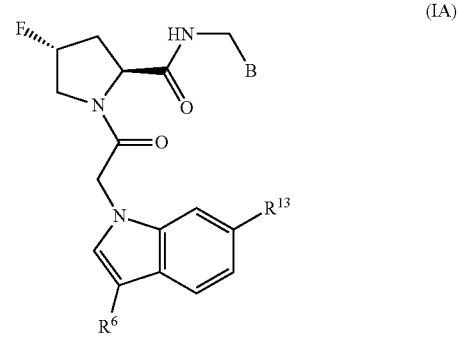

(IA)

where

B may carry any of the definitions set forth herein for this variable. In certain embodiments B is a 2-fluoro-3-chlorophenyl or a 2-fluoro-3-trifluoromethoxy-phenyl. Examples of such compounds include the compounds shown in Table 1. In any of the compounds shown in Table 1 the 2-fluoro-3-chloro-phenyl group may be replaced by a 2-fluoro-3-trifluoromethoxy-phenyl.

This disclosure includes compounds and salts of Formula IB, IC, and ID.

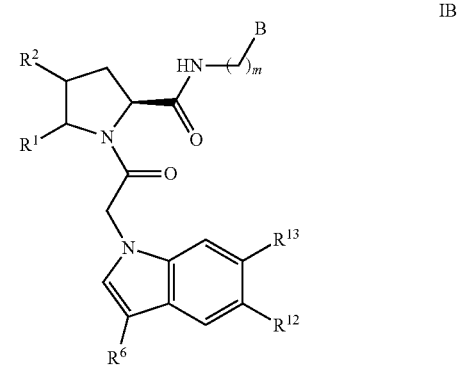

IB

-continued

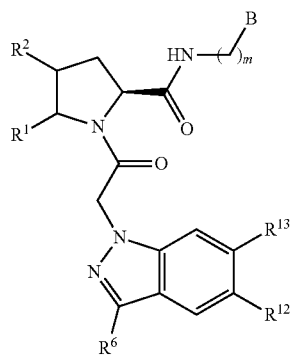

IC

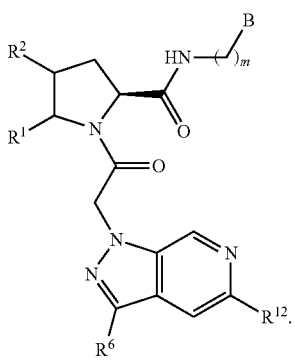

ID

In Formula IB, IC, and ID the variables may include any of the definitions set forth herein that results in a stable compound. In certain embodiments to the following conditions apply for Formula IB, IC, and ID.

$R^1$ is hydrogen and $R^2$ is fluoro.

$R^1$ and $R^2$ are joined to form a 3 membered ring.

m is 0.

B is pyridyl, optionally substituted with halogen, $C_1$-$C_2$alkoxy, and trifluoromethyl.

B is phenyl, substituted with 1, 2, or 3 substituents independently selected from halogen, $C_1$-$C_2$alkyl, $C_1$-$C_2$alkoxy, trifluoromethyl, and optionally substituted phenyl.

$R^{13}$ is hydrogen and $R^{12}$ is —NHC(O)NR$^{24}$R$^{25}$.

$R^{13}$ is hydrogen and $R^{12}$ is —CCR$^{23}$.

$R^{13}$ is hydrogen and $R^{12}$ is —NHC(O)NHR$^{23}$.

$R^{13}$ is hydrogen and $R^{12}$ is —C(O)R$^{23}$.

TABLE 1

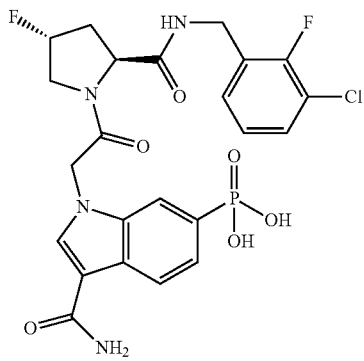

TABLE 1-continued

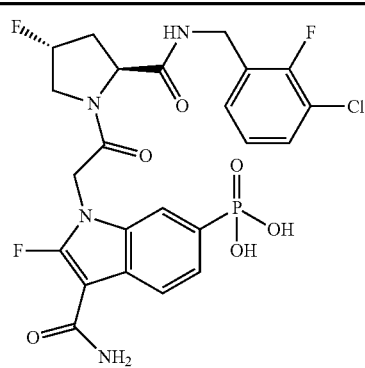

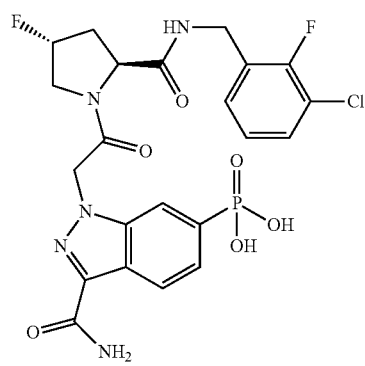 [SMILES: NC(=O)c1nn(CC(=O)N2C[C@H](F)C[C@H]2C(=O)NCc2cccc(Cl)c2F)c2cc(P(=O)(O)O)ccc12]

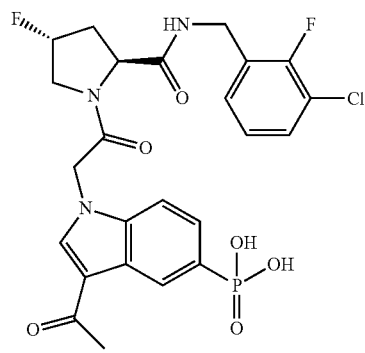 [SMILES: CC(=O)c1cn(CC(=O)N2C[C@H](F)C[C@H]2C(=O)NCc2cccc(Cl)c2F)c2ccc(P(=O)(O)O)cc12]

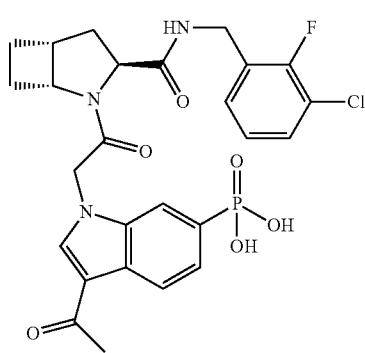 [SMILES: CC(=O)c1cn(CC(=O)N2[C@@H]3CC[C@@H]3C[C@H]2C(=O)NCc2cccc(Cl)c2F)c2cc(P(=O)(O)O)ccc12]

TABLE 1-continued
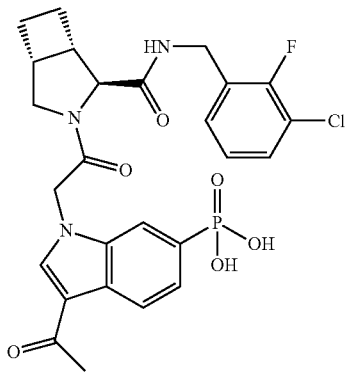 [SMILES: CC(=O)c1cn(CC(=O)N2C[C@@H]3CC[C@@H]3[C@H]2C(=O)NCc2cccc(Cl)c2F)c2cc(P(=O)(O)O)ccc12]
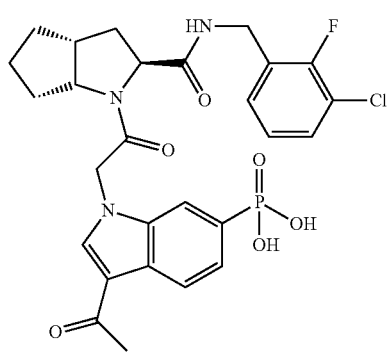
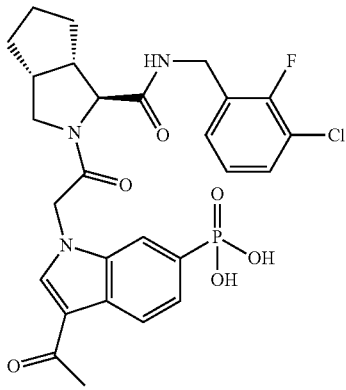 [SMILES: CC(=O)c1cn(CC(=O)N2C[C@@H]3CCC[C@@H]3[C@H]2C(=O)NCc2cccc(Cl)c2F)c2cc(P(=O)(O)O)ccc12]
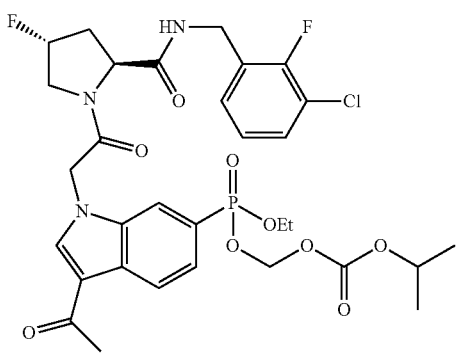 [SMILES: CCOP(=O)(OCOC(=O)OC(C)C)c1ccc2c(C(C)=O)cn(CC(=O)N3C[C@H](F)C[C@H]3C(=O)NCc3cccc(Cl)c3F)c2c1]
TABLE 1-continued
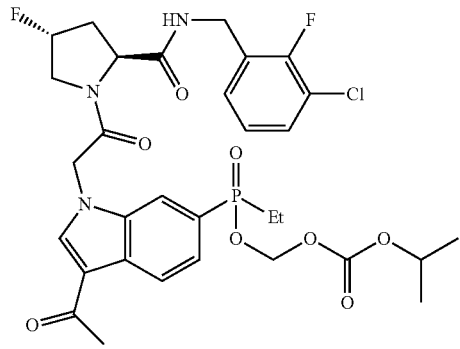 [SMILES: CCP(=O)(OCOC(=O)OC(C)C)c1ccc2c(C(C)=O)cn(CC(=O)N3C[C@H](F)C[C@H]3C(=O)NCc3cccc(Cl)c3F)c2c1]
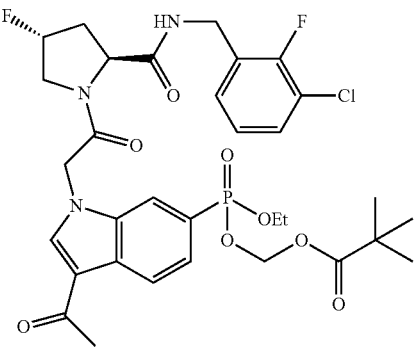 [SMILES: CCOP(=O)(OCOC(=O)C(C)(C)C)c1ccc2c(C(C)=O)cn(CC(=O)N3C[C@H](F)C[C@H]3C(=O)NCc3cccc(Cl)c3F)c2c1]
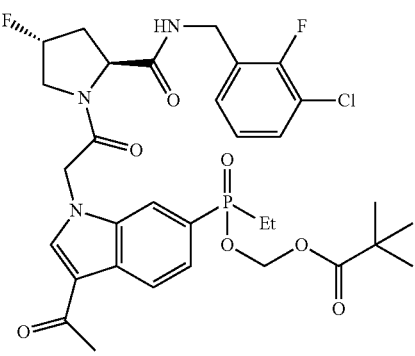 [SMILES: CCP(=O)(OCOC(=O)C(C)(C)C)c1ccc2c(C(C)=O)cn(CC(=O)N3C[C@H](F)C[C@H]3C(=O)NCc3cccc(Cl)c3F)c2c1]
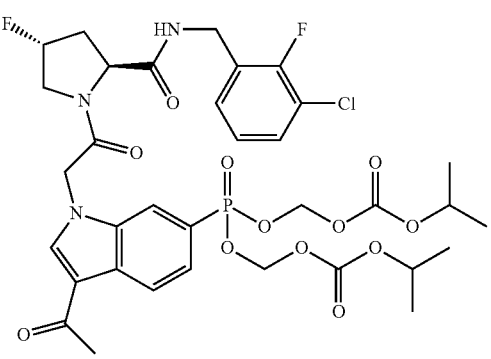 [SMILES: CC(=O)c1cn(CC(=O)N2C[C@H](F)C[C@H]2C(=O)NCc2cccc(Cl)c2F)c2cc(P(=O)(OCOC(=O)OC(C)C)OCOC(=O)OC(C)C)ccc12]

TABLE 1-continued
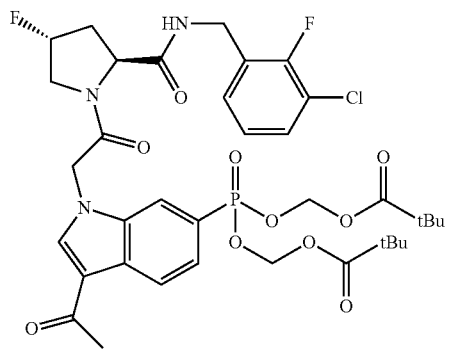 [SMILES: CC(=O)c1cn(CC(=O)N2C[C@H](F)C[C@H]2C(=O)NCc2cccc(Cl)c2F)c2cc(P(=O)(OCOC(=O)C(C)(C)C)OCOC(=O)C(C)(C)C)ccc12]
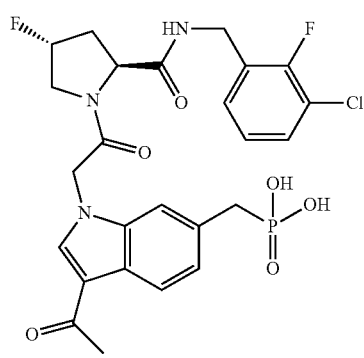
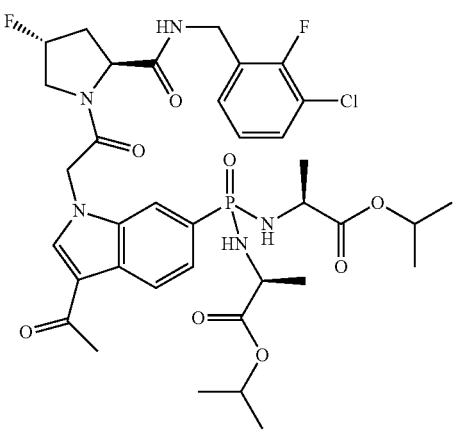 [SMILES: CC(=O)c1cn(CC(=O)N2C[C@H](F)C[C@H]2C(=O)NCc2cccc(Cl)c2F)c2cc(P(=O)(N[C@@H](C)C(=O)OC(C)C)N[C@@H](C)C(=O)OC(C)C)ccc12]
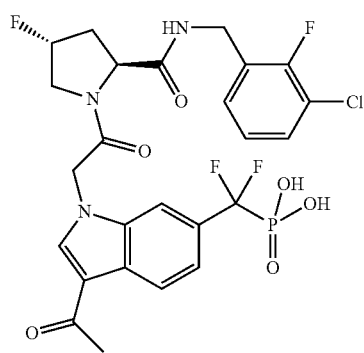
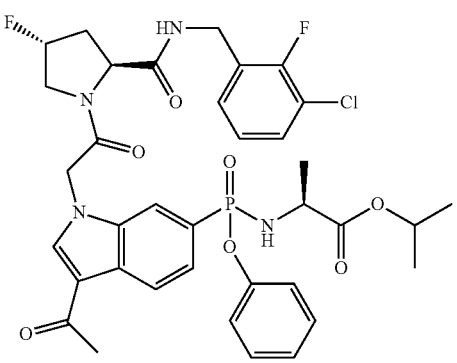 [SMILES: CC(=O)c1cn(CC(=O)N2C[C@H](F)C[C@H]2C(=O)NCc2cccc(Cl)c2F)c2cc(P(=O)(N[C@@H](C)C(=O)OC(C)C)Oc3ccccc3)ccc12]
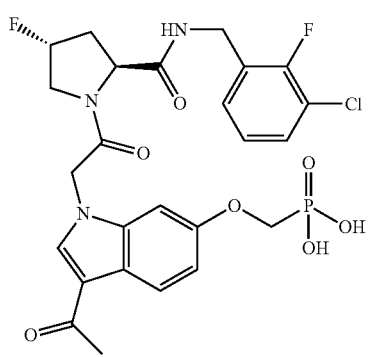 [SMILES: CC(=O)c1cn(CC(=O)N2C[C@H](F)C[C@H]2C(=O)NCc2cccc(Cl)c2F)c2cc(OCP(=O)(O)O)ccc12]
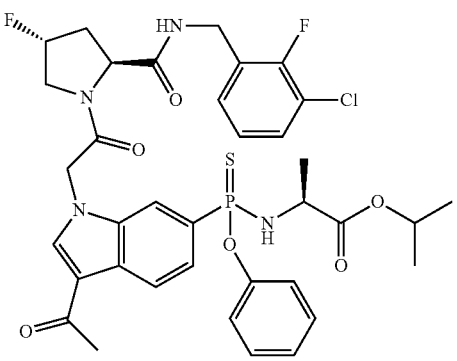
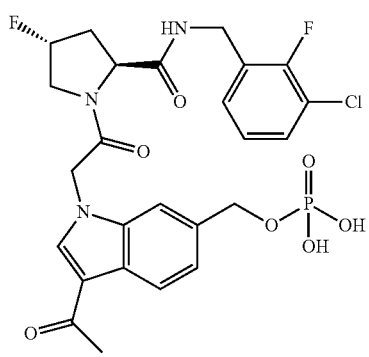 [SMILES: CC(=O)c1cn(CC(=O)N2C[C@H](F)C[C@H]2C(=O)NCc2cccc(Cl)c2F)c2cc(COP(=O)(O)O)ccc12]

TABLE 1-continued
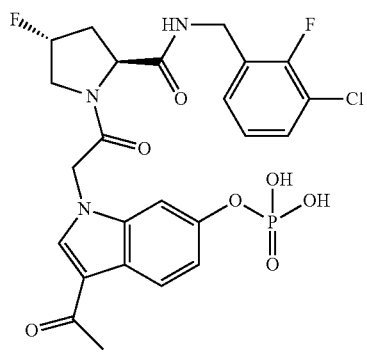 [SMILES: CC(=O)c1cn(CC(=O)N2C[C@H](F)C[C@H]2C(=O)NCc2cccc(Cl)c2F)c2cc(OP(=O)(O)O)ccc12]
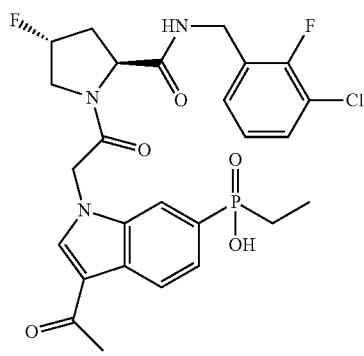 [SMILES: CCP(=O)(O)c1ccc2c(C(C)=O)cn(CC(=O)N3C[C@H](F)C[C@H]3C(=O)NCc3cccc(Cl)c3F)c2c1]
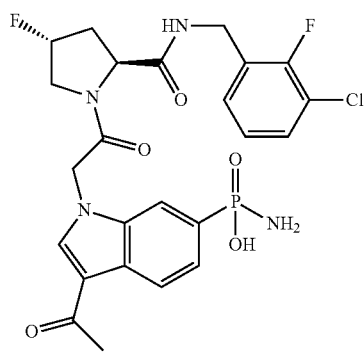 [SMILES: CC(=O)c1cn(CC(=O)N2C[C@H](F)C[C@H]2C(=O)NCc2cccc(Cl)c2F)c2cc(P(N)(=O)O)ccc12]
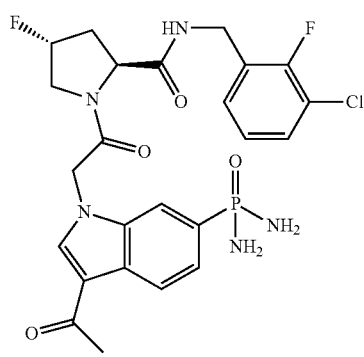 [SMILES: CC(=O)c1cn(CC(=O)N2C[C@H](F)C[C@H]2C(=O)NCc2cccc(Cl)c2F)c2cc(P(N)(N)=O)ccc12]
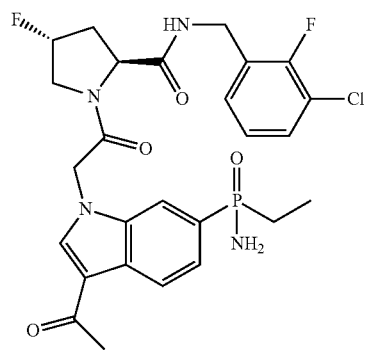 [SMILES: CCP(N)(=O)c1ccc2c(C(C)=O)cn(CC(=O)N3C[C@H](F)C[C@H]3C(=O)NCc3cccc(Cl)c3F)c2c1]
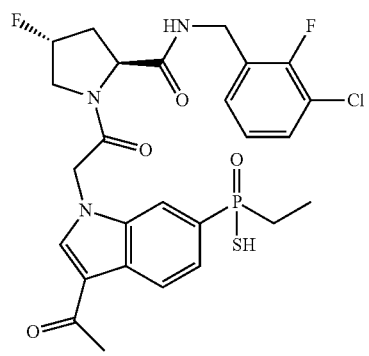 [SMILES: CCP(=O)(S)c1ccc2c(C(C)=O)cn(CC(=O)N3C[C@H](F)C[C@H]3C(=O)NCc3cccc(Cl)c3F)c2c1]
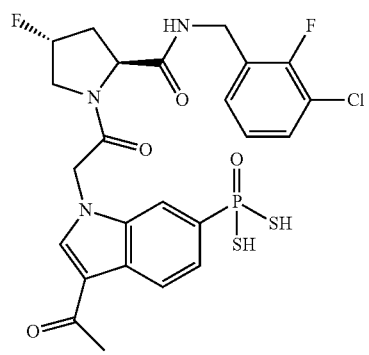 [SMILES: CC(=O)c1cn(CC(=O)N2C[C@H](F)C[C@H]2C(=O)NCc2cccc(Cl)c2F)c2cc(P(=O)(S)S)ccc12]
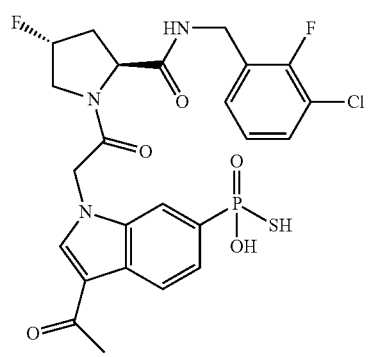 [SMILES: CC(=O)c1cn(CC(=O)N2C[C@H](F)C[C@H]2C(=O)NCc2cccc(Cl)c2F)c2cc(P(=O)(O)S)ccc12]

TABLE 1-continued
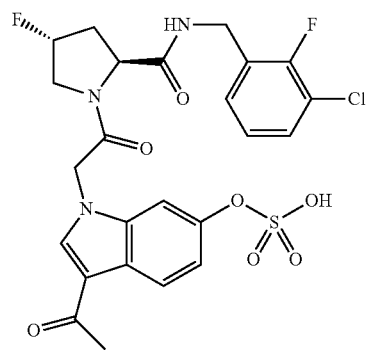 [SMILES: CC(=O)c1cn(CC(=O)N2C[C@H](F)C[C@H]2C(=O)NCc2cccc(Cl)c2F)c2cc(OS(=O)(=O)O)ccc12]
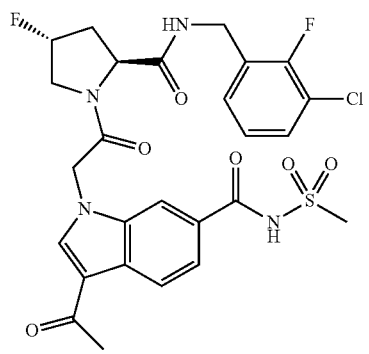
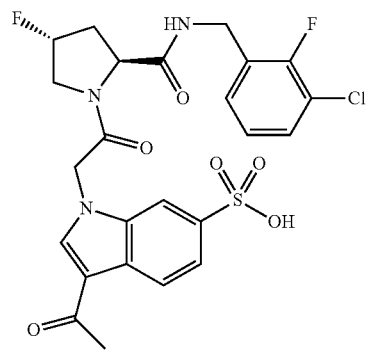 [SMILES: CC(=O)c1cn(CC(=O)N2C[C@H](F)C[C@H]2C(=O)NCc2cccc(Cl)c2F)c2cc(S(=O)(=O)O)ccc12]
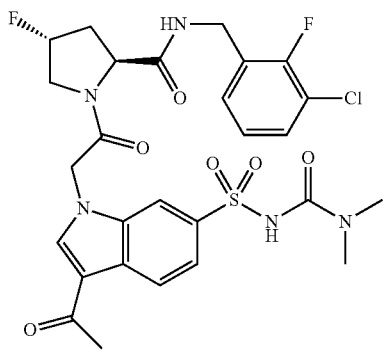
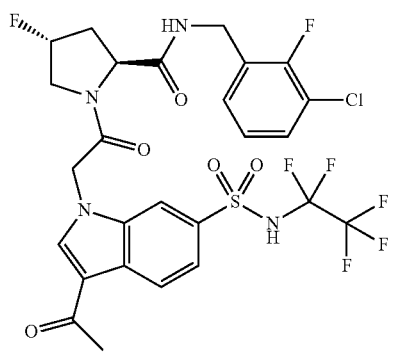 [SMILES: CC(=O)c1cn(CC(=O)N2C[C@H](F)C[C@H]2C(=O)NCc2cccc(Cl)c2F)c2cc(S(=O)(=O)NC(F)(F)C(F)(F)F)ccc12]
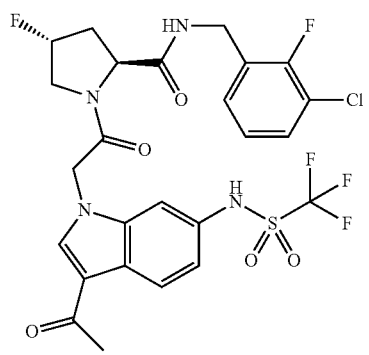
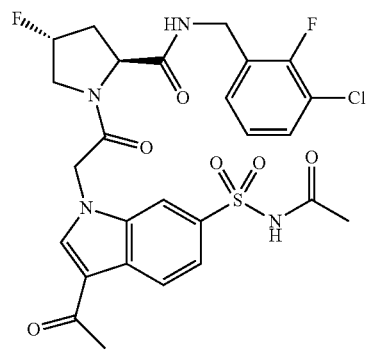 [SMILES: CC(=O)NS(=O)(=O)c1ccc2c(C(C)=O)cn(CC(=O)N3C[C@H](F)C[C@H]3C(=O)NCc3cccc(Cl)c3F)c2c1]
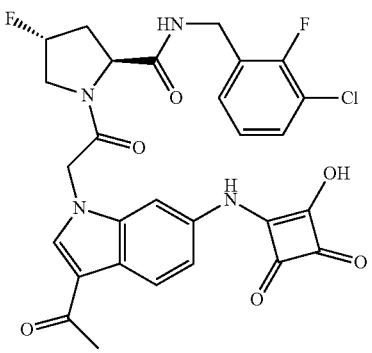 [SMILES: CC(=O)c1cn(CC(=O)N2C[C@H](F)C[C@H]2C(=O)NCc2cccc(Cl)c2F)c2cc(Nc3c(O)c(=O)c3=O)ccc12]

TABLE 1-continued
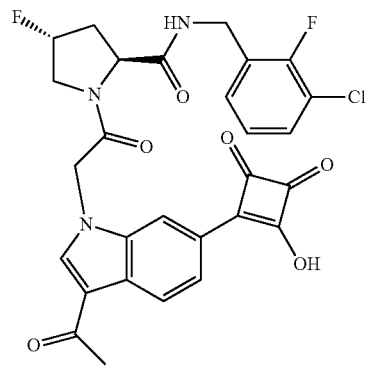 [SMILES: CC(=O)c1cn(CC(=O)N2C[C@H](F)C[C@H]2C(=O)NCc2cccc(Cl)c2F)c2cc(-c3c(O)c(=O)c3=O)ccc12]
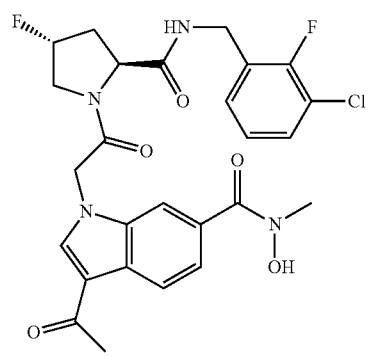 [SMILES: CC(=O)c1cn(CC(=O)N2C[C@H](F)C[C@H]2C(=O)NCc2cccc(Cl)c2F)c2cc(C(=O)N(C)O)ccc12]
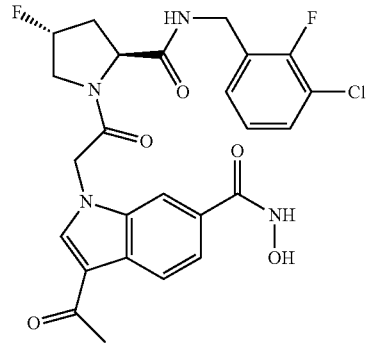 [SMILES: CC(=O)c1cn(CC(=O)N2C[C@H](F)C[C@H]2C(=O)NCc2cccc(Cl)c2F)c2cc(C(=O)NO)ccc12]
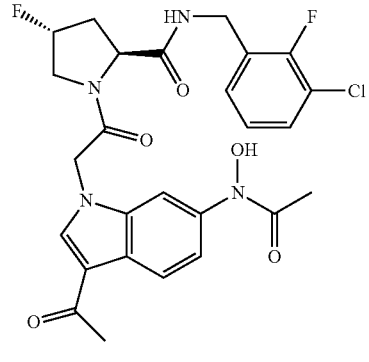 [SMILES: CC(=O)c1cn(CC(=O)N2C[C@H](F)C[C@H]2C(=O)NCc2cccc(Cl)c2F)c2cc(N(O)C(C)=O)ccc12]
TABLE 1-continued
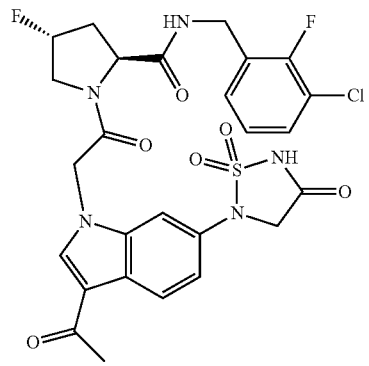 [SMILES: CC(=O)c1cn(CC(=O)N2C[C@H](F)C[C@H]2C(=O)NCc2cccc(Cl)c2F)c2cc(N3CC(=O)NS3(=O)=O)ccc12]
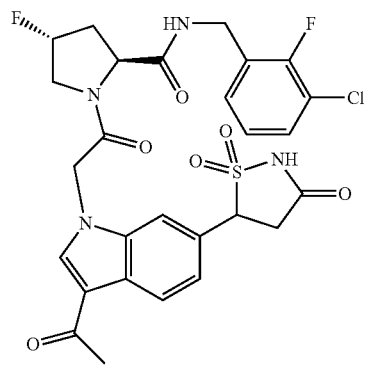 [SMILES: CC(=O)c1cn(CC(=O)N2C[C@H](F)C[C@H]2C(=O)NCc2cccc(Cl)c2F)c2cc(C3CC(=O)NS3(=O)=O)ccc12]
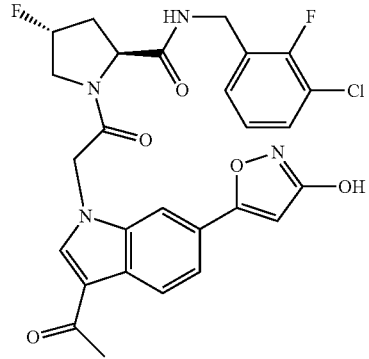 [SMILES: CC(=O)c1cn(CC(=O)N2C[C@H](F)C[C@H]2C(=O)NCc2cccc(Cl)c2F)c2cc(-c3cc(O)no3)ccc12]
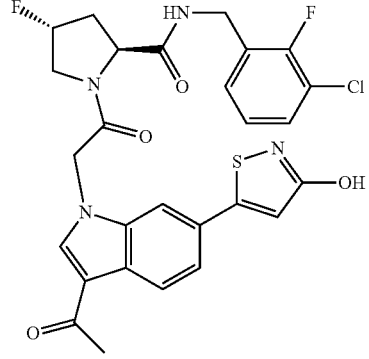 [SMILES: CC(=O)c1cn(CC(=O)N2C[C@H](F)C[C@H]2C(=O)NCc2cccc(Cl)c2F)c2cc(-c3cc(O)ns3)ccc12]

TABLE 1-continued
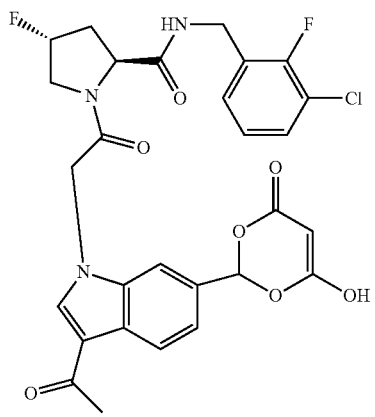 [SMILES: CC(=O)c1cn(CC(=O)N2C[C@H](F)C[C@H]2C(=O)NCc2cccc(Cl)c2F)c2cc(C3OC(=O)C=C(O)O3)ccc12]
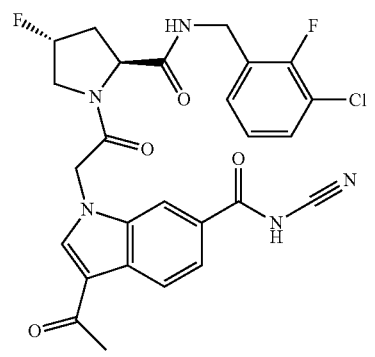 [SMILES: CC(=O)c1cn(CC(=O)N2C[C@H](F)C[C@H]2C(=O)NCc2cccc(Cl)c2F)c2cc(C(=O)NC#N)ccc12]
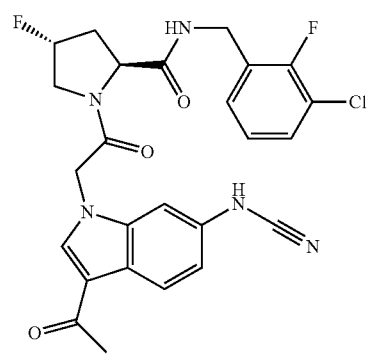 [SMILES: CC(=O)c1cn(CC(=O)N2C[C@H](F)C[C@H]2C(=O)NCc2cccc(Cl)c2F)c2cc(NC#N)ccc12]
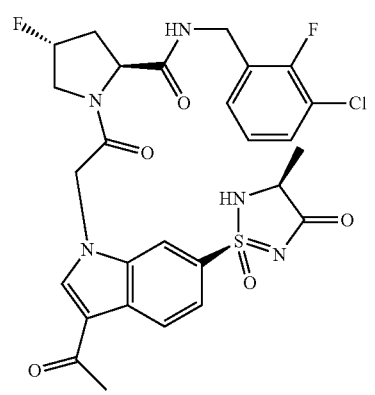 [SMILES: CC(=O)c1cn(CC(=O)N2C[C@H](F)C[C@H]2C(=O)NCc2cccc(Cl)c2F)c2cc([S@]3(=O)=NC(=O)[C@H](C)N3)ccc12]
TABLE 1-continued
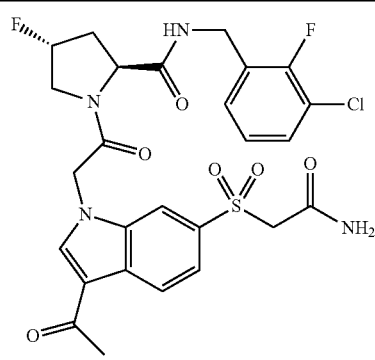
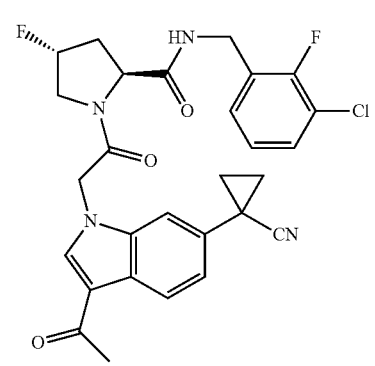 [SMILES: CC(=O)c1cn(CC(=O)N2C[C@H](F)C[C@H]2C(=O)NCc2cccc(Cl)c2F)c2cc(C3(C#N)CC3)ccc12]
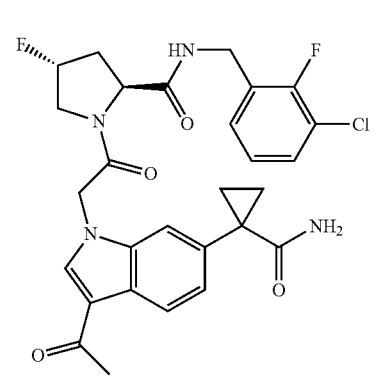 [SMILES: CC(=O)c1cn(CC(=O)N2C[C@H](F)C[C@H]2C(=O)NCc2cccc(Cl)c2F)c2cc(C3(C(N)=O)CC3)ccc12]
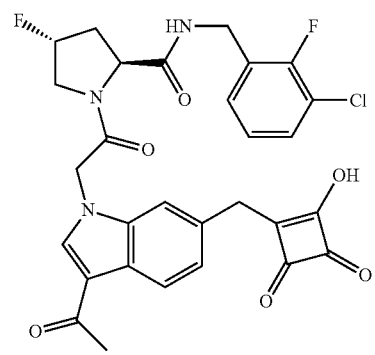 [SMILES: CC(=O)c1cn(CC(=O)N2C[C@H](F)C[C@H]2C(=O)NCc2cccc(Cl)c2F)c2cc(Cc3c(O)c(=O)c3=O)ccc12]

TABLE 1-continued
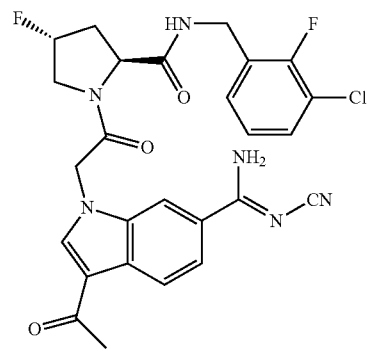
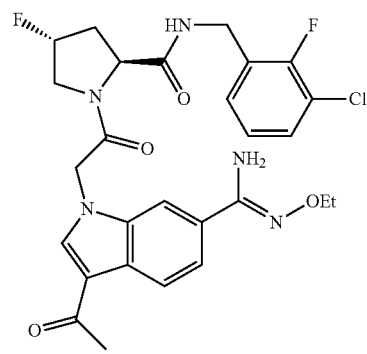 [SMILES: CC(=O)c1cn(CC(=O)N2C[C@H](F)C[C@H]2C(=O)NCc2cccc(Cl)c2F)c2cc(/C(N)=N/C#N)ccc12]
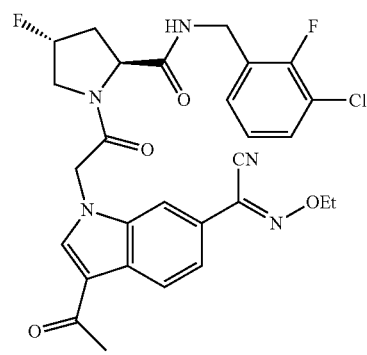 [SMILES: CCO/N=C(\C#N)c1ccc2c(C(C)=O)cn(CC(=O)N3C[C@H](F)C[C@H]3C(=O)NCc3cccc(Cl)c3F)c2c1]
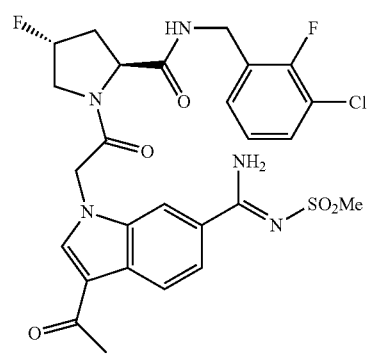 [SMILES: CC(=O)c1cn(CC(=O)N2C[C@H](F)C[C@H]2C(=O)NCc2cccc(Cl)c2F)c2cc(/C(N)=N/S(C)(=O)=O)ccc12]
TABLE 1-continued
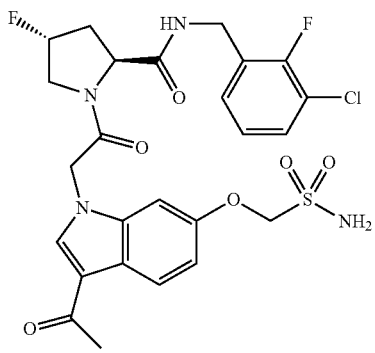 [SMILES: CC(=O)c1cn(CC(=O)N2C[C@H](F)C[C@H]2C(=O)NCc2cccc(Cl)c2F)c2cc(OCS(N)(=O)=O)ccc12]
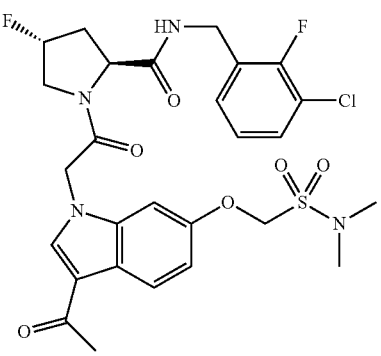 [SMILES: CC(=O)c1cn(CC(=O)N2C[C@H](F)C[C@H]2C(=O)NCc2cccc(Cl)c2F)c2cc(OCS(=O)(=O)N(C)C)ccc12]
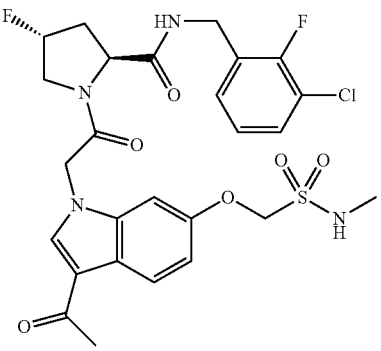 [SMILES: CNS(=O)(=O)COc1ccc2c(C(C)=O)cn(CC(=O)N3C[C@H](F)C[C@H]3C(=O)NCc3cccc(Cl)c3F)c2c1]
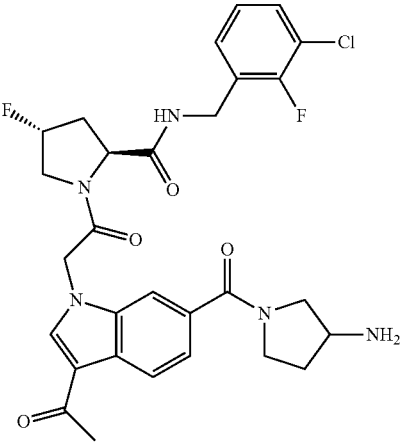 [SMILES: CC(=O)c1cn(CC(=O)N2C[C@H](F)C[C@H]2C(=O)NCc2cccc(Cl)c2F)c2cc(C(=O)N3CCC(N)C3)ccc12]

TABLE 1-continued
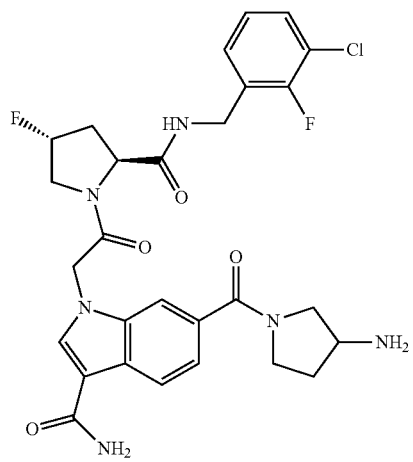 [SMILES: NC(=O)c1cn(CC(=O)N2C[C@H](F)C[C@H]2C(=O)NCc2cccc(Cl)c2F)c2cc(C(=O)N3CCC(N)C3)ccc12]
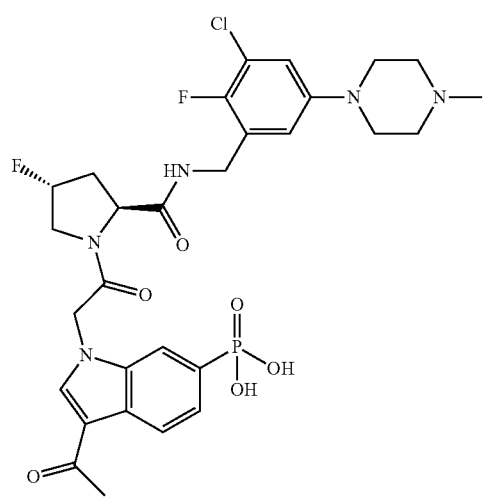 [SMILES: CC(=O)c1cn(CC(=O)N2C[C@H](F)C[C@H]2C(=O)NCc2cc(N3CCN(C)CC3)cc(Cl)c2F)c2cc(P(=O)(O)O)ccc12]
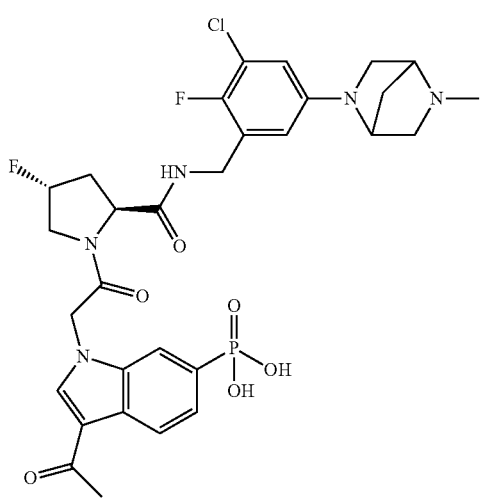 [SMILES: CC(=O)c1cn(CC(=O)N2C[C@H](F)C[C@H]2C(=O)NCc2cc(N3CC4CC3CN4C)cc(Cl)c2F)c2cc(P(=O)(O)O)ccc12]
TABLE 1-continued
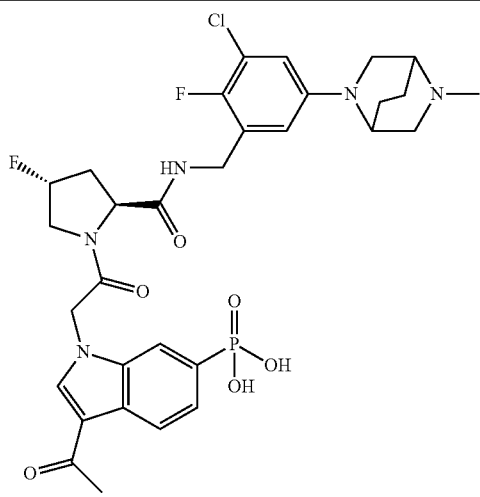
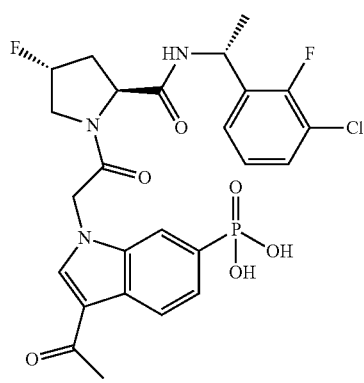 [SMILES: CC(=O)c1cn(CC(=O)N2C[C@H](F)C[C@H]2C(=O)N[C@H](C)c2cccc(Cl)c2F)c2cc(P(=O)(O)O)ccc12]
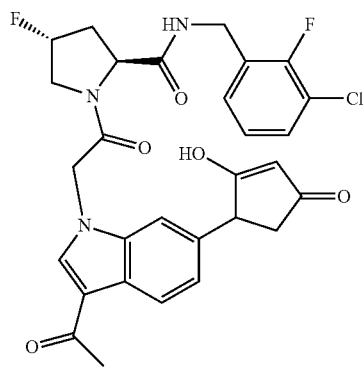 [SMILES: CC(=O)c1cn(CC(=O)N2C[C@H](F)C[C@H]2C(=O)NCc2cccc(Cl)c2F)c2cc(C3CC(=O)C=C3O)ccc12]
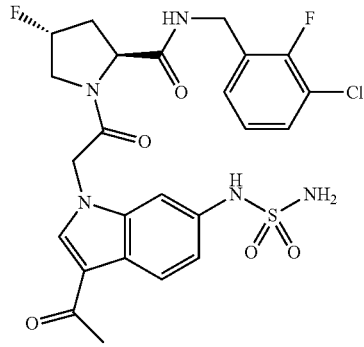 [SMILES: CC(=O)c1cn(CC(=O)N2C[C@H](F)C[C@H]2C(=O)NCc2cccc(Cl)c2F)c2cc(NS(N)(=O)=O)ccc12]

TABLE 1-continued

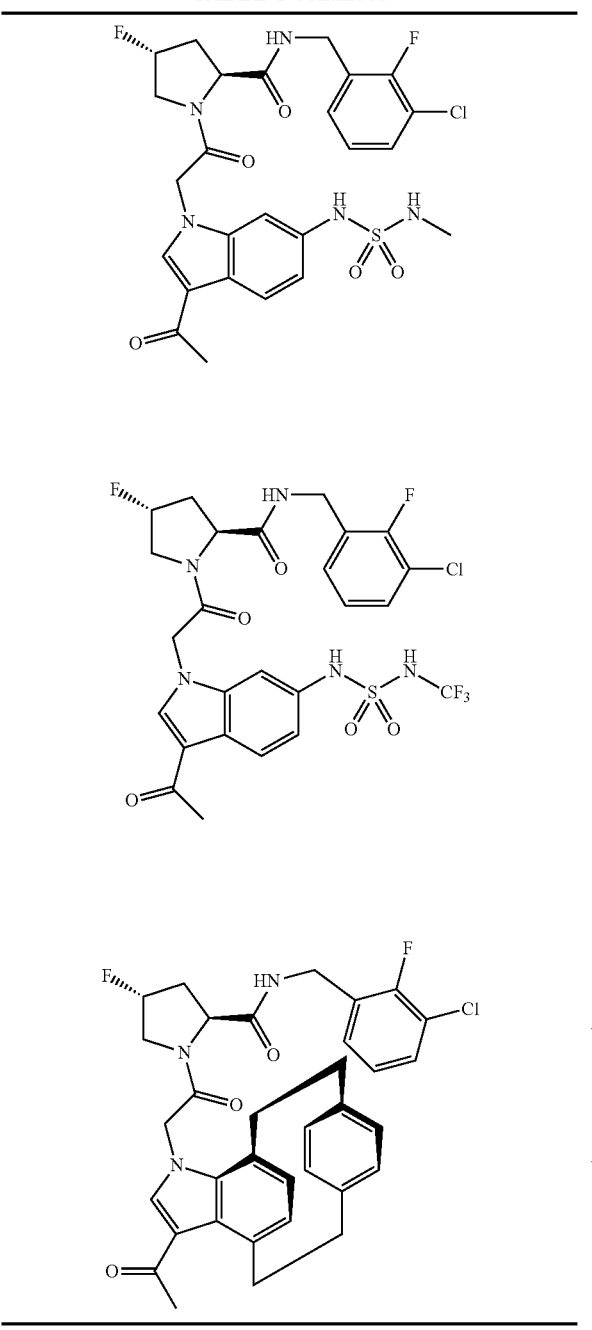

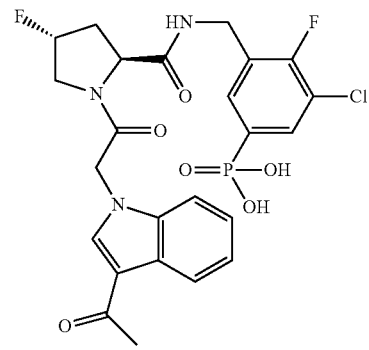

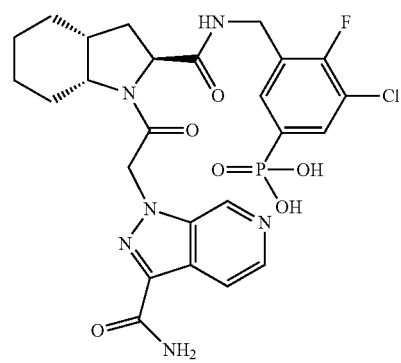

The disclosure also includes compounds and salts of Formula IA in which $R^{13}$ is hydrogen, halogen, hydroxyl, nitro, $C_2$-$C_6$alkanoyl, $C_1$-$C_6$alkoxy, $C_1$-$C_6$thioalkyl, ($C_3$-$C_7$cycloalkyl)$C_0$-$C_4$alkyl, ($C_3$-$C_7$cycloalkyl)$C_0$-$C_4$alkoxy, $C_1$-$C_2$haloalkyl, or $C_1$-$C_2$haloalkoxy and B is an aryl or heteroaryl group such as a phenyl or pyridyl substituted with at least one phosphate, thiophosphate, phosphoamide, or phosphothioamide group and optionally substituted with additional substituents independently chosen from halogen, hydroxyl, nitro, $C_2$-$C_6$alkanoyl, $C_1$-$C_6$alkoxy, $C_1$-$C_6$thioalkyl, ($C_3$-$C_7$cycloalkyl)$C_0$-$C_4$alkyl, ($C_3$-$C_7$cycloalkyl)$C_0$-$C_4$alkoxy, $C_1$-$C_2$haloalkyl, or $C_1$-$C_2$haloalkoxy.

Examples of such compounds include:

The disclosure also includes boron containing compounds. These compounds may be compounds of Formula IA in which the $R^{13}$ substituent is a boron containing substituent such as —B(OH)$_2$ and also compounds of Formula I in which A is a benzoazoborale group. For example

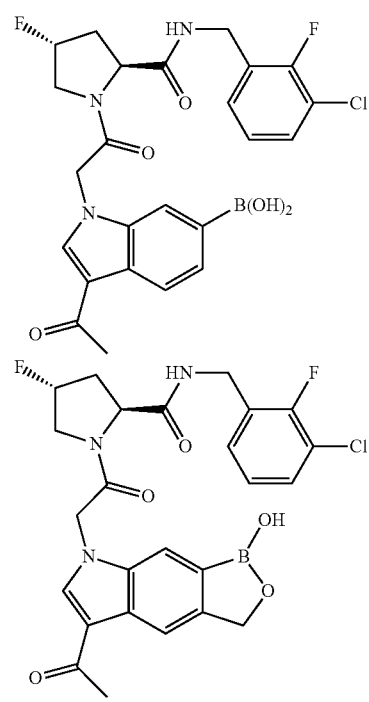

-continued

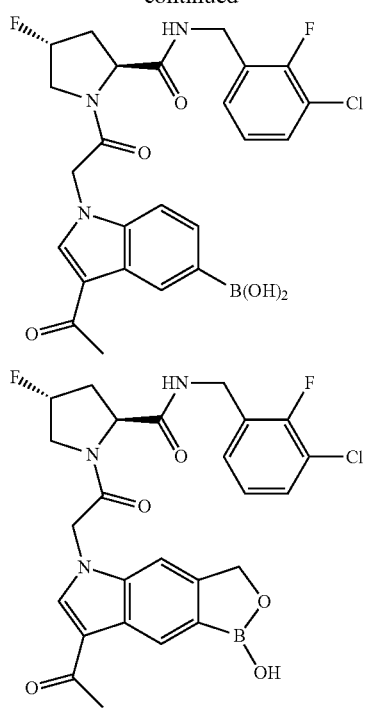

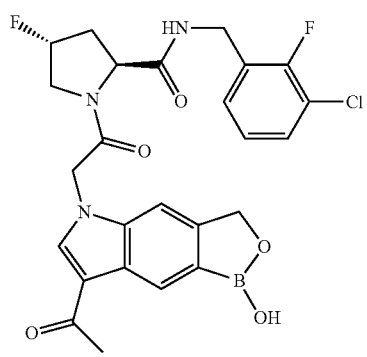

The disclosure also includes compounds which contain an azulene ring. These compounds are compounds of Formula IE. In certain embodiments B is a 2-fluoro-3-chlorophenyl or a 2-fluoro-3-trifluoromethoxy-phenyl. In any of the azulene containing compounds shown below the 2-fluoro-3-chloro-phenyl group may be replaced by a 2-fluoro-3-trifluoromethoxy-phenyl.

Formula IE

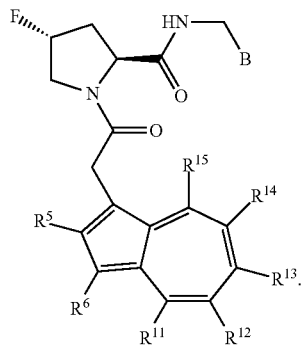

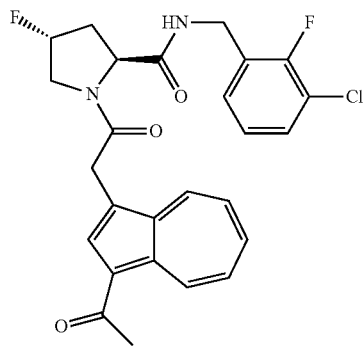 [SMILES: CC(=O)c1cc(CC(=O)N2C[C@H](F)C[C@H]2C(=O)NCc2cccc(Cl)c2F)c2ccc(O)ccc1-2]

-continued

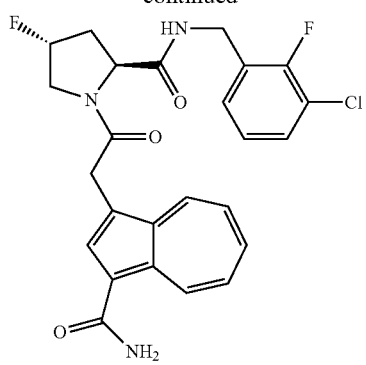


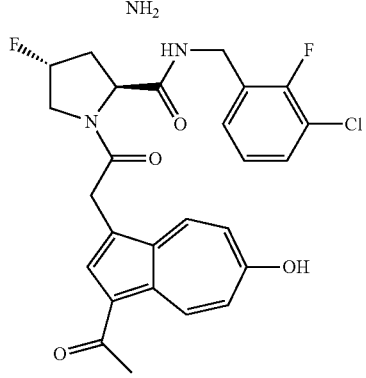

The disclosure includes compounds of Formula I in which $R^1$ and $R^2$ are joined to a 3- to 6-membered heterocycloalkyl group and $R^{1'}$, $R^{2'}$, $R^3$, and $R^{3'}$ are all hydrogen. The disclosure also includes compounds in which $R^2$ and $R^3$ are joined to a 3- to 6-membered heterocycloalkyl group and $R^1$, $R^{1'}$, $R^{2'}$, and $R^{3'}$ are all hydrogen.

Examples of such compounds include:

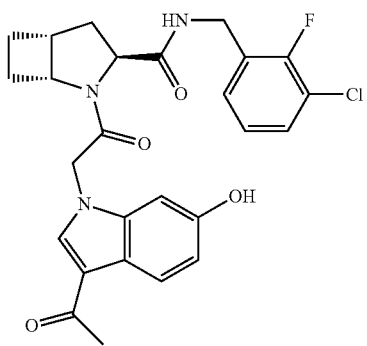

51
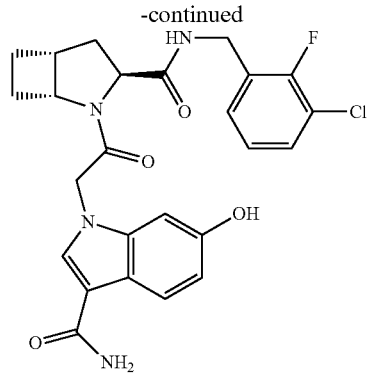
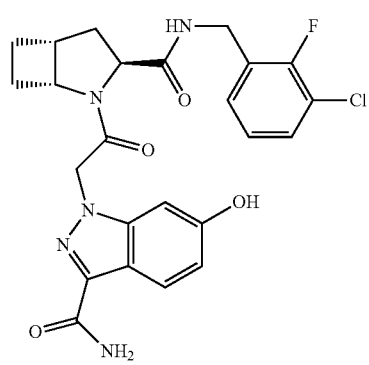
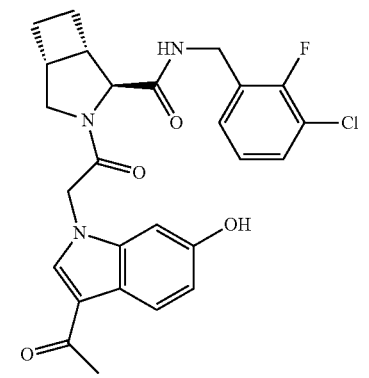
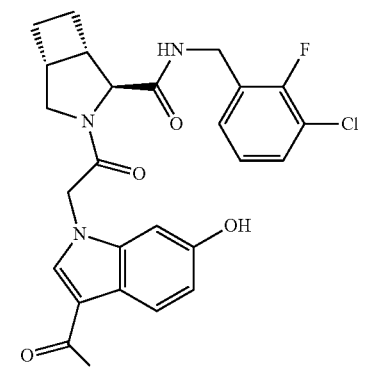
52
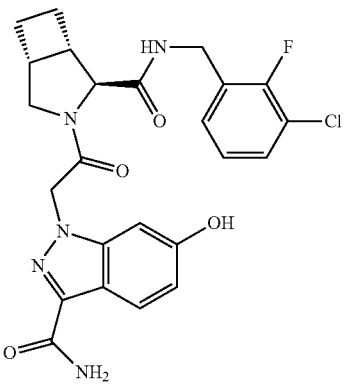
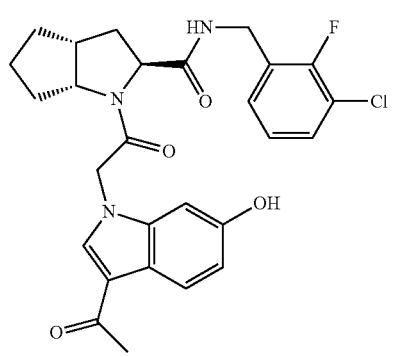
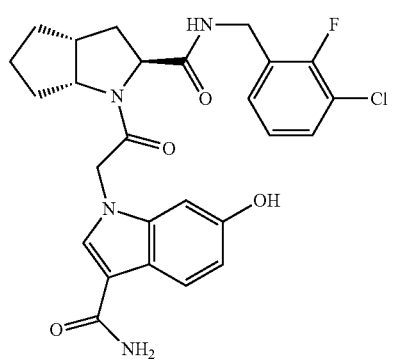
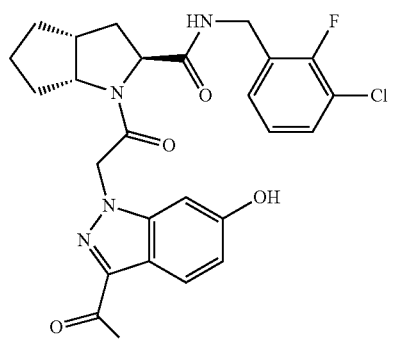

-continued

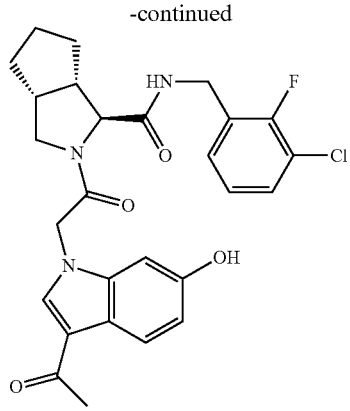

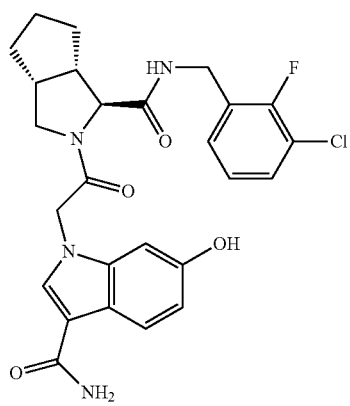

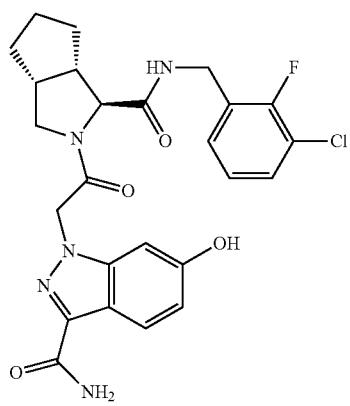

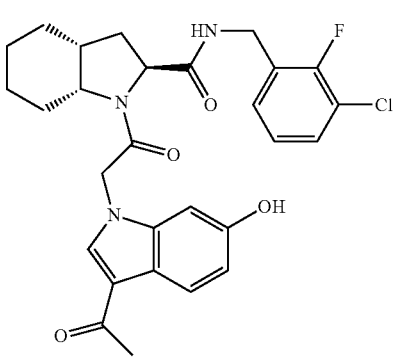

-continued

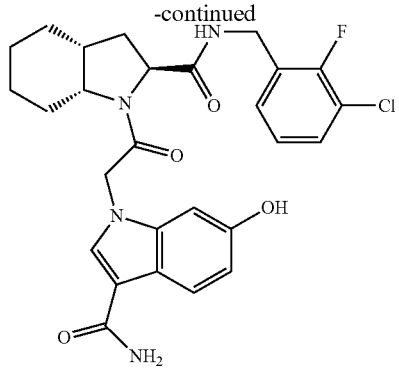

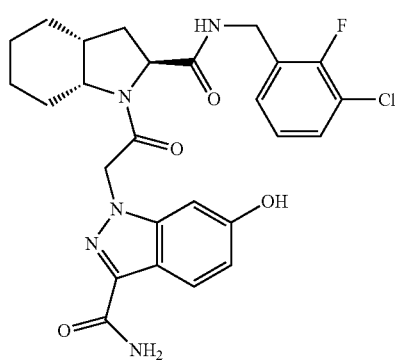 [SMILES: NC(=O)c1nn(CC(=O)N2[C@@H]3CCCC[C@@H]3C[C@H]2C(=O)NCc2cccc(Cl)c2F)c2cc(O)ccc12]

The disclosure further includes compounds and salts of Formula I in which the group A is 2-fluoro-3-chloro-phenyl. The 2-fluoro-3-chloro-phenyl group may be replaced by another carbocyclic or heterocyclic group such as 2-bromo-pyridin-6-yl, 1-(2,2,2-trifluroehtyl)-1H-pyrazol-3-yl, 2,2-dichlorocyclopropylmethyl, 2-fluoro-3-trimethylsilylphenyl.

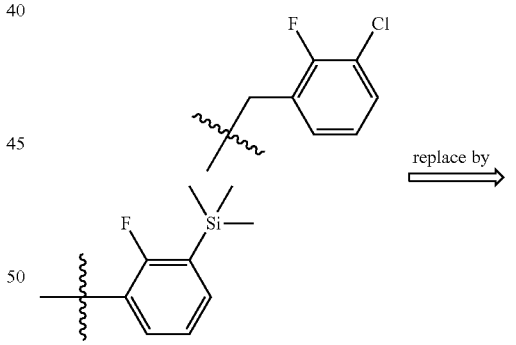

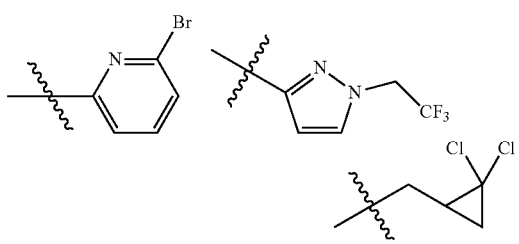

The disclosure further includes compounds and salts of Formula I, in which A is a heterocyclic group chosen from:

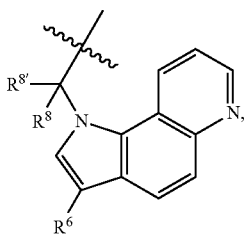
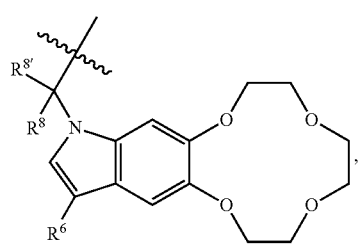
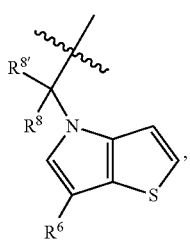 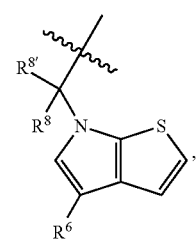
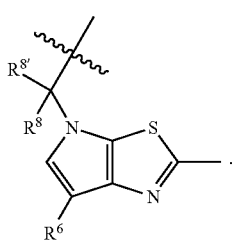
Examples of such compounds include:
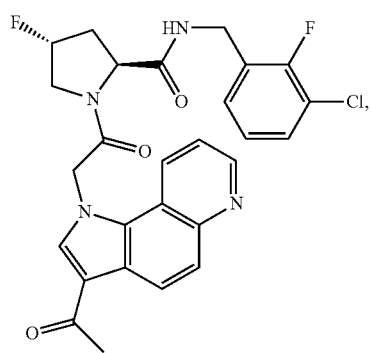
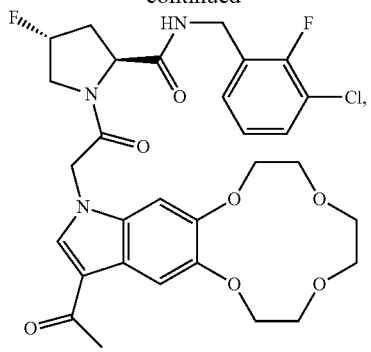
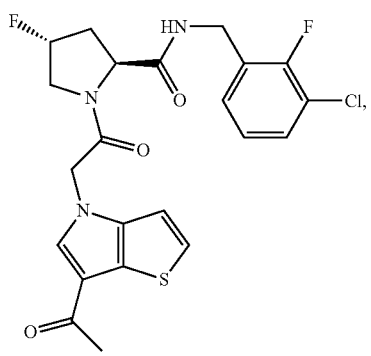
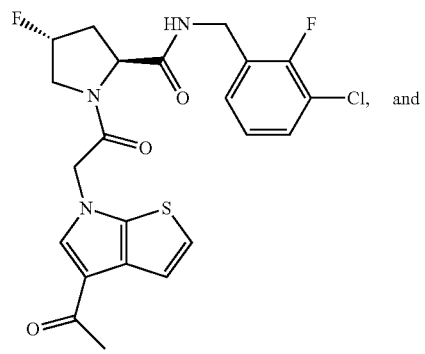 and
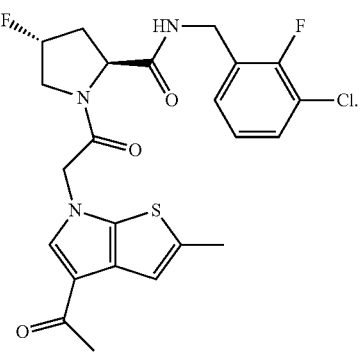

Additional compounds of the disclosure include:

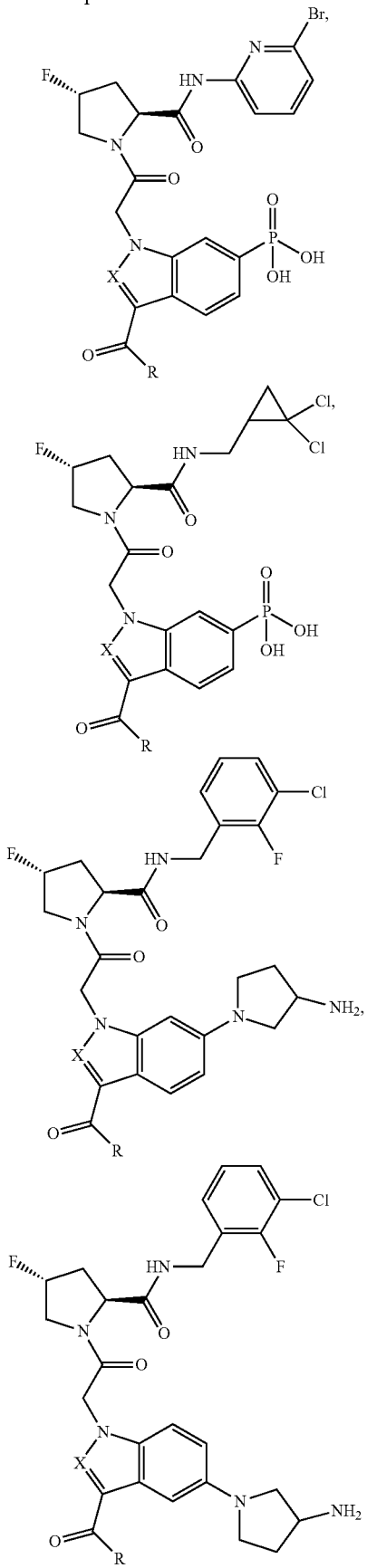

in which R is methyl, or amino and X is N, CH or CF.

The disclosure includes compounds of Formula I in which the central pyrrolidine is vinyl substituted.

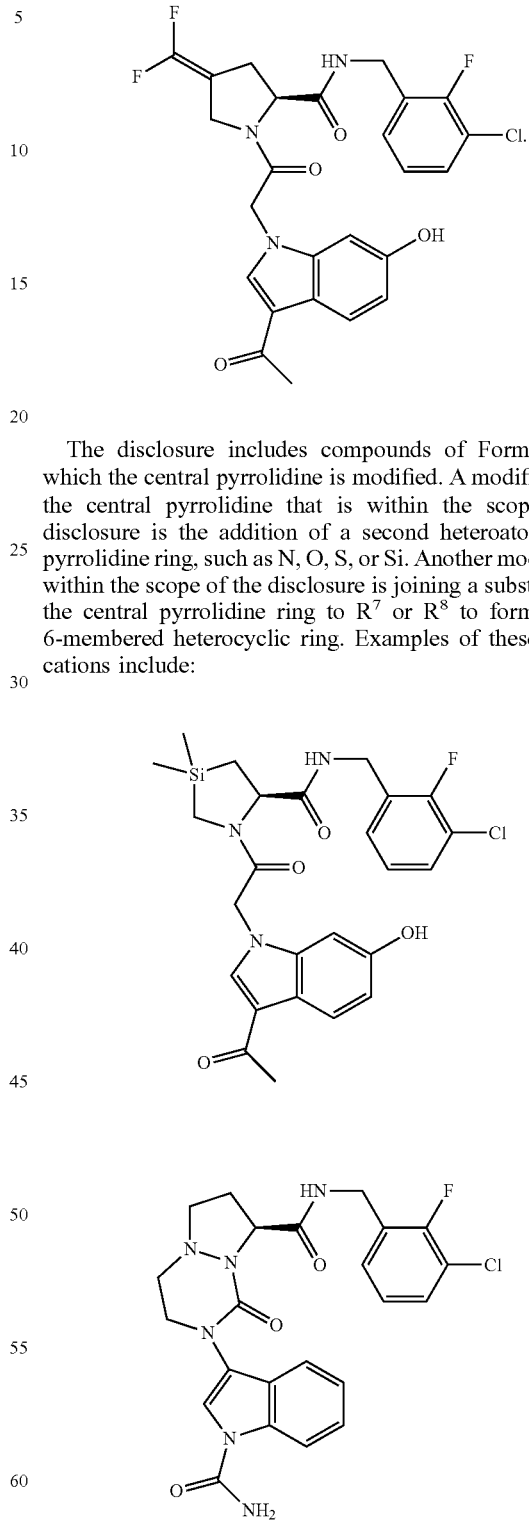

The disclosure includes compounds of Formula I, in which the central pyrrolidine is modified. A modification to the central pyrrolidine that is within the scope of the disclosure is the addition of a second heteroatom to the pyrrolidine ring, such as N, O, S, or Si. Another modification within the scope of the disclosure is joining a substituent on the central pyrrolidine ring to $R^7$ or $R^8$ to form a 5- to 6-membered heterocyclic ring. Examples of these modifications include:

Prodrugs of Formula I are also within the scope of the disclosure. Prodrugs of Formula I include compounds in which the $R_{13}$ substituent is a long-chain phosphoether group. Examples of such compounds include:

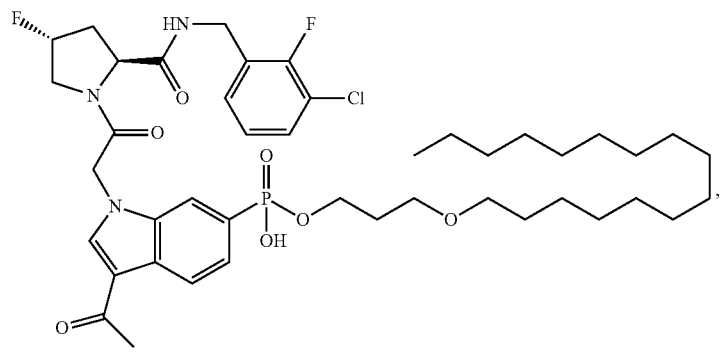

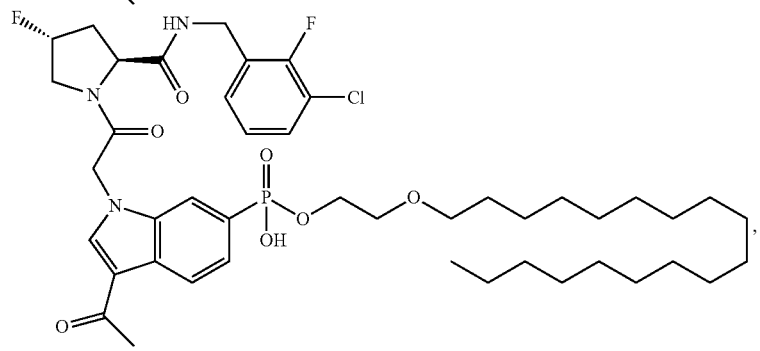

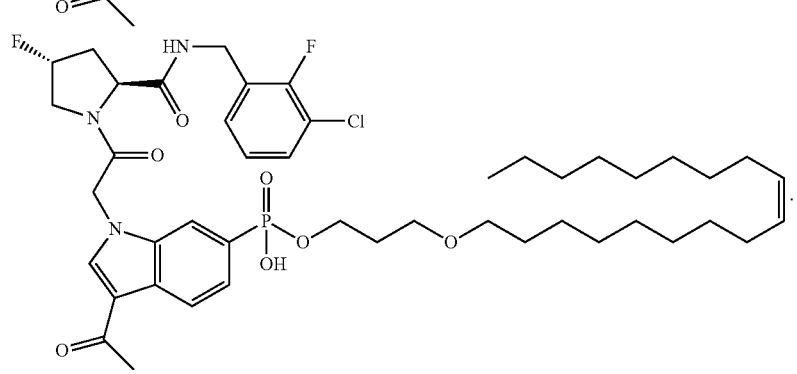

PHARMACEUTICAL PREPARATIONS

Compounds disclosed herein can be administered as the neat chemical, but are preferably administered as a pharmaceutical composition. Accordingly, the disclosure provides pharmaceutical compositions comprising a compound or pharmaceutically acceptable salt of Formula I, together with at least one pharmaceutically acceptable carrier. The pharmaceutical composition/combination may contain a compound or salt of Formula I as the only active agent, but is preferably contains at least one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound of Formula I and an additional active agent. For example the pharmaceutical composition may contain a molar ratio of about 0.5:1, about 1:1, about 2:1, about 3:1 or from about 1.5:1 to about 4:1 of an another anti-inflammatory agent.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula. Some embodiments contain from about 25 wt. % to about 50 wt. % or from about 5 wt. % to about 75 wt. % of the compound of Formula I.

Methods of Treatment

The compounds and pharmaceutical compositions disclosed herein are useful for treating and preventing inflammatory disorders and disorders of the Complement cascade in patients. Inflammatory disorders that may be treated or prevented by the compounds and compositions of this disclosure include inflammatory effects of sepsis, systemic inflammatory response syndrome (SIRS), ischemia/reperfusion injury (I/R injury), psoriasis, myasthenia gravis, system lupus erythematosus (SLE), paroxysmal nocturnal hemoglobinuria (PNH), hereditary angioedema, multiple sclerosis, trauma, burn injury, capillary leak syndrome, obesity, diabetes, Alzheimer's dementia, stroke, schizophrenia, epilepsy, age-related macular degeneration, glaucoma, diabetic retinopathy, asthma, allergy, acute respiratory distress syndrome (ARDS), atypical hemolytic uremic syndrome (aHUS), hemolytic uremic syndrome (HUS), cystic fibrosis, myocardial infarction, lupus nephritides, Crohn's disease, rheumatoid arthritis, atherosclerosis, transplant rejection, prevention of fetal loss, biomaterial reactions (e.g. in hemodialysis, inplants), C3 glomerulonephritis, abdominal aortic aneurysm, and vasculitis. "Prevention" as used in this disclosure means decreasing the likelihood of the appearance of symptoms in a patient administered the compound prophylactically as compared to the likelihood of the appearance of symptoms in patients not administered the compound or decreasing the severity of symptoms in a patient administered the compound prophylactically as compared to the severity of symptoms experienced by patients with the disorder or condition who were not administered the compound.

This disclosure provides methods of treating or preventing an inflammatory disorder, by providing an effective amount of a compound or pharmaceutically acceptable salt of Formula I to patient infected with a Factor D mediated inflammatory disorder. A compound or salt of Formula I may be provided as the only active agent or may be provided together with one or more additional active agents.

An effective amount of a pharmaceutical composition/combination of the invention may be an amount sufficient to (a) inhibit the progression of an inflammatory disorder; (b) cause a regression of the inflammatory disorder; or (c) cause a cure of inflammatory disorder.

An effective amount of a compound or pharmaceutical composition described herein will also provide a sufficient concentration of the active agent when administered to a patient to provide a clinical benefit. Such an amount may be ascertained experimentally, for example by assaying blood concentration of the agent, or theoretically, by calculating bioavailability. The amount of an active agent sufficient to inhibit an inflammatory disorder may be determined with a conventional assay for Complement Factor D inhibition.

EXAMPLES

Abbreviations

AcOEt, EtOAc ethyl acetate
ACN acetonitrile
(Boc)$_2$O di-tert-butyl dicarbonate
DCM dichloromethane
DIEA, DIPEA N,N-diisopropylethylamine
DMA N,N-dimethylacetamide
DMF N,N-dimethylformamide
DPPA diphenyl phosphoryl azide
HATU O-(7-Azabenzotriazole-1-yl)-1,1,3,3-tetramethyluroniumhexafluorophosphate
NEt$_3$ triethylamine
$^i$Pr$_2$NEt N,N-diisopropylethylamine
TEA triethylamine
TFA trifluoroacetic acid
Tf$_2$O trifluoromethanesulfonic anhydride
THF tetrahydrofuran
tBuOK potassium tert-butoxide
TMSBr bromotrimethylsilane General Methods All nonaqueous reactions were performed under an atmosphere of dry argon gas using oven-dried glassware and anhydrous solvents. The progress of reactions and the purity of target compounds were determined using one of the following two UPLC methods: (1) Waters ACQUITY UPLC BEH C18 1.7 μm 2.1×50 mm column with an isocratic elution of 0.24 min at 85:15 water:acetonitrile containing 0.05% formic acid followed by a 3.26-min linear gradient elution from 85:15 to 15:85 at a flow rate of 0.8 mL/min with UV (PDA), ELS, and MS (SQ in EI mode) detection (method 1); and (2) Waters ACQUITY UPLC BEH C18 1.7 μm 2.1×150 mm column with an isocratic elution of 0.31 min at 95:5 water:acetonitrile containing 0.05% formic acid followed by a 16.40-min linear gradient elution from 95:5 to 10:90 at a flow rate of 0.43 mL/min with UV (PDA), ELS, and MS (SQ in EI mode) detection (method 2).

Example 1

Synthesis of Intermediates 1A. (2S,4R)-Tert-Butyl 2-((3-Chloro-2-Fluorobenzyl)Carbamoyl)-4-Fluoropyrrolidine-1-Carboxylate

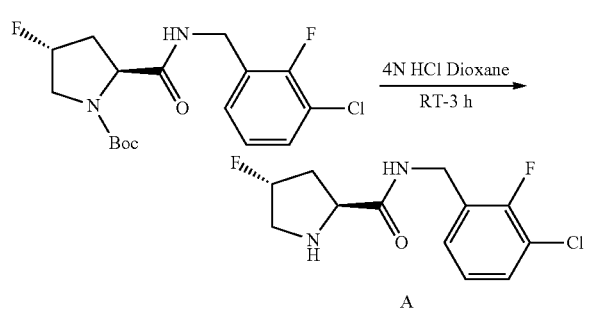

(2S,4R)-1-(tert-butoxycarbonyl)-4-fluoropyrrolidine-2-carboxylic acid (2.33 gm, 10 mmol) was dissolved in DMF (50 ml) and $^i$Pr$_2$NEt (8.6 ml, 5 eq.) was added, followed by the addition of (3-chloro-2-fluorophenyl) methanamine (3.18 gm 20 mmol) at 5° C. Then HATU (8 gm, 2.1 eq) was added slowly at same temperature. The reaction mixture was then stirred for 18 h at RT. After completion of the reaction monitored by HPLC, The reaction mixture was diluted with 1M citric acid solution (200 ml+NaCl solid 20 gm) and extracted with DCM (150 mL×2), the organic layer was then washed with an aqueous solution of NaHCO$_3$ (100 ml) and washed with water (100 ml), brine (100 ml) and dried over Na$_2$SO$_4$ and concentrated under reduced pressure. The remaining residue was purified by column chromatography (eluted with DCM/EtOAc) to give (2S,4R)-tert-butyl 2-((3-chloro-2-fluorobenzyl)carbamoyl)-4-fluoropyrrolidine-1-carboxylate.

1B. (2S,4R)—N-(3-Chloro-2-Fluorobenzyl)-4-Fluoropyrrolidine-2-Carboxamide Hydrochloride (A)

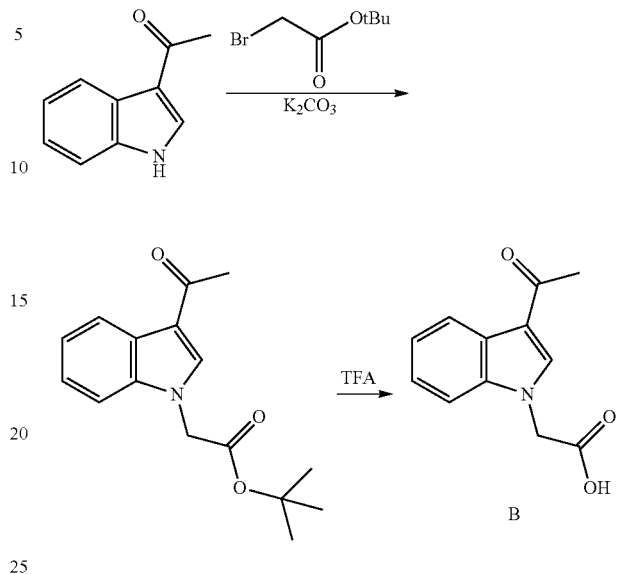

(2S,4R)-tert-butyl 2-((3-chloro-2-fluorobenzyl)carbamoyl)-4-fluoropyrrolidine-1-carboxylate (500 mg) was taken in 4N HCl dioxane (30 ml) and resulting reaction mixture was stirred at rt for 3 h. After completion of the reaction monitored by HPLC solvent was removed under reduced pressure. The residue, A, was used for next reaction.

1C. 2-(3-Acetyl-1H-Indol-1-Yl)Acetic Acid (B)

A mixture of 3-Acetylindole (10.09 g) and t-butylbromoacetate (13.71 g) were reflux in acetonitrile in presence of potassium carbonate (9.7 g) for 24 h. The reaction mixture was cooled to room temperature and filtered and evaporated to dryness. The residue was purified by chromatography over silica gel and eluted with a mixture of ethylacetate in methylene chloride to give tert-butyl 2-(3-acetyl-1H-indol-1-yl)acetate.

Tert-butyl 2-(3-acetyl-1H-indol-1-yl)acetate was stirred overnight in a mixture of trifluoroacetic acid in methylene chloride and diluted with methanol and evaporated to dryness. The residue was treated with 1M sodium hydroxide and extracted with methylene chloride. The aqueous layer was acidified with 6M HCl and the residue filtered, washed with water and dried to give 2-(3-acetyl-1H-indol-1-yl) acetic acid (B).

1D. 1-(3-Amino-1H-Indol-1-Yl)Ethanone Hydrochloride (C)

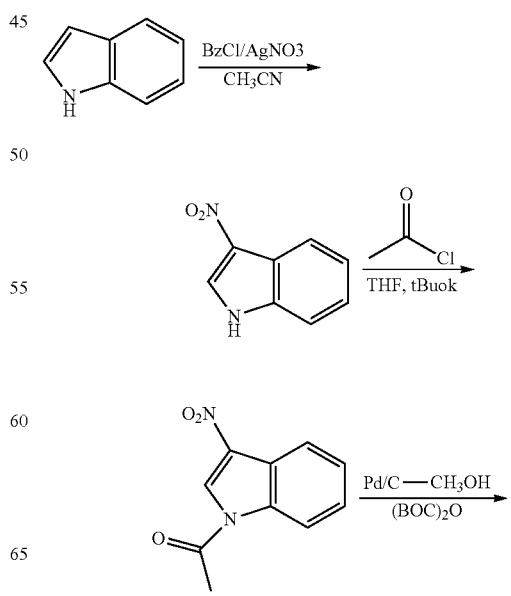

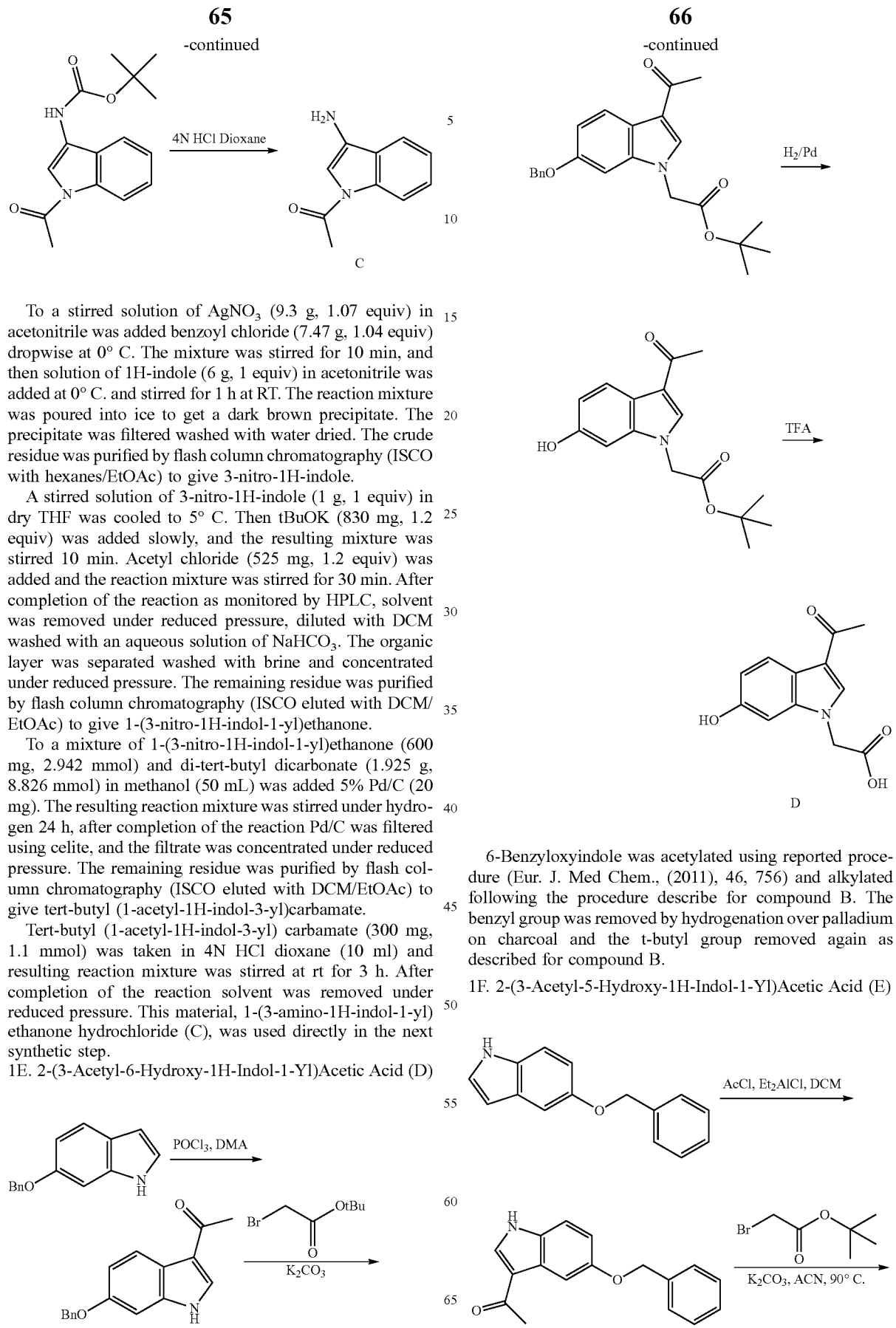

To a stirred solution of AgNO₃ (9.3 g, 1.07 equiv) in acetonitrile was added benzoyl chloride (7.47 g, 1.04 equiv) dropwise at 0° C. The mixture was stirred for 10 min, and then solution of 1H-indole (6 g, 1 equiv) in acetonitrile was added at 0° C. and stirred for 1 h at RT. The reaction mixture was poured into ice to get a dark brown precipitate. The precipitate was filtered washed with water dried. The crude residue was purified by flash column chromatography (ISCO with hexanes/EtOAc) to give 3-nitro-1H-indole.

A stirred solution of 3-nitro-1H-indole (1 g, 1 equiv) in dry THF was cooled to 5° C. Then tBuOK (830 mg, 1.2 equiv) was added slowly, and the resulting mixture was stirred 10 min. Acetyl chloride (525 mg, 1.2 equiv) was added and the reaction mixture was stirred for 30 min. After completion of the reaction as monitored by HPLC, solvent was removed under reduced pressure, diluted with DCM washed with an aqueous solution of NaHCO₃. The organic layer was separated washed with brine and concentrated under reduced pressure. The remaining residue was purified by flash column chromatography (ISCO eluted with DCM/EtOAc) to give 1-(3-nitro-1H-indol-1-yl)ethanone.

To a mixture of 1-(3-nitro-1H-indol-1-yl)ethanone (600 mg, 2.942 mmol) and di-tert-butyl dicarbonate (1.925 g, 8.826 mmol) in methanol (50 mL) was added 5% Pd/C (20 mg). The resulting reaction mixture was stirred under hydrogen 24 h, after completion of the reaction Pd/C was filtered using celite, and the filtrate was concentrated under reduced pressure. The remaining residue was purified by flash column chromatography (ISCO eluted with DCM/EtOAc) to give tert-butyl (1-acetyl-1H-indol-3-yl)carbamate.

Tert-butyl (1-acetyl-1H-indol-3-yl) carbamate (300 mg, 1.1 mmol) was taken in 4N HCl dioxane (10 ml) and resulting reaction mixture was stirred at rt for 3 h. After completion of the reaction solvent was removed under reduced pressure. This material, 1-(3-amino-1H-indol-1-yl)ethanone hydrochloride (C), was used directly in the next synthetic step.

1E. 2-(3-Acetyl-6-Hydroxy-1H-Indol-1-Yl)Acetic Acid (D)

6-Benzyloxyindole was acetylated using reported procedure (Eur. J. Med Chem., (2011), 46, 756) and alkylated following the procedure describe for compound B. The benzyl group was removed by hydrogenation over palladium on charcoal and the t-butyl group removed again as described for compound B.

1F. 2-(3-Acetyl-5-Hydroxy-1H-Indol-1-Yl)Acetic Acid (E)

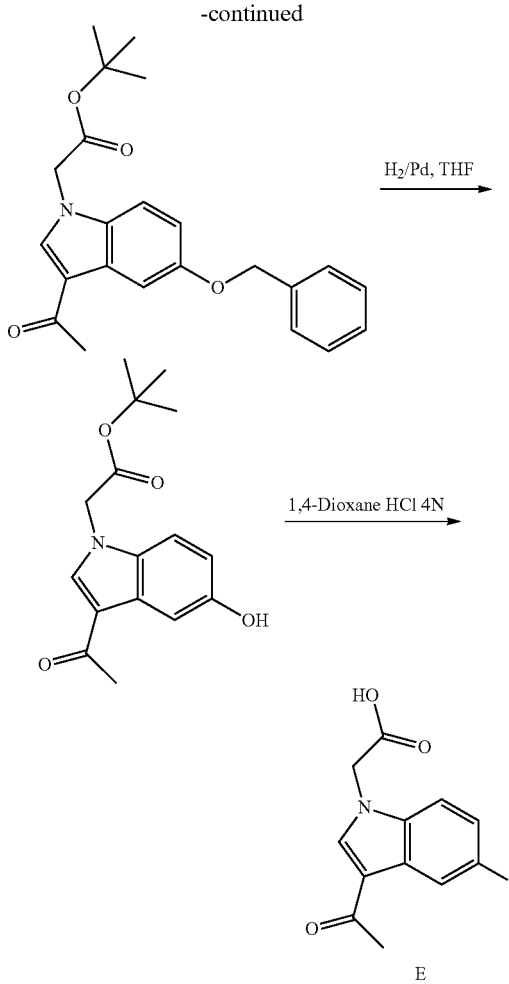

of Celite and washed with CH₂Cl₂ and MeOH. The filtrate was concentrated under reduced pressure and the remaining residue was purified by flash column chromatography (silica gel eluted with DCM/EtOAc) to give tert-Butyl 2-(3-acetyl-5-hydroxy-1H-indol-1-yl)acetate.

Tert-Butyl 2-(3-acetyl-5-hydroxy-1H-indol-1-yl)acetate (814 mg, 2.8 mmol) was taken up in 4 N HCl dioxane (10 mL) and the resulting reaction mixture was stirred at RT for 48 h. The solvent was then removed under reduced pressure to give 2-(3-acetyl-5-hydroxy-1H-indol-1-yl)acetic acid (E) which could be used directly in the next synthetic step.

Example 2

Synthesis of (2S,3aS,7aS)-1-(2-(3-Acetyl-1H-Indol-1-Yl)Acetyl)-N-(3-Chloro-2-Fluorobenzyl)Octahydro-1H-Indole-2-Carboxamide. (Compound 1)

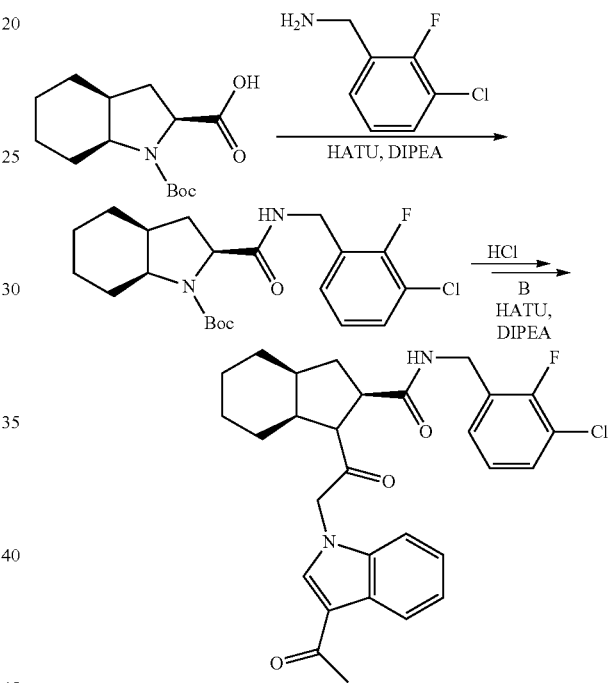

To a stirred solution of 5-(benzyloxy)-1H-indole (11.08 g, 1 equiv) in 200 mL DCM was added diethylaluminium chloride (1 M solution in Hexane; 74.6 mL, 1.5 equiv) drop wise at 0° C. The mixture was stirred for 30 min, and then a solution of acetyl chloride (5.3 mL, 1.5 equiv) in 150 mL DCM was added at 0° C. and the reaction was stirred for 1 h at 0° C. A 5% aqueous citric acid solution was added at 0° C. and the reaction was stirred for 15 min at RT. The precipitate was filtered and washed with water, and the organic filtrate was dried and concentrated under reduced pressure. The residue was purified by flash column chromatography (silica gel eluted with DCM/CH₃OH) to give 1-(5-(Benzyloxy)-1H-indol-3-yl)ethanone.

To a suspension of 1-(5-(benzyloxy)-1H-indol-3-yl)ethanone (6.5 gm, 1 equiv) and K₂CO₃ (3.72 gm, 1.1 equiv) in 50 mL acetonitrile was added tert-butyl 2-bromoacetate (3.92 mL, 1.1 equiv) dropwise at RT. The resulting mixture was then heated to reflux for 18 h. After cooling to RT, the mixture was diluted with DCM (100 mL), and then filtered through the celite pad; filtrate was concentrated under reduced pressure. The remaining residue was purified by flash column chromatography (silica gel eluted with DCM/EtOAc) to give tert-Butyl 2-(3-acetyl-5-(benzyloxy)-1H-indol-1-yl)acetate.

To tert-Butyl 2-(3-acetyl-5-(benzyloxy)-1H-indol-1-yl) acetate (6 g) in THF (80 mL) was added Pd/C (0.05 equiv). The reaction mixture was stirred at RT for 5 h under H₂ (1 atm). The reaction mixture was then filtered through a pad 1-[Bis(dimethylamino)methylene]-1H-1,2,3-triazolo[4,5-b]pyridinium 3-oxid hexafluorophosphate (296 mg) was added in portions to a cooled (0° C.) mixture of (2S,3aS,7aS)-1-(tert-butoxycarbonyl)octahydro-1H-indole-2-carboxylic acid (200 mg), 3-chloro-2-fluorobenzylamine (124 mg), and N,N-diisopropylethylamine (520 μL) in N,N-dimethylformamide (5 mL). The resulting mixture was stirred for 45 min at 0° C., warmed to rt, and stirred at rt for 1.5 h. The reaction mixture was diluted with a 1 M aq. solution of citric acid (50 mL) and extracted with dichloromethane (3×100 mL). The combined organic extracts were concentrated to approximately 50 mL under reduced pressure, washed with a saturated aq solution of sodium bicarbonate (2×25 mL), washed with brine (25 mL), dried over sodium sulfate, and evaporated under reduced pressure. The remaining residue was purified by flash column chromatography on silica (ethyl acetate/hexanes gradient, 0 to 60% v/v) to give (2S,3aS,7aS)-tert-Butyl 2-((3-chloro-2-fluorobenzyl)carbamoyl)octahydro-1H-indole-1-carboxylate as a solid. LC-MS (method 1): $t_R$ 2.63 min, m/z found 411 ([M+H]+)⁺.

(2S,3aS,7aS)-tert-Butyl 2-((3-chloro-2-fluorobenzyl)carbamoyl)octahydro-1H-indole-1-carboxylate (105 mg) was dissolved in a hydrogen chloride solution (4.0 M in dioxane, 5 mL). After stirring at rt for 1 h, the reaction mixture was evaporated under reduced pressure to give a solid, which was then treated with methanol (10 mL) and evaporated under reduced pressure. Treatment with methanol and subsequent evaporation was repeated twice. The resulting solid, (2S,3aS,7aS)—N-(3-Chloro-2-fluorobenzyl)octahydro-1H-indole-2-carboxamide hydrochloride, was dried in vacuo overnight and used directly in the next synthetic step. LC-MS (method 1): $t_R$ 1.28 min, m/z found 311 ([M+H])$^+$.

1-[Bis(dimethylamino)methylene]-1H-1,2,3-triazolo[4,5-b]pyridinium 3-oxid hexafluorophosphate (98 mg) was added in one portion to a mixture of (2S,3aS,7aS)—N-(3-chloro-2-fluorobenzyl)octahydro-1H-indole-2-carboxamide hydrochloride (from above), compound B (56 mg), and N,N-diisopropylethylamine (180 µL) in N,N-dimethylformamide (2 mL) at rt. The resulting mixture was stirred for 15 min and concentrated under reduced pressure to approximately half the original volume. The resulting mixture was diluted with ethyl acetate (40 mL), washed with a 1 M aq solution of citric acid (10 mL), washed with a saturated aq solution of sodium bicarbonate (10 mL), washed with brine (10 mL), dried over sodium sulfate, and evaporated under reduced pressure. The remaining residue was purified by flash column chromatography on silica (methanol/dichloromethane gradient, 0 to 10% v/v) to give, (2S,3aS,7aS)-1-(2-(3-Acetyl-1H-indol-1-yl)acetyl)-N-(3-chloro-2-fluorobenzyl)octahydro-1H-indole-2-carboxamide, as a solid foam. LC-MS (method 1): $t_R$ 2.33 min, m/z found 510 ([M+H]+)$^+$.

Example 3

Synthesis of (2S,4R)—N2-(1-Acetyl-1H-Indol-3-Yl)-N1-(3-Chloro-2-Fluorobenzyl)-4-Fluoropyrrolidine-1,2-Dicarboxamide (Compound 3)

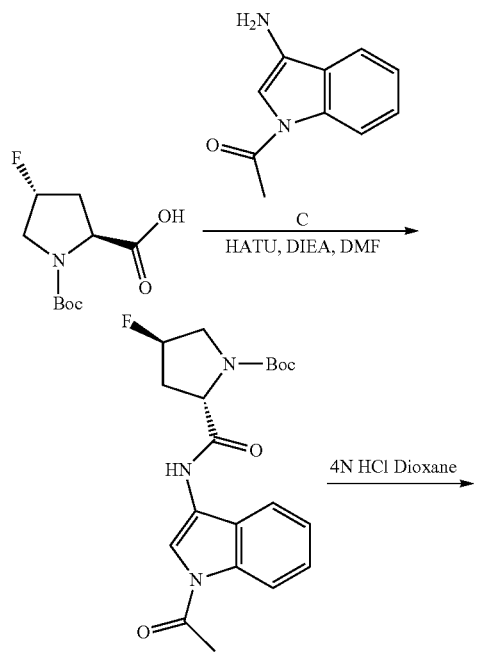

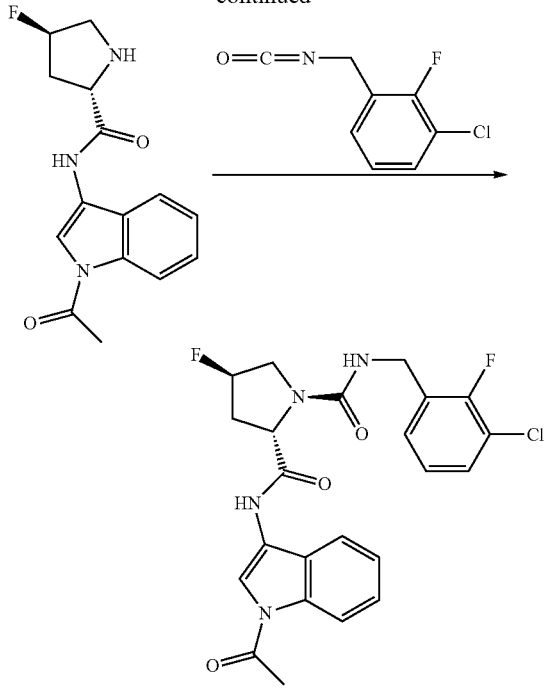

1-(3-amino-1H-indol-1-yl)ethanone hydrochloride (C). (411 mg 1.96 mmol) was dissolved in DMF (25 ml) and $^i$Pr$_2$NEt (900 µl, 5 eq.) was added, which was followed by the addition of (2S,4R)-1-(tert-butoxycarbonyl)-4-fluoropyrrolidine-2-carboxylic acid (456 mg, 1.96 mmol) at 5° C. Then HATU (878 mg, 2.1 eq) was added slowly at same temperature. The reaction mixture was then stirred for 18 h at RT. After completion of the reaction monitored by HPLC, the reaction mixture was diluted with 1M citric acid solution (100 ml+NaCl solid 10 gm) and extracted with DCM (50 mL×2). The organic layer was then washed with an aqueous solution of NaHCO$_3$ (40 ml), washed with water (40 ml), and then brine (40 ml), and dried over Na$_2$SO$_4$ and concentrated under reduced pressure. The remaining residue was purified by flash column chromatography (ISCO eluted with DCM/EtOAc) to give (2S,4R)-tert-butyl 2-((1-acetyl-1H-indol-3-yl)carbamoyl)-4-fluoropyrrolidine-1-carboxylate.

(2S,4R)-tert-butyl 2-((1-acetyl-1H-indol-3-yl)carbamoyl)-4-fluoropyrrolidine-1-carboxylate (78 mg) was taken in 4N HCl dioxane (5 ml) and resulting reaction mixture was stirred at rt for 3 h after completion of the reaction monitored by HPLC solvent was removed under reduced pressure. The residue, (2S,4R)—N-(1-acetyl-1H-indol-3-yl)-4-fluoropyrrolidine-2-carboxamide hydrochloride, was used as is for the next reaction.

(2S,4R)—N-(1-acetyl-1H-indol-3-yl)-4-fluoropyrrolidine-2-carboxamide hydrochloride was dissolved in THF (5 ml) and NEt$_3$ (140 µl, 5 eq.) was added, which was followed by the addition of at 5° C. Then 1-chloro-2-fluoro-3-(isocyanatomethyl) benzene (100 mg, 2.1 eq, freshly prepared from 2-(3-chloro-2-fluorophenyl) acetic acid) was added slowly at same temperature. The reaction mixture was then stirred for 30 min at RT. After completion of the reaction monitored by HPLC, The reaction mixture was diluted with 5 ml water and extracted with ethyl acetate (50 ml), the organic layer dried over Na$_2$SO$_4$ and concentrated under reduced pressure. The remaining residue was purified by flash column chromatography (eluted with DCM/EtOAc) to give (2S,4R)—N2-(1-acetyl-1H-indol-3-yl)-N1-(3-chloro- 2-fluorobenzyl)-4-fluoropyrrolidine-1,2-dicarboxamide. HPLC: $t_R$ 2.07 min. MS m/z calcd for $C_{23}H_{21}ClF_2N_4O_3$ ([M]+), 474; found, 475 ([M+1]+). $^1$H-NMR (DMSO-D6, 400 MHz): δ2.2-2.1 (m, 1H), 2.60 (s, 3H), 3.79-3.72 (m, 2H), 4.34-4.28 (m, 2H), 4.72 (t, J=9.2 Hz 1H), 4.52-5.38 (m, 1H), 7.18-7.09 (m, 2H), 7.46-7.30 (m, 4H), 7.92 (d, J=7.6 Hz, 1H), 8.14 (s, 1H), 8.36 (d, J=8.4 Hz, 1H), 10.3 (s, 1H).

Example 4

Synthesis of (2S,4R)—N-(3-Chloro-2-Fluorobenzyl)-1-(2-(3-(Cyclopropanecarbonyl)-1H-Indol-1-Yl)Acetyl)-4-Fluoropyrrolidine-2-Carboxamide. (Compound 25)

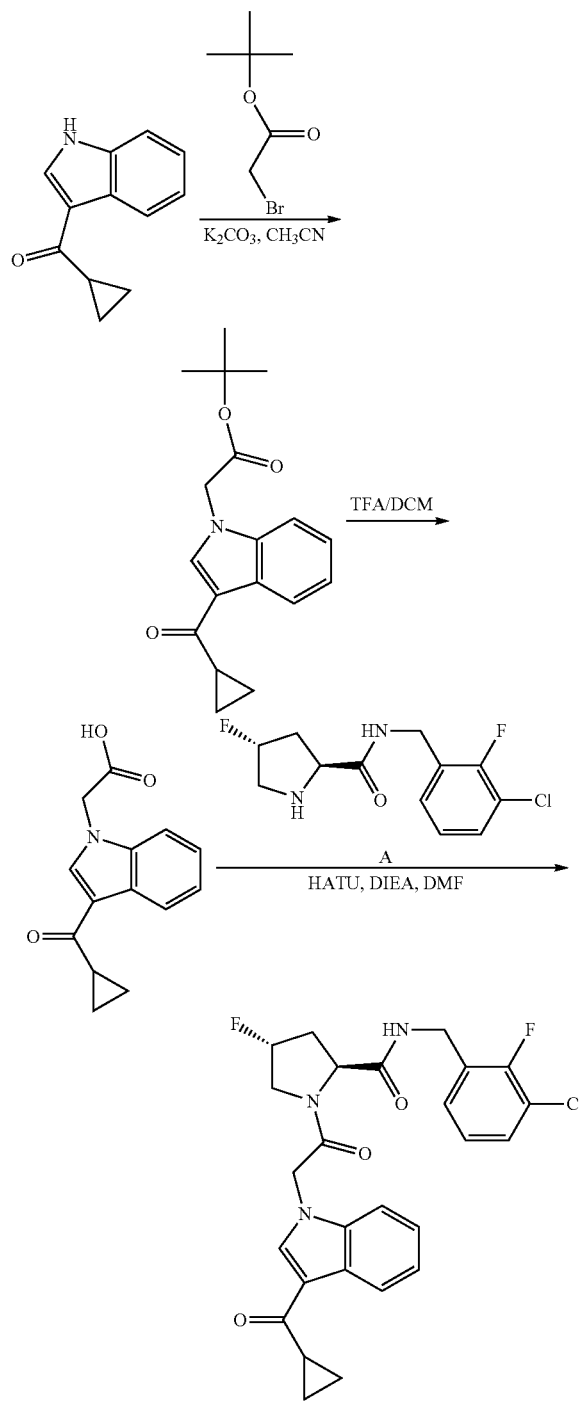

To a suspension of cyclopropyl(1H-indol-3-yl)methanone (3 gm, 16.22 mmol) and potassium carbonate (2.463 gm, 1.1 equiv) in 50 ml acetonitrile was added tert-butyl 2-bromoacetate (2.6 ml, 1.1 equiv) dropwise at RT. The resulting mixture was then heated to reflux for 18 h. After cooling to RT, the mixture was diluted with DCM (100 ml), and then filtered through the celite pad; filtrate was concentrated under reduced pressure. The remaining residue was purified by flash column chromatography (eluted with DCM/EtOAc) to give tert-butyl 2-(3-(cyclopropanecarbonyl)-1H-indol-1-yl)acetate.

Tert-butyl 2-(3-(cyclopropanecarbonyl)-1H-indol-1-yl)acetate (198 mg, 0.66 mmol) was dissolved in CH$_2$Cl$_2$ (5 mL) and TFA (5 mL) was added slowly at 5° C. The reaction mixture was stirred 3 h at RT. After completion of the reaction monitored by HPLC solvent was removed under reduced pressure. The residue, 2-(3-(cyclopropanecarbonyl)-1H-indol-1-yl)acetic acid was used for next reaction.

2-(3-(cyclopropanecarbonyl)-1H-indol-1-yl)acetic acid was dissolved in DMF (10 ml) and $^i$Pr$_2$NEt (490 μl, 5 eq.) was added, which was followed by the addition of A (187 mg, 0.6 mmol) at 5° C. Then HATU (478 mg, 2.1 eq) was added slowly at same temperature. The reaction mixture was then stirred for 18 h at RT. After completion of the reaction monitored by HPLC, the reaction mixture was diluted with water and extracted with DCM (50 mL). The organic layer was then washed with an aqueous solution of NaHCO$_3$ (20 ml) and washed with water (20 ml), brine (20 ml) and dried over Na$_2$SO$_4$ and concentrated under reduced pressure. The remaining residue was purified by flash column chromatography (eluted with DCM/EtOAc) to give (200 mg). HPLC: $t_R$ 2.02 min. MS m/z calcd for $C_{26}H_{24}ClF_2N_3O_3$ ([M]+), 499; found, 500 ([M+1]+). $^1$H-NMR (DMSO-D6, 400 MHz): δ, 0.91-0.87 (m, 2H), 1.00-0.98 (m, 2H), 2.2-2.0 (m, 1H), 2.59-2.57 (m, 2H), 3.9-4.05 (m, 1H), 4.47-4.28 (m, 4H), 5.22-5.17 (m, 1H), 5.42-5.38 (m, 2H), 6.99-6.95 (m, 1H), 7.23-7.19 (m, 3H), 7.48-7.40 (m, 1H), 8.22-8.20 (m, 1H), 8.42 (s, 1H), 8.6-8.5- (m, J=8. 1H).

Example 5

Synthesis of (S)—N1-(1-Carbamoyl-1H-Indol-3-Yl)-N2-(3-Chloro-2-Fluorobenzyl)Indoline-1,2-Dicarboxamide. (Compound 2)

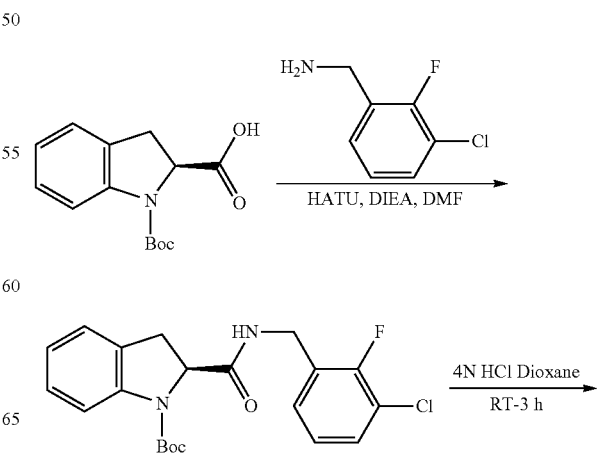

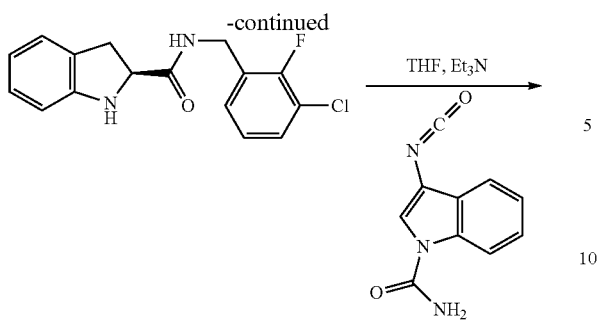

(S)-1-(tert-butoxycarbonyl)indoline-2-carboxylic acid (2.63 gm, 10 mmol) was dissolved in DMF (50 ml) and $^i$Pr$_2$NEt (8.6 ml, 5 eq.) was added, which was followed by the addition of (3-chloro-2-fluorophenyl) methanamine (3.18 gm 20 mmol) at 5° C. Then HATU (8 gm, 2.1 eq) was added slowly at same temperature. The reaction mixture was then stirred for 18 h at RT. After completion of the reaction monitored by HPLC, The reaction mixture was diluted with 1M citric acid solution (200 ml+NaCl solid 20 gm) and extracted with DCM (150 mL×2), the organic layer was then washed with an aqueous solution of NaHCO$_3$ (100 ml) and washed with water (100 ml), brine (100 ml) and dried over Na$_2$SO$_4$ and concentrated under reduced pressure. The remaining residue was purified by flash column chromatography (ISCO eluted with DCM/EtOAc) to give (S)-tert-butyl 2-((3-chloro-2-fluorobenzyl)carbamoyl)indoline-1-carboxylate.

(S)-tert-butyl 2-((3-chloro-2-fluorobenzyl)carbamoyl)indoline-1-carboxylate (300 mg) was taken in 4N HCl dioxane (30 ml) and resulting reaction mixture was stirred at rt for 3 h. After completion of the reaction monitored by HPLC solvent was removed under reduced pressure. The residue, (S)—N-(3-chloro-2-fluorobenzyl)indoline-2-carboxamide hydrochloride, was used for next reaction.

(S)—N-(3-chloro-2-fluorobenzyl)indoline-2-carboxamide hydrochloride (50 mg, 0.147 mmol) was dissolved in THF (5 ml) and NEt$_3$ (100 µl, 5 eq.) was added, which was followed by the addition of 3-isocyanato-1H-indole-1-carboxamide (33 mg, 1.1 eq, freshly prepared) added slowly at 5° C. The reaction mixture was then stirred for 30 min at RT. After completion of the reaction monitored by HPLC, the reaction mixture was diluted with 5 ml water and extracted with ethyl acetate (50 ml), the organic layer dried over Na$_2$SO$_4$ and concentrated under reduced pressure. The remaining residue was purified by flash column chromatography (ISCO eluted with DCM/CH$_3$OH) to give (S)—N1-(1-carbamoyl-1H-indol-3-yl)-N2-(3-chloro-2-fluorobenzyl) indoline-1,2-dicarboxamide. HPLC: t$_R$ 2.04 min. MS m/z calcd for C$_{26}$H$_{21}$ClFN$_5$O$_3$ ([M]+), 505; found, 506 ([M+1]+). $^1$H-NMR (DMSO-D6, 400 MHz): δ, 3.19-3.15 (m, 1H), 3.36 (s, 3H), 3.6-3.7 (m, 1H), 4.43 (d, J=5.6 Hz, 2H), 5.45-5.41 (m, 1H), 6.88-6.86 (m, 1H), 6.90-6.88 (m, 1H), 7.34-6.97 (m, 5H), 7.45-7.43 (m, 1H), 7.50 (br, 2H), 7.68 (d, J=7.6 Hz, 1H), 7.91 (d, J=8 Hz, 1H), 8.11 (s, 1H), 8.35 (d, J=8.4 Hz 1H); 8.65 (s, 1H). 8.81-8.75 (m, 1H).

Example 6

Synthesis of (2S,4R)-1-(2-(3-Acetyl-6-Hydroxy-1H-Indol-1-Yl)Acetyl)-N-(3-Chloro-2-Fluorobenzyl)-4-Fluoropyrrolidine-2-Carboxamide

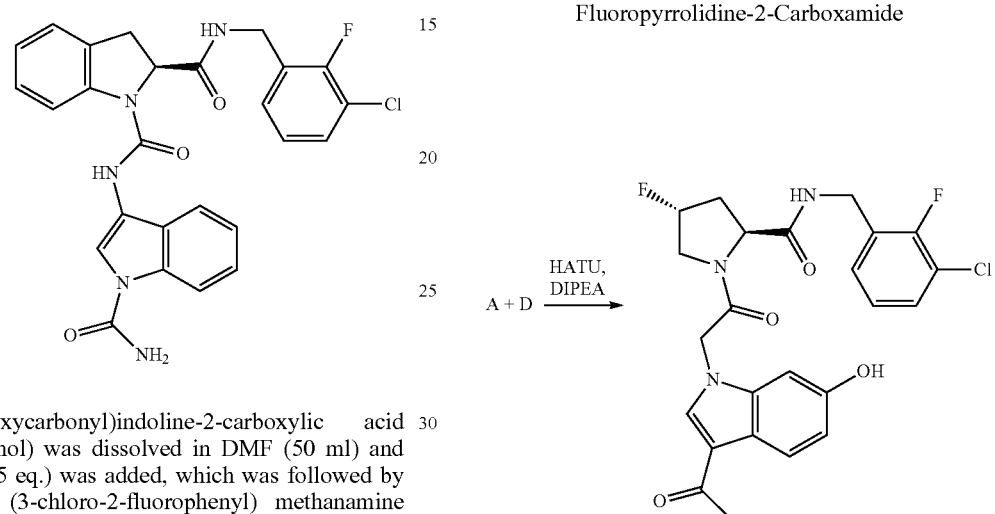

Compounds A (3.6 g) and D (2.5 g) were coupled following procedure described in Example 2 to give (2S,4R)-1-(2-(3-acetyl-6-hydroxy-1H-indol-1-yl)acetyl)-N-(3-chloro-2-fluorobenzyl)-4-fluoropyrrolidine-2-carboxamide.

Example 7

Synthesis of Diethyl (3-Acetyl-1-(2-((2S,4R)-2-((3-Chloro-2-Fluorobenzyl)Carbamoyl)-4-Fluoropyrrolidin-1-Yl)-2-Oxoethyl)-1H-Indol-6-Yl)Phosphonate (Compound 48)

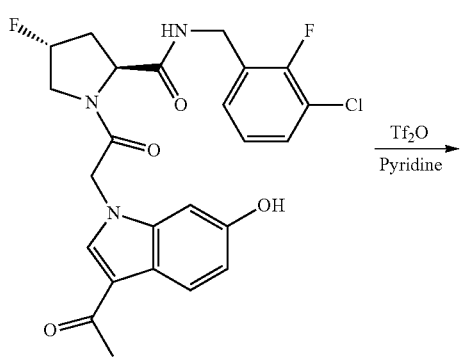

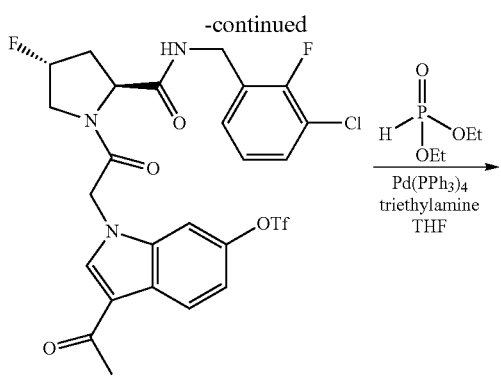

dol-6-yl)phosphonate, (as a solid. LC-MS (method 1): $t_R$ 1.84 min, m/z found 610 ([M+H])+. LC-MS (method 2): $t_R$ 7.15 min, m/z found 610 ([M+H]+)+.

Example 8

Synthesis of Ethyl Hydrogen (3-Acetyl-1-(2-((2S, 4R)-2-((3-Chloro-2-Fluorobenzyl) Carbamoyl)-4-Fluoropyrrolidin-1-Yl)-2-Oxoethyl)-1H-Indol-6-Yl) Phosphonate. (Compound 52)

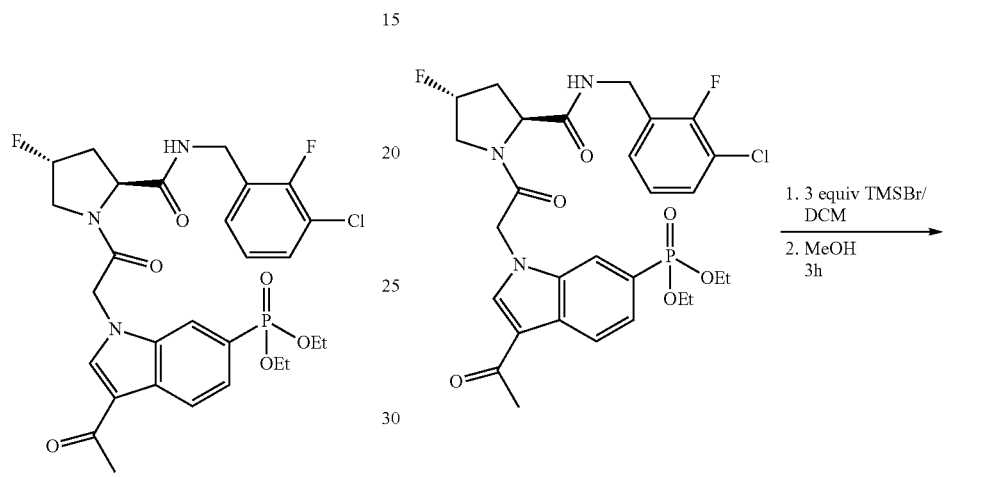

Under an atmosphere of argon gas, trifluoromethanesulfonic anhydride (250 µL) was added dropwise to a cooled (0° C.) solution of (2S,4R)-1-(2-(3-acetyl-6-hydroxy-1H-indol-1-yl)acetyl)-N-(3-chloro-2-fluorobenzyl)-4-fluoropyrrolidine-2-carboxamide (551 mg) in pyridine (10 mL). The resulting solution was stirred at 0° C. for 2.5 h, allowed to warm to rt, and concentrated under reduced pressure to give an oil. This material was dissolved in ethyl acetate (75 mL), and the resulting solution was washed with a 1 M aq. solution of citric acid (2×25 mL), washed with brine (25 mL), dried over sodium sulfate, and evaporated under reduce pressure to give the crude product. This material was purified by flash column chromatography on silica (methanol/dichloromethane gradient, 0 to 5% v/v) to give, 3-Acetyl-1-(2-((2S,4R)-2-((3-chloro-2-fluorobenzyl)carbamoyl)-4-fluoropyrrolidin-1-yl)-2-oxoethyl)-1H-indol-6-yl trifluoromethanesulfonate, as a solid. LC-MS (method 1): $t_R$ 2.39 min, m/z found 622 ([M+H]+)+.

Under an atmosphere of argon gas, a mixture of 3-acetyl-1-(2-((2S,4R)-2-((3-chloro-2-fluorobenzyl)carbamoyl)-4-fluoropyrrolidin-1-yl)-2-oxoethyl)-1H-indol-6-yl trifluoromethanesulfonate (526 mg), diethyl phosphite (1.2 mL), triethylamine (217 µL), and tetrakis(triphenylphosphine)palladium(0) (100 mg) in tetrahydrofuran (30 mL) was stirred at 100° C. in a sealed tube for 18 h. The reaction mixture was allowed to cool to room temperature and concentrated under reduced pressure. The remaining residue was purified by flash column chromatography on silica (methanol/dichloromethane gradient, 0 to 5% v/v) to give, diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate, (as a solid. LC-MS (method 1): $t_R$ 1.84 min, m/z found 610 ([M+H])+. LC-MS (method 2): $t_R$ 7.15 min, m/z found 610 ([M+H]+)+.

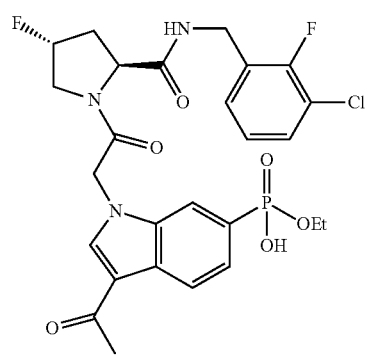

Under an atmosphere of argon gas at rt, bromotrimethylsilane (132 mg) was added to a solution of diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate (200 mg) in dichloromethane (5 mL) at rt. The resulting solution was stirred for 3 h and evaporated to dryness under reduced pressure. The reaction was stopped at 3 h when the majority of the product was the monoethyl phosphonate. The residue was treated with a mixture of dichloromethane and methanol (3:1 v/v, 15 mL) and evaporated under reduced pressure. This treatment was repeated once, and the remaining solid was washed with ethyl acetate (15 mL), and dried in vacuo overnight. Ethyl hydrogen (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate was purified by HPLC to give 25 mg of solid. LC-MS: $t_R$ 1.20 min, m/z found 582 ([M+H]+)+.

Example 9

Synthesis of (3-Acetyl-1-(2-((2S,4R)-2-((3-Chloro-2-Fluorobenzyl) Carbamoyl)-4-Fluoropyrrolidin-1-Yl)-2-Oxoethyl)-1H-Indol-6-Yl)Phosphonic Acid. (Compound 68)

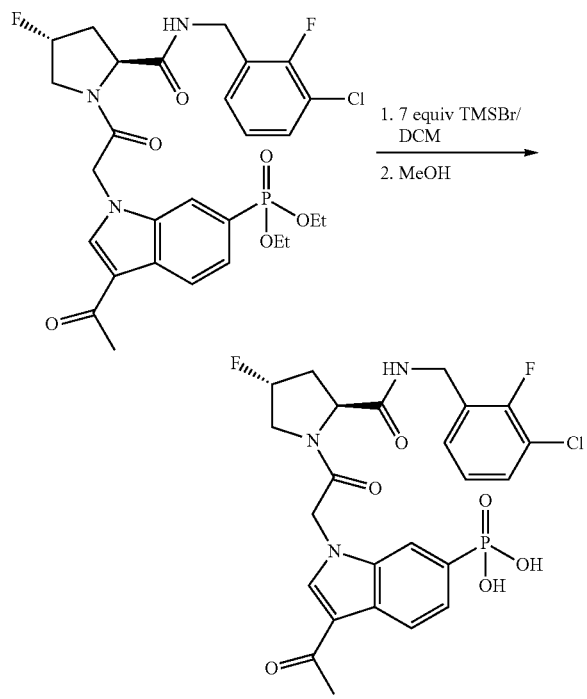

Under an atmosphere of argon gas at rt, bromotrimethylsilane (233 mg) was added to a solution of diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate (150 mg) in dichloromethane (5 mL) at rt. The resulting solution was stirred for 18 h and evaporated to dryness under reduced pressure. The remaining residue was treated with a mixture of dichloromethane and methanol (3:1 v/v, 15 mL) and evaporated under reduced pressure. This treatment was repeated once, and the remaining solid was washed with ethyl acetate (15 mL), and dried in vacuo overnight to give 132 mg of (3-Acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonic acid. LC-MS (method 1): $t_R$ 1.06 min, m/z found 554 ([M+H]+)$^+$. LC-MS (method 2): $t_R$ 5.40 min, m/z found 554 ([M+H]$^+$).

Example 10

Synthesis of Diethyl(((3-Acetyl-1-(2-((2S,4R)-2-((3-Chloro-2-Fluorobenzyl)Carbamoyl)-4-Fluoropyrrolidin-1-Yl)-2-Oxoethyl)-1H-Indol-6-Yl)Oxy)Methyl) Phosphonate (Compound 66)

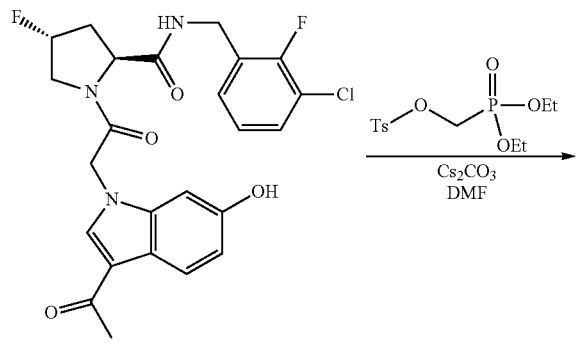

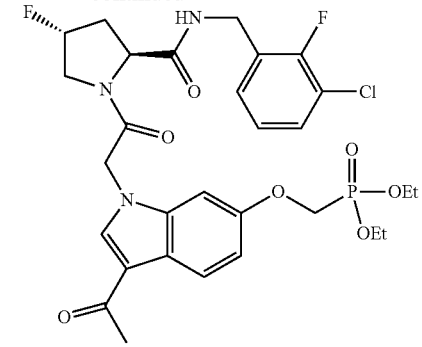

(2S,4R)-1-(2-(3-acetyl-6-hydroxy-1H-indol-1-yl)acetyl)-N-(3-chloro-2-fluorobenzyl)-4-fluoropyrrolidine-2-carboxamide (100 mg, 0.204 mmol), Tosylate (98.8 mg, 0.307 mmol), Cs$_2$CO$_3$ (200 mg, 0.614 mmol) in dimethylformamide (2 mL) was stirred for 15 hr at 50° C. Solvent was removed in vacuo and the residue was purified by HPLC to afford diethyl(((3-acetyl-1-(2-((2S,4R)-2-((3-chloro-2-fluorobenzyl)carbamoyl)-4-fluoropyrrolidin-1-yl)-2-oxoethyl)-1H-indol-6-yl)oxy)methyl)phosphonate. LC-MS (method 1): $t_R$ 1.86 min, m/z found 640 ([M+H]+)$^+$.

Example 11

Synthesis of 3-((2S,4R)-2-(5-(3-Chlorophenyl)-1H-Imidazol-2-Yl)-4-Fluoropyrrolidine-1-Carboxamido)-1H-Indole-1-Carboxamide (Compound 11)

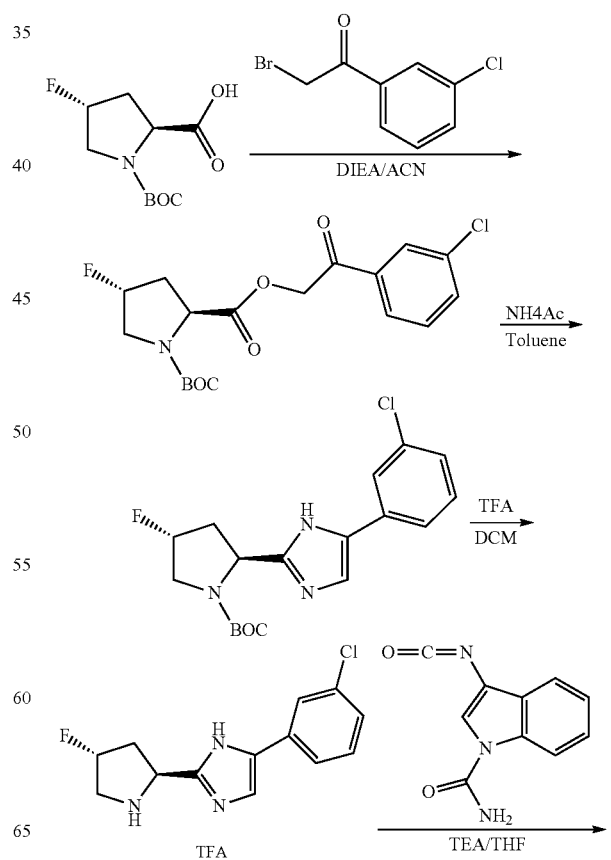

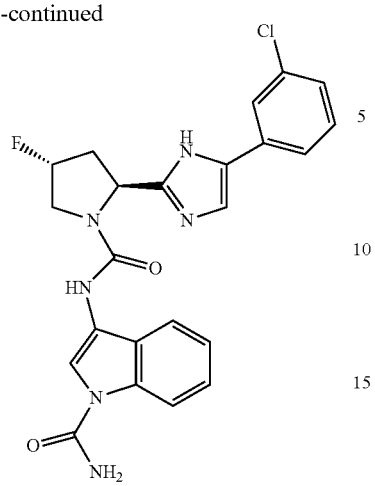

(2S,4R)-1-(tert-butoxycarbonyl)-4-fluoropyrrolidine-2-carboxylic acid (1.103 g, 4.73 mmol) and 2-bromo-1-(3-chlorophenyl)ethanone (1.007 g, 4.30 mmol) were dissolved in acetonitrile (20 ml), into which diisopropylethylamine (0.822 ml, 4.73 mmol) was added at rt and the mixture was stirred overnight. After solvent was removed on a rotavapor, the residue was dissolved in AcOEt and washed with water and brine. After removing AcOEt, (2S,4R)-1-tert-butyl 2-(2-(3-chlorophenyl)-2-oxoethyl) 4-fluoropyrrolidine-1,2-dicarboxylate was obtained as colorless syrups.

(2S,4R)-1-tert-butyl 2-(2-(3-chlorophenyl)-2-oxoethyl) 4-fluoropyrrolidine-1,2-dicarboxylate was mixed with ammoniumacetate (3.53 g, 45.8 mmol) and refluxed in toluene (25 ml) for 5 hr. The mixture was diluted with AcOEt and washed with water and brine. After removing solvent, the crude was purified by chromatography over silica gel. (2S,4R)-tert-butyl 2-(5-(3-chlorophenyl)-1H-imidazol-2-yl)-4-fluoropyrrolidine-1-carboxylate (1.58 g) was obtained as yellow foam.

(2S,4R)-tert-butyl 2-(5-(3-chlorophenyl)-1H-imidazol-2-yl)-4-fluoropyrrolidine-1-carboxylate (0.14 g, 0.38 mmol) was treated with TFA (1 ml) in DCM (4 ml) at rt for 2 hr. volatiles were removed by evaporation. The residue was coevaporated with tolene (10 ml×2) to get 5-(3-chlorophenyl)-2-((2S,4R)-4-fluoropyrrolidin-2-yl)-1H-imidazole.

5-(3-chlorophenyl)-2-((2S,4R)-4-fluoropyrrolidin-2-yl)-1H-imidazole is dissolved in THF (5 ml) and TEA (0.266 ml, 1.9 mmol). Into the mixture, 3-isocyanato-1H-indole-1-carboxamide (0.0844 g, 0.42 mmol) was added at rt. After 2 hr, the mixture was concentrated and the residue was purified by chromatography over silica gel to give 3-((2S,4R)-2-(5-(3-chlorophenyl)-1H-imidazol-2-yl)-4-fluoropyrrolidine-1-carboxamido)-1H-indole-1-carboxamide (0.110 g) as white foam. $^1$H-NMR (DMSO-$d_6$, 400 MHz) 12.45 (s, 1H); 8.47 (s, 1H); 8.33 (d, J=8.4 Hz, 1H); 7.99 (s, 1H); 7.86 (s, 1H); 7.78-7.69 (m, 3H); 7.04-7.33 (m, 3H); 7.26-7.20 (m, 2H); 7.00 t, J=7.2 Hz); 5.512 (d, J=53 Hz, 1H); 5.25 (t, J=7.6 Hz, 1H); 4.40 (t, J=7.2 Hz, 1H); 4.13 (dd, J=22 Hz, 12 Hz, 1H); 3.84 (dd, J=37 Hz, 11 Hz, 1H); 2.74-2.66 (m, 2H).

Example 12

Diethyl (1-(2-((2S,4R)-2-((3-Chloro-2-Fluorobenzyl)Carbamoyl)-4-Fluoropyrrolidin-1-Yl)-2-Oxoethyl)-1H-Pyrazolo [3,4-C]Pyridin-3-Yl)Phosphonate (Compound 61)

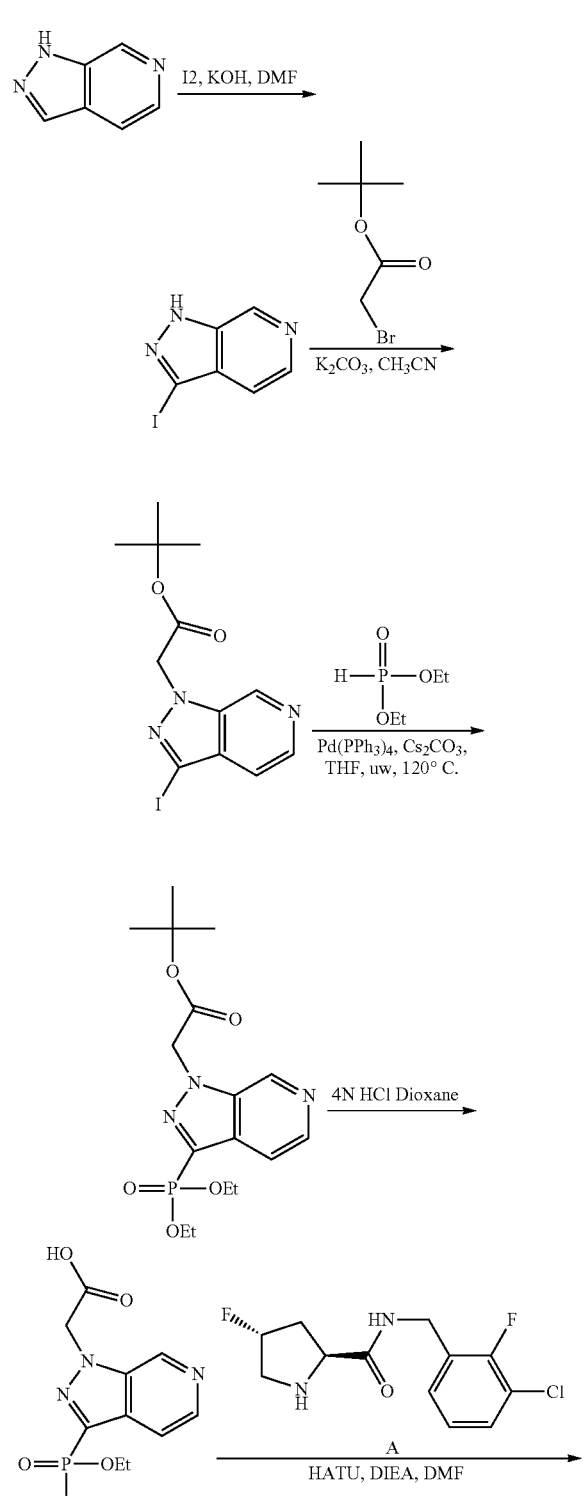

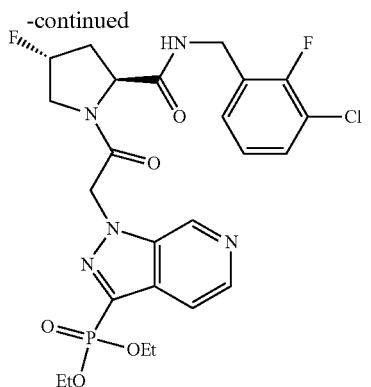

To a solution of 1H-pyrazolo [3,4-c]pyridine (4.94 g) in DMF (60 mL) were added iodine (15.8 gm) and potassium hydroxide (5.85 gm). The reaction mixture was stirred at RT for 16 h. The mixture was diluted with 10% sodium thiosulfate and water, then extracted (2×) with EtOAc. The combined organic extracts were washed with brine, then dried and concentrated under reduced pressure to give 3-lodo-1H-pyrazolo[3,4-c]pyridine.

To a suspension of 3-iodo-1H-pyrazolo[3,4-c]pyridine (6.89 g) and potassium carbonate (8.16 g) in acetonitrile (60 mL) was added tert-butyl bromoacetate (4.5 mL) dropwise at RT and the resulting mixture was heated to reflux for 24 h. The mixture was cooled to RT and filtered, the solid was washed with $CH_3CN$ and the filtrate was concentrated under vacuum. The remaining residue was purified by column chromatography (eluted with DCM/EtOAc) to give Tert-butyl 2-(3-iodo-1H-pyrazolo[3,4-c]pyridin-1-yl)acetate.

To a suspension of Tert-butyl 2-(3-iodo-1H-pyrazolo[3, 4-c]pyridin-1-yl)acetate (100 mg, 0.278 mmol), Cesium carbonate (108 mg, 1.2 eq) and diethyl phosphonate (38 mg, 1.1 equiv) in 5 ml THF are added. After initial heating in microwave, the reaction temperature was maintained for 15 min at 115° C. After cooling to RT, reaction mixture was concentrated under reduced pressure. The remaining residue was purified by flash column chromatography (ISCO eluted with $DCM/CH_3OH$) to give tert-butyl 2-(3-(diethoxyphosphoryl)-1H-pyrazolo[3,4-c]pyridin-1-yl)acetate (62 mg).

tert-butyl 2-(3-(diethoxyphosphoryl)-1H-pyrazolo[3,4-c] pyridin-1-yl)acetate (63 mg, 0.17 mmol) was taken in 4N HCl dioxane (5 ml) and resulting reaction mixture was stirred at rt for 24 h. After completion of the reaction monitored by HPLC, solvent was removed under reduced pressure. The residue, 2-(3-(diethoxyphosphoryl)-1H-pyrazolo[3,4-c]pyridin-1-yl)acetic acid, was used for next reaction.

2-(3-(diethoxyphosphoryl)-1H-pyrazolo[3,4-c]pyridin-1-yl)acetic acid (0.170 mmol) from previous reaction was dissolved in DMF (10 ml) and $iPr_2NEt$ (140 μl, 5 equiv) was added This was followed by the addition of A (47.7 mg, 0.154 mmol) at 5° C. Then HATU (136 mg, 2.1 equiv) was added slowly at same temperature. The reaction mixture was then stirred for 18 h at RT. After completion of the reaction monitored by HPLC, The reaction mixture was diluted with water and extracted with DCM (50 mL), the organic layer was then washed with an aqueous solution of $NaHCO_3$ (20 ml) and washed with water (20 ml), brine (20 ml) and dried over $Na_2SO_4$ and concentrated under reduced pressure. The remaining residue was purified by flash column chromatography (ISCO eluted with $DCM/CH_3OH$) to give diethyl (1-(2-((2S,4R)-2-((3-chloro-2-fluorobenzyl)carbamoyl)-4-fluoropyrrolidin-1-yl)-2-oxoethyl)-1H-pyrazolo[3,4-c]pyridin-3-yl)phosphonate (80 mg).). HPLC: tR 0.82 min. MS m/z calcd for $C_{24}H_{27}ClF_2N_5O_5P$ ([M]+), 570; found, 572 ([M+2]+). 1H-NMR (DMSO-D6, 400 MHz): δ, 1.28-1.23 (m, 6H), 2.2-2.0 (m, 1H), 4.05-3.85 (m, 1H), 4.17-4.08 (m, 4H), 4.46-4.24 (m, 3H), 5.58-5.45 (m, 1H), 5.71 (d, J=17.2 Hz, 1H), 5.94 (d, J=17.2 Hz, 1H), 7.00-6.96 (m, 1H), 7.21-7.19 (m, 1H), 7.44-7.40 (m, 1H), 7.85 (d, J=5.6 Hz, 1H), 8.40 (d, J=5.6 Hz, 1H), 8.62-8.59 (m, 1H), 9.16 (s, 1H).

Example 13

Synthesis of (1-(2-((2S,4R)-2-((3-Chloro-2-Fluorobenzyl)Carbamoyl)-4-Fluoropyrrolidin-1-Yl)-2-Oxoethyl)-1H-Pyrazolo [3,4-C]Pyridin-3-Yl)Phosphonic Acid (Compound 65)

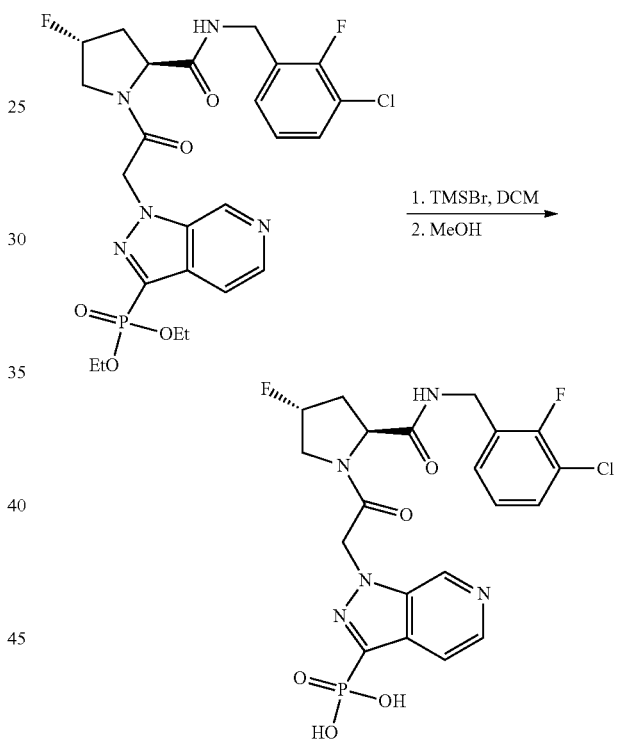

To a mixture of 27 (20 mg, 0.037 mmol) in 3 ml DCM under argon was added bromotrimethylsilane (54 μl, 10.5 equiv). The mixture was stirred at rt for 3 days and solvents were removed under reduced pressure. Then the product was dissolved in $CH_3OH/DCM$, then solvents removed under reduced pressure to yield 1-(2-((2S,4R)-2-((3-chloro-2-fluorobenzyl)carbamoyl)-4-fluoropyrrolidin-1-yl)-2-oxoethyl)-1H-pyrazolo[3,4-c]pyridin-3-yl)phosphonic acid quatintatively. HPLC: tR 0.72 min MS m/z calcd for $C_{20}H_{19}ClF_2N_5O_5P$ ([M]+), 513; found, 514 ([M+1]+). $^1$H-NMR (DMSO-$d_6$, 400 MHz): δ, 2.2-2.0 (m, 1H), 4.08-3.98 (m, 1H), 4.51-4.18 (m, 3H), 5.64-5.51 (m, 1H), 5.35-5.79 (m, 3H), 6.03 (d, J=17.2 Hz, 1H), 7.07-7.03 (m, 1H), 7.28-7.24 (m, 1H), 7.48-7.45 (m, 1H), 8.30 (d, J=6 Hz, 1H), 8.57 (d, J=5.6 Hz, 1H), 8.69 (t, J=5.6 Hz 1H), 9.16 (s, 1H); 9.58 (s, 1H).

Example 14

Synthesis of 3-Acetyl-1-(2-((2S,4R)-2-((3-Chloro-2-Fluorobenzyl)Carbamoyl)-4-Fluoropyrrolidin-1-Yl)-2-Oxoethyl)-1H-Indol-5-Yl Cyclopropylcarbamate (Compound 110)

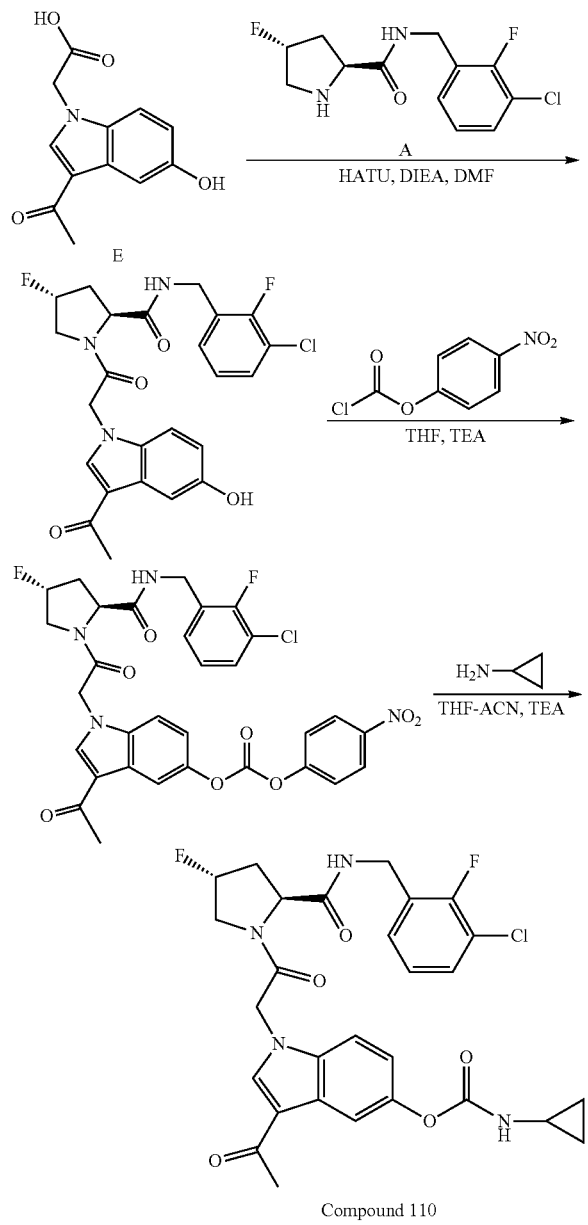

Compound 110

2-(3-acetyl-5-hydroxy-1H-indol-1-yl)acetic acid (2.8 mmol) E was dissolved in DMF (20 mL) and $^i$Pr$_2$NEt (2.076 mL, 5 equiv) was added, followed by the addition of (2S,4R)—N-(3-chloro-2-fluorobenzyl)-4-fluoropyrrolidine-2-carboxamide hydrochloride A (788 mg, 2.54 mmol) at 5° C. HATU (2.026 g, 2.1 equiv) was then added slowly at the same temperature and the reaction mixture was stirred for 18 h at RT. The reaction mixture was then diluted with 1 M citric acid solution (100 mL, containing 10 g NaCl) and extracted with DCM (2×50 mL). The organic layer was washed with an aqueous solution of NaHCO$_3$ (40 mL), washed with water (40 mL), washed with brine (40 mL), dried over Na$_2$SO$_4$, and concentrated under reduced pressure. The remaining residue was purified by flash column chromatography (silica gel eluted with DCM/EtOAc) to give (2S,4R)—N-(3-chloro-2-fluorobenzyl)-1-(2-(3-acetyl-5-hydroxy-1H-indol-1-yl)acetyl)-4-fluoropyrrolidine-2-carboxamide.

(2S,4R)—N-(3-chloro-2-fluorobenzyl)-1-(2-(3-acetyl-5-hydroxy-1H-indol-1-yl)acetyl)-4-fluoropyrrolidine-2-carboxamide (220 mg, 1 equiv) was dissolved in THF (20 mL) and NEt$_3$ (100 µl, 1.7 equiv) was added, followed by the addition of 4-nitrophenyl chloroformate (136 mg, 1.5 equiv) at 0° C. The reaction mixture was then stirred for 18 h at RT, diluted with 5 mL water, and extracted with ethyl acetate (50 mL). The organic layer was dried over Na$_2$SO$_4$ and concentrated under reduced pressure. The remaining residue was purified by flash column chromatography (silica gel eluted with DCM/EtOAc) to give 3-Acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate.

3-Acetyl-1-(2-((2S,4R)-2-((3-chloro-2-fluorobenzyl)carbamoyl)-4-fluoropyrrolidin-1-yl)-2-oxoethyl)-1H-indol-5-yl (4-nitrophenyl) carbonate was dissolved in a mixture of THF (5 mL), ACN (5 mL), and cyclopropanamine (12.86 µl, 2 equiv), followed by the addition of NEt$_3$ (30 µl, 3 equiv) at 0° C. The reaction mixture was then stirred for 24 h at RT. The reaction mixture was then concentrated under reduced pressure and the remaining residue was purified by flash column chromatography (silica gel eluted with DCM/CH$_3$OH) to give (2S,4R)—N2-(1-acetyl-1H-indol-3-yl)-N1-(3-chloro-2-fluorobenzyl)-4-fluoropyrrolidine-1,2-dicarboxamide. $^1$H NMR (400 MHz, DMSO-d$_6$, 300 K): (major rotamer) δ 0.53 (s, br, 2H), 0.65 (d, J=5.6 Hz, 2H), 2.04-2.18 (m, 1H), 2.42 (s, 3H), 2.54-2.58 (m, 1H), 3.90 (ddd, J=22, 9.6, 3.2 Hz, 1H), 4.14 (dd, J=8.8, 12.4 Hz, 1H), 4.32 (dd, J=22.4, 6.0 Hz, 1H), 4.40-4.49 (m, 2H), 5.18 (d, J=17.2 Hz, 1H), 5.39 (d, J=17.2 Hz, 1H), 5.51 (d, J=52.8 Hz, 1H), 6.92-7.01 (m, 2H), 7.16-7.24 (m, 1H), 7.40-7.45 (m, 2H), 7.82-7.87 (m, 2H), 8.22 (s, 1H), 8.60 (t, J=5.6 Hz, 1H). $^{19}$F NMR (376 MHz, DMSO-d$_6$, 300 K): (major rotamer) 6-121.3, −176.1. LC (method 1): t$_R$=1.73 min. LC/MS (EI) m/z: [M+H]$^+$ calcd for C$_{28}$H$_{27}$ClF$_2$N$_4$O$_5$, 573; found, 573.

Example 15

Synthesis of (2S,4R)—N2-(1-Acetyl-1H-Indol-3-Yl)-N1-(3-Chloro-2-Fluorobenzyl)-4-Fluoropyrrolidine-1,2-Dicarboxamide (Compound F)

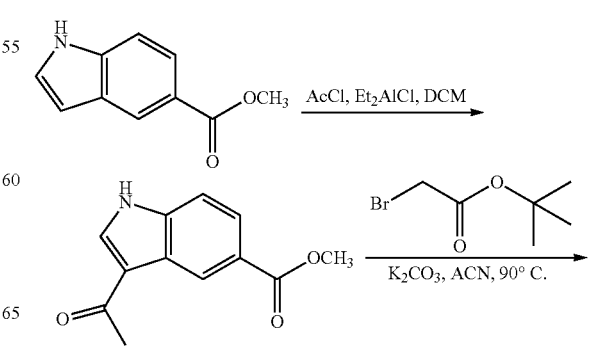

-continued

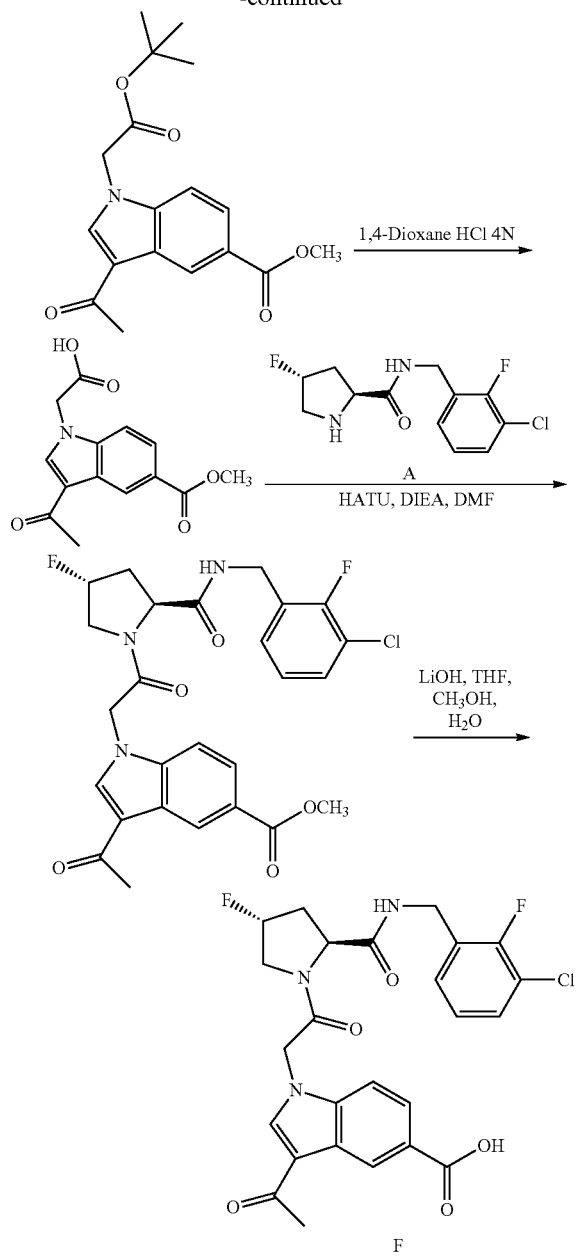

To a stirred solution of methyl 1H-indole-5-carboxylate (10 g, 1 equiv) in 200 mL DCM was added diethylaluminium chloride (1 M solution in hexane; 85.71 mL, 1.5 equiv) dropwise at 0° C. The mixture was stirred for 30 min and then a solution of acetyl chloride (6 mL, 1.5 equiv) in 150 mL DCM was added at 0° C. and stirred for 1 h at 0° C. A 5% aqueous citric acid solution was added at 0° C. and the reaction mixture was stirred for 15 min at RT. The precipitate was collected by filtration, washed with water, and dried. The residue was purified by flash column chromatography (silica gel eluted with DCM/CH$_3$OH) to give Methyl 3-acetyl-1H-indole-5-carboxylate.

To a suspension of methyl 3-acetyl-1H-indole-5-carboxylate (6 g, 1 equiv) and K$_2$CO$_3$ (4.19 g, 1.1 equiv) in 50 mL acetonitrile was added tert-butyl 2-bromoacetate (4.42 mL, 1.1 equiv) dropwise at RT. The resulting mixture was then heated to reflux for 18 h. After cooling to RT, the mixture was diluted with DCM (100 mL), filtered through a pad of Celite; and the filtrate was concentrated under reduced pressure. The remaining residue was purified by flash column chromatography (silica gel eluted with DCM/EtOAc) to give Methyl 3-acetyl-1-(2-(tert-butoxy)-2-oxoethyl)-1H-indole-5-carboxylate (12).

Methyl 3-acetyl-1-(2-(tert-butoxy)-2-oxoethyl)-1H-indole-5-carboxylate (3 g, 9.06 mmol) was taken up in 4 N HCl dioxane (50 mL) and the resulting reaction mixture was stirred at RT for 48 h. The solvent was then removed under reduced pressure and the remaining material 2-(3-Acetyl-5-(methoxycarbonyl)-1H-indol-1-yl)acetic acid was used directly in the next synthetic step.

2-(3-Acetyl-5-(methoxycarbonyl)-1H-indol-1-yl)acetic acid (2 g, 1 equiv) was dissolved in DMF (50 mL) and $^i$Pr$_2$NEt (3.95 mL, 5 equiv) was added, followed by the sequential addition of (2S,4R)—N-(3-chloro-2-fluorobenzyl)-4-fluoropyrrolidine-2-carboxamide hydrochloride A (2.254 g, 1 equiv) and HATU (5.8 g, 2.1 equiv) slowly at 5° C. The reaction mixture was then stirred for 18 h at RT, diluted with 1 M citric acid solution (100 mL, containing 10 g NaCl), and extracted with DCM (50 mL×2). The organic layer was washed with an aqueous solution of NaHCO$_3$ (40 mL), washed with water (40 mL), washed with brine (40 mL), dried over Na$_2$SO$_4$, and concentrated under reduced pressure. The remaining residue was purified by flash column chromatography (silica gel eluted with DCM/CH$_3$OH) to give methyl 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylate.

Methyl 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylate (3.86 g, 1 equiv) was taken up in a mixture of THF (20 mL) and methanol (20 mL), and then LiOH (1.832 g, 6 equiv) in water (20 mL) was added. The resulting reaction mixture was stirred at RT for 48 h. The solvent was then removed under reduced pressure and water (30 mL) was added. Acidification with 4 N HCl produced a white precipitate that was collected by filtration and dried in vacuo. This material 3-Acetyl-1-(2-((2S,4R)-2-((3-chloro-2-fluorobenzyl)carbamoyl)-4-fluoropyrrolidin-1-yl)-2-oxoethyl)-1H-indole-5-carboxylic acid (F) was used directly in the next synthetic step.

Example 16

Synthesis of Cyclopropyl (3-Acetyl-1-(2-((2S,4R)-2-((3-Chloro-2-Fluorobenzyl) Carbamoyl)-4-Fluoropyrrolidin-1-Yl)-2-Oxoethyl)-1H-Indol-5-Yl)Carbamate (Compound 187)

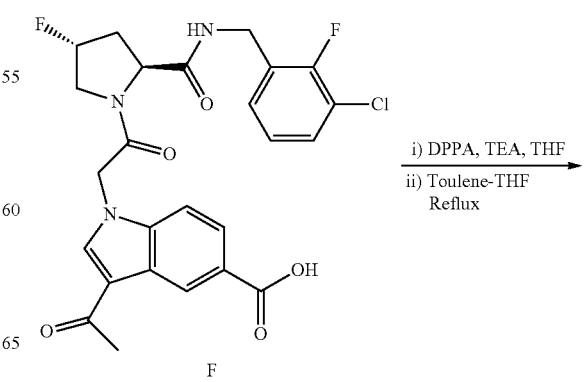

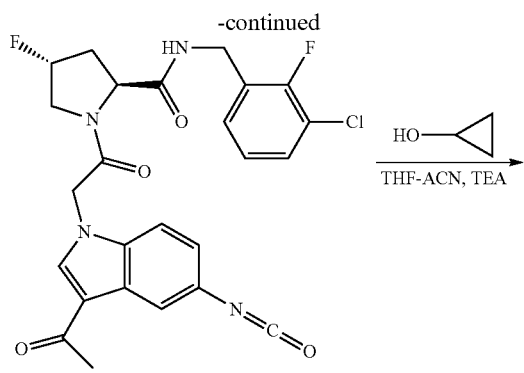

$t_R$=1.78 min. LC/MS (EI) m/z: [M+H]$^+$ calcd for $C_{28}H_{27}ClF_2N_4O_5$, 573; found, 573.

Example 17

Synthesis of N-(3-Acetyl-1-(2-((2S,4R)-2-((3-Chloro-2-Fluorobenzyl)Carbamoyl)-4-Fluoropyrrolidin-1-Yl)-2-Oxoethyl)-1H-Indol-5-Yl)-3,3-Difluoropiperidine-1-Carboxamide (Compound 191)

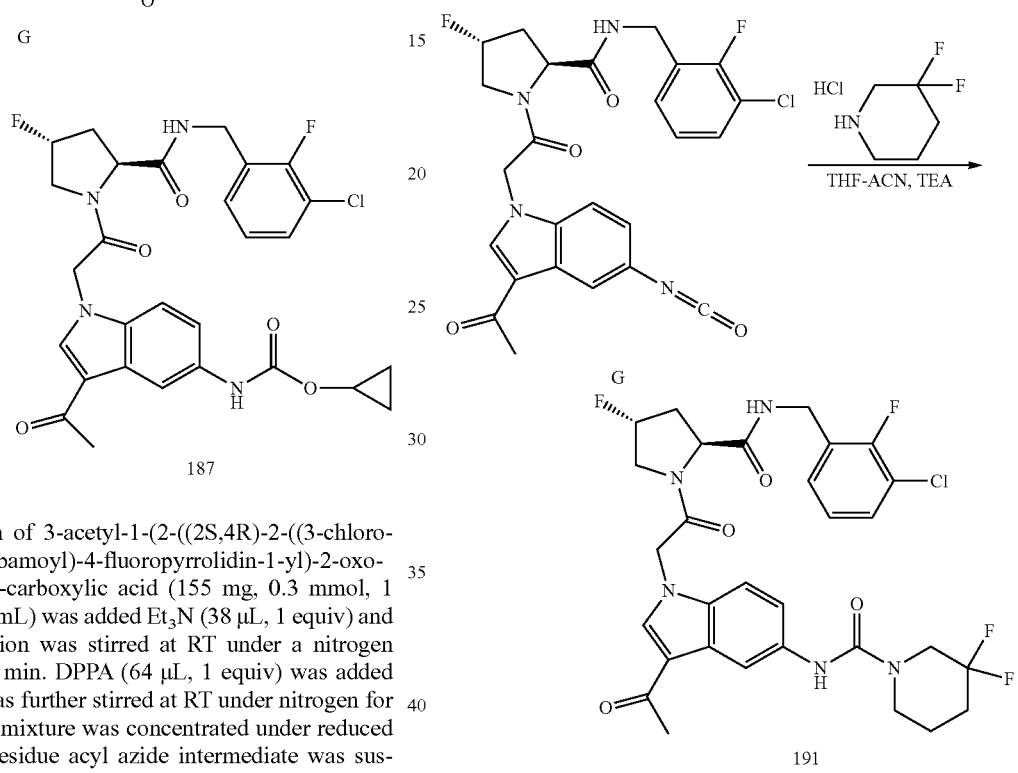

To a suspension of 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylic acid (155 mg, 0.3 mmol, 1 equiv) in THF (20 mL) was added Et$_3$N (38 μL, 1 equiv) and the resulting solution was stirred at RT under a nitrogen atmosphere for 15 min. DPPA (64 μL, 1 equiv) was added and the reaction was further stirred at RT under nitrogen for 18 h. The reaction mixture was concentrated under reduced pressure and the residue acyl azide intermediate was suspended in a mixture of toluene (20 mL) and THF (5 mL). This mixture was refluxed under nitrogen for 4 h and evaporated to dryness under reduce pressure. The remaining crude isocyanate (2S,4R)-1-(2-(3-Acetyl-5-isocyanato-1H-indol-1-yl)acetyl)-N-(3-chloro-2-fluorobenzyl)-4-fluoropyrrolidine-2-carboxamide (G) was used directly in the next step.

Compound G was dissolved in a mixture of THF (7 mL), ACN (3 mL), and cyclopropanol (35 mg, 2 equiv), followed by the addition of NEt$_3$ (76 μL, 2 equiv) at 0° C. The reaction mixture was then stirred for 24 h at RT. The reaction mixture was concentrated under reduced pressure and the remaining residue was purified by flash column chromatography (silica gel eluted with DCM/CH$_3$OH) to give product cyclopropyl (3-acetyl-1-(2-((2S,4R)-2-((3-chloro-2-fluorobenzyl)carbamoyl)-4-fluoropyrrolidin-1-yl)-2-oxoethyl)-1H-indol-5-yl)carbamate (187). $^1$H NMR (400 MHz, DMSO-d$_6$, 300 K): (major rotamer) δ 0.68-0.72 (m, 4H), 2.00-2.17 (m, 1H), 2.40 (s, 3H), 2.49-2.56 (m, 1H), 3.89 (ddd, J=22.8, 9.6, 2.8 Hz, 1H), 4.05-4.14 (m, 1H), 4.32 (dd, J=20.8, 6.0 Hz, 1H), 4.42-4.49 (m, 2H), 5.12 (d, J=17.2 Hz, 1H), 5.33 (d, J=17.2 Hz, 1H), 5.50 (d, J=52.8 Hz, 1H), 6.97-7.01 (m, 1H), 7.15-7.45 (m, 4H), 8.18 (s, 1H), 8.31 (s, 1H), 8.59 (t, J=5.6 Hz, 1H), 9.49 (s, 1H). $^{19}$F NMR (376 MHz, DMSO-d$_6$, 300 K): (major rotamer) δ −121.8, −176.1. LC (method 1):

Compound G from the previous reaction was dissolved in a mixture of THF (7 mL), ACN (3 mL), and 3,3-difluoropiperidine hydrochloride (51.81 mg, 1.1 equiv), followed by the addition of NEt$_3$ (76 μL, 2 equiv) at 0° C. The reaction mixture was then stirred for 24 h at RT. The reaction mixture was concentrated under reduced pressure and the remaining residue was purified by flash column chromatography (silica gel eluted with DCM/CH$_3$OH) to give N-(3-Acetyl-1-(2-((2S,4R)-2-((3-chloro-2-fluorobenzyl)carbamoyl)-4-fluoropyrrolidin-1-yl)-2-oxoethyl)-1H-indol-5-yl)-3,3-difluoropiperidine-1-carboxamide. $^1$H NMR (400 MHz, DMSO-d$_6$, 300 K): (major rotamer) δ 1.69-1.76 (m, 2H), 2.01-2.17 (m, 3H), 2.41 (s, 3H), 3.52 (t, J=5.2 Hz, 1H), 3.78-3.95 (m, 3H), 4.13 (dd, J=9.2, 12.4 Hz, 1H), 4.32 (dd, J=20.4, 6.0 Hz, 1H), 4.42-4.49 (m, 2H), 5.12 (d, J=17.2 Hz, 1H), 5.33 (d, J=17.2 Hz, 1H), 5.50 (d, J=52.8 Hz, 1H), 6.99-7.03 (m, 1H), 7.22-7.25 (m, 1H), 7.29-7.48 (m, 3H), 8.16 (s, 1H), 8.19 (d, J=2 Hz, 1H), 8.59 (t, J=6 Hz, 1H), 8.62 (s, 1H). $^{19}$F NMR (376 MHz, DMSO-d$_6$, 300 K): (major rotamer) δ −101.06, −121.25, −176.1. LC (method 1): $t_R$=1.82 min. LC/MS (EI) m/z: [M+H]$^+$ calcd for $C_{30}H_{30}ClF_4N_5O_4$, 636; found, 636.

Example 18
Synthesis of (2S,4R)-1-(2-(3-Acetyl-5-(Pyrimidin-2-Ylethynyl)-1H-Indol-1-Yl)Acetyl)-N-(3-Chloro-2-Fluorobenzyl)-4-Fluoropyrrolidine-2-Carboxamide (Compound 158)
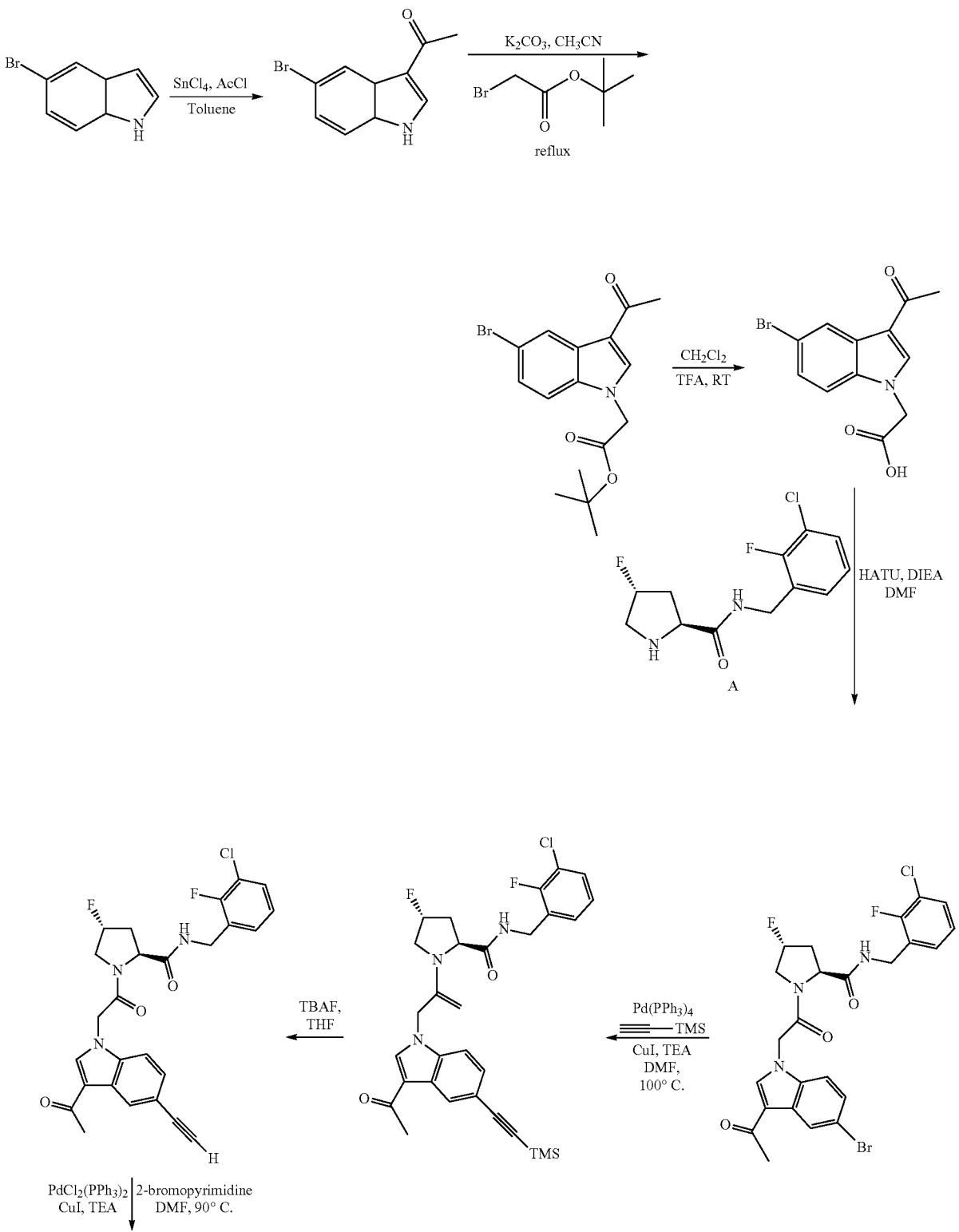

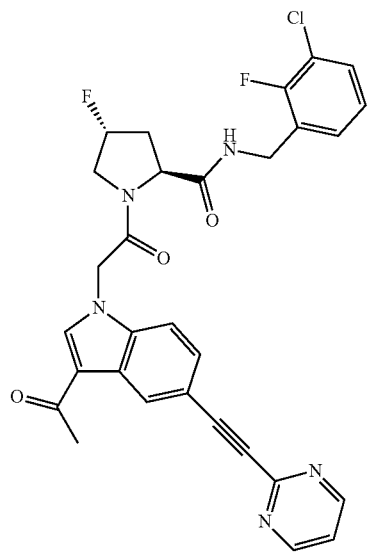

158

1-(5-Bromo-1H-indol-3-yl)ethanone (2) was prepared from 5-bromoindole according to the procedure published by MacKay et al. (MacKay, J. A.; Bishop, R.; Rawal, V. H. Org. Lett. 2005, 7, 3421-3424.)

A mixture of 3.9 g (16.4 mmol) of 1-(5-bromo-1H-indol-3-yl)ethanone, 2.63 mL (18.02 mmol) of tert-butyl bromoacetate and 2.50 g (18.02 mmol) potassium carbonate in anhydrous acetonitrile (80 mL) was refluxed for 5 h. The reaction mixture was then cooled to RT and the solvent was removed under reduced pressure. The residue was taken in 1:1 mixture of $CH_2Cl_2$ and water (100 mL: 100 mL). The two layers were separated and the organic layer was washed with water (2×100 mL). Finally, the organic layer was dried ($Na_2SO_4$) and concentrated. The resulting residue was stirred with 50 mL of heptane for 30 min., cooled in an ice bath and filtered, washing the solid with cold heptane (10 mL). This cream colored solid was dried under high vacuum to give 5.6 g of product tert-Butyl 2-(3-acetyl-5-bromo-1H-indol-1-yl)acetate.

4.5 g of tert-Butyl 2-(3-acetyl-5-bromo-1H-indol-1-yl)acetate was stirred in 1:1 mixture of $CH_2C_2$-TFA (90 mL) at RT for 4 h. The volatiles were removed under reduced pressure. The residue was dissolved in 45 mL of DMF. 4.16 g (13.4 mmol) of hydrochloride salt of 5 was added to this solution, followed by 11 mL of N,N-diisopropylethylamine (63.7 mmol). The reaction mixture was cooled in an ice bath and 5.82 g of (15.3 mmol) HATU was added. Following the addition of HATU, the cooling bath was removed and the reaction mixture was stirred overnight at RT. This reaction mixture was then poured in 450 mL of 1.0 M aq. citric acid solution. The separated product was isolated by filtration and the solid was washed thoroughly with water. This gray solid was dried under high vacuum to give 7.4 g of product (2S,4R)-1-(2-(3-Acetyl-5-bromo-1H-indol-1-yl)acetyl)-N-(3-chloro-2-fluorobenzyl)-4-fluoropyrrolidine-2-carboxamide.

A mixture of 1 g (1.8 mmol) of (2S,4R)-1-(2-(3-Acetyl-5-bromo-1H-indol-1-yl)acetyl)-N-(3-chloro-2-fluorobenzyl)-4-fluoropyrrolidine-2-carboxamide, 0.419 g (0.36 mmol) of tetrakis(triphenylphosphine)palladium(0), 0.138 g 0.72 mmol) of cuprous iodide in DMF (10 mL) was deoxygenated by bubbling argon in a pressure vessel. Triethylamine (2.53 mL, 18.1 mmol) and 2.56 mL (18.1 mmol) of ethynyltrimethylsilane were added under argon. The pressure vessel was capped and heated at 100° C. overnight. Then the reaction mixture was cooled to RT and the solvent was removed under reduced pressure. The residue was purified by column chromatography (silica gel, 0-2% MeOH in $CH_2Cl_2$) to give 0.56 g of (2S,4R)-1-(2-(3-Acetyl-5-((trimethylsilyl)ethynyl)-1H-indol-1-yl)acetyl)-N-(3-chloro-2-fluorobenzyl)-4-fluoropyrrolidine-2-carboxamide as a yellow solid.

To a solution of (2S,4R)-1-(2-(3-Acetyl-5-((trimethylsilyl)ethynyl)-1H-indol-1-yl)acetyl)-N-(3-chloro-2-fluorobenzyl)-4-fluoropyrrolidine-2-carboxamide (0.5 g, 1 mmol) in THF (5 mL) was added 1.5 mL of 1.0 M tetrabutylammonium fluoride in THF at RT. The reaction mixture was stirred for 1 h. The solvent was removed under reduced pressure and the residue was purified by column chromatography (silica gel, 0-2% MeOH in $CH_2Cl_2$) to give 0.26 g of (2S,4R)-1-(2-(3-Acetyl-5-ethynyl-1H-indol-1-yl)acetyl)-N-(3-chloro-2-fluorobenzyl)-4-fluoropyrrolidine-2-carboxamide as a light yellow solid.

A mixture of 0.16 g (1.0 mmol) of 2-bromopyrimidine, 0.141 g (0.2 mmol) of $PdCl_2(PPh_3)_2$, 0.043 g (0.23 mmol) of cuprous iodide in DMF (4 mL) was deoxygenated by bubbling argon in a pressure vessel. Triethylamine (2.0 mL) and 0.250 g (0.5 mmol) of (2S,4R)-1-(2-(3-Acetyl-5-ethynyl-1H-indol-1-yl)acetyl)-N-(3-chloro-2-fluorobenzyl)-4-fluoropyrrolidine-2-carboxamide were added under argon. The pressure vessel was capped and heated at 100° C. overnight. Then the reaction mixture was cooled to RT and the solvent was removed under reduced pressure. The residue was purified by column chromatography (silica gel, 0-4.5% MeOH in $CH_2Cl_2$) to give 35 mg of the desired product (2S,4R)-1-(2-(3-Acetyl-5-(pyrimidin-2-ylethynyl)-1H-indol-1-yl)acetyl)-N-(3-chloro-2-fluorobenzyl)-4-fluoropyrrolidine-2-carboxamide (158) as a light red solid. $^1$H NMR (400 MHz, DMSO-$d_6$, 300 K): (major rotamer) δ 1.99-2.18 (m, 1H), 2.46 (s, 3H), 3.92 (ddd, J=24.4, 12.4, 2.8 Hz, 1H), 4.26 (dd, J=12.8, 20.8 Hz, 1H), 4.32 (dd, J=28.4, 6.0 Hz, 1H), 4.39-4.49 (m, 2H), 5.24 (d, J=17.2 Hz, 1H), 5.45 (d, J=17.2 Hz, 1H), 5.51 (d, J=52.8 Hz, 1H), 6.96 (t, J=7.2 Hz, 1H), 7.23 (t, J=6.4 Hz, 1H), 7.40-7.51 (m, 4H), 7.59 (d, J=8.4 Hz, 1H), 8.36 (s, 1H), 8.47 (d, J=0.8 Hz, 1H), 8.61 (t, J=5.6 Hz, 1H), 8.85 (d, J=4.8 Hz, 2H). $^{31}$F NMR (376 MHz, DMSO-$d_6$, 300 K): (major rotamer) δ−121.7, −176.1. LC (method 1): $t_R$=1.73 min. LC/MS (EI) m/z: [M+H]$^+$ calcd for $C_{30}H_{24}ClF_2N_5O_3$, 575.9; found, 576.4.

Example 19

Synthesis of 3-Acetyl-1-(2-((2S,4R)-2-((3-Chloro-2-Fluorobenzyl)Carbamoyl)-4-Fluoropyrrolidin-1-Yl)-2-Oxoethyl)-N-Cyclopropylsulfonyl)-1H-Indole-6-Carboxamide (Compound 129)

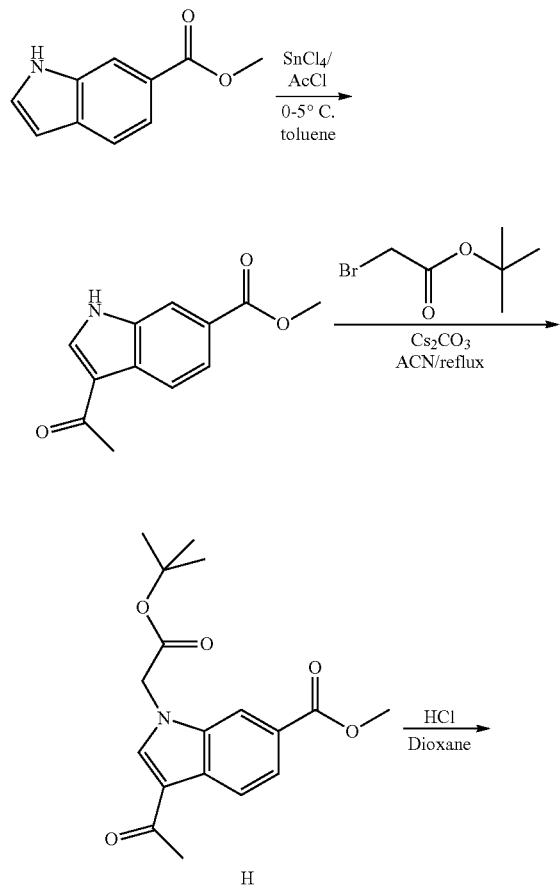

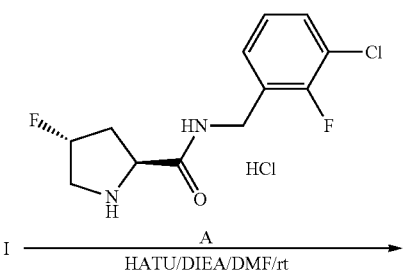

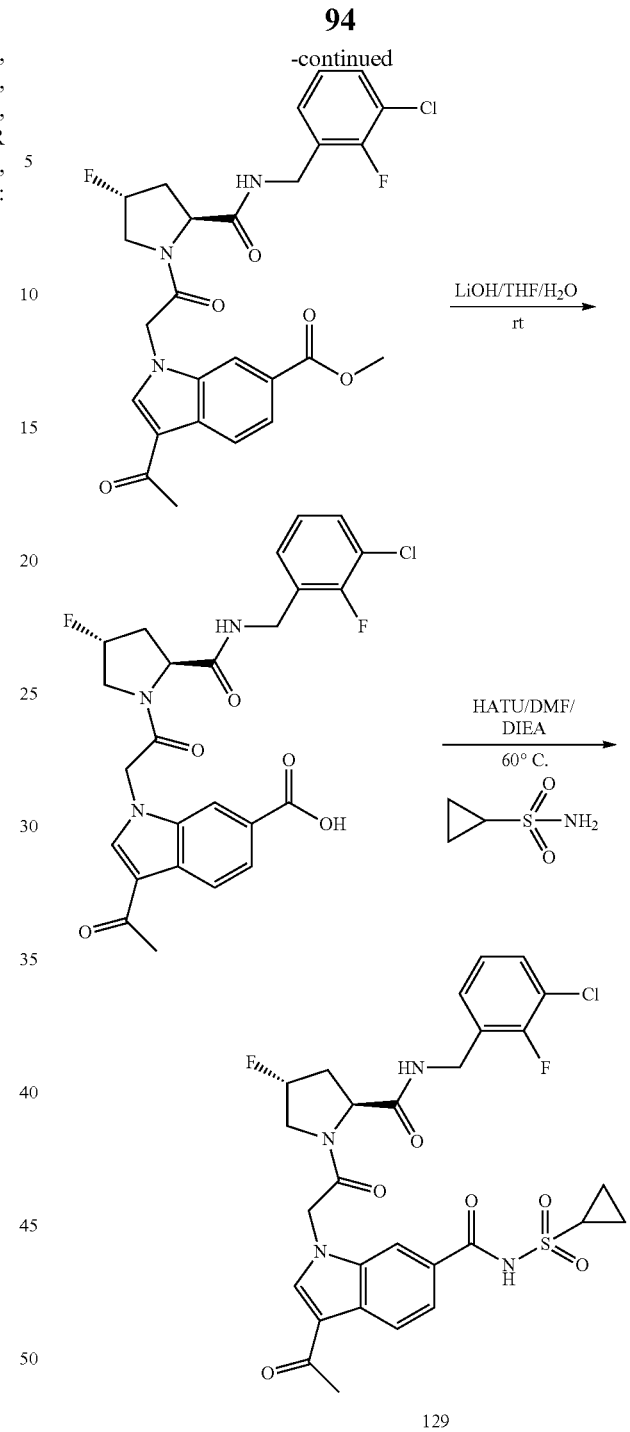

Methyl 3-acetyl-1H-indole-6-carboxylate was prepared according to the procedure published by MacKay et al. (MacKay, J. A.; Bishop, R.; Rawal, V. H. *Org. Lett.* 2005, 7, 3421-3424.)

A mixture of 150 mg (0.68 mmol) of methyl 3-acetyl-1H-indole-6-carboxylate, 0.12 mL (0.76 mmol) of tert-butyl bromoacetate, and 249 mg (0.76 mmol) cesium carbonate in anhydrous acetonitrile (15 mL) was refluxed for 18 h. The reaction mixture was then cooled to RT and the solvent was removed under reduced pressure. The residue was taken in a 2:1 mixture of EtOAc and water (30 mL: 15 mL). The two layers were separated and the organic layer was washed with brine (2×15 mL). Finally, the organic layer was dried (Na₂SO₄) and concentrated to obtain 283 mg of product methyl 3-acetyl-1-(2-tert-butoxy)-2-oxoethyl)-1H-indole-6-carboxylate (H) as a yellow solid.

100 mg of methyl 3-acetyl-1-(2-tert-butoxy)-2-oxoethyl)-1H-indole-6-carboxylate (0.3 mmol) was stirred in 4 N HCl in dioxane (15 mL) at RT for 18 h. The volatiles were removed under reduced pressure. The residue (intermediate I) was dissolved in 5 mL of DMF. To this solution was added 140 mg (0.36 mmol) of TFA salt of A, followed by 0.26 mL of N,N-diisopropylethylamine (1.5 mmol). Then 137 mg of (0.36 mmol) HATU was added and the reaction mixture was stirred overnight at RT. The reaction mixture was diluted with EtOAc (20 mL) and water (15 mL). The organic layer was separated, washed with brine (3×15 mL), dried (Na₂SO₄), concentrated in vacuo, and the residue was purified by column chromatography (silica gel, 0-10% MeOH in CH₂Cl₂) to give 128 mg of methyl-3-acetyl-1-(2-((2S,4R)-2-((3-chloro-2-fluorobenzyl)carbamoyl)-4-fluoropyrrolidin-1-yl)-2-oxoethyl-1H-indole-6-carboxylate as a yellow solid.

A mixture of 128 mg (0.24 mmol) of methyl-3-acetyl-1-(2-((2S,4R)-2-((3-chloro-2-fluorobenzyl)carbamoyl)-4-fluoropyrrolidin-1-yl)-2-oxoethyl-1H-indole-6-carboxylate in THF (5 mL) and 1 N LiOH (10 mL) was stirred at RT for 18 h. The solvent (THF) was removed under reduced pressure and the remaining water layer was washed with EtOAc (5 mL), acidified by 2 N HCl, and extracted with EtOAc (20 mL). The organic layer was washed with water, dried, and concentrated to obtain 126 mg of product 3-Acetyl-1-(2-((2S,4R)-2-((3-chloro-2-fluorobenzyl)carbamoyl)-4-fluoropyrrolidin-1-yl)-2-oxoethyl-1H-indole-6-carboxylic acid as a yellow solid.

To a stirred solution of 177 mg (0.34 mmol) of 3-Acetyl-1-(2-((2S,4R)-2-((3-chloro-2-fluorobenzyl)carbamoyl)-4-fluoropyrrolidin-1-yl)-2-oxoethyl-1H-indole-6-carboxylic acid in DMF (8 mL) was added 207 mg (1.71 mmol) of cyclopropanesulfonamide, 390 mg (1.03 mmol) of HATU, and 0.4 mL (2.4 mmol) DIEA. The reaction mixture was heated to 60° C. for 36 h. The reaction mixture was then cooled to RT and the solvent was removed under reduced pressure. The residue was purified by preparative HPLC to give 63 mg of the desired product 3-Acetyl-1-(2-((2S,4R)-2-((3-chloro-2-fluorobenzyl)carbamoyl)-4-fluoropyrrolidin-1-yl)-2-oxoethyl)-N-cyclopropylsulfonyl)-1H-indole-6-carboxamide (129) as a white solid. $^1$H NMR (400 MHz, DMSO-d₆, 300 K): (major rotamer) δ 1.12 (m, 4H), 2.11 (m, 1H), 2.48 (s, 3H), 3.15 (m, 1H), 3.92 (m, 1H), 4.16 (m, 2H), 4.32 (m, 2H), 4.49 (m, 2H), 5.48 (m, 2H), 6.92 (t, 1H), 7.21 (t, 1H), 7.43 (t, 1H), 7.81 (d, 1H), 8.30 (d, 1H), 8.44 (s, 1H), 8.65 (t, 1H). $^{31}$F NMR (376 MHz, DMSO-d₆, 300 K): (major rotamer) δ −121.6, −176.0. LC (method 1): $t_R$=1.52 min. LC/MS (EI) m/z: [M+H]⁺ calcd for $C_{28}H_{27}ClF_2N_4O_6S$, 621.05; found, 621.00.

Example 20

Synthesis of (S)-3-Acetyl-1-2(-(3-((3-Chlorobenzyl)Carbamoyl)Morpholino)-2-Oxoethyl)-1H-Indole-6-Carboxylic Acid (Compound 160)

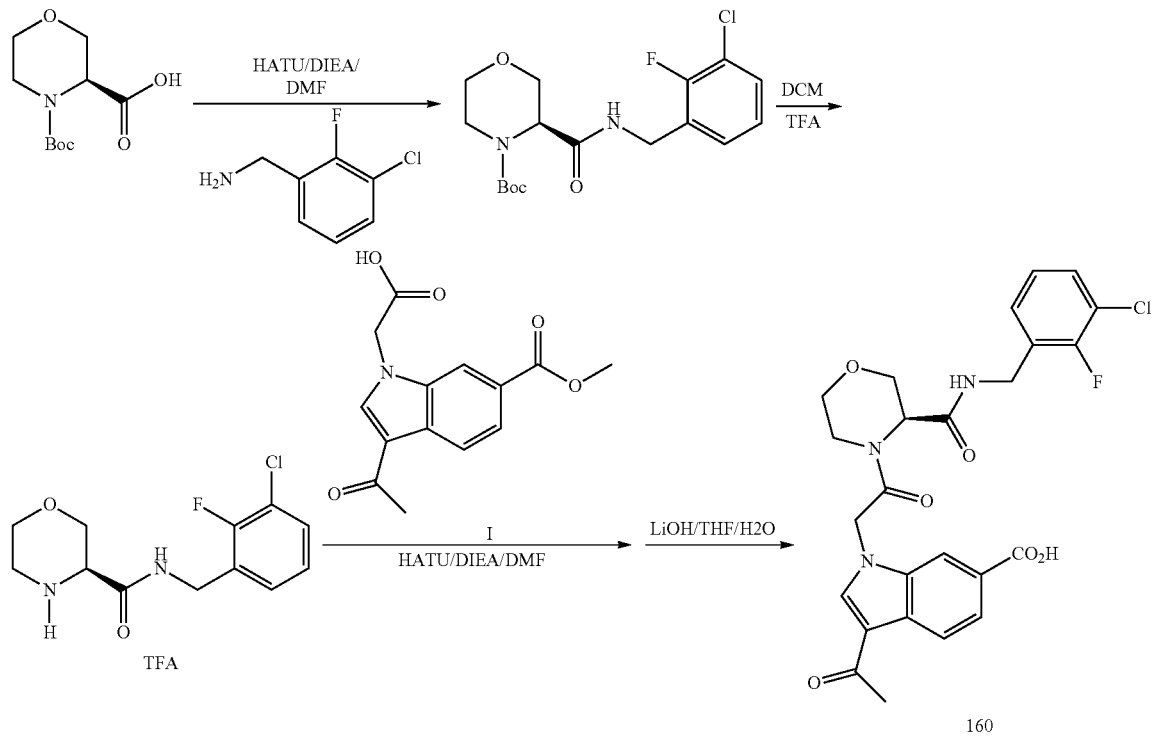

160

2-(3-Acetyl-6-(methoxycarbonyl)-1H-indol-1-yl)acetic acid-6-carboxylate I was prepared from H with HCl in dioxane according to the procedure in example 19.

273 mg (1.18 mmol) of (S)-4-Boc-morpholine-3-carboxylic acid was added to a solution of (3-chloro-2-flurophenyl)methanamine, 208 mg, 1.3 mmol) in DMF (10 mL), followed by addition of 0.41 mL of N,N-diisopropylethylamine (2.4 mmol), and 538 mg (1.4 mmol) of HATU. The reaction mixture was stirred overnight at RT. The reaction mixture was diluted with EtOAc (50 mL) and water (20 mL). The organic layer was separated, washed with brine (3×15 mL), dried (Na$_2$SO$_4$), concentrated in vacuo, and the remaining residue was purified by column chromatography (silica gel, 0-80% EtOAc in hexanes) to give 399 mg of a yellow oil. The coupling product obtained was deprotected with TFA in DCM at RT to form the TFA salt of (S)—N-(3-Chloro-2-fluorobenzyl)morpholine-3-carboxamide.

To a stirred solution of 261 mg (0.54 mmol) of (S)—N-(3-Chloro-2-fluorobenzyl)morpholine-3-carboxamide in DMF (7 mL) was added 155 mg (0.56 mmol) of 11 (2-(3-acetyl-6-(methoxycarbonyl)-1H-indol-1-yl)acetic acid-6-carboxylate), 244 mg (0.64 mmol) of HATU, and 0.28 mL (1.61 mmol) DIEA. The reaction mixture was stirred 18 h at room temperature. The reaction mixture was then diluted with EtOAc (45 mL) and water (25 mL). The organic layer was separated, washed with brine (3×25 mL), dried, and evaporated to dryness under reduced pressure. The residue was dissolved in THF (5 mL) and hydrolyzed with LiOH solution (1 N, 10 mL). The THF was removed under reduced pressure, and the remaining water layer was acidified with 1 N HCl and extracted with EtOAc (20 mL). The EtOAc layer was dried and concentrated in vacuo. The residue was purified by HPLC (C18, 10-100% acetonitrile in water) to give 57 mg of the desired product (S)-3-Acetyl-1-2(-(3-((3-chlorobenzyl)carbamoyl)morpholino)-2-oxoethyl)-1H-indole-6-carboxylic acid (160) as a white solid. $^1$H NMR (400 MHz, DMSO-d$_6$, 300 K): (major rotamer) δ 2.25 (s, 3H), 3.52 (m, 1H), 3.85 (dd, 2H), 4.21 (d, 1H), 4.34 (dd, 2H), 4.55 (m, 1H), 4.62 (m, 1H), 5.44 (m, 2H), 7.06 (t, 1H), 7.20 (t, 1H), 7.48 (t, 1H), 7.76 (d, 1H), 8.18 (d, 1H), 8.31 (s, 1H), 8.59 (t, 1H). $^{31}$F NMR (376 MHz, DMSO-d$_6$, 300 K): (major rotamer) 8-121.53. LC (method 1): t$_R$=1.46 min. LC/MS (EI) m/z: [M+H]$^+$ calcd for C$_{25}$H$_{23}$ClF$_2$N$_3$O$_6$, 515.92; found, 516.00.

Example 21

Additional Compounds

Table 2 shows compounds of Examples 2 to 20 with biological data and shows additional compounds prepared by the methods shown in Examples 1 to 13. Routine changes in starting materials and reaction conditions, readily apparent to those of skill in the art, were used to make the particular compounds disclosed in Table 2. Three *'s are used to denote compounds with an IC$_{50}$ less than 1 micromolar, two 's indicate compound with an IC$_{50}$ between 1 micromolar and 10 micromolar, and one * denotes compounds with an IC$_{50}$ greater than 10 micromolar, ND indicates "No Data." A standard Factor D inhibition assay, such as the assay of Example 22, is used to determine the IC$_{50}$'s for the compounds.

| Cmp. No. | Structure | Name | IC$_{50}$ (μM) | RT min (Method 1 or 2) | M + 1 |
|---|---|---|---|---|---|
| 1 | 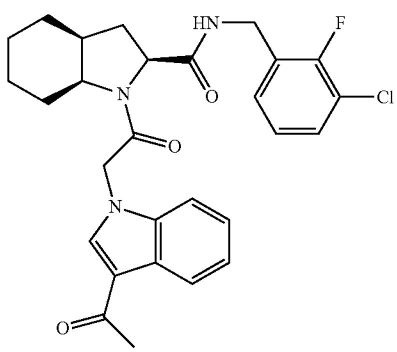 [SMILES: CC(=O)c1cn(CC(=O)N2[C@H](C(=O)NCc3cccc(Cl)c3F)C[C@@H]3CCCC[C@@H]32)c2ccccc12] | (2S,3aS,7aS)-1-(2-(3-acetyl-1H-indol-1-yl)acetyl)-N-(3-chloro-2-fluorobenzyl)octahydro-1H-indole-2-carboxamide | *** | 2.33 | 510 |
| 2 | 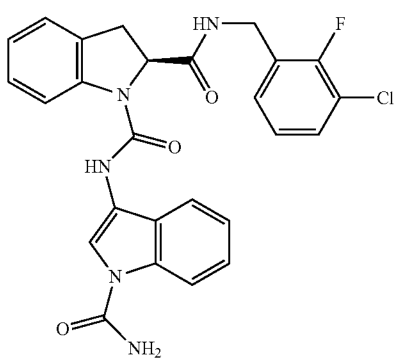 [SMILES: NC(=O)n1cc(NC(=O)N2c3ccccc3C[C@H]2C(=O)NCc2cccc(Cl)c2F)c2ccccc21] | (S)-N1-(1-carbamoyl-1H-indol-3-yl)-N2-(3-chloro-2-fluorobenzyl)indoline-1,2-dicarboxamide | ** | 2.04 | 506 |

-continued

| Cmp. No. | Structure | Name | IC$_{50}$ (μM) | RT min (Method 1 or 2) | M + 1 |
|---|---|---|---|---|---|
| 3 | 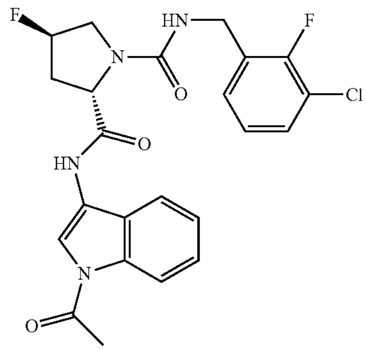 [SMILES: CC(=O)n1cc(NC(=O)[C@@H]2C[C@@H](F)CN2C(=O)NCc2cccc(Cl)c2F)c2ccccc21] | (2S,4R)-N2-(1-acetyl-1H-indol-3-yl)-N1-(3-chloro-2-fluorobenzyl)-4-fluoropyrrolidine-1,2-dicarboxamide | * | 2.07 | 475 |
| 4 | 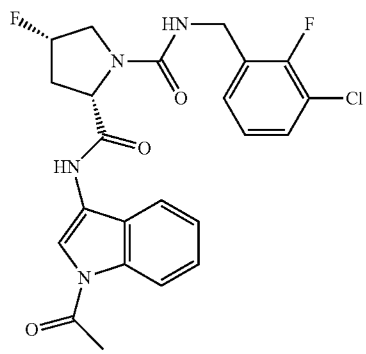 [SMILES: CC(=O)n1cc(NC(=O)[C@@H]2C[C@H](F)CN2C(=O)NCc2cccc(Cl)c2F)c2ccccc21] | (2S,4S)-N2-(1-acetyl-1H-indol-3-yl)-N1-(3-chloro-2-fluorobenzyl)-4-fluoropyrrolidine-1,2-dicarboxamide | * | 2.05 | 475 |
| 5 | 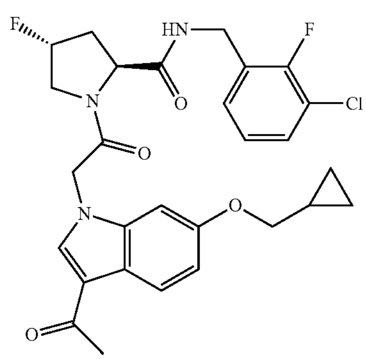 [SMILES: CC(=O)c1cn(CC(=O)N2C[C@H](F)C[C@H]2C(=O)NCc2cccc(Cl)c2F)c2cc(OCC3CC3)ccc12] | (2S,4R)-1-(2-(3-acetyl-6-(cyclopropylmethoxy)-1H-indol-1-yl)acetyl)-N-(3-chloro-2-fluorobenzyl)-4-fluoropyrrolidine-2-carboxamide | *** | 2.14 | 544 |
| 6 | 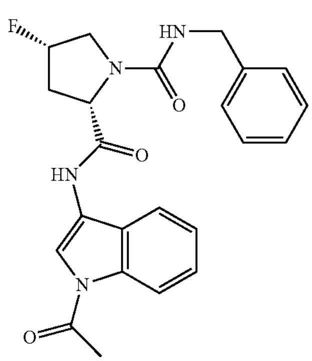 [SMILES: CC(=O)n1cc(NC(=O)[C@@H]2C[C@H](F)CN2C(=O)NCc2ccccc2)c2ccccc21] | (2S,4S)-N2-(1-acetyl-1H-indol-3-yl)-N1-benzyl-4-fluoropyrrolidine-1,2-dicarboxamide | * | 1.78 | 423 |

-continued

| Cmp. No. | Structure | Name | IC$_{50}$ (μM) | RT min (Method 1 or 2) | M + 1 |
|---|---|---|---|---|---|
| 7 | 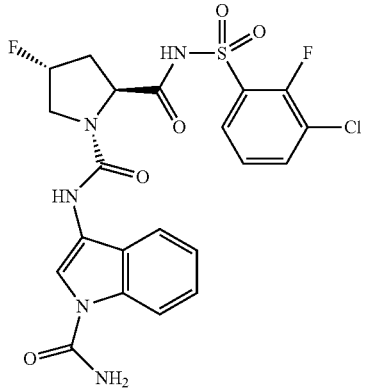 | (2S,4R)-N1-(1-carbamoyl-1H-indol-3-yl)-N2-((3-chloro-2-fluorophenyl)sulfonyl)-4-fluoropyrrolidine-1,2-dicarboxamide | * | 1.33 | 526 |
| 8 | 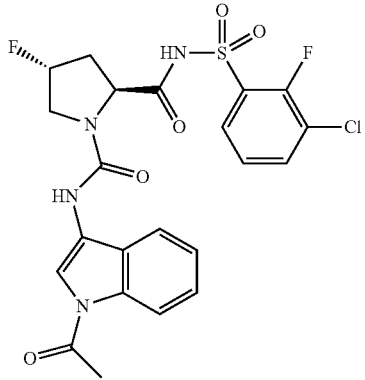 [SMILES: CC(=O)n1cc(NC(=O)N2C[C@H](F)C[C@H]2C(=O)NS(=O)(=O)c2cccc(Cl)c2F)c2ccccc21] | (2S,4R)-N1-(1-acetyl-1H-indol-3-yl)-N2-((3-chloro-2-fluorophenyl)sulfonyl)-4-fluoropyrrolidine-1,2-dicarboxamide | * | 1.67 | 525 |
| 9 | 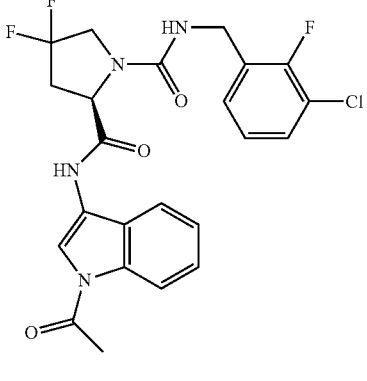 | (R)-N2-(1-acetyl-1H-indol-3-yl)-N1-(3-chloro-2-fluorobenzyl)-4,4-difluoropyrrolidine-1,2-dicarboxamide | * | 2.25 | 493 |
| 10 | 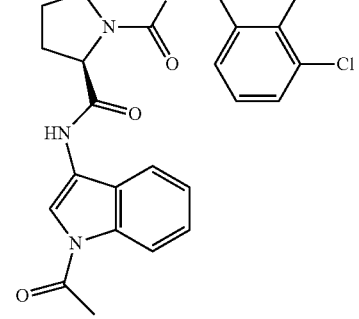 | (R)-N2-(1-acetyl-1H-indol-3-yl)-N1-(3-chloro-2-fluorobenzyl)pyrrolidine-1,2-dicarboxamide | * | 2.14 | 457 |

-continued

| Cmp. No. | Structure | Name | IC$_{50}$ (μM) | RT min (Method 1 or 2) | M + 1 |
|---|---|---|---|---|---|
| 11 | 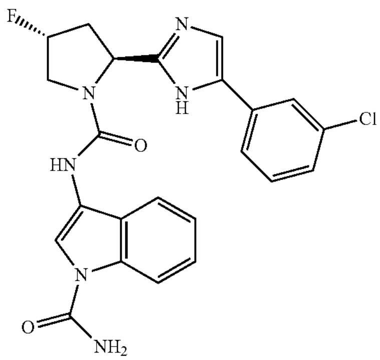 | 3-((2S,4R)-2-(5-(3-chlorophenyl)-1H-imidazol-2-yl)-4-fluoropyrrolidine-1-carboxamido)-1H-indole-1-carboxamide | ** | 1.49 | 467 |
| 12 | 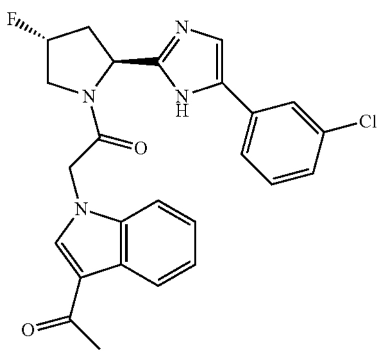 | 2-(3-acetyl-1H-indol-1-yl)-1-((2S,4R)-2-(5-(3-chlorophenyl)-1H-imidazol-2-yl)-4-fluoropyrrolidin-1-yl)ethanone | * | 1.46 | 465 |
| 13 | 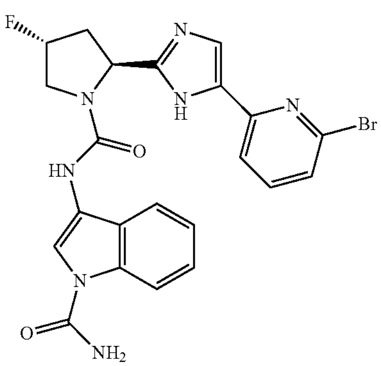 [SMILES: NC(=O)n1cc(NC(=O)N2C[C@H](F)C[C@H]2c2ncc(-c3cccc(Br)n3)[nH]2)c2ccccc21] | 3-((2S,4R)-2-(5-(6-bromopyridin-2-yl)-1H-imidazol-2-yl)-4-fluoropyrrolidine-1-carboxamido)-1H-indole-1-carboxamide | ** | 1.34 | 512 |
| 14 | 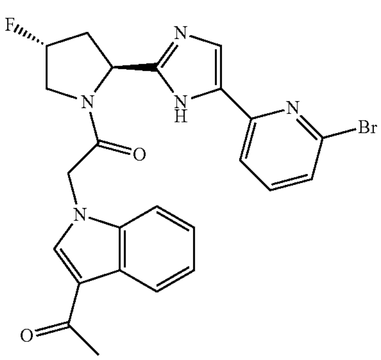 [SMILES: CC(=O)c1cn(CC(=O)N2C[C@H](F)C[C@H]2c2ncc(-c3cccc(Br)n3)[nH]2)c2ccccc12] | 2-(3-acetyl-1H-indol-1-yl)-1-((2S,4R)-2-(5-(6-bromopyridin-2-yl)-1H-imidazol-2-yl)-4-fluoropyrrolidin-1-yl)ethanone | ** | 1.43 | 512 |

-continued

| Cmp. No. | Structure | Name | IC$_{50}$ (μM) | RT min (Method 1 or 2) | M + 1 |
|---|---|---|---|---|---|
| 15 | 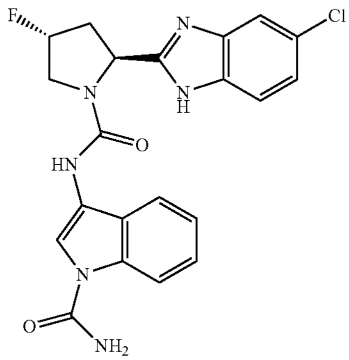 [SMILES: NC(=O)n1cc(NC(=O)N2C[C@H](F)C[C@H]2c2nc3cc(Cl)ccc3[nH]2)c2ccccc21] | 3-((2S,4R)-2-(5-chloro-1H-benzo[d]imidazol-2-yl)-4-fluoropyrrolidine-1-carboxamido)-1H-indole-1-carboxamide | ** | 1.42 | 441 |
| 16 | 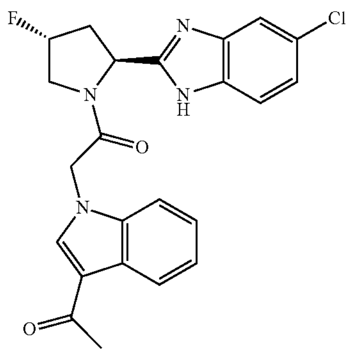 [SMILES: CC(=O)c1cn(CC(=O)N2C[C@H](F)C[C@H]2c2nc3cc(Cl)ccc3[nH]2)c2ccccc12] | 2-(3-acetyl-1H-indol-1-yl)-1-((2S,4R)-2-(5-chloro-1H-benzo[d]imidazol-2-yl)-4-fluoropyrrolidin-1-yl)ethanone | * | 1.54 | 439 |
| 17 | 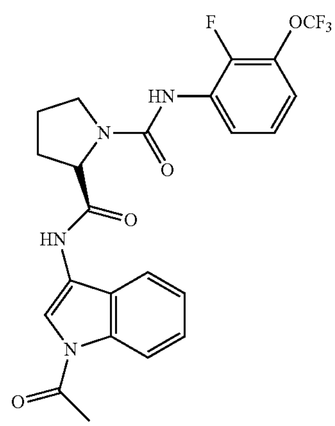 | (R)-N2-(1-acetyl-1H-indol-3-yl)-N1-(2-fluoro-3-(trifluoromethoxy)phenyl)pyrrolidine-1,2-dicarboxamide | * | 2.30 | 493 |
| 18 | 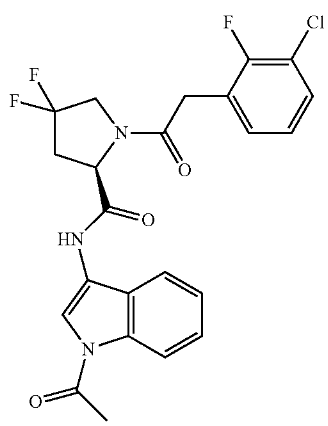 [SMILES: CC(=O)n1cc(NC(=O)[C@H]2CC(F)(F)CN2C(=O)Cc2cccc(Cl)c2F)c2ccccc21] | (R)-N-(1-acetyl-1H-indol-3-yl)-1-(2-(3-chloro-2-fluorophenyl)acetyl)-4,4-difluoropyrrolidine-2-carboxamide | * | 2.28 | 478 |

-continued
| Cmp. No. | Structure | Name | IC$_{50}$ (μM) | RT min (Method 1 or 2) | M + 1 |
|---|---|---|---|---|---|
| 19 | 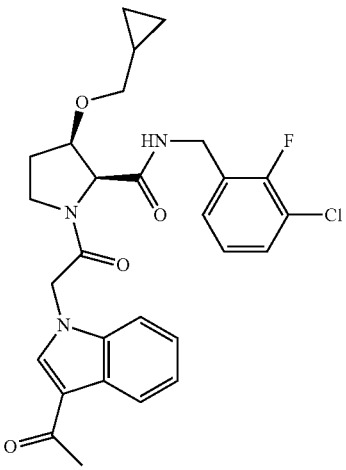 [SMILES: CC(=O)c1cn(CC(=O)N2CC[C@@H](OCC3CC3)[C@H]2C(=O)NCc2cccc(Cl)c2F)c2ccccc12] | (2S,3R)-1-(2-(3-acetyl-1H-indol-1-yl)acetyl)-N-(3-chloro-2-fluorobenzyl)-3-(cyclopropylmethoxy)pyrrolidine-2-carboxamide | *** | 2.12 | 526 |
| 20 | 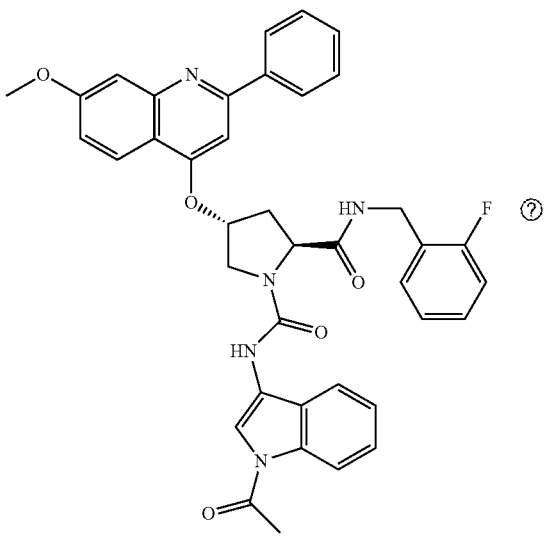 [SMILES: COc1ccc2c(O[C@@H]3C[C@@H](C(=O)NCc4ccccc4F)N(C(=O)Nc4cn(C(C)=O)c5ccccc45)C3)cc(-c3ccccc3)nc2c1] | (2S,4R)-N1-(1-acetyl-1H-indol-3-yl)-N2-(3-chloro-2-fluorobenzyl)-4-((7-methoxy-2-phenylquinolin-4-yl)oxy)pyrrolidine-1,2-dicarboxamide | * | Method 2, 6.93 | 706 |
| 21 | 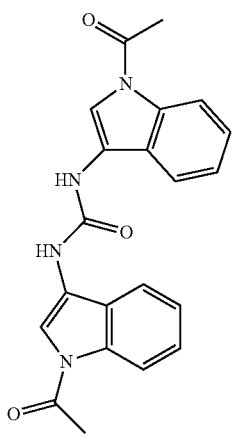 [SMILES: CC(=O)n1cc(NC(=O)Nc2cn(C(C)=O)c3ccccc23)c2ccccc21] | 1,3-bis(1-acetyl-1H-indol-3-yl)urea | * | 1.98 | 375 |

-continued

| Cmp. No. | Structure | Name | IC$_{50}$ (μM) | RT min (Method 1 or 2) | M + 1 |
|---|---|---|---|---|---|
| 22 | 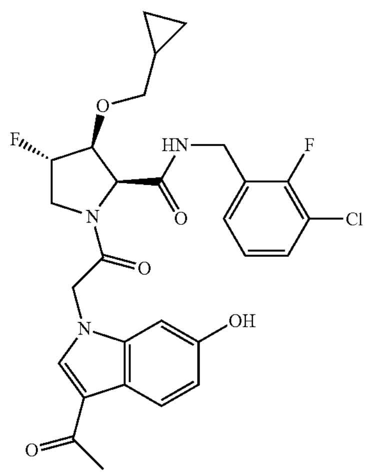 [SMILES: CC(=O)c1cn(CC(=O)N2C[C@H](F)[C@@H](OCC3CC3)[C@H]2C(=O)NCc2cccc(Cl)c2F)c2cc(O)ccc12] | (2S,3S,4S)-1-(2-(3-acetyl-6-hydroxy-1H-indol-1-yl)acetyl)-N-(3-chloro-2-fluorobenzyl)-3-(cyclopropylmethoxy)-4-fluoropyrrolidine-2-carboxamide | *** | 1.91 | 560 |
| 23 | 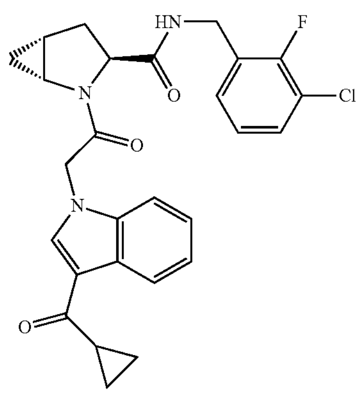 [SMILES: O=C(c1cn(CC(=O)N2[C@@H]3C[C@@H]3C[C@H]2C(=O)NCc2cccc(Cl)c2F)c2ccccc12)C1CC1] | (1R,3S,5R)-N-(3-chloro-2-fluorobenzyl)-2-(2-(3-(cyclopropanecarbonyl)-1H-indol-1-yl)acetyl)-2-azabicyclo[3.1.0]hexane-3-carboxamide | *** | 2.07 | 494 |
| 24 | 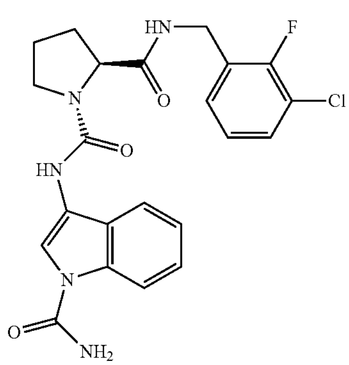 | (1R,2R)-N1-(1-carbamoyl-1H-indol-3-yl)-N2-(3-chloro-2-fluorobenzyl)cyclopentane-1,2-dicarboxamide | ** | 1.87 | 457 |

| Cmp. No. | Structure | Name | IC$_{50}$ (μM) | RT min (Method 1 or 2) | M + 1 |
|---|---|---|---|---|---|
| 25 | 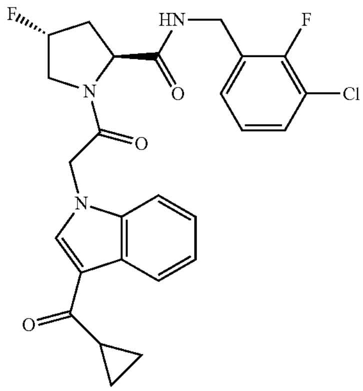 [SMILES: O=C(c1cn(CC(=O)N2C[C@H](F)C[C@H]2C(=O)NCc2cccc(Cl)c2F)c2ccccc12)C1CC1] | (2S,4R)-N-(3-chloro-2-fluorobenzyl)-1-(2-(3-(cyclopropanecarbonyl)-1H-indol-1-yl)acetyl)-4-fluoropyrrolidine-2-carboxamide | *** | 2.02 | 500 |
| 26 | mix | (2S)-1-(2-(3-acetyl-6-hydroxy-1H-indol-1-yl)acetyl)-N-(3-chloro-2-fluorobenzyl)-3-(cyclopropylmethoxy)-4-fluoropyrrolidine-2-carboxamide and (2R)-1-(2-(3-acetyl-6-hydroxy-1H-indol-1-yl)acetyl)-N-(3-chloro-2-fluorobenzyl)-4-(cyclopropylmethoxy)-3-fluoropyrrolidine-2-carboxamide | *** | 1.82 and 1.86 | 560 |

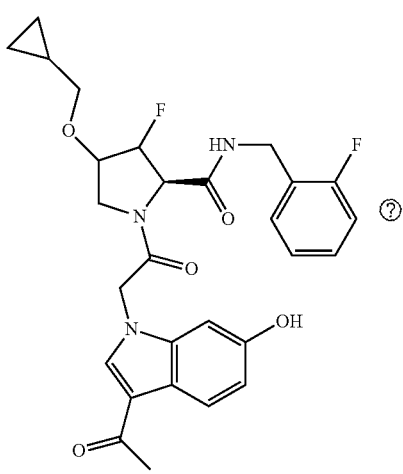 [SMILES: CC(=O)c1cn(CC(=O)N2CC(OCC3CC3)C(F)[C@H]2C(=O)NCc2ccccc2F)c2cc(O)ccc12]

-continued

| Cmp. No. | Structure | Name | IC$_{50}$ (μM) | RT min (Method 1 or 2) | M + 1 |
| --- | --- | --- | --- | --- | --- |
| 27 | 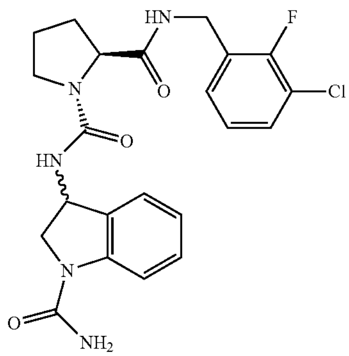 | (1R,2R)-N1-(1-carbamoylindolin-3-yl)-N2-(3-chloro-2-fluorobenzyl)cyclopentane-1,2-dicarboxamide | * | 1.35 | 459 |
| 28 | 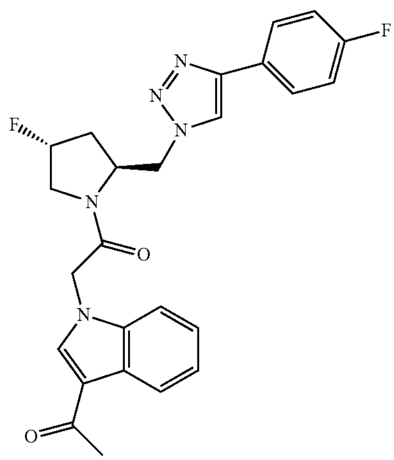 [SMILES: CC(=O)c1cn(CC(=O)N2C[C@H](F)C[C@H]2Cn2cc(-c3ccc(F)cc3)nn2)c2ccccc12] | 2-(3-acetyl-1H-indol-1-yl)-1-((2S,4R)-4-fluoro-2-((4-(4-fluorophenyl)-1H-1,2,3-triazol-1-yl)methyl)pyrrolidin-1-yl)ethanone | * | 1.72 | 464 |
| 29 | 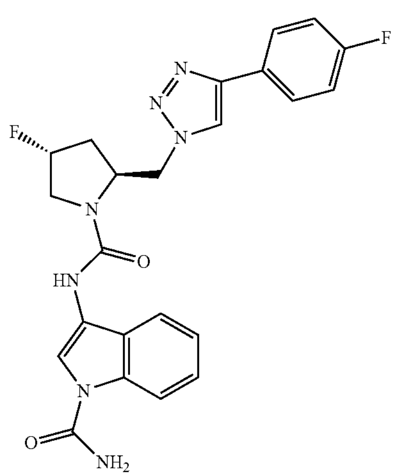 [SMILES: NC(=O)n1cc(NC(=O)N2C[C@H](F)C[C@H]2Cn2cc(-c3ccc(F)cc3)nn2)c2ccccc21] | 3-((2S,4R)-4-fluoro-2-((4-(4-fluorophenyl)-1H-1,2,3-triazol-1-yl)methyl)pyrrolidine-1-carboxamido)-1H-indole-1-carboxamide | * | 1.60 | 466 |

| Cmp. No. | Structure | Name | IC$_{50}$ (μM) | RT min (Method 1 or 2) | M + 1 |
|---|---|---|---|---|---|
| 30 | 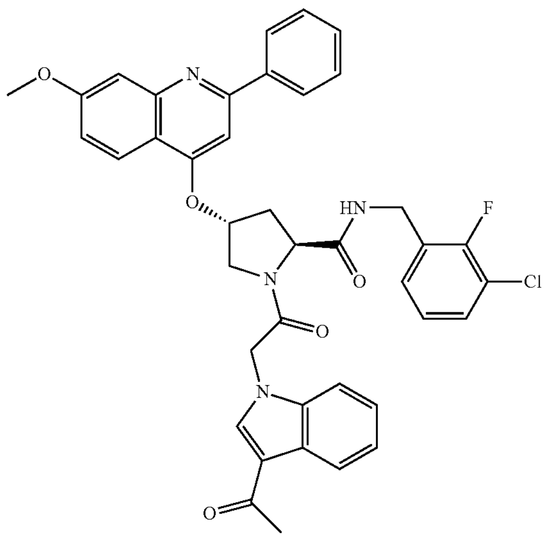 [SMILES: COc1ccc2c(O[C@@H]3C[C@@H](C(=O)NCc4cccc(Cl)c4F)N(C(=O)Cn4cc(C(C)=O)c5ccccc54)C3)cc(-c3ccccc3)nc2c1] | (2S,4R)-1-(2-(3-acetyl-1H-indol-1-yl)acetyl)-N-(3-chloro-2-fluorobenzyl)-4-((7-methoxy-2-phenylquinolin-4-yl)oxy)pyrrolidine-2-carboxamide | * | Method 2, 6.18 | 705 |
| 31 | 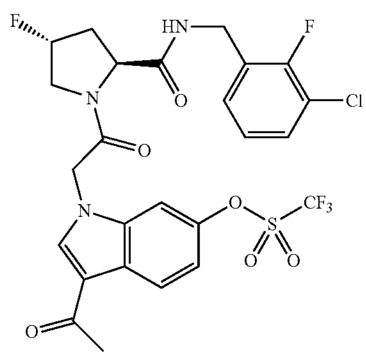 | 3-Acetyl-1-(2-((2S,4R)-2-((3-chloro-2-fluorobenzyl)carbamoyl)-4-fluoropyrrolidin-1-yl)-2-oxoethyl)-1H-indol-6-yl trifluoromethanesulfonate | *** | 2.24 | 622 |
| 32 | 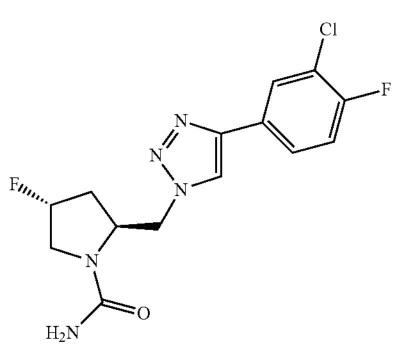 [SMILES: NC(=O)N1C[C@H](F)C[C@H]1Cn1cc(-c2ccc(F)c(Cl)c2)nn1] | (2S,4R)-2-((4-(3-chloro-4-fluorophenyl)-1H-1,2,3-triazol-1-yl)methyl)-4-fluoropyrrolidine-1-carboxamide | * | 1.15 | 342 |

-continued

| Cmp. No. | Structure | Name | IC$_{50}$ (μM) | RT min (Method 1 or 2) | M + 1 |
|---|---|---|---|---|---|
| 33 | 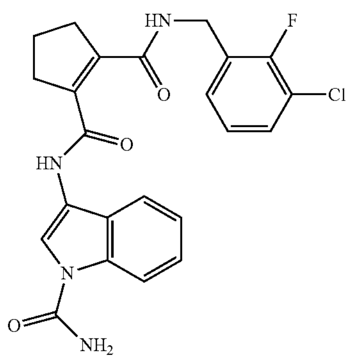 [SMILES: NC(=O)n1cc(NC(=O)C2=C(C(=O)NCc3cccc(Cl)c3F)CCC2)c2ccccc21] | N1-(1-carbamoyl-1H-indol-3-yl)-N2-(3-chloro-2-fluorobenzyl)cyclopent-1-ene-1,2-dicarboxamide | * | 1.97 | 455 |
| 34 | 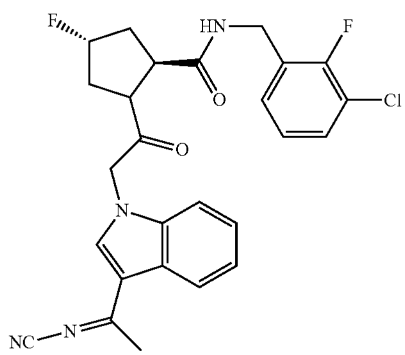 [SMILES: CC(=NC#N)c1cn(CC(=O)C2C[C@H](F)C[C@H]2C(=O)NCc2cccc(Cl)c2F)c2ccccc12] | (2S,4R)-N-(3-chloro-2-fluorobenzyl)-1-(2-(3-(1-(cyanoimino)ethyl)-1H-indol-1-yl)acetyl)-4-fluoropyrrolidine-2-carboxamide | ** | 1.48 | 498 |
| 35 | 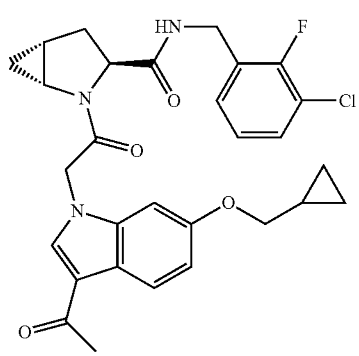 [SMILES: CC(=O)c1cn(CC(=O)N2[C@@H]3C[C@@H]3C[C@H]2C(=O)NCc2cccc(Cl)c2F)c2cc(OCC3CC3)ccc12] | (1R,3S,5R)-2-(2-(3-acetyl-6-(cyclopropylmethoxy)-1H-indol-1-yl)acetyl)-N-(3-chloro-2-fluorobenzyl)-2-azabicyclo[3.1.0]hexane-3-carboxamide | *** | 1.46 | 538 |
| 36 | 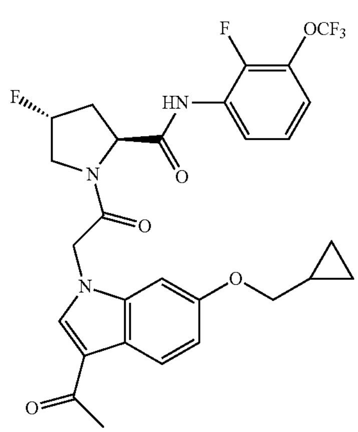 [SMILES: CC(=O)c1cn(CC(=O)N2C[C@H](F)C[C@H]2C(=O)Nc2cccc(OC(F)(F)F)c2F)c2cc(OCC3CC3)ccc12] | (2S,4R)-1-(2-(3-acetyl-6-(cyclopropylmethoxy)-1H-indol-1-yl)acetyl)-4-fluoro-N-(2-fluoro-3-(trifluoromethoxy)phenyl)pyrrolidine-2-carboxamide | *** | 1.66 | 580 |

-continued

| Cmp. No. | Structure | Name | IC$_{50}$ (μM) | RT min (Method 1 or 2) | M + 1 |
|---|---|---|---|---|---|
| 37 | 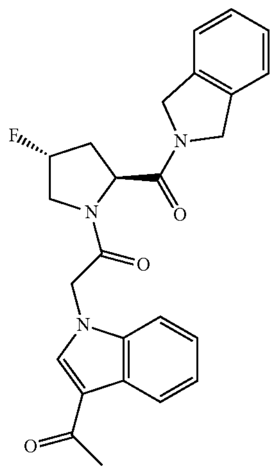 [SMILES: CC(=O)c1cn(CC(=O)N2C[C@H](F)C[C@H]2C(=O)N2Cc3ccccc3C2)c2ccccc12] | 2-(3-acetyl-1H-indol-1-yl)-1-((2S,4R)-4-fluoro-2-(isoindoline-2-carbonyl)pyrrolidin-1-yl)ethanone | * | 0.95 | 434 |
| 38 | 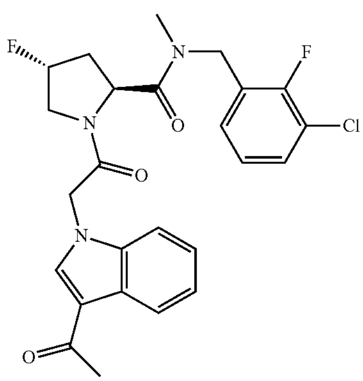 [SMILES: CC(=O)c1cn(CC(=O)N2C[C@H](F)C[C@H]2C(=O)N(C)Cc2cccc(Cl)c2F)c2ccccc12] | (2S,4R)-1-(2-(3-acetyl-1H-indol-1-yl)acetyl)-N-(3-chloro-2-fluorobenzyl)-4-fluoro-N-methylpyrrolidine-2-carboxamide | * | 1.35 | 488 |
| 39 | 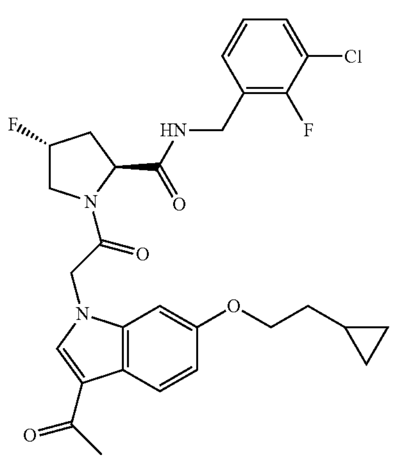 [SMILES: CC(=O)c1cn(CC(=O)N2C[C@H](F)C[C@H]2C(=O)NCc2cccc(Cl)c2F)c2cc(OCCC3CC3)ccc12] | (2S,4R)-1-(2-(3-acetyl-6-(2-cyclopropylethoxy)-1H-indol-1-yl)acetyl)-N-(3-chloro-2-fluorophenyl)-4-fluoropyrrolidine-2-carboxamide | *** | 1.70 | 558 |

-continued

| Cmp. No. | Structure | Name | IC$_{50}$ (μM) | RT min (Method 1 or 2) | M + 1 |
|---|---|---|---|---|---|
| 40 | 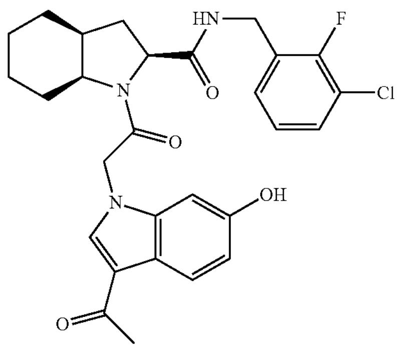 [SMILES: CC(=O)c1cn(CC(=O)N2[C@H](C(=O)NCc3cccc(Cl)c3F)C[C@@H]3CCCC[C@@H]32)c2cc(O)ccc12] | (2S,3aS,7aS)-1-(2-(3-acetyl-6-hydroxy-1H-indol-1-yl)acetyl)-N-(3-chloro-2-fluorobenzyl)octahydro-1H-indole-2-carboxamide | *** | 1.30 | 526 |
| 41 | 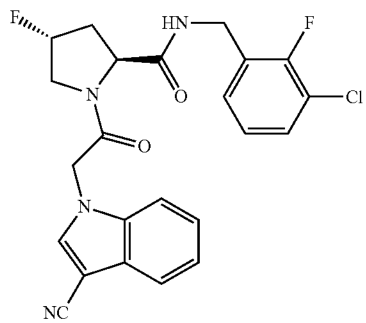 [SMILES: N#Cc1cn(CC(=O)N2C[C@H](F)C[C@H]2C(=O)NCc2cccc(Cl)c2F)c2ccccc12] | (2S,4R)-N-(3-chloro-2-fluorobenzyl)-1-(2-(3-cyano-1H-indol-1-yl)acetyl)-4-fluoropyrrolidine-2-carboxamide | *** | 1.38 | 457 |
| 42 | 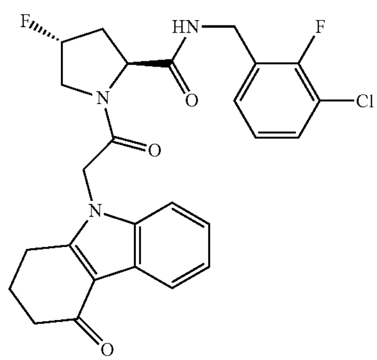 [SMILES: O=C1CCCc2c1c1ccccc1n2CC(=O)N1C[C@H](F)C[C@H]1C(=O)NCc1cccc(Cl)c1F] | (2S,4R)-N-(3-chloro-2-fluorobenzyl)-4-fluoro-1-(2-(4-oxo-3,4-dihydro-1H-carbazol-9(2H)-yl)acetyl)pyrrolidine-2-carboxamide | *** | 1.18 | 500 |
| 43 | 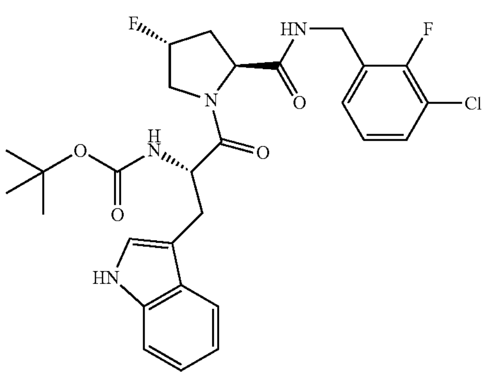 [SMILES: CC(C)(C)OC(=O)N[C@@H](Cc1c[nH]c2ccccc12)C(=O)N1C[C@H](F)C[C@H]1C(=O)NCc1cccc(Cl)c1F] | tert-butyl ((S)-1-((2S,4R)-2-((3-chloro-2-fluorobenzyl)carbamoyl)-4-fluoropyrrolidin-1-yl)-3-(1H-indol-3-yl)-1-oxopropan-2-yl)carbamate | * | 1.66 | 561 |

-continued

| Cmp. No. | Structure | Name | IC$_{50}$ (μM) | RT min (Method 1 or 2) | M + 1 |
|---|---|---|---|---|---|
| 44 | 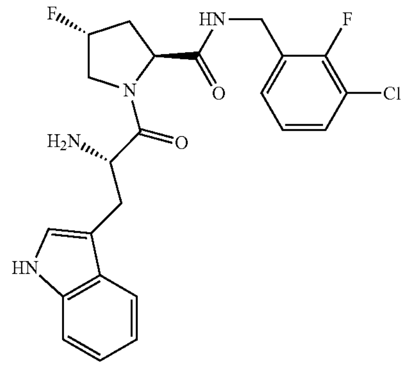 [SMILES: N[C@@H](Cc1c[nH]c2ccccc12)C(=O)N1C[C@H](F)C[C@H]1C(=O)NCc1cccc(Cl)c1F] | (2S,4R)-1-((S)-2-amino-3-(1H-indol-3-yl)propanoyl)-N-(3-chloro-2-fluorobenzyl)-4-fluoropyrrolidine-2-carboxamide | * | 0.40 | 461 |
| 45 | 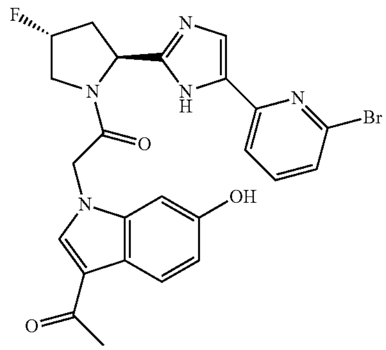 [SMILES: CC(=O)c1cn(CC(=O)N2C[C@H](F)C[C@H]2c2ncc(-c3cccc(Br)n3)[nH]2)c2cc(O)ccc12] | 2-(3-acetyl-6-hydroxy-1H-indol-1-yl)-1-((2S,4R)-2-(5-(6-bromopyridin-2-yl)-1H-imidazol-2-yl)-4-fluoropyrrolidin-1-yl)ethanone | ** | 0.93 | 526 |
| 46 | 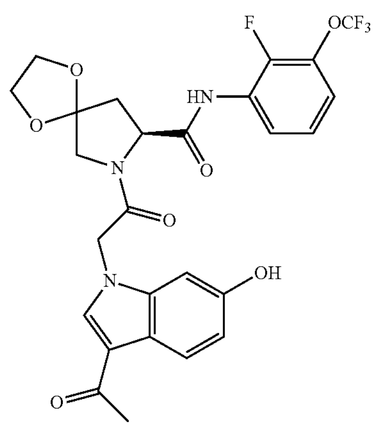 [SMILES: CC(=O)c1cn(CC(=O)N2CC3(C[C@H]2C(=O)Nc2cccc(OC(F)(F)F)c2F)OCCO3)c2cc(O)ccc12] | (S)-7-(2-(3-acetyl-6-hydroxy-1H-indol-1-yl)acetyl)-N-(2-fluoro-3-(trifluoromethoxy)phenyl)-1,4-dioxa-7-azaspiro[4.4]nonane-8-carboxamide | ** | 1.21 | 566 |
| 47 | 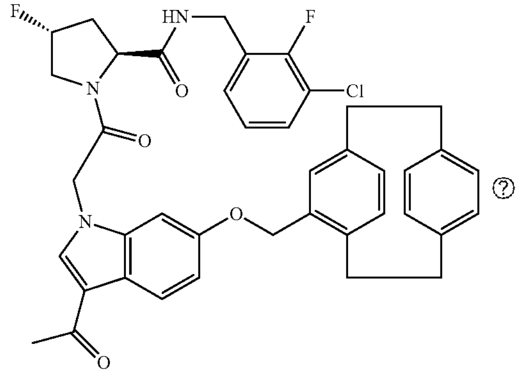 [SMILES: CC(=O)c1cn(CC(=O)N2C[C@H](F)C[C@H]2C(=O)NCc2cccc(Cl)c2F)c2cc(OCc3cc4ccc3CCc3ccc(cc3)CC4)ccc12] | | ** | 2.25 | 710 |

| Cmp. No. | Structure | Name | IC$_{50}$ (μM) | RT min (Method 1 or 2) | M + 1 |
|---|---|---|---|---|---|
| 48 | 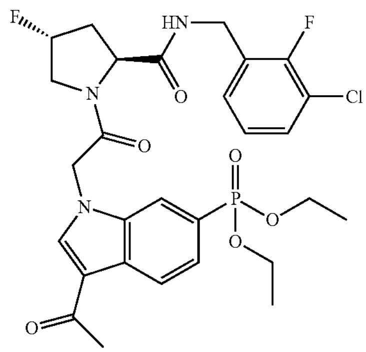 [SMILES: CCOP(=O)(OCC)c1ccc2c(C(C)=O)cn(CC(=O)N3C[C@H](F)C[C@H]3C(=O)NCc3cccc(Cl)c3F)c2c1] | diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate | *** | 1.83 | 610 |
| 49 | 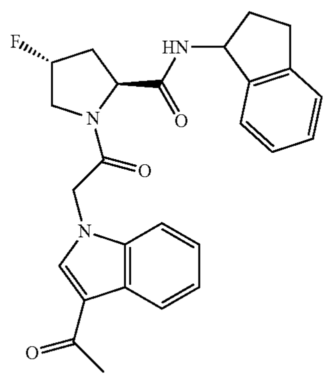 [SMILES: CC(=O)c1cn(CC(=O)N2C[C@H](F)C[C@H]2C(=O)NC2CCc3ccccc32)c2ccccc12] | (2S,4R)-1-(2-(3-acetyl-1H-indol-1-yl)acetyl)-N-(2,3-dihydro-1H-inden-1-yl)-4-fluoropyrrolidine-2-carboxamide | ** | 1.06 | 448 |
| 50 | 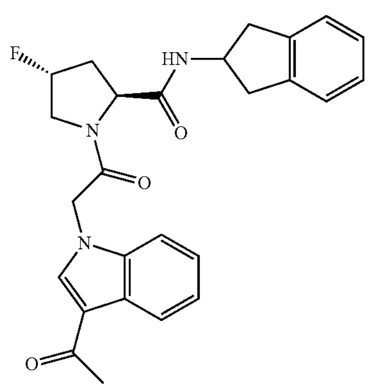 [SMILES: CC(=O)c1cn(CC(=O)N2C[C@H](F)C[C@H]2C(=O)NC2Cc3ccccc3C2)c2ccccc12] | (2S,4R)-1-(2-(3-acetyl-1H-indol-1-yl)acetyl)-N-(2,3-dihydro-1H-inden-2-yl)-4-fluoropyrrolidine-2-carboxamide | *** | 1.05 | 448 |
| 51 | 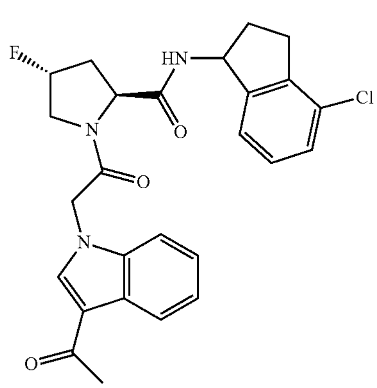 [SMILES: CC(=O)c1cn(CC(=O)N2C[C@H](F)C[C@H]2C(=O)NC2CCc3c(Cl)cccc32)c2ccccc12] | (2S,4R)-1-(2-(3-acetyl-1H-indol-1-yl)acetyl)-N-(4-chloro-2,3-dihydro-1H-inden-1-yl)-4-fluoropyrrolidine-2-carboxamide | ** | 1.15 | 482 |

| Cmp. No. | Structure | Name | IC$_{50}$ (μM) | RT min (Method 1 or 2) | M + 1 |
|---|---|---|---|---|---|
| 52 | 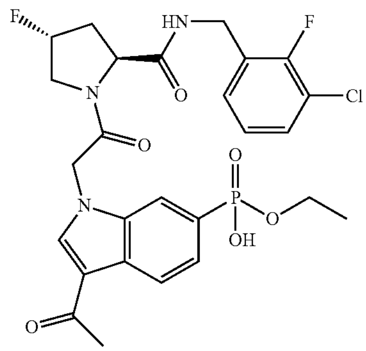 [SMILES: CCOP(=O)(O)c1ccc2c(C(C)=O)cn(CC(=O)N3C[C@H](F)C[C@H]3C(=O)NCc3cccc(Cl)c3F)c2c1] | ethyl hydrogen (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate | *** | 1.20 | 582 |
| 53 | 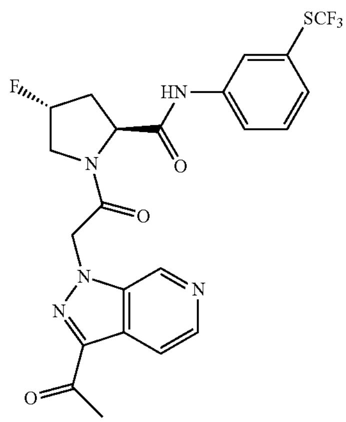 | (2S,4R)-1-(2-(3-acetyl-1H-pyrazolo[3,4-c]pyridin-1-yl)acetyl)-4-fluoro-N-(3-((trifluoromethyl)thio)phenyl)pyrrolidine-2-carboxamide | *** | 1.16 | 511 |
| 54 | 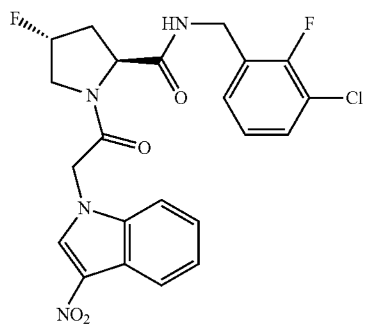 [SMILES: O=C(NCc1cccc(Cl)c1F)[C@@H]1C[C@@H](F)CN1C(=O)Cn1cc([N+](=O)[O-])c2ccccc21] | (2S,4R)-N-(3-chloro-2-fluorobenzyl)-4-fluoro-1-(2-(3-nitro-1H-indol-1-yl)acetyl)pyrrolidine-2-carboxamide | *** | 1.37 | 477 |
| 55 | 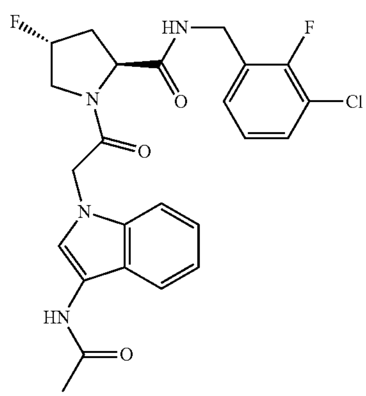 [SMILES: CC(=O)Nc1cn(CC(=O)N2C[C@H](F)C[C@H]2C(=O)NCc2cccc(Cl)c2F)c2ccccc12] | (2S,4R)-1-(2-(3-acetamido-1H-indol-1-yl)acetyl)-N-(3-chloro-2-fluorobenzyl)-4-fluoropyrrolidine-2-carboxamide | *** | 1.01 | 489 |

| Cmp. No. | Structure | Name | IC$_{50}$ (μM) | RT min (Method 1 or 2) | M + 1 |
|---|---|---|---|---|---|
| 56 | 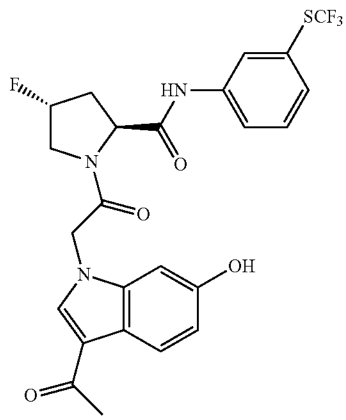 | (2S,4R)-1-(2-(3-acetyl-6-hydroxy-1H-indol-1-yl)acetyl)-4-fluoro-N-(3-((trifluoromethyl)thio)phenyl)pyrrolidine-2-carboxamide | *** | 1.09 | 524 |
| 57 | 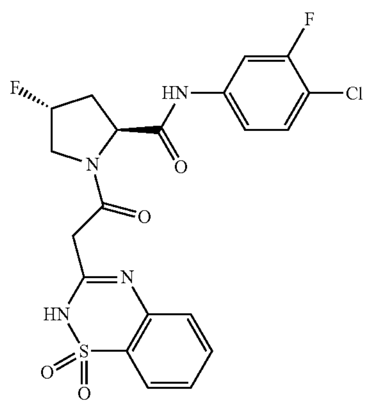 [SMILES: O=C(Nc1ccc(Cl)c(F)c1)[C@@H]1C[C@@H](F)CN1C(=O)CC1=Nc2ccccc2S(=O)(=O)N1] | (2S,4R)-N-(3-chloro-2-fluorobenzyl)-1-(2-(1,1-dioxido-2H-benzo[e][1,2,4]thiadiazin-3-yl)acetyl)-4-fluoropyrrolidine-2-carboxamide | ** | 0.86 | 497 |
| 58 | 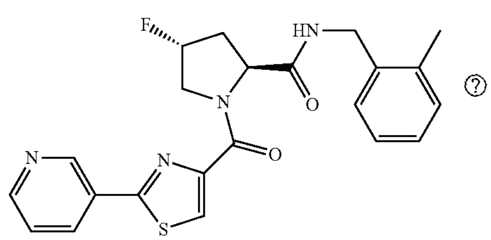 [SMILES: Cc1ccccc1CNC(=O)[C@@H]1C[C@@H](F)CN1C(=O)c1csc(-c2cccnc2)n1] | (2S,4R)-N-(3-chloro-2-fluorobenzyl)-4-fluoro-1-(2-(pyridin-3-yl)thiazole-4-carbonyl)pyrrolidine-2-carboxamide | * | 0.77 | 463 |
| 59 | 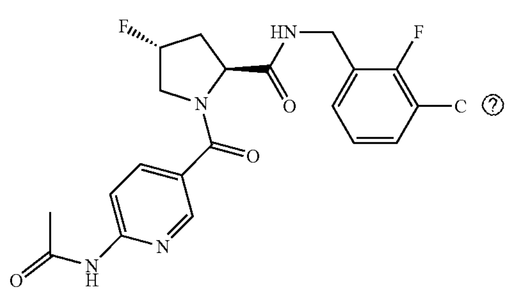 [SMILES: CC(=O)Nc1ccc(C(=O)N2C[C@H](F)C[C@H]2C(=O)NCc2cccc(C)c2F)cn1] | (2S,4R)-1-(6-acetamidonicotinoyl)-N-(3-chloro-2-fluorobenzyl)-4-fluoropyrrolidine-2-carboxamide | * | 0.55 | 437 |

-continued

| Cmp. No. | Structure | Name | IC$_{50}$ (μM) | RT min (Method 1 or 2) | M + 1 |
|---|---|---|---|---|---|
| 60 | 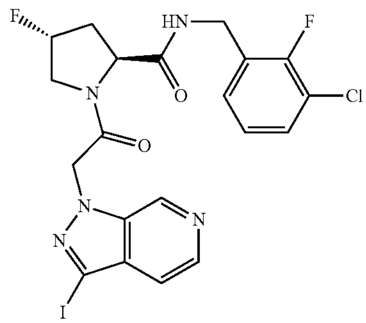 [SMILES: O=C(NCc1cccc(Cl)c1F)[C@@H]1C[C@@H](F)CN1C(=O)Cn1nc(I)c2ccncc21] | (2S,4R)-N-(3-chloro-2-fluorobenzyl)-4-fluoro-1-(2-(3-iodo-1H-pyrazolo[3,4-c]pyridin-1-yl)acetyl)pyrrolidine-2-carboxamide | *** | 1.00 | 562 |
| 61 | 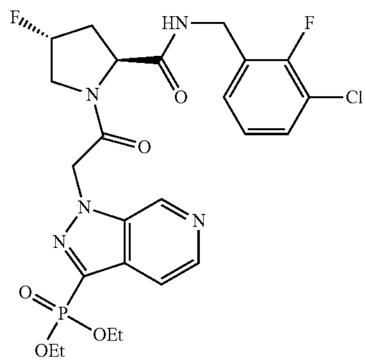 | diethyl (1-(2-((2S,4R)-2-((3-chloro-2-fluorobenzyl)carbamoyl)-4-fluoropyrrolidin-1-yl)-2-oxoethyl)-1H-pyrazolo[3,4-c]pyridin-3-yl)phosphonate | ** | 0.82 | 572 |
| 62 | 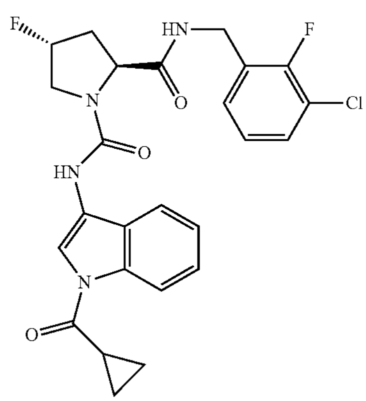 [SMILES: O=C(NCc1cccc(Cl)c1F)[C@@H]1C[C@@H](F)CN1C(=O)Nc1cn(C(=O)C2CC2)c2ccccc12] | (2S,4R)-N2-(3-chloro-2-fluorobenzyl)-N1-(1-(cyclopropanecarbonyl)-1H-indol-3-yl)-4-fluoropyrrolidine-1,2-dicarboxamide | *** | 1.28 | 501 |
| 63 | 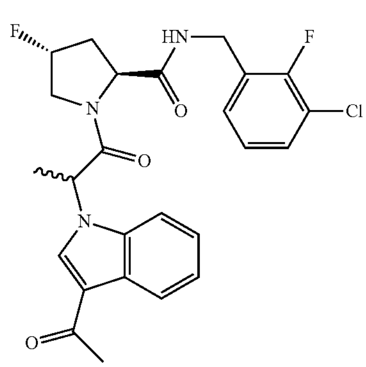 | (2S,4R)-1-(2-(3-acetyl-1H-indol-1-yl)propanoyl)-N-(3-chloro-2-fluorobenzyl)-4-fluoropyrrolidine-2-carboxamide | * | 1.17 | 488 |

-continued

| Cmp. No. | Structure | Name | IC$_{50}$ (μM) | RT min (Method 1 or 2) | M + 1 |
|---|---|---|---|---|---|
| 64 | 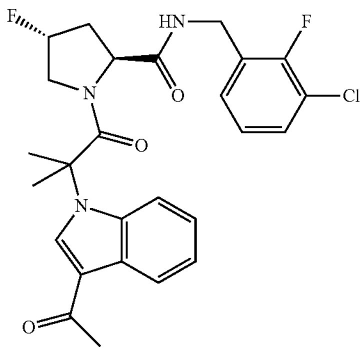 [SMILES: CC(=O)c1cn(C(C)(C)C(=O)N2C[C@H](F)C[C@H]2C(=O)NCc2cccc(Cl)c2F)c2ccccc12] | (2S,4R)-1-(2-(3-acetyl-1H-indol-1-yl)-2-methylpropanoyl)-N-(3-chloro-2-fluorobenzyl)-4-fluoropyrrolidine-2-carboxamide | * | 1.96 | 502 |
| 65 | 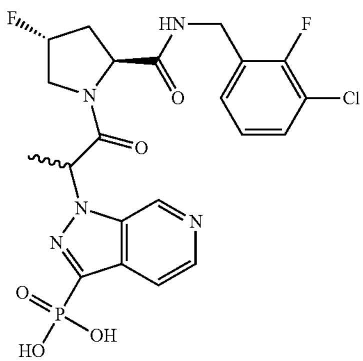 [SMILES: CC(C(=O)N1C[C@H](F)C[C@H]1C(=O)NCc1cccc(Cl)c1F)n1nc(P(=O)(O)O)c2ccncc21] | (1-(2-((2S,4R)-2-((3-chloro-2-fluorobenzyl)carbamoyl)-4-fluoropyrrolidin-1-yl)-2-oxoethyl)-1H-pyrazolo[3,4-c]pyridin-3-yl)phosphonic acid | * | 0.72 | 514 |
| 66 | 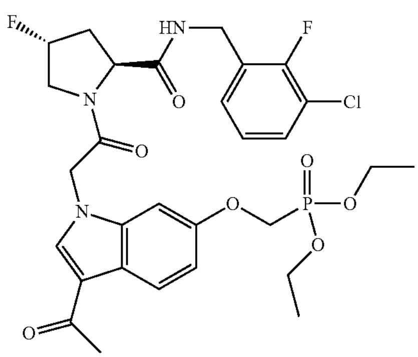 [SMILES: CCOP(=O)(COc1ccc2c(C(C)=O)cn(CC(=O)N3C[C@H](F)C[C@H]3C(=O)NCc3cccc(Cl)c3F)c2c1)OCC] | diethyl (((3-acetyl-1-(2-((2S,4R)-2-((3-chloro-2-fluorobenzyl)carbamoyl)-4-fluoropyrrolidin-1-yl)-2-oxoethyl)-1H-indol-6-yl)oxy)methyl)phosphonate | *** | 1.84 | 640 |
| 67 | 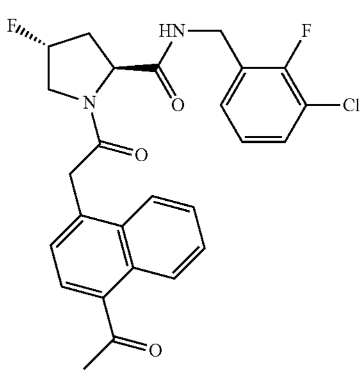 [SMILES: CC(=O)c1ccc(CC(=O)N2C[C@H](F)C[C@H]2C(=O)NCc2cccc(Cl)c2F)c2ccccc12] | (2S,4R)-1-(2-(4-acetylnaphthalen-1-yl)acetyl)-N-(3-chloro-2-fluorobenzyl)-4-fluoropyrrolidine-2-carboxamide | ** | 2.04 | 485 |

| Cmp. No. | Structure | Name | IC$_{50}$ (μM) | RT min (Method 1 or 2) | M + 1 |
|---|---|---|---|---|---|
| 68 | 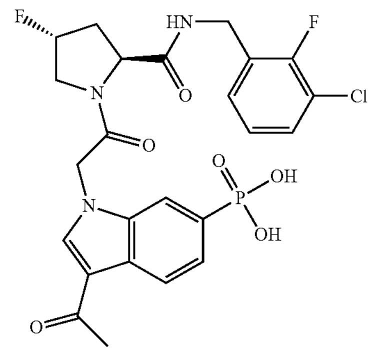 [SMILES: CC(=O)c1cn(CC(=O)N2C[C@H](F)C[C@H]2C(=O)NCc2cccc(Cl)c2F)c2cc(P(=O)(O)O)ccc12] | (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonic acid | *** | 1.07 | 554 |
| 69 | 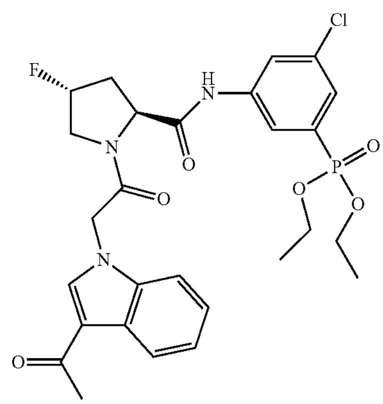 [SMILES: CCOP(=O)(OCC)c1cc(Cl)cc(NC(=O)[C@@H]2C[C@@H](F)CN2C(=O)Cn2cc(C(C)=O)c3ccccc32)c1] | diethyl (3-((2S,4R)-1-(2-(3-acetyl-1H-indol-1-yl)acetyl)-4-fluoropyrrolidine-2-carboxamido)-5-chlorophenyl)phosphonate | ** | 1.89 | 578 |
| 70 | 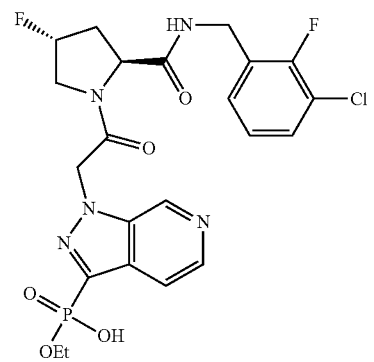 [SMILES: CCOP(=O)(O)c1nn(CC(=O)N2C[C@H](F)C[C@H]2C(=O)NCc2cccc(Cl)c2F)c2cnccc12] | ethyl hydrogen (1-(2-((2S,4R)-2-((3-chloro-2-fluorobenzyl)carbamoyl)-4-fluoropyrrolidin-1-yl)-2-oxoethyl)-1H pyrazolo[3,4-c]pyridin-3-yl)phosphonate | ** | 0.86 | 542 |
| 71 | 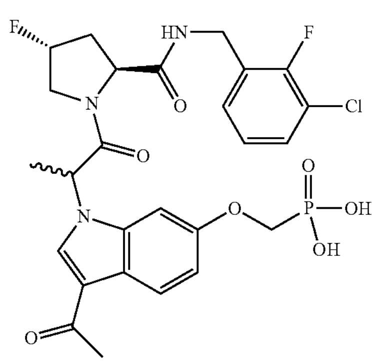 [SMILES: CC(=O)c1cn(C(C)C(=O)N2C[C@H](F)C[C@H]2C(=O)NCc2cccc(Cl)c2F)c2cc(OCP(=O)(O)O)ccc12] | (((3-acetyl-1-(2-((2S,4R)-2-((3-chloro-2-fluorobenzyl)carbamoyl)-4-fluoropyrrolidin-1-yl)-2-oxoethyl)-1H-indol-6-yl)oxy)methyl)phosphonic acid | *** | 1.03 | 584 |

| Cmp. No. | Structure | Name | IC$_{50}$ (μM) | RT min (Method 1 or 2) | M + 1 |
|---|---|---|---|---|---|
| 72 | 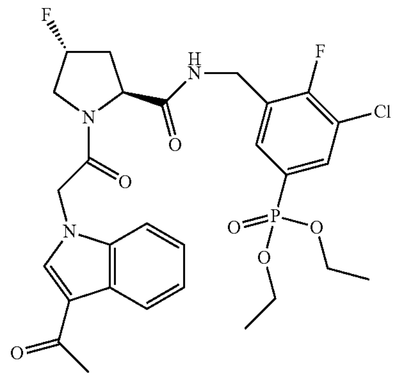 [SMILES: CCOP(=O)(OCC)c1cc(Cl)c(F)c(CNC(=O)[C@@H]2C[C@@H](F)CN2C(=O)Cn2cc(C(C)=O)c3ccccc32)c1] | diethyl 3-(((3R,5S)-1-(2-(3-acetyl-1H-indol-1-yl)acetyl)-3-fluoropyrrolidine-5-carboxamido)methyl)-5-chloro-4-fluorophenylphosphonate | *** | 1.82 | 610 |
| 73 | 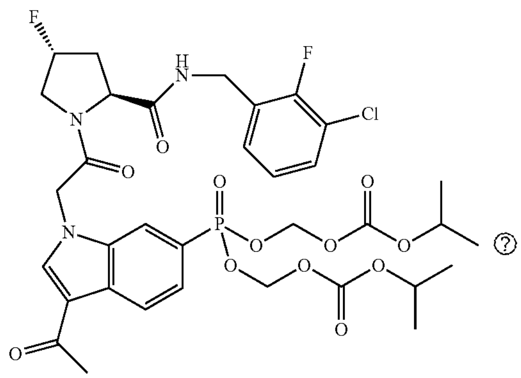 [SMILES: CC(=O)c1cn(CC(=O)N2C[C@H](F)C[C@H]2C(=O)NCc2cccc(Cl)c2F)c2cc(P(=O)(OCOC(=O)OC(C)C)OCOC(=O)OC(C)C)ccc12] | Di-isopropoxycarboxymethyl 1-(2-((2S,4R)-2-((3-chloro-2-fluorobenzyl)carbamoyl)-4-fluoropyrrolidin-1-yl)-2-oxoethyl)-3-acetyl-1H-indol-6-ylphosphonate | *** | 2.31 | 786 |
| 74 | 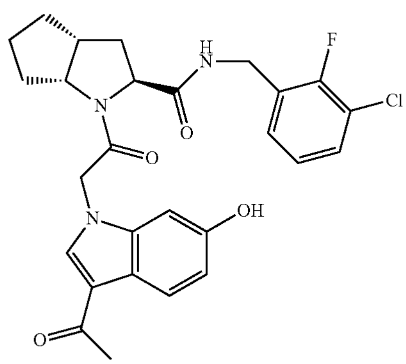 [SMILES: CC(=O)c1cn(CC(=O)N2[C@@H]3CCC[C@@H]3C[C@H]2C(=O)NCc2cccc(Cl)c2F)c2cc(O)ccc12] | (2S,3aR,6aR)-N-(3-chloro-2-fluorobenzyl)-1-(2-(3-acetyl-6-hydroxy-1H-indol-1-yl)acetyl)-octahydrocyclopenta[b]pyrrole-2-carboxamide | *** | 1.88 | 512 |
| 75 | 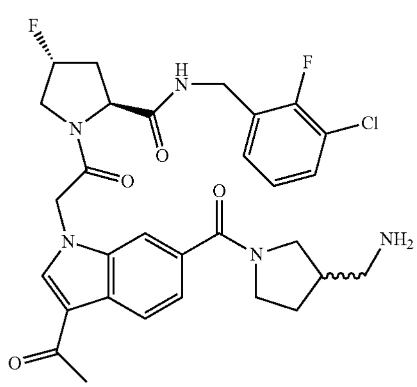 [SMILES: CC(=O)c1cn(CC(=O)N2C[C@H](F)C[C@H]2C(=O)NCc2cccc(Cl)c2F)c2cc(C(=O)N3CCC(CN)C3)ccc12] | (2S,4R)-N-(3-chloro-2-fluorobenzyl)-1-(2-(3-acetyl-6-(3-(aminomethyl)pyrrolidine-1-carbonyl)-1H-indol-1-yl)acetyl)-4-fluoropyrrolidine-2-carboxamide | *** | 1.02 | 600 |

-continued

| Cmp. No. | Structure | Name | IC$_{50}$ (μM) | RT min (Method 1 or 2) | M + 1 |
|---|---|---|---|---|---|
| 76 | 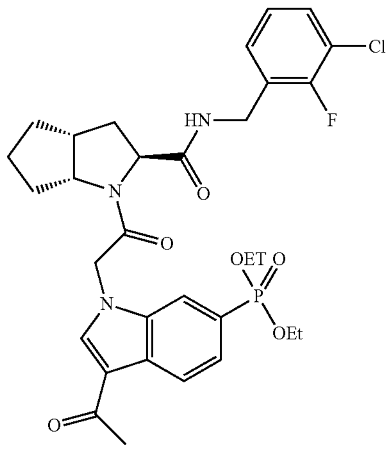 | diethyl 1-(2-((2S,3aR,6aR)-2-((3-chloro-2-fluorobenzyl)carbamoyl)-hexahydrocyclopenta[b]pyrrol-1(2H)-yl)-2-oxoethyl)-3-acetyl-1H-indol-6-ylphosphonate | *** | 2.13 | 632 |
| 77 | 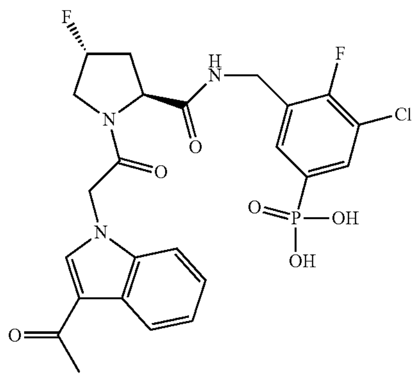 [SMILES: CC(=O)c1cn(CC(=O)N2C[C@H](F)C[C@H]2C(=O)NCc2cc(P(=O)(O)O)cc(Cl)c2F)c2ccccc12] | 3-(((3R,5S)-1-(2-(3-acetyl-1H-indol-1-yl)acetyl)-3-fluoropyrrolidine-5-carboxamido)methyl)-5-chloro-4-fluorophenylphosphonic acid | *** | 0.98 | 554 |
| 78 | 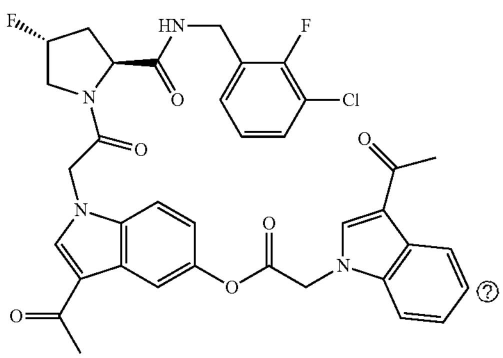 [SMILES: CC(=O)c1cn(CC(=O)Oc2ccc3c(c2)c(C(C)=O)cn3CC(=O)N2C[C@H](F)C[C@H]2C(=O)NCc2cccc(Cl)c2F)c2ccccc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl 2-(3-acetyl-5-hydroxy-1H-indol-1-yl)acetate | *** | 1.77 | 705 |
| 79 | 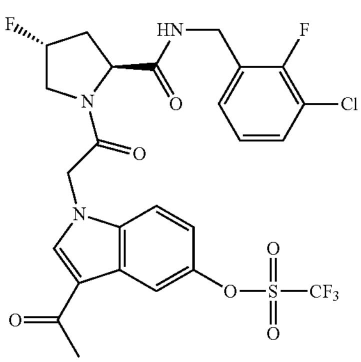 [SMILES: CC(=O)c1cn(CC(=O)N2C[C@H](F)C[C@H]2C(=O)NCc2cccc(Cl)c2F)c2ccc(OS(=O)(=O)C(F)(F)F)cc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl trifluoromethanesulfonate | *** | 2.37 | 622 |

| Cmp. No. | Structure | Name | IC$_{50}$ (μM) | RT min (Method 1 or 2) | M + 1 |
|---|---|---|---|---|---|
| 80 | 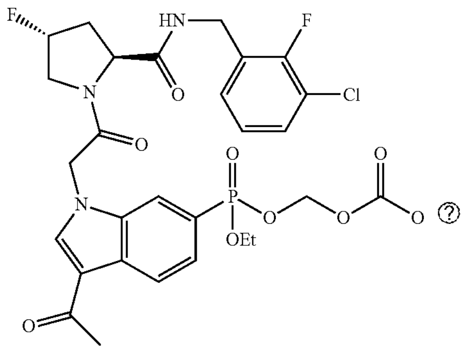 [SMILES: CCOP(=O)(OCOC(=O)O)c1ccc2c(C(C)=O)cn(CC(=O)N3C[C@H](F)C[C@H]3C(=O)NCc3cccc(Cl)c3F)c2c1] | ((1-(2-((2S,4R)-2-((3-chloro-2-fluorobenzyl)carbamoyl)-4-fluoropyrrolidin-1-yl)-2-oxoethyl)-3-acetyl-1H-indol-6-yl)(ethoxy)phosphoryloxy)methyl isoproply carbonate | *** | 2.08 | 698 |
| 81 | 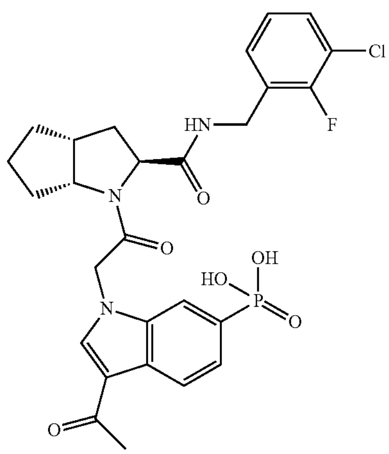 [SMILES: CC(=O)c1cn(CC(=O)N2[C@@H]3CCC[C@@H]3C[C@H]2C(=O)NCc2cccc(Cl)c2F)c2cc(P(=O)(O)O)ccc12] | 1-(2-((2S,3aR,6aR)-2-((3-chloro-2-fluorobenzyl)carbamoyl)-hexahydrocyclopenta[b]pyrrol-1(2H)-yl)-2-oxoethyl)-3-acetyl-1H-indol-6-ylphosphonic acid | *** | 1.43 | 576 |
| 82 | 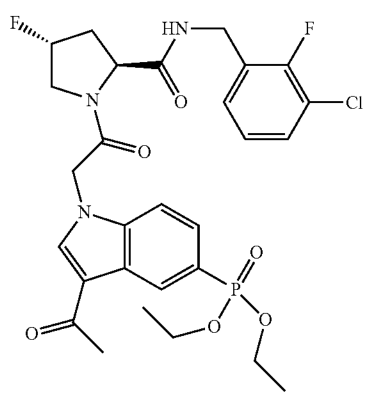 [SMILES: CCOP(=O)(OCC)c1ccc2c(c1)c(C(C)=O)cn2CC(=O)N1C[C@H](F)C[C@H]1C(=O)NCc1cccc(Cl)c1F] | diethyl 1-(2-((2S,4R)-2-((3-chloro-2-fluorobenzyl)carbamoyl)-4-fluoropyrrolidin-1-yl)-2-oxoethyl)-3-acetyl-1H-indol-5-ylphosphonate | *** | 1.74 | 610 |
| 83 | 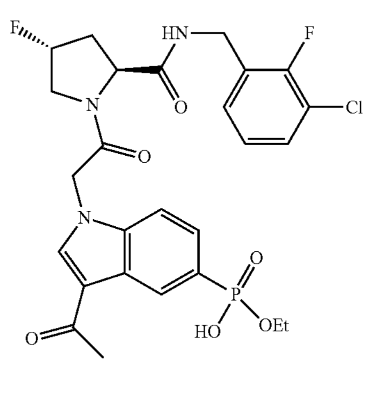 [SMILES: CCOP(=O)(O)c1ccc2c(c1)c(C(C)=O)cn2CC(=O)N1C[C@H](F)C[C@H]1C(=O)NCc1cccc(Cl)c1F] | ethyl hydrogen 1-(2-((2S,4R)-2-((3-chloro-2-fluorobenzyl)carbamoyl)-4-fluoropyrrodin-1-yl)-2-oxoethyl)-3-acetyl-1H-indol-5-ylphosphonate | * | 1.19 | 582 |

| Cmp. No. | Structure | Name | IC$_{50}$ (μM) | RT min (Method 1 or 2) | M + 1 |
|---|---|---|---|---|---|
| 84 | 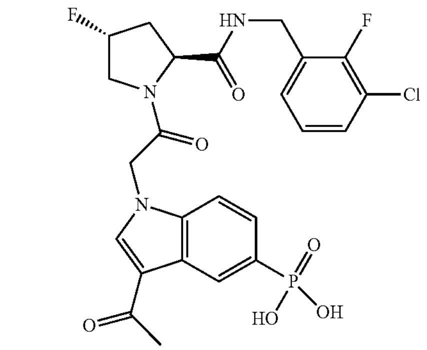 | 1-(2-((2S,4R)-2-((3-chloro-2-fluorobenzyl)carbamoyl)-4-fluoropyrrolidin-1-yl)-2-oxoethyl)-3-acetyl-1H-indol-5-ylphosphonic acid | *** | 1.04 | 554 |
| 85 | 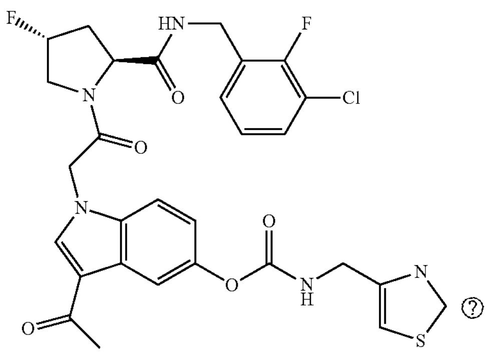 [SMILES: CC(=O)c1cn(CC(=O)N2C[C@H](F)C[C@H]2C(=O)NCc2cccc(Cl)c2F)c2ccc(OC(=O)NCC3=CSCN3)cc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl thiazol-4-ylmethylcarbamate | *** | 1.64 | 630 |
| 86 | 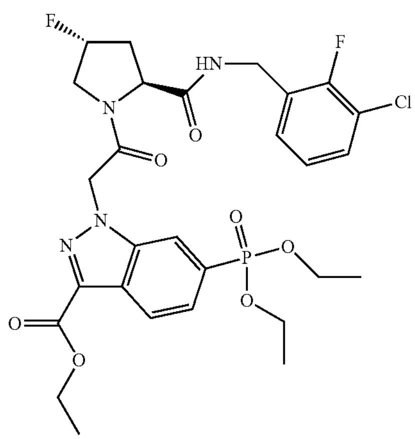 [SMILES: CCOC(=O)c1nn(CC(=O)N2C[C@H](F)C[C@H]2C(=O)NCc2cccc(Cl)c2F)c2cc(P(=O)(OCC)OCC)ccc12] | ethyl 1-(2-((2S,4R)-2-((3-chloro-2-fluorobenzyl)carbamoyl)-4-fluoropyrrolidin-1-yl)-2-oxoethyl)-6-(diethoxyphosphoryl)-1H-indazole-3-carboxylate | * | 2.15 | 641 |
| 87 | 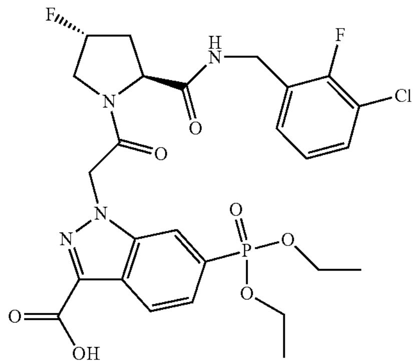 [SMILES: CCOP(=O)(OCC)c1ccc2c(C(=O)O)nn(CC(=O)N3C[C@H](F)C[C@H]3C(=O)NCc3cccc(Cl)c3F)c2c1] | 1-(2-((2S,4R)-2-((3-chloro-2-fluorobenzyl)carbamoyl)-4-fluoropyrrolidin-1-yl)-2-oxoethyl)-6-(diethoxyphosphoryl)-1H-indazole-3-carboxylic acid | * | 1.65 | 613 |

-continued

| Cmp. No. | Structure | Name | IC$_{50}$ (μM) | RT min (Method 1 or 2) | M + 1 |
|---|---|---|---|---|---|
| 88 | 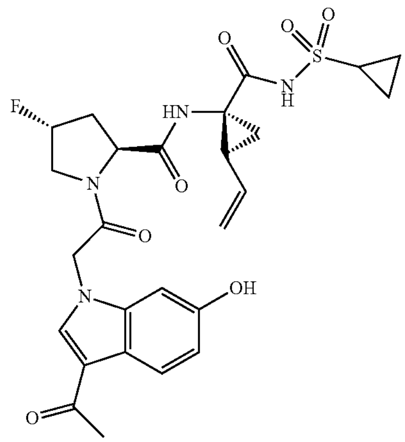 [SMILES: C=C[C@@H]1C[C@]1(NC(=O)[C@@H]1C[C@@H](F)CN1C(=O)Cn1cc(C(C)=O)c2ccc(O)cc21)C(=O)NS(=O)(=O)C1CC1] | (2S,4R)-1-(2-(3-acetyl-6-hydroxy-1H-indol-1-yl)acetyl)-N-((1R)-1-(cyclopropylsulfonylcarbamoyl)-2-vinylcyclopropyl)-4-fluoropyrrolidine-2-carboxamide | ** | 1.16 | 561 |
| 89 | 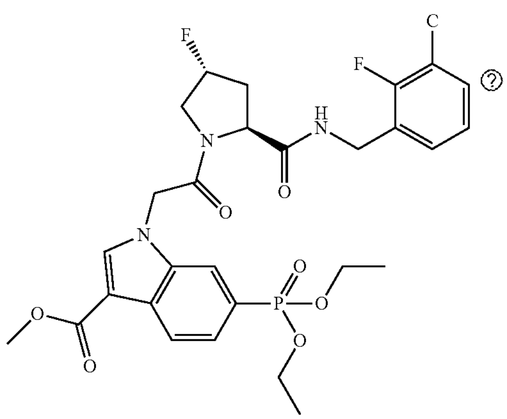 [SMILES: CCOP(=O)(OCC)c1ccc2c(C(=O)OC)cn(CC(=O)N3C[C@H](F)C[C@H]3C(=O)NCc3cccc(C)c3F)c2c1] | methyl 1-(2-((2S,4R)-2-((3-chloro-2-fluorobenzyl)carbamoyl)-4-fluoropyrrolidin-1-yl)-2-oxoethyl)-6-(diethoxyphosphoryl)-1H-indole-3-carboxylate | *** | 2.03 | 626 |
| 90 | 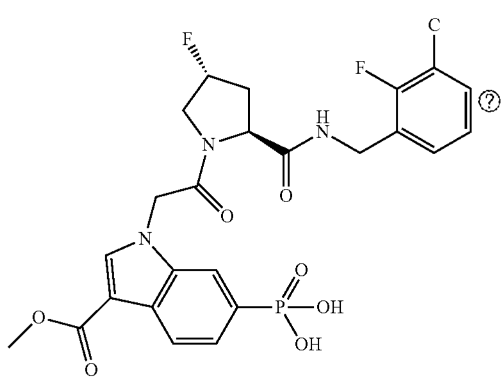 [SMILES: COC(=O)c1cn(CC(=O)N2C[C@H](F)C[C@H]2C(=O)NCc2cccc(C)c2F)c2cc(P(=O)(O)O)ccc12] | 1-(2-((2S,4R)-2-((3-chloro-2-fluorobenzyl)carbamoyl)-4-fluoropyrrolidin-1-yl)-2-oxoethyl)-3-(methoxycarbonyl)-1H-indol-6-ylphosphonic acid | *** | 1.22 | 570 |

| Cmp. No. | Structure | Name | IC$_{50}$ (μM) | RT min (Method 1 or 2) | M + 1 |
|---|---|---|---|---|---|
| 91 | 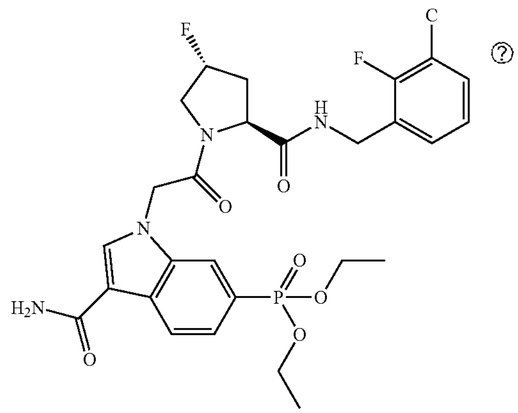 [SMILES: CCOP(=O)(OCC)c1ccc2c(C(N)=O)cn(CC(=O)N3C[C@H](F)C[C@H]3C(=O)NCc3cccc(C)c3F)c2c1] | diethyl 1-(2-((2S,4R)-2-((3-chloro-2-fluorobenzyl)carbamoyl)-4-fluoropyrrolidin-1-yl)-2-oxoethyl)-3-carbamoyl-1H-indol-6-ylphosphonate | *** | 1.54 | 611 |
| 92 | 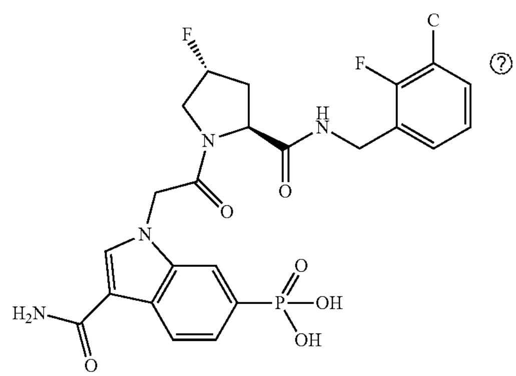 [SMILES: Cc1cccc(CNC(=O)[C@@H]2C[C@@H](F)CN2C(=O)Cn2cc(C(N)=O)c3ccc(P(=O)(O)O)cc32)c1F] | 1-(2-((2S,4R)-2-((3-chloro-2-fluorobenzyl)carbamoyl)-4-fluoropyrrolidin-1-yl)-2-oxoethyl)-3-carbamoyl-1H-indol-6-ylphosphonic acid | *** | 0.72 | 555 |
| 93 | 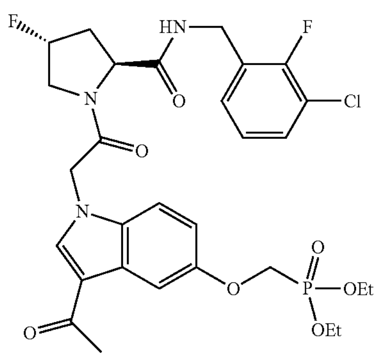 [SMILES: CCOP(=O)(COc1ccc2c(c1)c(C(C)=O)cn2CC(=O)N1C[C@H](F)C[C@H]1C(=O)NCc1cccc(Cl)c1F)OCC] | diethyl (1-(2-((2S,4R)-2-((3-chloro-2-fluorobenzyl)carbamoyl)-4-fluoropyrrolidin-1-yl)-2-oxoethyl)-3-acetyl-1H-indol-5-yloxy)methylphosphonate | *** | 1.79 | 640 |
| 94 | 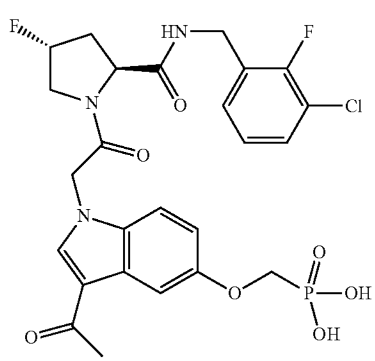 [SMILES: CC(=O)c1cn(CC(=O)N2C[C@H](F)C[C@H]2C(=O)NCc2cccc(Cl)c2F)c2ccc(OCP(=O)(O)O)cc12] | (1-(2-((2S,4R)-2-((3-chloro-2-fluorobenzyl)carbamoyl)-4-fluoropyrrolidin-1-yl)-2-oxoethyl)-3-acetyl-1H-indol-5-yloxy)methylphosphonic acid | *** | 1.02 | 584 |

-continued

| Cmp. No. | Structure | Name | IC$_{50}$ (µM) | RT min (Method 1 or 2) | M + 1 |
|---|---|---|---|---|---|
| 95 | 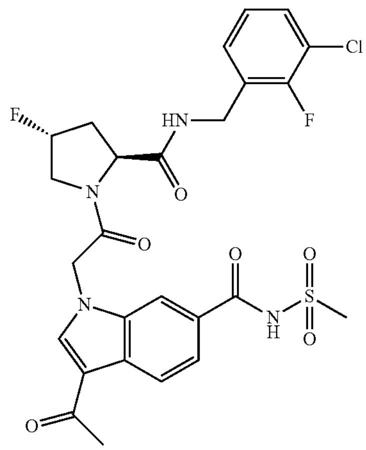 [SMILES: CC(=O)c1cn(CC(=O)N2C[C@H](F)C[C@H]2C(=O)NCc2cccc(Cl)c2F)c2cc(C(=O)NS(C)(=O)=O)ccc12] | 1-(2-((2S,4R)-2-((3-chloro-2-fluorobenzyl)carbamoyl)-4-fluoropyrrolidin-1-yl)-2-oxoethyl)-3-acetyl-N-(methylsulfonyl)-1H-indole-6-carboxamide | *** | 1.60 | 595 |
| 96 | 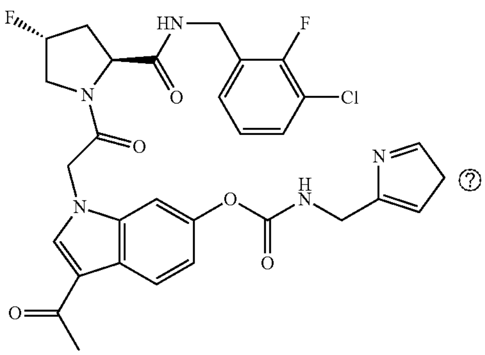 [SMILES: CC(=O)c1cn(CC(=O)N2C[C@H](F)C[C@H]2C(=O)NCc2cccc(Cl)c2F)c2cc(OC(=O)NCC3=CCC=N3)ccc12] | 1-(2-((2S,4R)-2-((3-chloro-2-fluorobenzyl)carbamoyl)-4-fluoropyrrolidin-1-yl)-2-oxoethyl)-3-acetyl-1H-indol-6-yl thiazol-4-ylmethylcarbamate | *** | 1.68 | 630 |
| 97 | 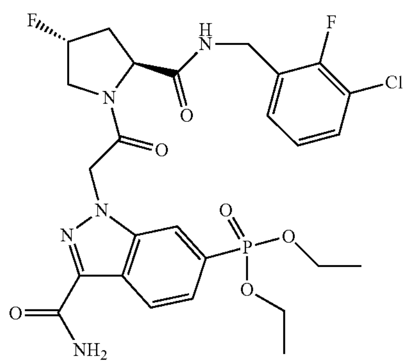 [SMILES: CCOP(=O)(OCC)c1ccc2c(C(N)=O)nn(CC(=O)N3C[C@H](F)C[C@H]3C(=O)NCc3cccc(Cl)c3F)c2c1] | diethyl 1-(2-((2S,4R)-2-((3-chloro-2-fluorobenzyl)carbamoyl)-4-fluoropyrrolidin-1-yl)-2-oxoethyl)-3-carbamoyl-1H-indazol-6-ylphosphonate | *** | 1.59 | 612 |
| 98 | 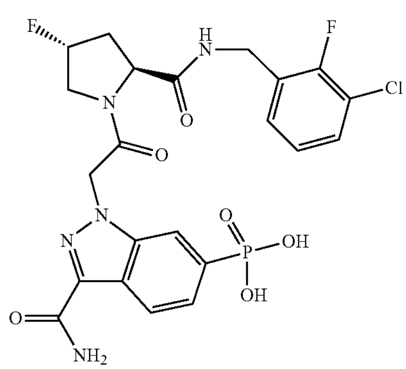 [SMILES: NC(=O)c1nn(CC(=O)N2C[C@H](F)C[C@H]2C(=O)NCc2cccc(Cl)c2F)c2cc(P(=O)(O)O)ccc12] | 1-(2-((2S,4R)-2-((3-chloro-2-fluorobenzyl)carbamoyl)-4-fluoropyrrolidin-1-yl)-2-oxoethyl)-3-carbamoyl-1H-indazol-6-ylphosphonic acid | *** | 0.70 | 556 |

| Cmp. No. | Structure | Name | IC$_{50}$ (μM) | RT min (Method 1 or 2) | M + 1 |
|---|---|---|---|---|---|
| 99 | 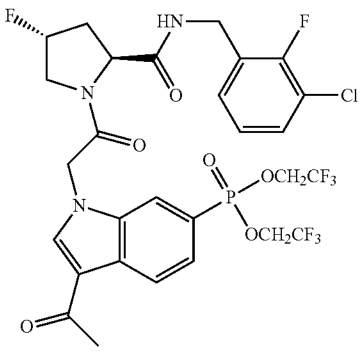 | bis(2,2,2-trifluoroethyl) 1-(2-((2S,4R)-2-((3-chloro-2-fluorobenzyl)carbamoyl)-4-fluoropyrrolidin-1-yl)-2-oxoethyl)-3-acetyl-1H-indol-6-ylphosphonate | *** | 2.26 | 718 |
| 100 | 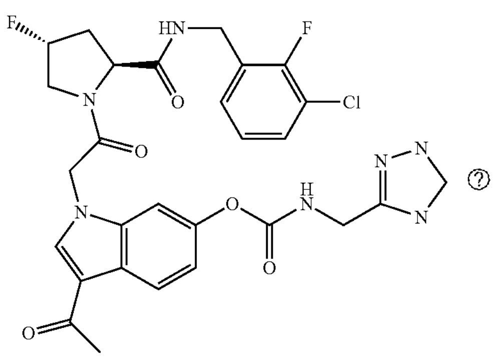 [SMILES: CC(=O)c1cn(CC(=O)N2C[C@H](F)C[C@H]2C(=O)NCc2cccc(Cl)c2F)c2cc(OC(=O)NCC3=NNCN3)ccc12] | 1-(2-((2S,4R)-2-((3-chloro-2-fluorobenzyl)carbamoyl)-4-fluoropyrrolidin-1-yl)-2-oxoethyl)-3-acetyl-1H-indol-6-yl (2H-tetrazol-5-yl)methylcarbamate | *** | 1.42 | 615 |
| 101 | 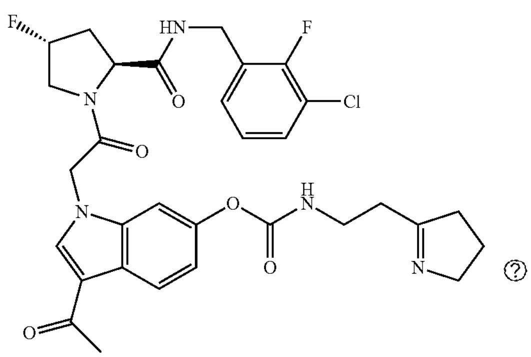 [SMILES: CC(=O)c1cn(CC(=O)N2C[C@H](F)C[C@H]2C(=O)NCc2cccc(Cl)c2F)c2cc(OC(=O)NCCC3=NCCC3)ccc12] | 1-(2-((2S,4R)-2-((3-chloro-2-fluorobenzyl)carbamoyl)-4-fluoropyrrolidin-1-yl)-2-oxoethyl)-3-acetyl-1H-indol-6-yl 2-(2H-tetrazol-5-yl)ethylcarbamate | *** | 1.45 | 629 |
| 102 | 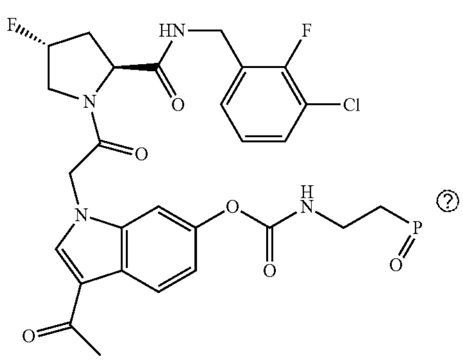 [SMILES: CC(=O)c1cn(CC(=O)N2C[C@H](F)C[C@H]2C(=O)NCc2cccc(Cl)c2F)c2cc(OC(=O)NCCP=O)ccc12] | 2-((1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)carbonyl)ethylphosphonic acid | *** | 1.16 | 641 |

-continued

| Cmp. No. | Structure | Name | IC$_{50}$ (μM) | RT min (Method 1 or 2) | M + 1 |
|---|---|---|---|---|---|
| 103 | 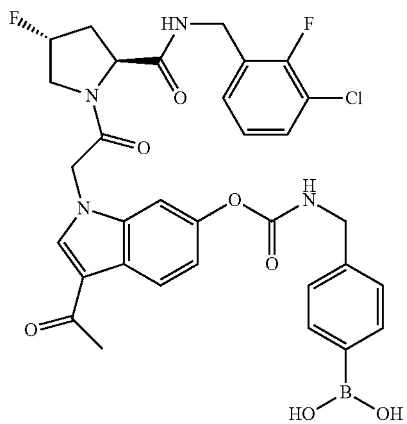 [SMILES: CC(=O)c1cn(CC(=O)N2C[C@H](F)C[C@H]2C(=O)NCc2cccc(Cl)c2F)c2cc(OC(=O)NCc3ccc(B(O)O)cc3)ccc12] | 4-(((1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)carbonyl)methyl)phenylboronic acid | *** | 1.65 | 667 |
| 104 | 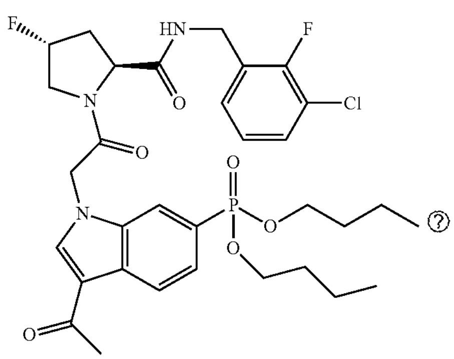 [SMILES: CCCCOP(=O)(OCCCC)c1ccc2c(C(C)=O)cn(CC(=O)N3C[C@H](F)C[C@H]3C(=O)NCc3cccc(Cl)c3F)c2c1] | dibutyl 1-(2-((2S,4R)-2-((3-chloro-2-fluorobenzyl)carbamoyl)-4-fluoropyrrolidin-1-yl)-2-oxoethyl)-3-acetyl-1H-indol-6-ylphosphonate | *** | 2.47 | 666 |
| 105 | 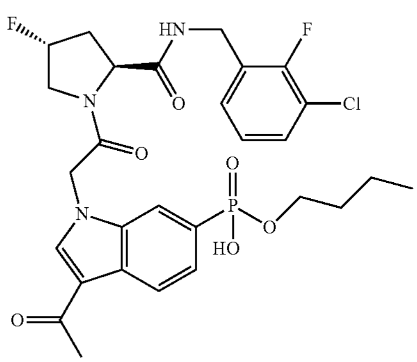 [SMILES: CCCCOP(=O)(O)c1ccc2c(C(C)=O)cn(CC(=O)N3C[C@H](F)C[C@H]3C(=O)NCc3cccc(Cl)c3F)c2c1] | butyl hydrogen 1-(2-((2S,4R)-2-((3-chloro-2-fluorobenzyl)carbamoyl)-4-fluoropyrrodin-1-yl)-2-oxoethyl)-3-acetyl-1H-indol-6-ylphosphonate | *** | 1.49 | 610 |
| 106 | 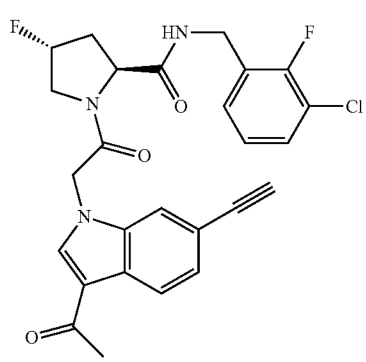 [SMILES: C#Cc1ccc2c(C(C)=O)cn(CC(=O)N3C[C@H](F)C[C@H]3C(=O)NCc3cccc(Cl)c3F)c2c1] | (2S,4R)-N-(3-chloro-2-fluorobenzyl)-1-(2-(3-acetyl-6-ethynyl-1H-indol-1-yl)acetyl)-4-fluoropyrrolidine-2-carboxamide | *** | 1.97 | 498 |

| Cmp. No. | Structure | Name | IC$_{50}$ (μM) | RT min (Method 1 or 2) | M + 1 |
|---|---|---|---|---|---|
| 107 | 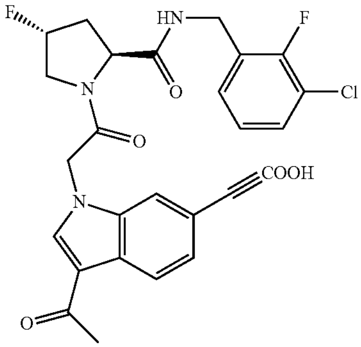 | 3-(1-(2-((2S,4R)-2-((3-chloro-2-fluorobenzyl)carbamoyl)-4-fluoropyrrolidin-1-yl)-2-oxoethyl)-3-acetyl-1H-indol-6-yl)propiolic acid | *** | 1.52 | 542 |
| 108 | 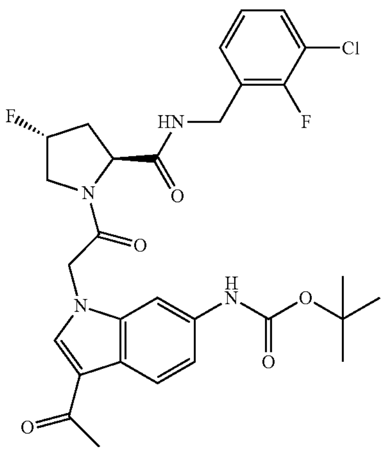 [SMILES: CC(=O)c1cn(CC(=O)N2C[C@H](F)C[C@H]2C(=O)NCc2cccc(Cl)c2F)c2cc(NC(=O)OC(C)(C)C)ccc12] | tert-butyl 1-(2-((2S,4R)-2-((3-chloro-2-fluorobenzyl)carbamoyl)-4-fluoropyrrolidin-1-yl)-2-oxoethyl)-3-acetyl-1H-indol-6-ylcarbamate | *** | 1.90 | 589 |
| 109 | 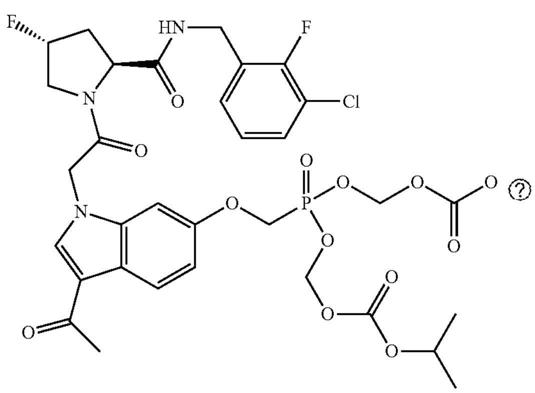 [SMILES: CC(=O)c1cn(CC(=O)N2C[C@H](F)C[C@H]2C(=O)NCc2cccc(Cl)c2F)c2cc(OCP(=O)(OCOC(=O)O)OCOC(=O)OC(C)C)ccc12] | Di(isopropoxycarboxymethyl)(1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)methylphosphonate | *** | 2.16 | 816 |
| 110 | 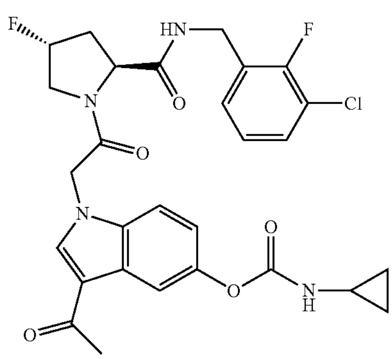 [SMILES: CC(=O)c1cn(CC(=O)N2C[C@H](F)C[C@H]2C(=O)NCc2cccc(Cl)c2F)c2ccc(OC(=O)NC3CC3)cc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl cyclopropylcarbamate | *** | 1.73 | 573 |

-continued

| Cmp. No. | Structure | Name | IC$_{50}$ (μM) | RT min (Method 1 or 2) | M + 1 |
|---|---|---|---|---|---|
| 111 | 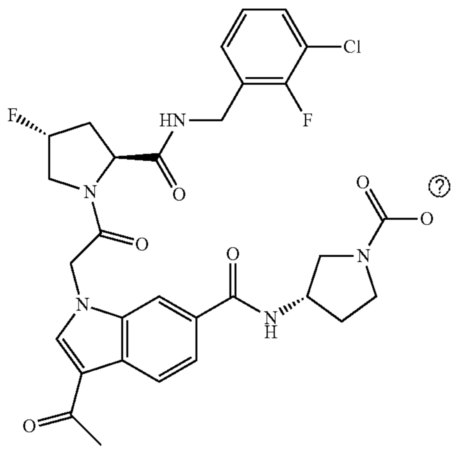 [SMILES: CC(=O)c1cn(CC(=O)N2C[C@H](F)C[C@H]2C(=O)NCc2cccc(Cl)c2F)c2cc(C(=O)N[C@H]3CCN(C(=O)O)C3)ccc12] | (S)-tert-butyl 3-(1-(2-((2S,4R)-2-((3-chloro-2-fluorobenzyl)carbamoyl)-4-fluoropyrrolidin-1-yl)-2-oxoethyl)-3-acetyl-1H-indole-6-carboxamido)pyrrolidine-1-carboxylate | *** | 1.92 | 686 |
| 112 | 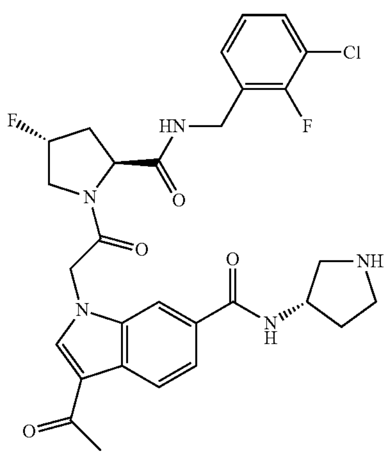 [SMILES: CC(=O)c1cn(CC(=O)N2C[C@H](F)C[C@H]2C(=O)NCc2cccc(Cl)c2F)c2cc(C(=O)N[C@H]3CCNC3)ccc12] | 1-(2-((2S,4R)-2-((3-chloro-2-fluorobenzyl)carbamoyl)-4-fluoropyrrolidin-1-yl)-2-oxoethyl)-3-acetyl-N-((S)-pyrrolidin-3-yl)-1H-indole-6-carboxamide | *** | 1.10 | 586 |
| 113 | 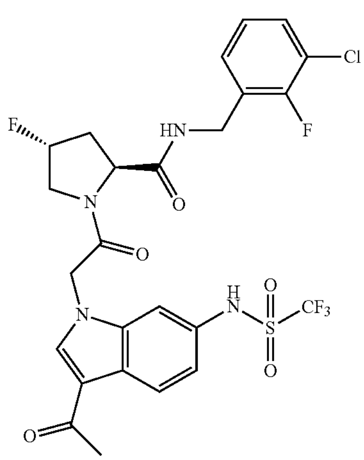 [SMILES: CC(=O)c1cn(CC(=O)N2C[C@H](F)C[C@H]2C(=O)NCc2cccc(Cl)c2F)c2cc(NS(=O)(=O)C(F)(F)F)ccc12] | (2S,4R)-N-(3-chloro-2-fluorobenzyl)-1-(2-(3-acetyl-6-(trifluoromethylsulfonamido)-1H-indol-1-yl)acetyl)-4-fluoropyrrolidine-2-carboxamide | *** | 1.54 | 621 |

-continued

| Cmp. No. | Structure | Name | IC₅₀ (μM) | RT min (Method 1 or 2) | M + 1 |
|---|---|---|---|---|---|
| 114 | 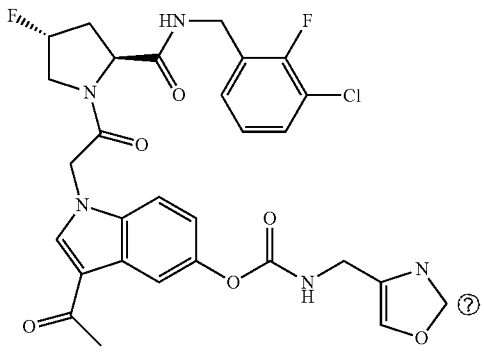 [SMILES: CC(=O)c1cn(CC(=O)N2C[C@H](F)C[C@H]2C(=O)NCc2cccc(Cl)c2F)c2ccc(OC(=O)NCC3=COCN3)cc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl oxazol-4-ylmethylcarbamate | *** | 1.55 | 614 |
| 115 | 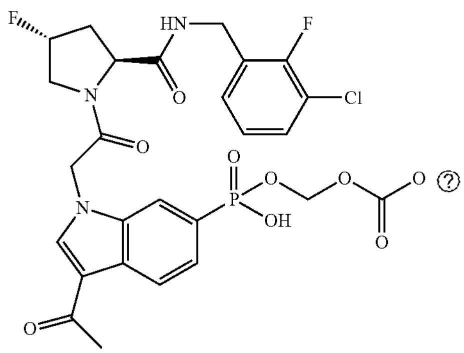 [SMILES: CC(=O)c1cn(CC(=O)N2C[C@H](F)C[C@H]2C(=O)NCc2cccc(Cl)c2F)c2cc(P(=O)(O)OCOC(=O)O)ccc12] | isopropoxycarboxymethyl hydrogen 1-(2-((2S,4R)-2-((3-chloro-2-fluorobenzyl)carbamoyl)-4-fluoropyrrolidin-1-yl)-2-oxoethyl)-3-acetyl-1H-indol-6-ylphosphonate | *** | 1.34 | 670 |
| 116 | 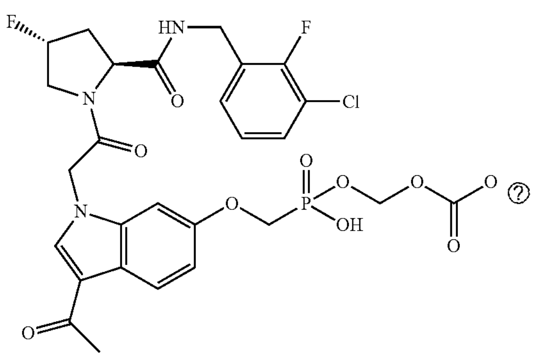 [SMILES: CC(=O)c1cn(CC(=O)N2C[C@H](F)C[C@H]2C(=O)NCc2cccc(Cl)c2F)c2cc(OCP(=O)(O)OCOC(=O)O)ccc12] | isopropoxycarboxymethyl hydrogen (1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)methylphosphonate | *** | 1.38 | 700 |
| 117 | 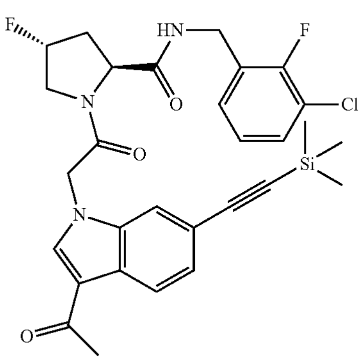 [SMILES: CC(=O)c1cn(CC(=O)N2C[C@H](F)C[C@H]2C(=O)NCc2cccc(Cl)c2F)c2cc(C#C[Si](C)(C)C)ccc12] | (2S,4R)-N-(3-chloro-2-fluorobenzyl)-1-(2-(3-acetyl-6-(2-(trimethylsilyl)ethynyl)-1H-indol-1-yl)acetyl)-4-fluoropyrrolidine-2-carboxamide | *** | 2.71 | 570 |

-continued

| Cmp. No. | Structure | Name | IC$_{50}$ (µM) | RT min (Method 1 or 2) | M + 1 |
|---|---|---|---|---|---|
| 118 | 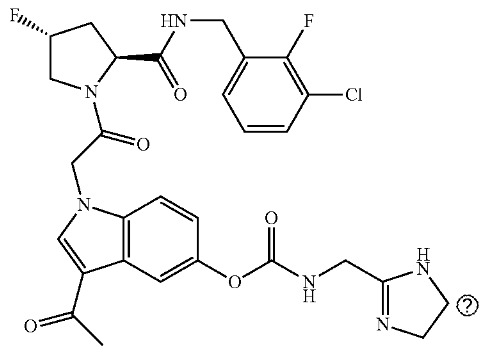 [SMILES: CC(=O)c1cn(CC(=O)N2C[C@H](F)C[C@H]2C(=O)NCc2cccc(Cl)c2F)c2ccc(OC(=O)NCC3=NCCN3)cc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl (1H-tetrazol-5-yl)methylcarbamate | *** | 1.37 | 615 |
| 119 | 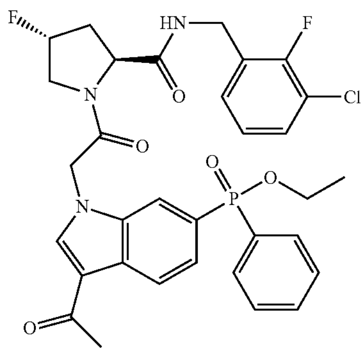 [SMILES: CCOP(=O)(c1ccccc1)c1ccc2c(C(C)=O)cn(CC(=O)N3C[C@H](F)C[C@H]3C(=O)NCc3cccc(Cl)c3F)c2c1] | ethyl 1-(2-((2S,4R)-2-((3-chloro-2-fluorobenzyl)carbamoyl)-4-fluoropyrrolidin-1-yl)-2-oxoethyl)-3-acetyl-1H-indol-6-yl(phenyl)phosphinate | *** | 1.97 | 642 |
| 120 | 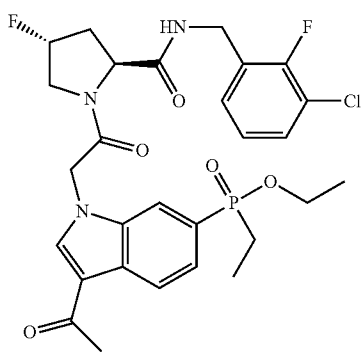 [SMILES: CCOP(=O)(CC)c1ccc2c(C(C)=O)cn(CC(=O)N3C[C@H](F)C[C@H]3C(=O)NCc3cccc(Cl)c3F)c2c1] | ethyl 1-(2-((2S,4R)-2-((3-chloro-2-fluorobenzyl)carbamoyl)-4-fluoropyrrolidin-1-yl)-2-oxoethyl)-3-acetyl-1H-indol-6-yl)ethyl)phosphinate | *** | 1.64 | 594 |
| 121 | 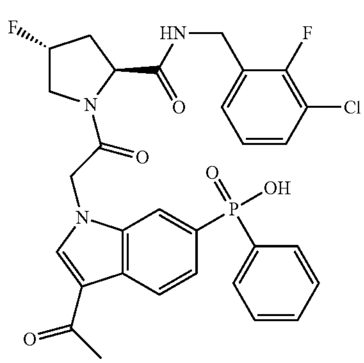 [SMILES: CC(=O)c1cn(CC(=O)N2C[C@H](F)C[C@H]2C(=O)NCc2cccc(Cl)c2F)c2cc(P(=O)(O)c3ccccc3)ccc12] | 1-(2-((2S,4R)-2-((3-chloro-2-fluorobenzyl)carbamoyl)-4-fluoropyrrolidin-1-yl)-2-oxoethyl)-3-acetyl-1H-indol-6-yl(phenyl)phosphinic acid | *** | 1.49 | 614 |

| Cmp. No. | Structure | Name | IC$_{50}$ (μM) | RT min (Method 1 or 2) | M + 1 |
|---|---|---|---|---|---|
| 122 | 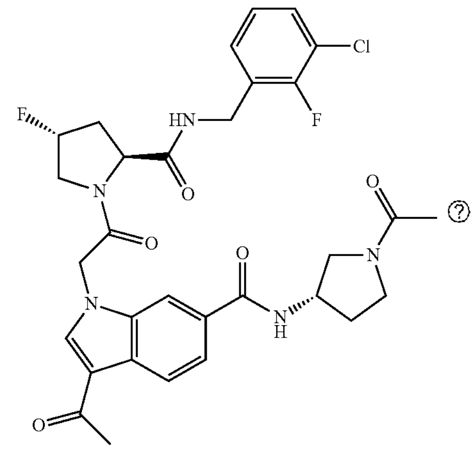 [SMILES: CC(=O)c1cn(CC(=O)N2C[C@H](F)C[C@H]2C(=O)NCc2cccc(Cl)c2F)c2cc(C(=O)N[C@H]3CCN(C(C)=O)C3)ccc12] | 1-(2-((2S,4R)-2-((3-chloro-2-fluorobenzyl)carbamoyl)-4-fluoropyrrolidin-1-yl)-2-oxoethyl)-3-acetyl-N-((S)-1-acetylpyrrolidin-3-yl)-1H-indole-6-carboxamide | *** | 1.30 | 628 |
| 123 | 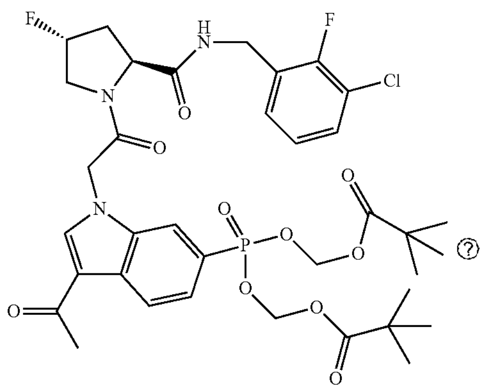 [SMILES: CC(=O)c1cn(CC(=O)N2C[C@H](F)C[C@H]2C(=O)NCc2cccc(Cl)c2F)c2cc(P(=O)(OCOC(=O)C(C)(C)C)OCOC(=O)C(C)(C)C)ccc12] | dipivaloyloxy 1-(2-((2S,4R)-2-((3-chloro-2-fluorobenzyl)carbamoyl)-4-fluoropyrrolidin-1-yl)-2-oxoethyl)-3-acetyl-1H-indol-6-ylphosphonate | *** | 2.41 | 782 |
| 124 | 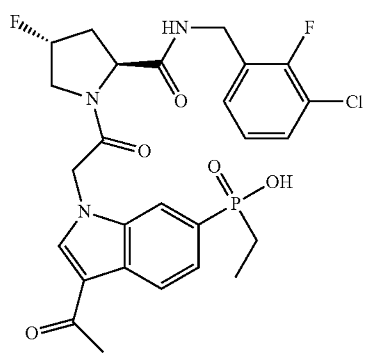 [SMILES: CCP(=O)(O)c1ccc2c(C(C)=O)cn(CC(=O)N3C[C@H](F)C[C@H]3C(=O)NCc3cccc(Cl)c3F)c2c1] | 1-(2-((2S,4R)-2-((3-chloro-2-fluorobenzyl)carbamoyl)-4-fluoropyrrolidin-1-yl)-2-oxoethyl)-3-acetyl-1H-indol-6-yl(ethyl)phosphinic acid | *** | 1.24 | 566 |
| 125 | 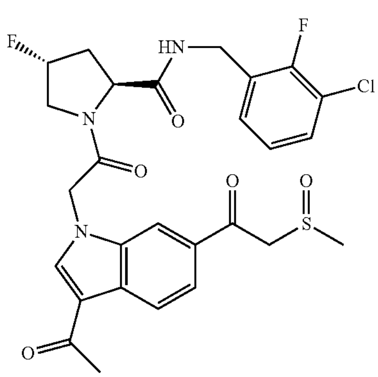 [SMILES: CC(=O)c1cn(CC(=O)N2C[C@H](F)C[C@H]2C(=O)NCc2cccc(Cl)c2F)c2cc(C(=O)CS(C)=O)ccc12] | (2S,4R)-N-(3-chloro-2-fluorobenzyl)-1-(2-(3-acetyl-6-(2-(methylsulfinyl)acetyl)-1H-indol-1-yl)acetyl)-4-fluoropyrrolidine-2-carboxamide | *** | 1.35 | 578 |

-continued

| Cmp. No. | Structure | Name | IC$_{50}$ (μM) | RT min (Method 1 or 2) | M + 1 |
|---|---|---|---|---|---|
| 126 | 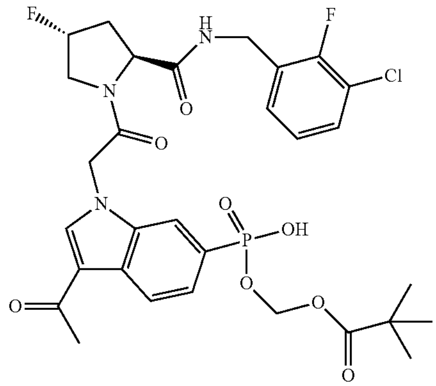 [SMILES: CC(=O)c1cn(CC(=O)N2C[C@H](F)C[C@H]2C(=O)NCc2cccc(Cl)c2F)c2cc(P(=O)(O)OCOC(=O)C(C)(C)C)ccc12] | pivaloyloxymethyl hydrogen 1-(2-((2S,4R)-2-((3-chloro-2-fluorobenzyl)carbamoyl)-4-fluoropyrrolidin-1-yl)-2-oxoethyl)-3-acetyl-1H-indol-6-ylphosphonate | *** | 1.14 | 668 |
| 127 | 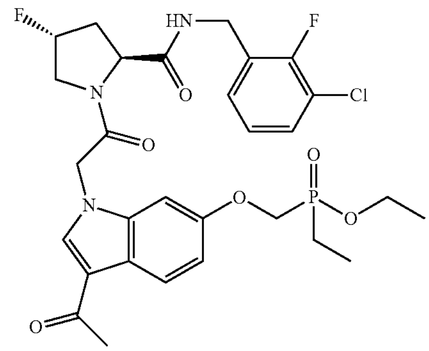 [SMILES: CCOP(=O)(CC)COc1ccc2c(C(C)=O)cn(CC(=O)N3C[C@H](F)C[C@H]3C(=O)NCc3cccc(Cl)c3F)c2c1] | ethyl (1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)methyl(ethyl)phosphinate | *** | 1.40 | 624 |
| 128 | 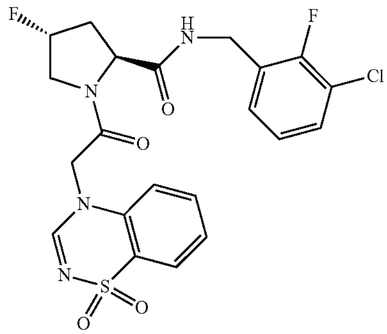 [SMILES: O=C(NCc1cccc(Cl)c1F)[C@@H]1C[C@@H](F)CN1C(=O)CN1C=NS(=O)(=O)c2ccccc21] | (2S,4R)-N-(3-chloro-2-fluorobenzyl)-4-fluoro-1-(4,4-dioxo-4-thio-2-(quinazolin-1(4H)-yl)acetyl)pyrrolidine-2-carboxamide | * | 1.25 | 497 |
| 129 | 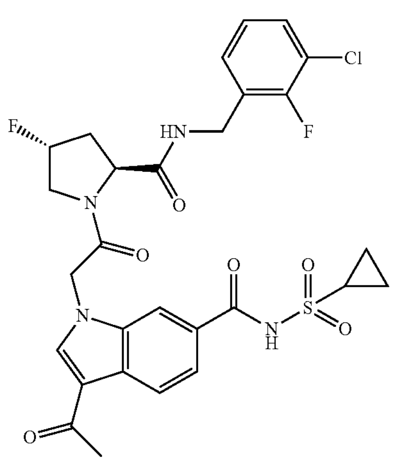 [SMILES: CC(=O)c1cn(CC(=O)N2C[C@H](F)C[C@H]2C(=O)NCc2cccc(Cl)c2F)c2cc(C(=O)NS(=O)(=O)C3CC3)ccc12] | 1-(2-((2S,4R)-2-((3-chloro-2-fluorobenzyl)carbamoyl)-4-fluoropyrrolidin-1-yl)-2-oxoethyl)-3-acetyl-N-(cyclopropylsulfonyl)-1H-indole-6-carboxamide | *** | 1.52 | 621 |

| Cmp. No. | Structure | Name | IC$_{50}$ (μM) | RT min (Method 1 or 2) | M + 1 |
|---|---|---|---|---|---|
| 130 | 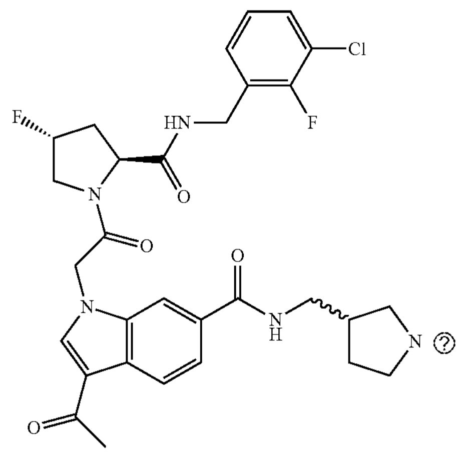 [SMILES: CC(=O)c1cn(CC(=O)N2C[C@H](F)C[C@H]2C(=O)NCc2cccc(Cl)c2F)c2cc(C(=O)NCC3CCNC3)ccc12] | 1-(2-((2S,4R)-2-((3-chloro-2-fluorobenzyl)carbamoyl)-4-fluoropyrrolidin-1-yl)-2-oxoethyl)-3-acetyl-N-(pyrrolidin-3-ylmethyl)-1H-indole-6-carboxamide | *** | 0.70 | 600 |
| 131 | 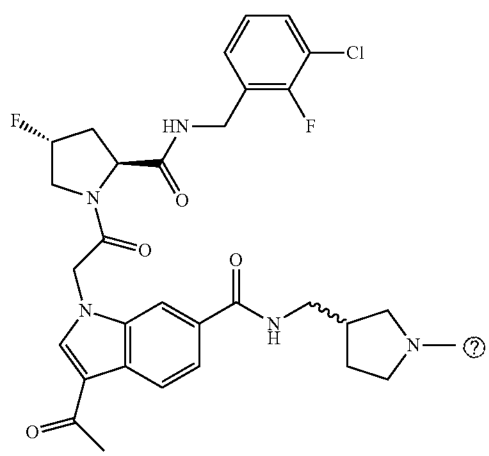 [SMILES: CC(=O)c1cn(CC(=O)N2C[C@H](F)C[C@H]2C(=O)NCc2cccc(Cl)c2F)c2cc(C(=O)NCC3CCN(C)C3)ccc12] | tert-butyl 3-((1-(2-((2S,4R)-2-((3-chloro-2-fluorobenzyl)carbamoyl)-4-fluoropyrrolidin-1-yl)-2-oxoethyl)-3-acetyl-1H-indole-6-carboxamido)methyl)pyrrolidine-1-carboxylate | *** | 1.77 | 700 |
| 132 | 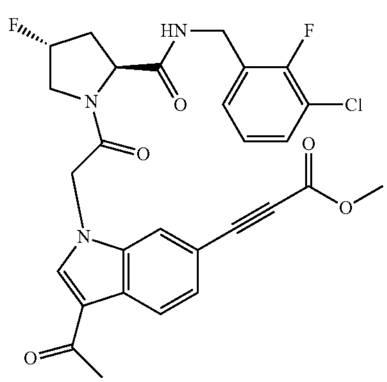 [SMILES: COC(=O)C#Cc1ccc2c(C(C)=O)cn(CC(=O)N3C[C@H](F)C[C@H]3C(=O)NCc3cccc(Cl)c3F)c2c1] | methyl 3-(1-(2-((2S,4R)-2-((3-chloro-2-fluorobenzyl)carbamoyl)-4-fluoropyrrolidin-1-yl)-2-oxoethyl)-3-acetyl-1H-indol-6-yl)propiolate | *** | 1.18 | 556 |

-continued

| Cmp. No. | Structure | Name | IC$_{50}$ (μM) | RT min (Method 1 or 2) | M + 1 |
|---|---|---|---|---|---|
| 133 | 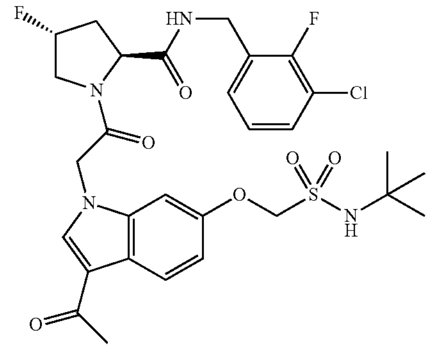 [SMILES: CC(=O)c1cn(CC(=O)N2C[C@H](F)C[C@H]2C(=O)NCc2cccc(Cl)c2F)c2cc(OCS(=O)(=O)NC(C)(C)C)ccc12] | (2S,4R)-N-(3-chloro-2-fluorobenzyl)-1-(2-(3-acetyl-6-(tert-butylaminosulfonylmethoxy)-1H-indol-1-yl)acetyl)-4-fluoropyrrolidine-2-carboxamide | *** | 1.83 | 639 |
| 134 | 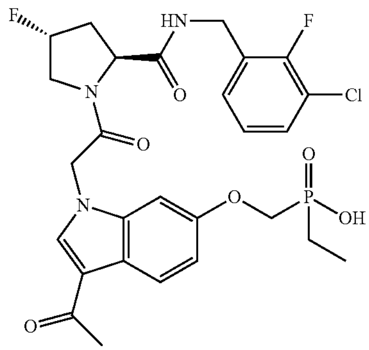 [SMILES: CCP(=O)(O)COc1ccc2c(C(C)=O)cn(CC(=O)N3C[C@H](F)C[C@H]3C(=O)NCc3cccc(Cl)c3F)c2c1] | (1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)methyl(ethyl)phosphinic acid | *** | 1.18 | 596 |
| 135 | 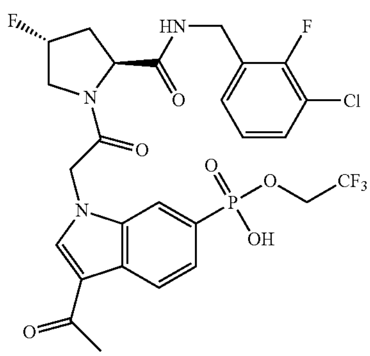 [SMILES: CC(=O)c1cn(CC(=O)N2C[C@H](F)C[C@H]2C(=O)NCc2cccc(Cl)c2F)c2cc(P(=O)(O)OCC(F)(F)F)ccc12] | 2,2,2-trifluoroethyl hydrogen 1-(2-((2S,4R)-2-((3-chloro-2-fluorobenzyl)carbamoyl)-4-fluoropyrrolidin-1-yl)-2-oxoethyl)-3-acetyl-1H-indol-6-ylphosphonate | *** | 1.08 | 636 |
| 136 | 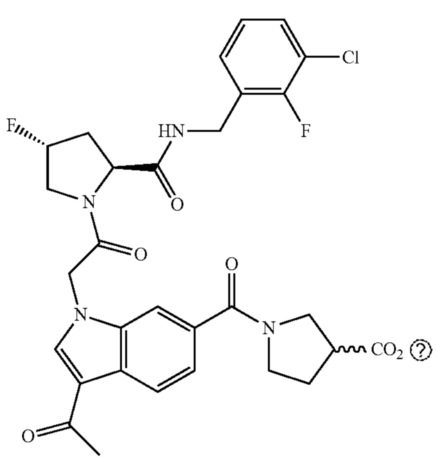 | methyl 1-(1-(2-((2S,4R)-2-((3-chloro-2-fluorobenzyl)carbamoyl)-4-fluoropyrrolidin-1-yl)-2-oxoethyl)-3-acetyl-1H-indole-6-carbonyl)pyrrolidine-3-carboxylate | *** | 1.28 | 629 |

| Cmp. No. | Structure | Name | IC$_{50}$ (μM) | RT min (Method 1 or 2) | M + 1 |
|---|---|---|---|---|---|
| 137 | 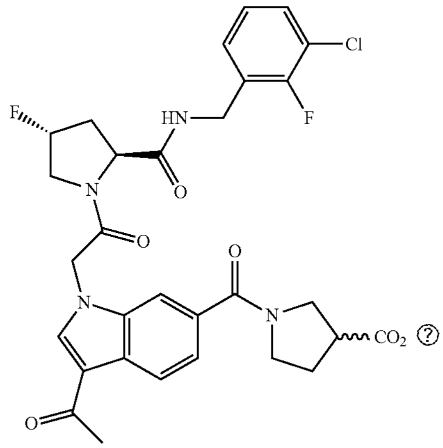 | 1-(1-(2-((2S,4R)-2-((3-chloro-2-fluorobenzyl)carbamoyl)-4-fluoropyrrolidin-1-yl)-2-oxoethyl)-3-acetyl-1H-indole-6-carbonyl)pyrrolidine-3-carboxylic acid | *** | 1.14 | 615 |
| 138 | 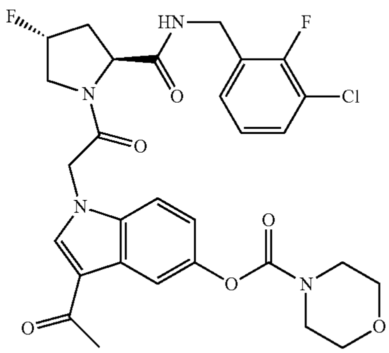 [SMILES: CC(=O)c1cn(CC(=O)N2C[C@H](F)C[C@H]2C(=O)NCc2cccc(Cl)c2F)c2ccc(OC(=O)N3CCOCC3)cc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl morpholine-4-carboxylate | *** | 1.39 | 603 |
| 139 | 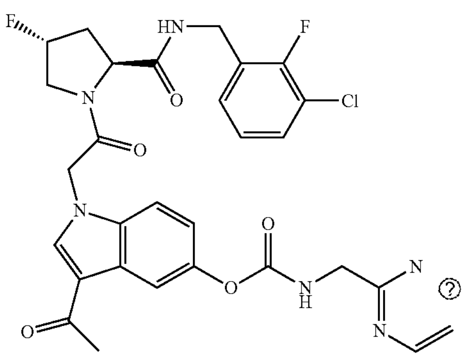 [SMILES: C=C/N=C(\N)CNC(=O)Oc1ccc2c(c1)c(C(C)=O)cn2CC(=O)N1C[C@H](F)C[C@H]1C(=O)NCc1cccc(Cl)c1F] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl pyrimidin-2-ylmethylcarbamate | *** | 1.10 | 625 |
| 140 | 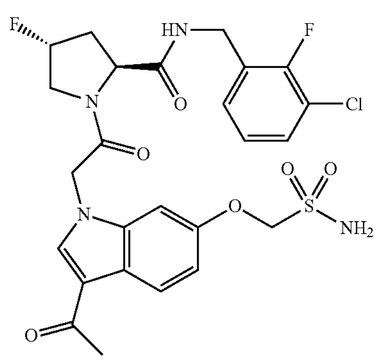 [SMILES: CC(=O)c1cn(CC(=O)N2C[C@H](F)C[C@H]2C(=O)NCc2cccc(Cl)c2F)c2cc(OCS(N)(=O)=O)ccc12] | (2S,4R)-N-(3-chloro-2-fluorobenzyl)-1-(2-(3-acetyl-6-(aminosulfonylmethoxy)-1H-indol-1-yl)acetyl)-4-fluoropyrrolidine-2-carboxamide | *** | 1.19 | 583 |

| Cmp. No. | Structure | Name | IC$_{50}$ (µM) | RT min (Method 1 or 2) | M + 1 |
|---|---|---|---|---|---|
| 141 | 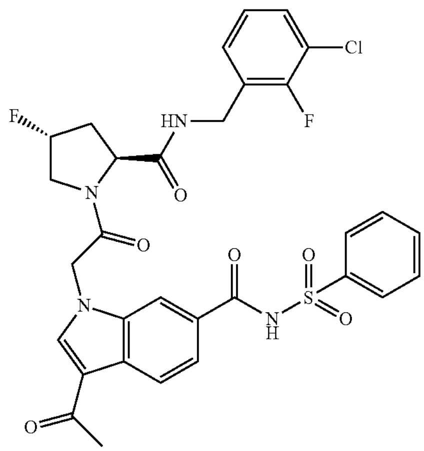 [SMILES: CC(=O)c1cn(CC(=O)N2C[C@H](F)C[C@H]2C(=O)NCc2cccc(Cl)c2F)c2cc(C(=O)NS(=O)(=O)c3ccccc3)ccc12] | 1-(2-((2S,4R)-2-((3-chloro-2-fluorobenzyl)carbamoyl)-4-fluoropyrrolidin-1-yl)-2-oxoethyl)-3-acetyl-N-(phenylsulfonyl)-1H-indole-6-carboxamide | *** | 1.71 | 657 |
| 142 | 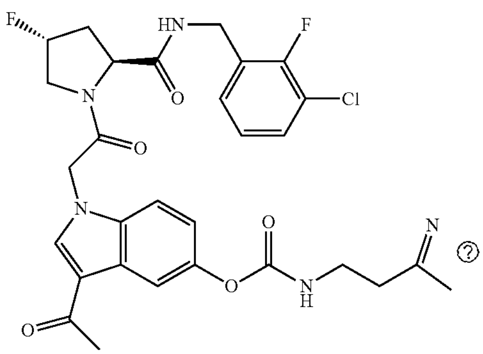 [SMILES: CC(=N)CCNC(=O)Oc1ccc2c(c1)c(C(C)=O)cn2CC(=O)N1C[C@H](F)C[C@H]1C(=O)NCc1cccc(Cl)c1F] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl 2-(2H-tetrazol-5-yl)ethylcarbamate | *** | 1.14 | 629 |
| 143 | 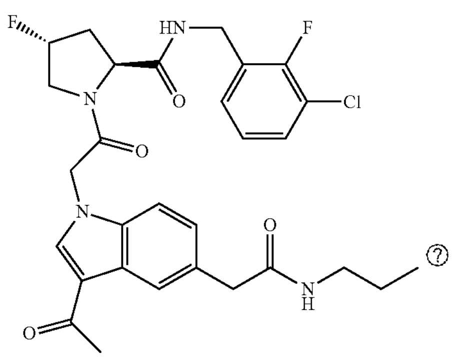 [SMILES: CCCNC(=O)Cc1ccc2c(c1)c(C(C)=O)cn2CC(=O)N1C[C@H](F)C[C@H]1C(=O)NCc1cccc(Cl)c1F] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl 2-(1H-imidazol-4-yl)ethylcarbamate | *** | 0.95 | 627 |
| 144 | 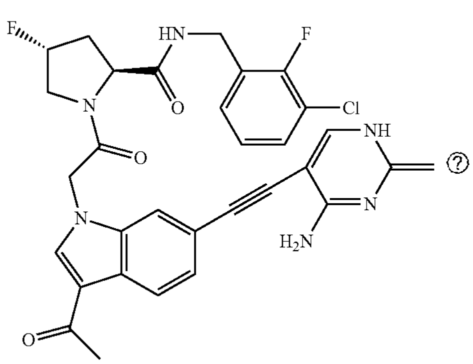 [SMILES: C=C1N=C(N)C(C#Cc2ccc3c(C(C)=O)cn(CC(=O)N4C[C@H](F)C[C@H]4C(=O)NCc4cccc(Cl)c4F)c3c2)=CN1] | (2S,4R)-N-(3-chloro-2-fluorobenzyl)-1-(2-(3-acetyl-6-(2-(4-amino-2-oxo-1,2-dihydropyrimidin-5-yl)ethynyl)-1H-indol-1-yl)acetyl)-4-fluoropyrrolidine-2-carboxamide | *** | 1.02 | 607 |

| Cmp. No. | Structure | Name | IC$_{50}$ (μM) | RT min (Method 1 or 2) | M + 1 |
|---|---|---|---|---|---|
| 145 | 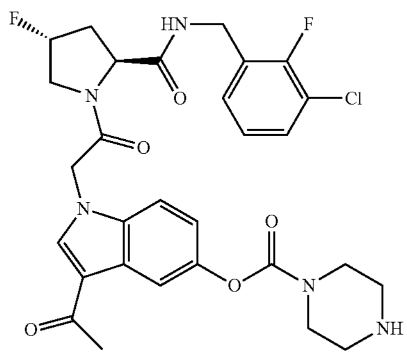 [SMILES: CC(=O)c1cn(CC(=O)N2C[C@H](F)C[C@H]2C(=O)NCc2cccc(Cl)c2F)c2ccc(OC(=O)N3CCNCC3)cc12] | 1-(2-((2S,4R)-2-((3-chloro-2-fluorobenzyl)carbamoyl)-4-fluoropyrrolidin-1-yl)-2-oxoethyl)-3-acetyl-1H-indol-5-yl piperazine-1-carboxylate | *** | 1.11 | 602 |
| 146 | 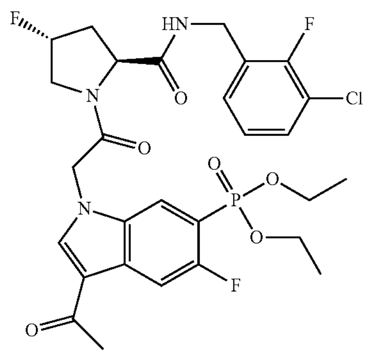 [SMILES: CCOP(=O)(OCC)c1cc2c(cc1F)c(C(C)=O)cn2CC(=O)N1C[C@H](F)C[C@H]1C(=O)NCc1cccc(Cl)c1F] | diethyl 1-(2-((2S,4R)-2-((3-chloro-2-fluorobenzyl)carbamoyl)-4-fluoropyrrolidin-1-yl)-2-oxoethyl)-3-acetyl-5-fluoro-1H-indol-6-ylphosphonate | *** | 1.41 | 628 |
| 147 | 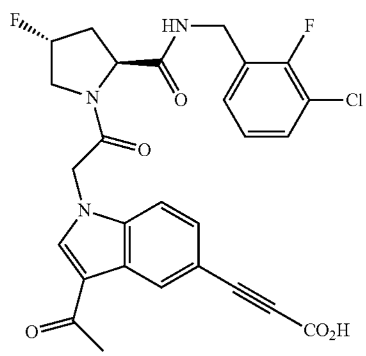 [SMILES: CC(=O)c1cn(CC(=O)N2C[C@H](F)C[C@H]2C(=O)NCc2cccc(Cl)c2F)c2ccc(C#CC(=O)O)cc12] | 3-(1-(2-((2S,4R)-2-((3-chloro-2-fluorobenzyl)carbamoyl)-4-fluoropyrrolidin-1-yl)-2-oxoethyl)-3-acetyl-1H-indol-5-yl)propiolic acid | *** | 1.26 | 532 542 |
| 148 | 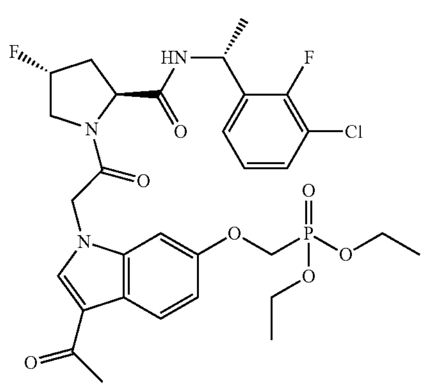 [SMILES: CCOP(=O)(COc1ccc2c(C(C)=O)cn(CC(=O)N3C[C@H](F)C[C@H]3C(=O)N[C@H](C)c3cccc(Cl)c3F)c2c1)OCC] | diethyl (1-(2-((2S,4R)-2-(((R)-1-(3-chloro-2-fluorophenyl)ethyl)carbamoyl)-4-fluoropyrrolidin-1-yl)-2-oxoethyl)-3-acetyl-1H-indol-6-yloxy)methylphosphonate | *** | 1.67 | 654 |

| Cmp. No. | Structure | Name | IC$_{50}$ (μM) | RT min (Method 1 or 2) | M + 1 |
|---|---|---|---|---|---|
| 149 | 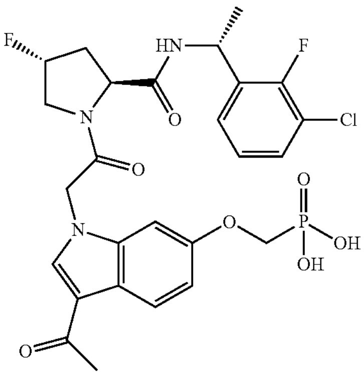 [SMILES: CC(=O)c1cn(CC(=O)N2C[C@H](F)C[C@H]2C(=O)N[C@H](C)c2cccc(Cl)c2F)c2cc(OCP(=O)(O)O)ccc12] | (1-(2-((2S,4R)-2-(((R)-1-(3-chloro-2-fluorophenyl)ethyl)carbamoyl)-4-fluoropyrrolidin-1-yl)-2-oxoethyl)-3-acetyl-1H-indol-6-yloxy)methylphosphonic acid | *** | 0.79 | 598 |
| 150 | 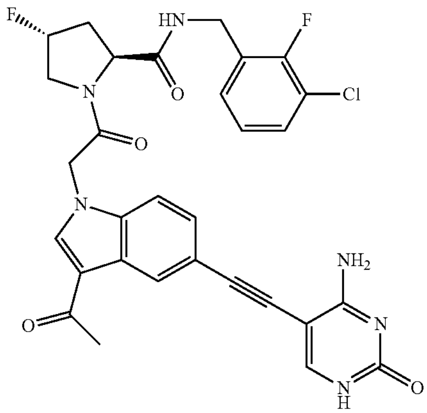 | (2S,4R)-N-(3-chloro-2-fluorobenzyl)-1-(2-(3-acetyl-5-(2-(4-amino-2-oxo-1,2-dihydropyrimidin-5-yl)ethynyl)-1H-indol-1-yl)acetyl)-4-fluoropyrrolidine-2-carboxamide | *** | 1.17 | 607 |
| 151 | 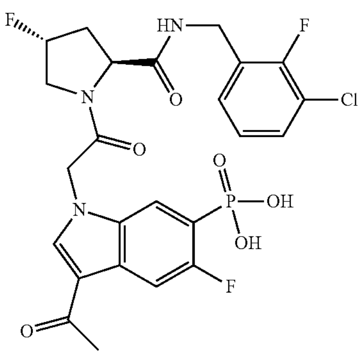 [SMILES: CC(=O)c1cn(CC(=O)N2C[C@H](F)C[C@H]2C(=O)NCc2cccc(Cl)c2F)c2cc(P(=O)(O)O)c(F)cc12] | 1-(2-((2S,4R)-2-((3-chloro-2-fluorobenzyl)carbamoyl)-4-fluoropyrrolidin-1-yl)-2-oxoethyl)-3-acetyl-5-fluoro-1H-indol-6-ylphosphonic acid | *** | 0.93 | 572 |
| 152 | 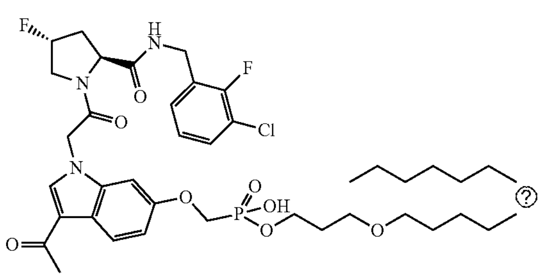 | 3-(hexadecyloxy)propyl hydrogen (1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)methylphosphonate | *** | 3.31 | 866 |

-continued

| Cmp. No. | Structure | Name | IC$_{50}$ (μM) | RT min (Method 1 or 2) | M + 1 |
|---|---|---|---|---|---|
| 153 | 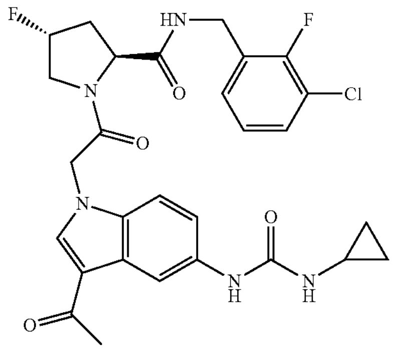 [SMILES: CC(=O)c1cn(CC(=O)N2C[C@H](F)C[C@H]2C(=O)NCc2cccc(Cl)c2F)c2ccc(NC(=O)NC3CC3)cc12] | 1-(1-(2-((2S,4R)-2-((3-chloro-2-fluorobenzyl)carbamoyl)-4-fluoropyrrolidin-1-yl)-2-oxoethyl)-3-acetyl-1H-indol-5-yl)-3-cyclopropylurea | *** | 1.24 | 572 |
| 154 | 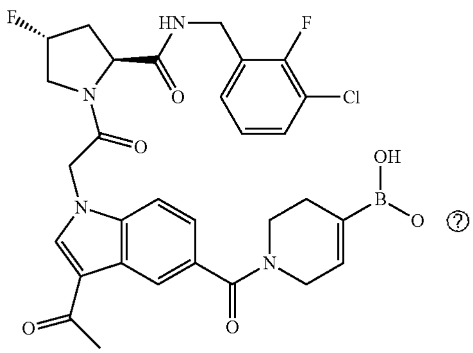 [SMILES: CC(=O)c1cn(CC(=O)N2C[C@H](F)C[C@H]2C(=O)NCc2cccc(Cl)c2F)c2ccc(C(=O)N3CC=C(B(O)O)CC3)cc12] | 1-(1-(2-((2S,4R)-2-((3-chloro-2-fluorobenzyl)carbamoyl)-4-fluoropyrrolidin-1-yl)-2-oxoethyl)-3-acetyl-1H-indole-5-carbonyl)-1,2,3,6-tetrahydropyridin-4-ylboronic acid | *** | 0.93 | 627 |
| 155 | 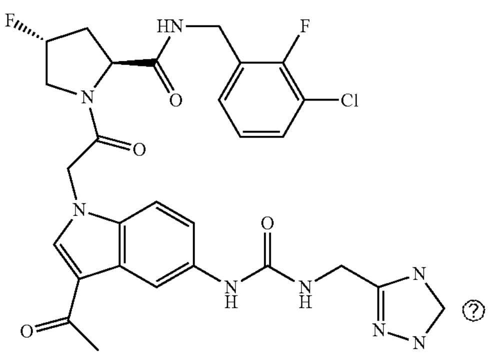 [SMILES: CC(=O)c1cn(CC(=O)N2C[C@H](F)C[C@H]2C(=O)NCc2cccc(Cl)c2F)c2ccc(NC(=O)NCC3=NNCN3)cc12] | 1-(1-(2-((2S,4R)-2-((3-chloro-2-fluorobenzyl)carbamoyl)-4-fluoropyrrolidin-1-yl)-2-oxoethyl)-3-acetyl-1H-indol-5-yl)-3-((2H-tetrazol-5-yl)methyl)urea | *** | 1.01 | 614 |
| 156 | 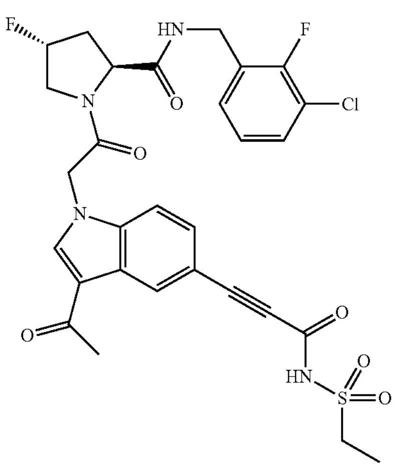 [SMILES: CCS(=O)(=O)NC(=O)C#Cc1ccc2c(c1)c(C(C)=O)cn2CC(=O)N1C[C@H](F)C[C@H]1C(=O)NCc1cccc(Cl)c1F] | (2S,4R)-N-(3-chloro-2-fluorobenzyl)-1-(2-(3-acetyl-5-(3-(ethylsulfonamido)-3-oxoprop-1-ynyl)-1H-indol-1-yl)acetyl)-4-fluoropyrrolidine-2-carboxamide | *** | 1.73 | 633 |

-continued

| Cmp. No. | Structure | Name | IC$_{50}$ (μM) | RT min (Method 1 or 2) | M + 1 |
|---|---|---|---|---|---|
| 157 | 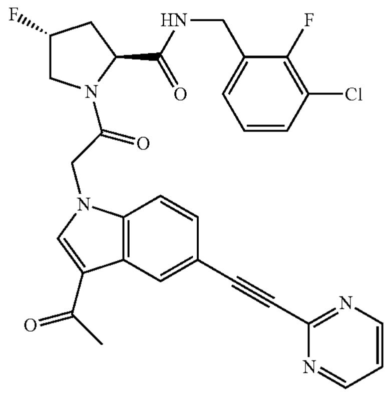 [SMILES: CC(=O)c1cn(CC(=O)N2C[C@H](F)C[C@H]2C(=O)NCc2cccc(Cl)c2F)c2ccc(C#Cc3ncccn3)cc12] | (2S,4R)-N-(3-chloro-2-fluorobenzyl)-1-(2-(3-acetyl-5-(2-(pyrimidin-2-yl)ethynyl)-1H-indol-1-yl)acetyl)-4-fluoropyrrolidine-2-carboxamide | *** | 1.74 | 576 |
| 158 | 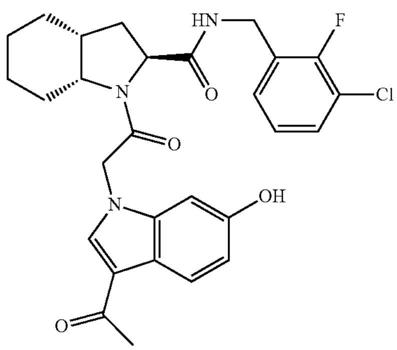 [SMILES: CC(=O)c1cn(CC(=O)N2[C@@H]3CCCC[C@@H]3C[C@H]2C(=O)NCc2cccc(Cl)c2F)c2cc(O)ccc12] | (2S,3aR,7aR)-N-(3-chloro-2-fluorobenzyl)-1-(2-(3-acetyl-6-hydroxy-1H-indol-1-yl)acetyl)-octahydro-1H-indole-2-carboxamide | ** | 1.93 | 526 |
| 159 | 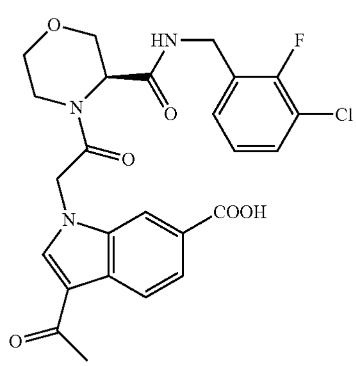 [SMILES: CC(=O)c1cn(CC(=O)N2CCOC[C@H]2C(=O)NCc2cccc(Cl)c2F)c2cc(C(=O)O)ccc12] | (S)-1-(2-(3-((3-chloro-2-fluorobenzyl)carbamoyl)morpholino)-2-oxoethyl)-3-acetyl-1H-indole-6-carboxylic acid | *** | 1.46 | 516 |
| 160 | 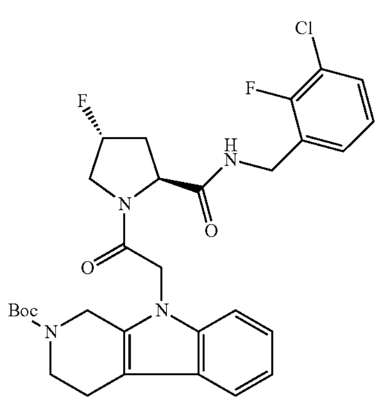 [SMILES: CC(C)(C)OC(=O)N1CCc2c(n(CC(=O)N3C[C@H](F)C[C@H]3C(=O)NCc3cccc(Cl)c3F)c3ccccc23)C1] | tert-butyl 9-(2-((2S,4R)-2-((3-chloro-2-fluorobenzyl)carbamoyl)-4-fluoropyrrolidin-1-yl)-2-oxoethyl)-3,4-dihydro-1H-pyrido[3,4-b]indole-2(9H)-carboxylate | * | 2.71 | 587 |

| Cmp. No. | Structure | Name | IC$_{50}$ (μM) | RT min (Method 1 or 2) | M + 1 |
|---|---|---|---|---|---|
| 161 | 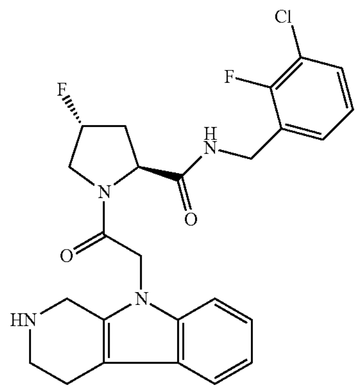 [SMILES: O=C(NCc1cccc(Cl)c1F)[C@@H]1C[C@@H](F)CN1C(=O)Cn1c2c(c3ccccc31)CCNC2] | (2S,4R)-N-(3-chloro-2-fluorobenzyl)-4-fluoro-1-(2-(1,2,3,4-tetrahydropyrido[3,4-b]indol-9-yl)acetyl)pyrrolidine-2-carboxamide | * | 1.38 | 487 |
| 162 | 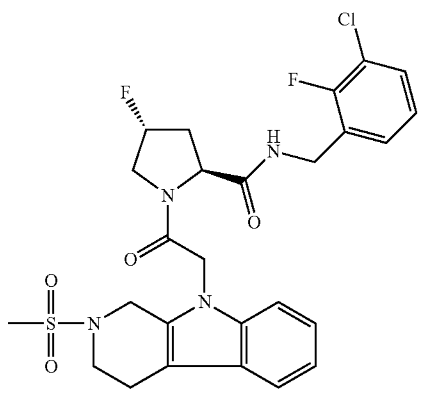 [SMILES: CS(=O)(=O)N1CCc2c(n(CC(=O)N3C[C@H](F)C[C@H]3C(=O)NCc3cccc(Cl)c3F)c3ccccc23)C1] | (2S,4R)-N-(3-chloro-2-fluorobenzyl)-4-fluoro-1-(2-(2-(methylsulfonyl)-1,2,3,4-tetrahydropyrido[3,4-b]indol-9-yl)acetyl)pyrrolidine-2-carboxamide | ** | 2.06 | 565 |
| 163 | 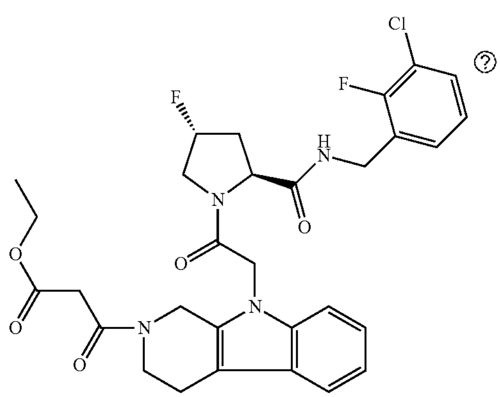 [SMILES: CCOC(=O)CC(=O)N1CCc2c(n(CC(=O)N3C[C@H](F)C[C@H]3C(=O)NCc3cccc(Cl)c3F)c3ccccc23)C1] | ethyl 3-(9-(2-((2S,4R)-2-((3-chloro-2-fluorobenzyl)carbamoyl)-4-fluoropyrrolidin-1-yl)-2-oxoethyl)-3,4-dihydro-1H-pyrido[3,4-b]indol-2(9H)-yl)-3-oxopropanoate | * | 2.16 | 601 |
| 164 | 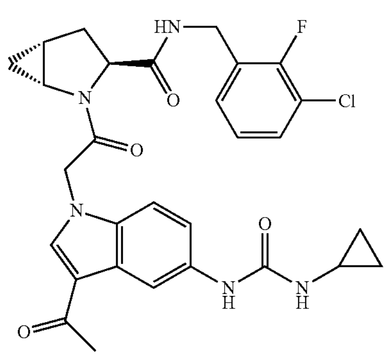 [SMILES: CC(=O)c1cn(CC(=O)N2[C@@H]3C[C@@H]3C[C@H]2C(=O)NCc2cccc(Cl)c2F)c2ccc(NC(=O)NC3CC3)cc12] | 1-(1-(2-((1R,3S,5R)-3-((3-chloro-2-fluorobenzyl)carbamoyl)-2-azabicyclo[3.1.0]hexan-2-yl)-2-oxoethyl)-3-acetyl-1H-indol-5-yl)-3-cyclopropylurea | *** | 1.52 | 566 |

| Cmp. No. | Structure | Name | IC$_{50}$ (μM) | RT min (Method 1 or 2) | M + 1 |
|---|---|---|---|---|---|
| 165 | 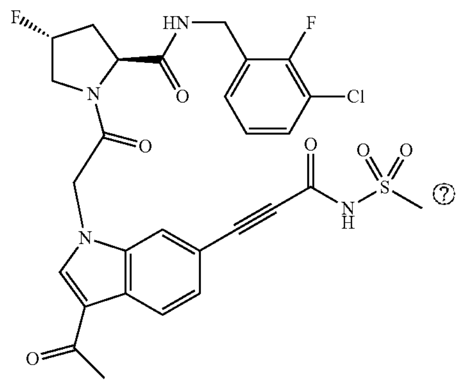 [SMILES: CC(=O)c1cn(CC(=O)N2C[C@H](F)C[C@H]2C(=O)NCc2cccc(Cl)c2F)c2cc(C#CC(=O)NS(C)(=O)=O)ccc12] | (2S,4R)-N-(3-chloro-2-fluorobenzyl)-1-(2-(3-acetyl-6-(3-(ethylsulfonamido)-3-oxoprop-1-ynyl)-1H-indol-1-yl)acetyl)-4-fluoropyrrolidine-2-carboxamide | *** | 1.73 | 633 |
| 166 | 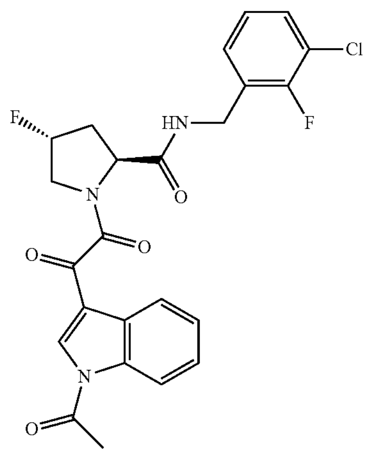 [SMILES: CC(=O)n1cc(C(=O)C(=O)N2C[C@H](F)C[C@H]2C(=O)NCc2cccc(Cl)c2F)c2ccccc21] | (2S,4R)-1-(2-(1-acetyl-1H-indol-3-yl)-2-oxoacetyl)-N-(3-chloro-2-fluorobenzyl)-4-fluoropyrrolidine-2-carboxamide | * | 2.31 | 488 |
| 167 | 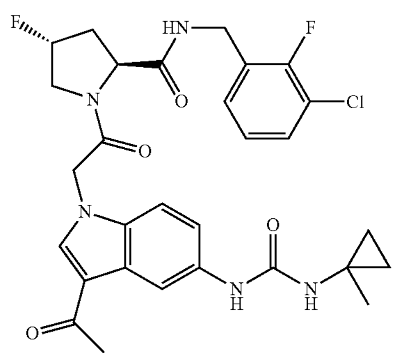 [SMILES: CC(=O)c1cn(CC(=O)N2C[C@H](F)C[C@H]2C(=O)NCc2cccc(Cl)c2F)c2ccc(NC(=O)NC3(C)CC3)cc12] | (2S,4R)-1-(2-(3-acetyl-5-(3-(1-methylcyclopropyl)ureido)-1H-indol-1-yl)acetyl)-N-(3-chloro-2-fluorobenzyl)-4-fluoropyrrolidine-2-carboxamide | *** | 1.66 | 586 |
| 168 | 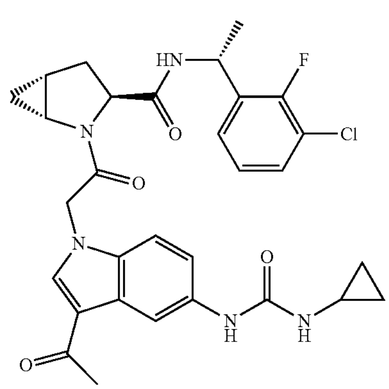 [SMILES: CC(=O)c1cn(CC(=O)N2[C@@H]3C[C@@H]3C[C@H]2C(=O)N[C@H](C)c2cccc(Cl)c2F)c2ccc(NC(=O)NC3CC3)cc12] | (1R,3S,5R)-2-(2-(3-acetyl-5-(3-cyclopropylureido)-1H-indol-1-yl)acetyl)-N-((R)-1-(3-chloro-2-fluorophenyl)ethyl)-2-azabicyclo[3.1.0]hexane-3-carboxamide | *** | 1.74 | 580 |

| Cmp. No. | Structure | Name | IC$_{50}$ (μM) | RT min (Method 1 or 2) | M + 1 |
|---|---|---|---|---|---|
| 169 | 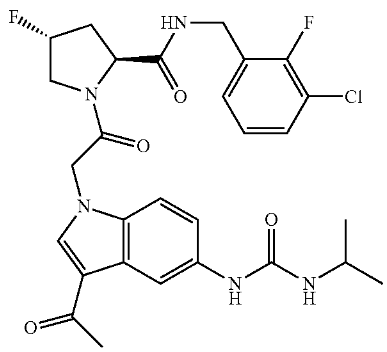 [SMILES: CC(=O)c1cn(CC(=O)N2C[C@H](F)C[C@H]2C(=O)NCc2cccc(Cl)c2F)c2ccc(NC(=O)NC(C)C)cc12] | (2S,4R)-1-(2-(3-acetyl-5-(3-isopropylureido)-1H-indol-1-yl)acetyl)-N-(3-chloro-2-fluorobenzyl)-4-fluoropyrrolidine-2-carboxamide | *** | 1.65 | 574 |
| 170 | 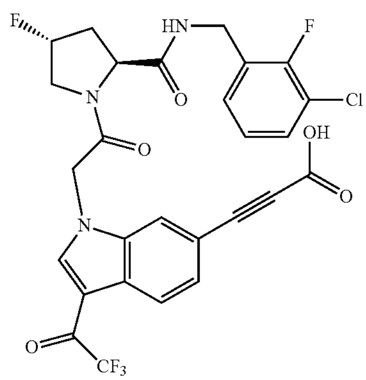 [SMILES: O=C(O)C#Cc1ccc2c(C(=O)C(F)(F)F)cn(CC(=O)N3C[C@H](F)C[C@H]3C(=O)NCc3cccc(Cl)c3F)c2c1] | 3-(1-(2-((2S,4R)-2-((3-chloro-2-fluorobenzyl)carbamoyl)-4-fluoropyrrolidin-1-yl)-2-oxoethyl)-3-(2,2,2-trifluoroacetyl)-1H-indol-6-yl)propiolic acid | *** | 2.11 | 596 |
| 171 | 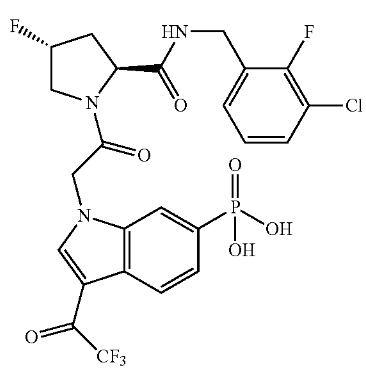 [SMILES: O=C(NCc1cccc(Cl)c1F)[C@@H]1C[C@@H](F)CN1C(=O)Cn1cc(C(=O)C(F)(F)F)c2ccc(P(=O)(O)O)cc21] | 1-(2-((2S,4R)-2-((3-chloro-2-fluorobenzyl)carbamoyl)-4-fluoropyrrolidin-1-yl)-2-oxoethyl)-3-(2,2,2-trifluoroacetyl)-1H-indol-6-ylphosphonic acid | *** | 1.54 | 608 |

-continued

| Cmp. No. | Structure | Name | IC$_{50}$ (μM) | RT min (Method 1 or 2) | M + 1 |
|---|---|---|---|---|---|
| 172 | 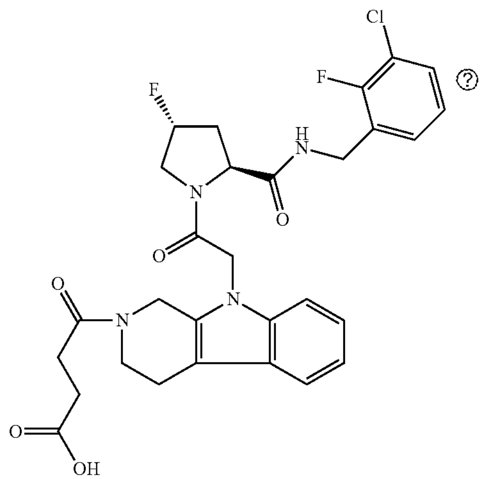 [SMILES: O=C(O)CCC(=O)N1CCc2c(n(CC(=O)N3C[C@H](F)C[C@H]3C(=O)NCc3cccc(Cl)c3F)c3ccccc23)C1] | 4-(9-(2-((2S,4R)-2-((3-chloro-2-fluorobenzyl)carbamoyl)-4-fluoropyrrolidin-1-yl)-2-oxoethyl)-3,4-dihydro-1H-pyrido[3,4-b]indol-2(9H)-yl)-4-oxobutanoic acid | * | 1.88 | 587 |
| 173 | 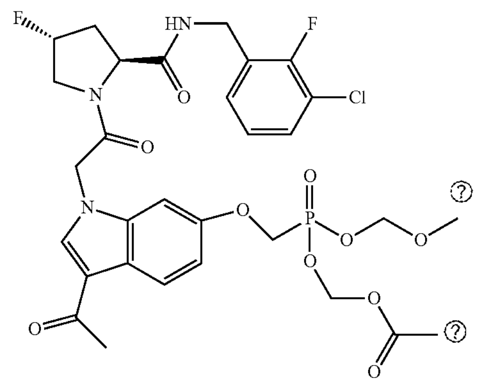 [SMILES: COCOP(=O)(COc1ccc2c(C(C)=O)cn(CC(=O)N3C[C@H](F)C[C@H]3C(=O)NCc3cccc(Cl)c3F)c2c1)OCOC(C)=O] | Di(pivaloylmethyl) (1-(2-((2S,4R)-2-((3-chloro-2-fluorobenzyl)carbamoyl)-4-fluoropyrrolidin-1-yl)-2-oxoethyl)-3-acetyl-1H-indol-6-yloxy)methylphosphonate | *** | 2.58 | 812 |
| 174 | 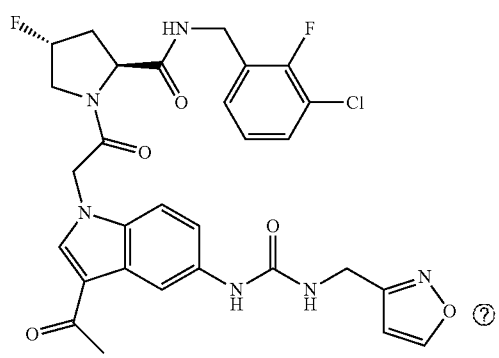 [SMILES: CC(=O)c1cn(CC(=O)N2C[C@H](F)C[C@H]2C(=O)NCc2cccc(Cl)c2F)c2ccc(NC(=O)NCc3ccon3)cc12] | 1-(1-(2-((2S,4R)-2-((3-chloro-2-fluorobenzyl)carbamoyl)-4-fluoropyrrolidin-1-yl)-2-oxoethyl)-3-acetyl-1H-indol-5-yl)-3-(isoxazol-3-ylmethyl)urea | *** | 1.49 | 613 |
| 175 | 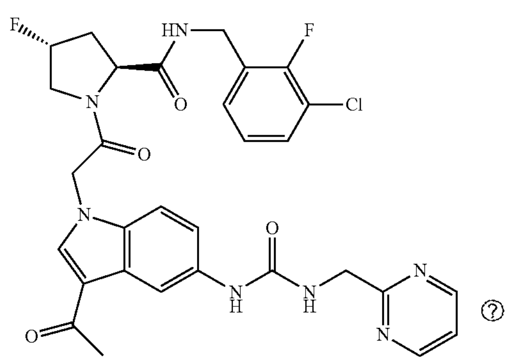 [SMILES: CC(=O)c1cn(CC(=O)N2C[C@H](F)C[C@H]2C(=O)NCc2cccc(Cl)c2F)c2ccc(NC(=O)NCc3ncccn3)cc12] | (2S,4R)-1-(2-(3-acetyl-5-(3-(pyrimidin-2-ylmethyl)ureido)-1H-indol-1-yl)acetyl)-N-(3-chloro-2-fluorobenzyl)-4-fluoropyrrolidine-2-carboxamide | *** | 1.35 | 624 |

| Cmp. No. | Structure | Name | IC$_{50}$ (μM) | RT min (Method 1 or 2) | M + 1 |
|---|---|---|---|---|---|
| 176 | 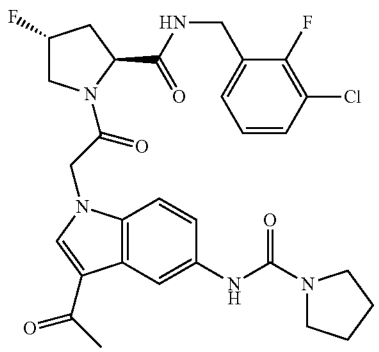 [SMILES: CC(=O)c1cn(CC(=O)N2C[C@H](F)C[C@H]2C(=O)NCc2cccc(Cl)c2F)c2ccc(NC(=O)N3CCCC3)cc12] | N-(3-acetyl-1-(2-((2S,4R)-2-((3-chloro-2-fluorobenzyl)carbamoyl)-4-fluoropyrrolidin-1-yl)-2-oxoethyl)-1H-indol-5-yl)pyrrolidine-1-carboxamide | *** | 1.61 | 586 |
| 177 | 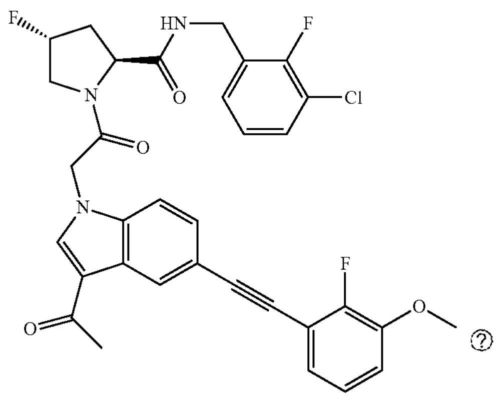 [SMILES: COc1cccc(C#Cc2ccc3c(c2)c(C(C)=O)cn3CC(=O)N2C[C@H](F)C[C@H]2C(=O)NCc2cccc(Cl)c2F)c1F] | (2S,4R)-1-(2-(3-acetyl-5-((2-fluoro-3-(trifluoromethoxy)phenyl)ethynyl)-1H-indol-1-yl)acetyl)-N-(3-chloro-2-fluorobenzyl)-4-fluoropyrrolidine-2-carboxamide | ** | 2.83 | 676 |
| 178 | 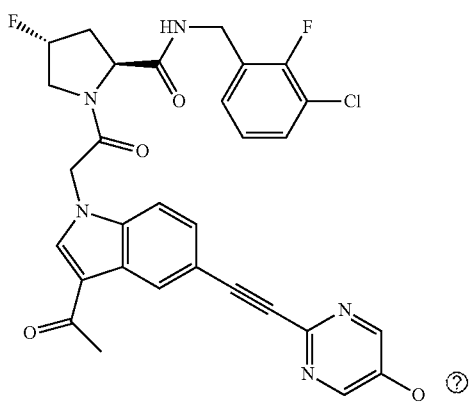 [SMILES: CC(=O)c1cn(CC(=O)N2C[C@H](F)C[C@H]2C(=O)NCc2cccc(Cl)c2F)c2ccc(C#Cc3ncc(O)cn3)cc12] | (2S,4R)-N-(3-chloro-2-fluorobenzyl)-1-(2-(3-acetyl-5-(2-(5-hydroxypyrimidin-2-yl)ethynyl)-1H-indol-1-yl)acetyl)-4-fluoropyrrolidine-2-carboxamide | *** | 1.44 | 592 |
| 179 | 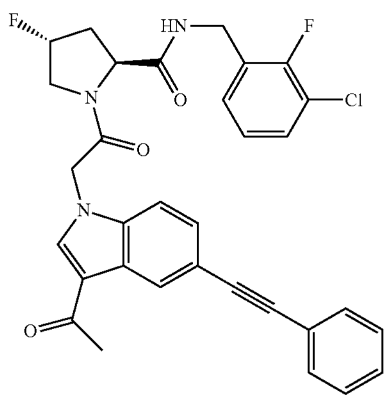 [SMILES: CC(=O)c1cn(CC(=O)N2C[C@H](F)C[C@H]2C(=O)NCc2cccc(Cl)c2F)c2ccc(C#Cc3ccccc3)cc12] | (2S,4R)-1-(2-(3-acetyl-5-(phenylethynyl)-1H-indol-1-yl)acetyl)-N-(3-chloro-2-fluorobenzyl)-4-fluoropyrrolidine-2-carboxamide | *** | 2.54 | 574 |

-continued

| Cmp. No. | Structure | Name | IC$_{50}$ (μM) | RT min (Method 1 or 2) | M + 1 |
|---|---|---|---|---|---|
| 180 | 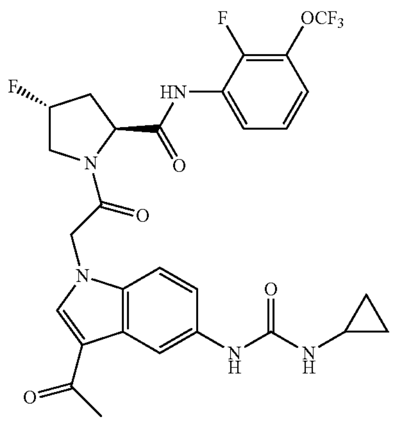 [SMILES: CC(=O)c1cn(CC(=O)N2C[C@H](F)C[C@H]2C(=O)Nc2cccc(OC(F)(F)F)c2F)c2ccc(NC(=O)NC3CC3)cc12] | (2S,4R)-1-(2-(3-acetyl-5-(3-cyclopropylureido)-1H-indol-1-yl)acetyl)-4-fluoro-N-(2-fluoro-3-(trifluoromethoxy)phenyl)pyrrolidine-2-carboxamide | *** | 1.80 | 608 |
| 181 | 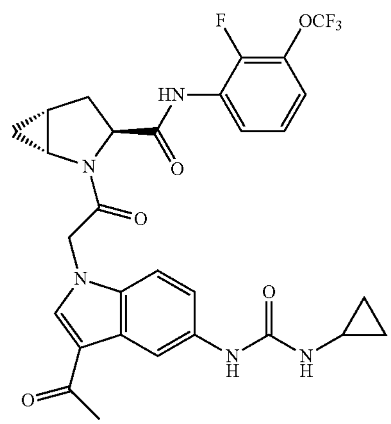 [SMILES: CC(=O)c1cn(CC(=O)N2[C@@H]3C[C@@H]3C[C@H]2C(=O)Nc2cccc(OC(F)(F)F)c2F)c2ccc(NC(=O)NC3CC3)cc12] | (1R,3S,5R)-2-(2-(3-acetyl-5-(3-cyclopropylureido)-1H-indol-1-yl)acetyl)-N-(2-fluoro-3-(trifluoromethoxy)phenyl)-2-azabicyclo[3.1.0]hexane-3-carboxamide | *** | 1.88 | 602 |
| 182 | 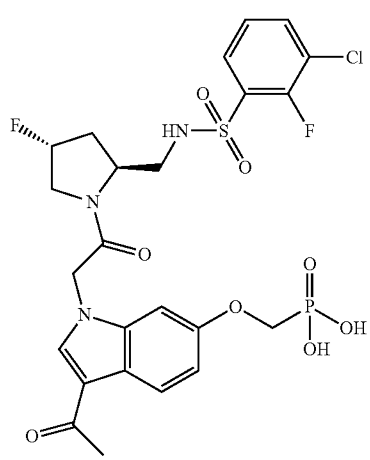 [SMILES: CC(=O)c1cn(CC(=O)N2C[C@H](F)C[C@H]2CNS(=O)(=O)c2cccc(Cl)c2F)c2cc(OCP(=O)(O)O)ccc12] | (((3-acetyl-1-(2-((2S,4R)-2-((3-chloro-2-fluorophenylsulfonamido)methyl)-4-fluoropyrrolidin-1-yl)-2-oxoethyl)-1H-indol-6-yl)oxy)methyl)phosphonic acid | *** | 1.11 | 620 |

| Cmp. No. | Structure | Name | IC$_{50}$ (μM) | RT min (Method 1 or 2) | M + 1 |
|---|---|---|---|---|---|
| 183 | 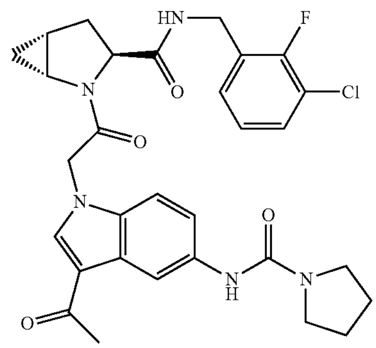 [SMILES: CC(=O)c1cn(CC(=O)N2[C@@H]3C[C@@H]3C[C@H]2C(=O)NCc2cccc(Cl)c2F)c2ccc(NC(=O)N3CCCC3)cc12] | (1R,3S,5R)-2-(2-(3-acetyl-5-(pyrrolidine-1-carboxamido)-1H-indol-1-yl)acetyl)-N-(3-chloro-2-fluorobenzyl)-2-azabicyclo[3.1.0]hexane-3-carboxamide | *** | 1.72 | 581 |
| 184 | 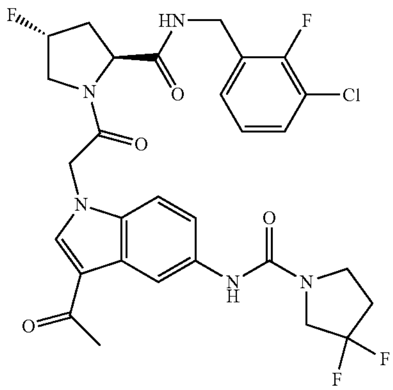 [SMILES: CC(=O)c1cn(CC(=O)N2C[C@H](F)C[C@H]2C(=O)NCc2cccc(Cl)c2F)c2ccc(NC(=O)N3CCC(F)(F)C3)cc12] | N-(3-acetyl-1-(2-((2S,4R)-2-((3-chloro-2-fluorobenzyl)carbamoyl)-4-fluoropyrrolidin-1-yl)-2-oxoethyl)-1H-indol-5-yl)-3,3-difluoropyrrolidine-1-carboxamide | *** | 1.77 | 622 |
| 185 | 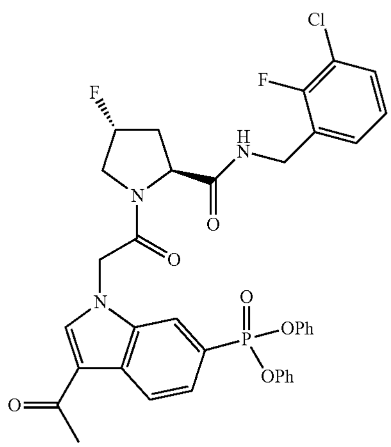 [SMILES: CC(=O)c1cn(CC(=O)N2C[C@H](F)C[C@H]2C(=O)NCc2cccc(Cl)c2F)c2cc(P(=O)(Oc3ccccc3)Oc3ccccc3)ccc12] | diphenyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate | *** | 2.44 | 707 |
| 186 | 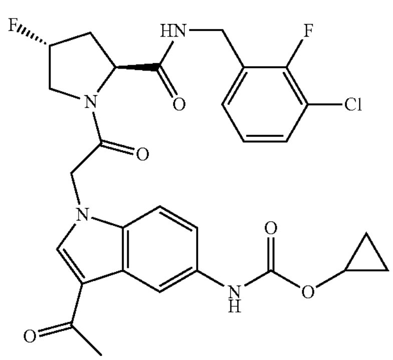 [SMILES: CC(=O)c1cn(CC(=O)N2C[C@H](F)C[C@H]2C(=O)NCc2cccc(Cl)c2F)c2ccc(NC(=O)OC3CC3)cc12] | cyclopropyl (3-acetyl-1-(2-((2S,4R)-2-((3-chloro-2-fluorobenzyl)carbamoyl)-4-fluoropyrrolidin-1-yl)-2-oxoethyl)-1H-indol-5-yl)carbamate | *** | 1.78 | 573 |

| Cmp. No. | Structure | Name | IC$_{50}$ (μM) | RT min (Method 1 or 2) | M + 1 |
|---|---|---|---|---|---|
| 187 | 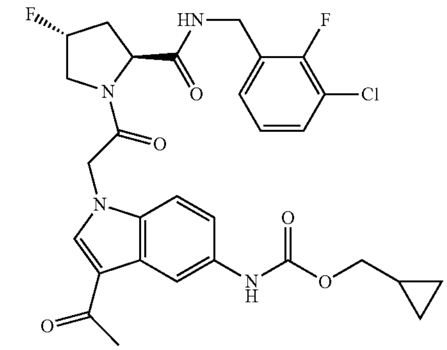 [SMILES: CC(=O)c1cn(CC(=O)N2C[C@H](F)C[C@H]2C(=O)NCc2cccc(Cl)c2F)c2ccc(NC(=O)OCC3CC3)cc12] | cyclopropylmethyl (3-acetyl-1-(2-((2S,4R)-2-((3-chloro-2-fluorobenzyl)carbamoyl)-4-fluoropyrrolidin-1-yl)-2-oxoethyl)-1H-indol-5-yl)carbamate | *** | 1.96 | 587 |
| 188 | 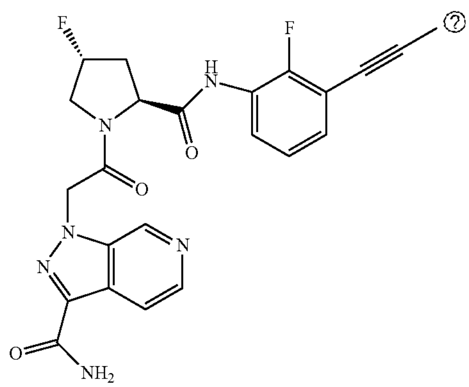 [SMILES: CC#Cc1cccc(NC(=O)[C@@H]2C[C@@H](F)CN2C(=O)Cn2nc(C(N)=O)c3ccncc32)c1F] | 1-(2-((2S,4R)-2-((3-ethynyl-2-fluorophenyl)carbamoyl)-4-fluoropyrrolidin-1-yl)-2-oxoethyl)-1H-pyrazolo[3,4-c]pyridine-3-carboxamide | *** | 0.91 | 453 |
| 189 | 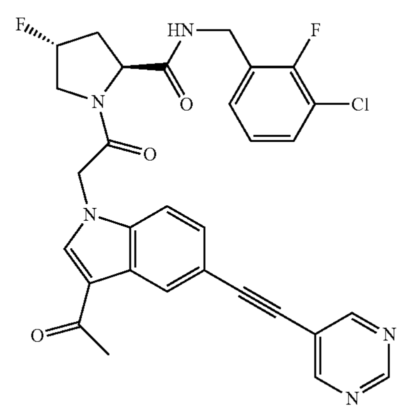 [SMILES: CC(=O)c1cn(CC(=O)N2C[C@H](F)C[C@H]2C(=O)NCc2cccc(Cl)c2F)c2ccc(C#Cc3cncnc3)cc12] | (2S,4R)-1-(2-(3-acetyl-5-(pyrimidin-5-ylethynyl)-1H-indol-1-yl)acetyl)-N-(3-chloro-2-fluorobenzyl)-4-fluoropyrrolidine-2-carboxamide | *** | 1.84 | 576 |
| 190 | 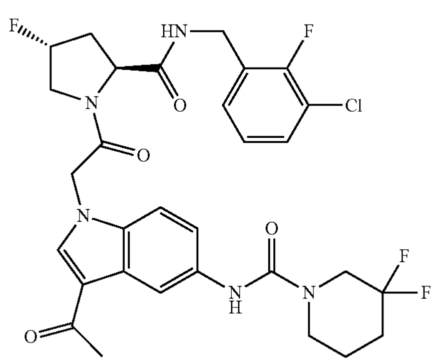 [SMILES: CC(=O)c1cn(CC(=O)N2C[C@H](F)C[C@H]2C(=O)NCc2cccc(Cl)c2F)c2ccc(NC(=O)N3CCCC(F)(F)C3)cc12] | N-(3-acetyl-1-(2-((2S,4R)-2-((3-chloro-2-fluorobenzyl)carbamoyl)-4-fluoropyrrolidin-1-yl)-2-oxoethyl)-1H-indol-5-yl)-3,3-difluoropiperidine-1-carboxamide | *** | 1.82 | 636 |

-continued

| Cmp. No. | Structure | Name | IC$_{50}$ (μM) | RT min (Method 1 or 2) | M + 1 |
|---|---|---|---|---|---|
| 191 | 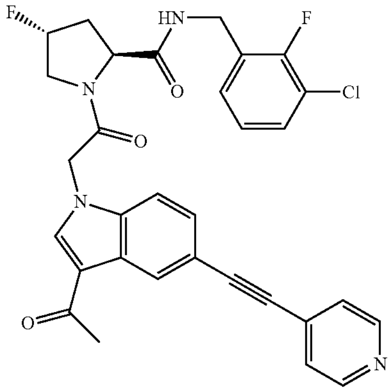 [SMILES: CC(=O)c1cn(CC(=O)N2C[C@H](F)C[C@H]2C(=O)NCc2cccc(Cl)c2F)c2ccc(C#Cc3ccncc3)cc12] | (2S,4R)-1-(2-(3-acetyl-5-(pyridin-4-ylethynyl)-1H-indol-1-yl)acetyl)-N-(3-chloro-2-fluorobenzyl)-4-fluoropyrrolidine-2-carboxamide | *** | 1.52 | 575 |
| 192 | 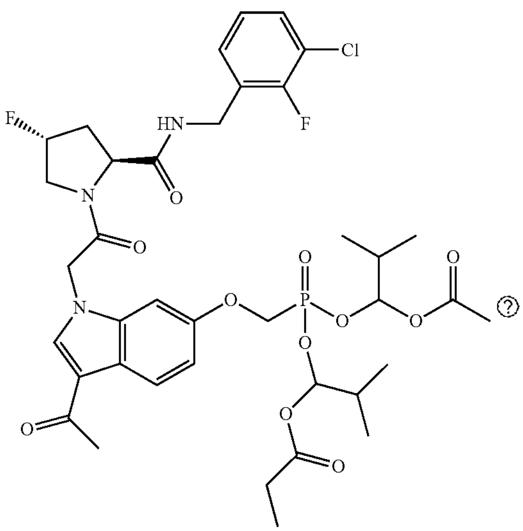 [SMILES: CCC(=O)OC(OP(=O)(COc1ccc2c(C(C)=O)cn(CC(=O)N3C[C@H](F)C[C@H]3C(=O)NCc3cccc(Cl)c3F)c2c1)OC(OC(C)=O)C(C)C)C(C)C] | (((((3-acetyl-1-(2-((2S,4R)-2-((3-chloro-2-fluorobenzyl)carbamoyl)-4-fluoropyrrolidin-1-yl)-2-oxoethyl)-1H-indol-6-yl)oxy)methyl)phosphoryl)bis(oxy))bis(2-methylpropane-1,1-diyl) dipropionate | *** | 2.79 | 840 |
| 193 | 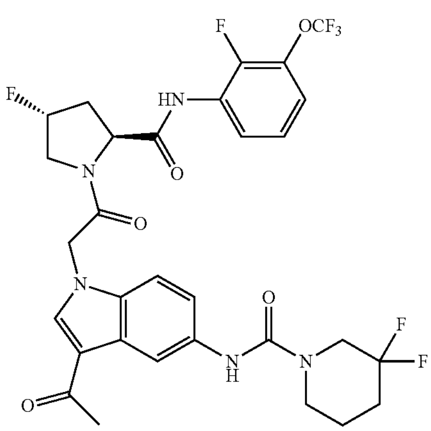 [SMILES: CC(=O)c1cn(CC(=O)N2C[C@H](F)C[C@H]2C(=O)Nc2cccc(OC(F)(F)F)c2F)c2ccc(NC(=O)N3CCCC(F)(F)C3)cc12] | N-(3-acetyl-1-(2-((2S,4R)-4-fluoro-2-((2-fluoro-3-(trifluoromethoxy)phenyl)carbamoyl)pyrrolidin-1-yl)-2-oxoethyl)-1H-indol-5-yl)-3,3-difluoropiperidine-1-carboxamide | *** | 2.06 | 672 |

| Cmp. No. | Structure | Name | IC$_{50}$ (μM) | RT min (Method 1 or 2) | M + 1 |
|---|---|---|---|---|---|
| 194 | 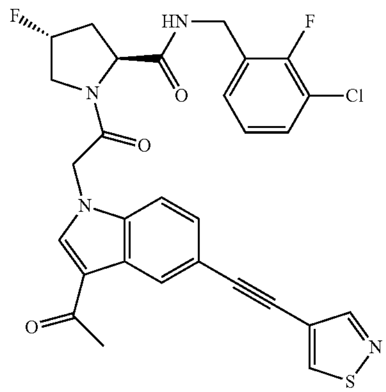 [SMILES: CC(=O)c1cn(CC(=O)N2C[C@H](F)C[C@H]2C(=O)NCc2cccc(Cl)c2F)c2ccc(C#Cc3cnsc3)cc12] | (2S,4R)-1-(2-(3-acetyl-5-(isothiazol-4-ylethynyl)-1H-indol-1-yl)acetyl)-N-(3-chloro-2-fluorobenzyl)-4-fluoropyrrolidine-2-carboxamide | *** | 2.18 | 581 |
| 195 | 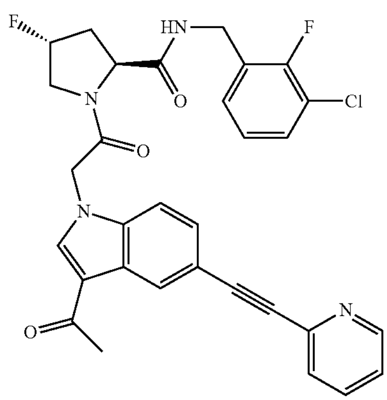 [SMILES: CC(=O)c1cn(CC(=O)N2C[C@H](F)C[C@H]2C(=O)NCc2cccc(Cl)c2F)c2ccc(C#Cc3ccccn3)cc12] | (2S,4R)-1-(2-(3-acetyl-5-(pyridin-2-ylethynyl)-1H-indol-1-yl)acetyl)-N-(3-chloro-2-fluorobenzyl)-4-fluoropyrrolidine-2-carboxamide | *** | 1.86 | 575 |
| 196 | 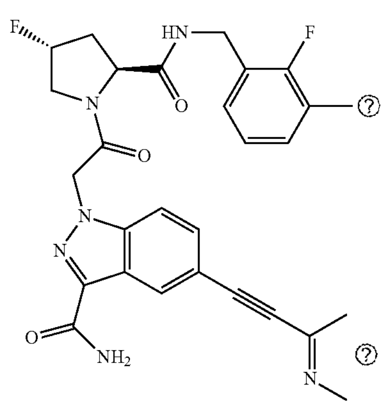 [SMILES: C/N=C(\C)C#Cc1ccc2c(c1)c(C(N)=O)nn2CC(=O)N1C[C@H](F)C[C@H]1C(=O)NCc1cccc(C)c1F] | 1-(2-((2S,4R)-2-((3-chloro-2-fluorobenzyl)carbamoyl)-4-fluoropyrrolidin-1-yl)-2-oxoethyl)-5-(2-(pyrimidin-2-yl)ethynyl)-1H-indazole-3-carboxamide | *** | 1.52 | 578 |

-continued

| Cmp. No. | Structure | Name | IC$_{50}$ (μM) | RT min (Method 1 or 2) | M + 1 |
|---|---|---|---|---|---|
| 197 | 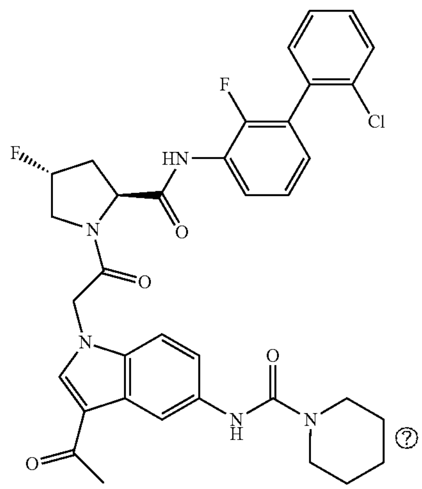 [SMILES: CC(=O)c1cn(CC(=O)N2C[C@H](F)C[C@H]2C(=O)Nc2cccc(-c3ccccc3Cl)c2F)c2ccc(NC(=O)N3CCCCC3)cc12] | N-(3-acetyl-1-(2-((2S,4R)-4-fluoro-2-((2-fluoro-3-(2-chlorophenyl)phenyl)carbamoyl)pyrrolidin-1-yl)-2-oxoethyl)-1H-indol-5-yl)-3,3-difluoropiperidine-1-carboxamide | *** | 2.25 | 698 |
| 198 | 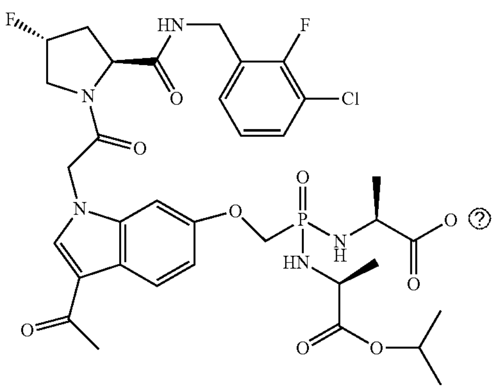 [SMILES: CC(=O)c1cn(CC(=O)N2C[C@H](F)C[C@H]2C(=O)NCc2cccc(Cl)c2F)c2cc(OCP(=O)(N[C@@H](C)C(=O)O)N[C@@H](C)C(=O)OC(C)C)ccc12] | | *** | 2.20 | 810 |
| 199 | 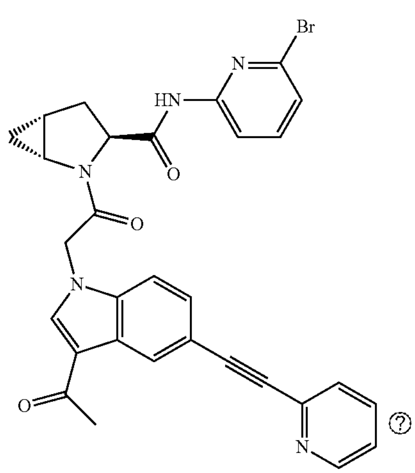 [SMILES: CC(=O)c1cn(CC(=O)N2[C@@H]3C[C@@H]3C[C@H]2C(=O)Nc2cccc(Br)n2)c2ccc(C#Cc3ccccn3)cc12] | (1R,3S,5R)-2-(2-(3-acetyl-5-(2-(pyrimidin-2-yl)ethynyl)-1H-indol-1-yl)acetyl)-N-(6-bromopyridin-2-yl)-2-aza-bicyclo[3.1.0]hexane-3-carboxamide | *** | 1.84 | 583 |

-continued

| Cmp. No. | Structure | Name | IC$_{50}$ (μM) | RT min (Method 1 or 2) | M + 1 |
|---|---|---|---|---|---|
| 200 | 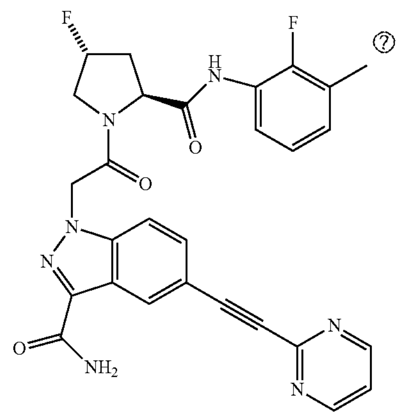 [SMILES: Cc1cccc(NC(=O)[C@@H]2C[C@@H](F)CN2C(=O)Cn2nc(C(N)=O)c3cc(C#Cc4ncccn4)ccc32)c1F] | 1-(2-((2S,4R)-4-fluoro-2-((2-fluoro-3-(2-chlorophenyl)phenyl)carbamoyl)pyrrolidin-1-yl)-2-oxoethyl)-5-(2-(pyrimidin-2-yl)ethynyl)-1H-indazole-3-carboxamide | *** | 1.99 | 640 |
| 201 | 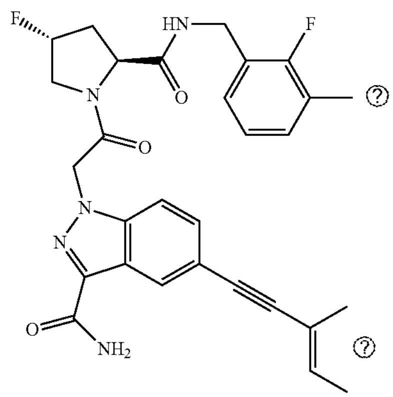 [SMILES: C/C=C(\C)C#Cc1ccc2c(c1)c(C(N)=O)nn2CC(=O)N1C[C@H](F)C[C@H]1C(=O)NCc1cccc(C)c1F] | 1-(2-((2S,4R)-2-((3-chloro-2-fluorobenzyl)carbamoyl)-4-fluoropyrrolidin-1-yl)-2-oxoethyl)-5-(2-(pyridin-2-yl)ethynyl)-1H-indazole-3-carboxamide | *** | 1.66 | 577 |
| 202 | 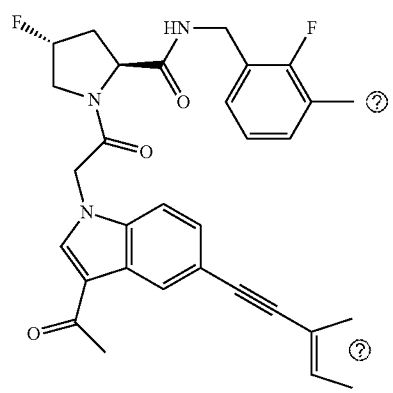 [SMILES: C/C=C(\C)C#Cc1ccc2c(c1)c(C(C)=O)cn2CC(=O)N1C[C@H](F)C[C@H]1C(=O)NCc1cccc(C)c1F] | (2S,4R)-N-(3-chloro-2-fluorobenzyl)-1-(2-(3-acetyl-5-(2-(3-cyano-1H-pyrazol-4-yl)ethynyl)-1H-indol-1-yl)acetyl)-4-fluoropyrrolidine-2-carboxamide | *** | 1.84 | 589 |
| 203 | 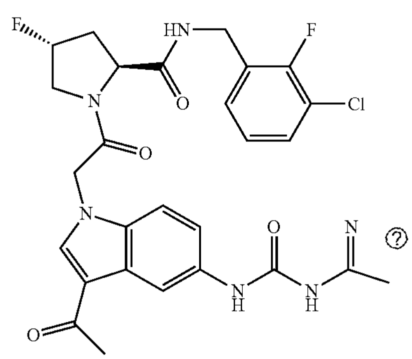 [SMILES: CC(=N)NC(=O)Nc1ccc2c(c1)c(C(C)=O)cn2CC(=O)N1C[C@H](F)C[C@H]1C(=O)NCc1cccc(Cl)c1F] | 1-(1-(2-((2S,4R)-2-((3-chloro-2-fluorobenzyl)carbamoyl)-4-fluoropyrrolidin-1-yl)-2-oxoethyl)-3-acetyl-1H-indol-5-yl)-3-(isoxazol-3-yl)urea | *** | 1.60 | 599 |

-continued

| Cmp. No. | Structure | Name | IC$_{50}$ (μM) | RT min (Method 1 or 2) | M + 1 |
|---|---|---|---|---|---|
| 204 | 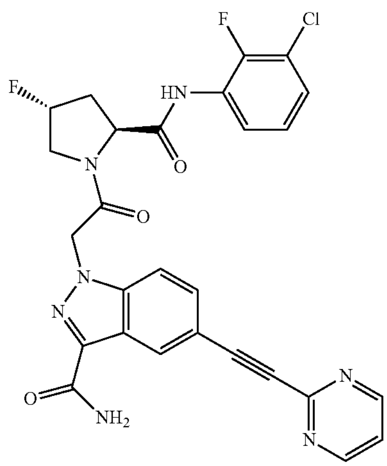 [SMILES: NC(=O)c1nn(CC(=O)N2C[C@H](F)C[C@H]2C(=O)Nc2cccc(Cl)c2F)c2ccc(C#Cc3ncccn3)cc12] | 1-(2-((2S,4R)-2-((3-chloro-2-fluorophenyl)carbamoyl)-4-fluoropyrrolidin-1-yl)-2-oxoethyl)-5-(pyrimidin-2-ylethynyl)-1H-indazole-3-carboxamide | *** | 1.56 | 564 |
| 205 | 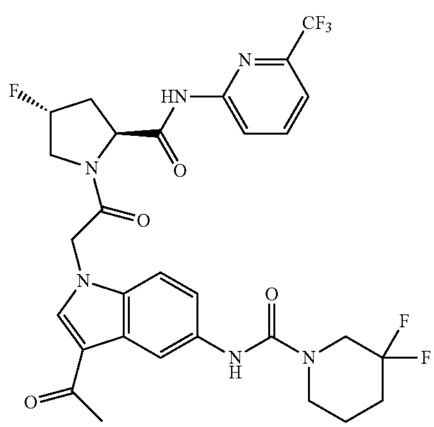 [SMILES: CC(=O)c1cn(CC(=O)N2C[C@H](F)C[C@H]2C(=O)Nc2cccc(C(F)(F)F)n2)c2ccc(NC(=O)N3CCCC(F)(F)C3)cc12] | N-(3-acetyl-1-(2-((2S,4R)-4-fluoro-2-((6-(trifluoromethyl)pyridin-2-yl)carbamoyl)pyrrolidin-1-yl)-2-oxoethyl)-1H-indol-5-yl)-3,3-difluoropiperidine-1-carboxamide | *** | 1.89 | 639 |
| 206 | 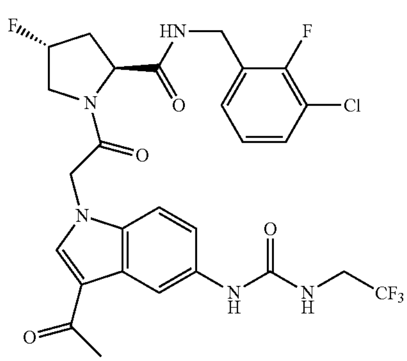 [SMILES: CC(=O)c1cn(CC(=O)N2C[C@H](F)C[C@H]2C(=O)NCc2cccc(Cl)c2F)c2ccc(NC(=O)NCC(F)(F)F)cc12] | (2S,4R)-1-(2-(3-acetyl-5-(3-(2,2,2-trifluoroethyl)ureido)-1H-indol-1-yl)acetyl)-N-(3-chloro-2-fluorobenzyl)-4-fluoropyrrolidine-2-carboxamide | *** | 1.72 | 614 |

| Cmp. No. | Structure | Name | IC$_{50}$ (μM) | RT min (Method 1 or 2) | M + 1 |
|---|---|---|---|---|---|
| 207 | 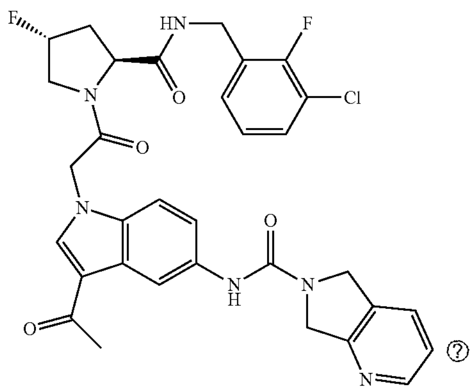 [SMILES: CC(=O)c1cn(CC(=O)N2C[C@H](F)C[C@H]2C(=O)NCc2cccc(Cl)c2F)c2ccc(NC(=O)N3Cc4cccnc4C3)cc12] | N-(3-acetyl-1-(2-((2S,4R)-2-((3-chloro-2-fluorobenzyl)carbamoyl)-4-fluoropyrrolidin-1-yl)-2-oxoethyl)-1H-indol-5-yl)-5H-pyrrolo[3,4-d]pyrimidine-6(7H)-carboxamide | *** | 1.38 | 636 |
| 208 | 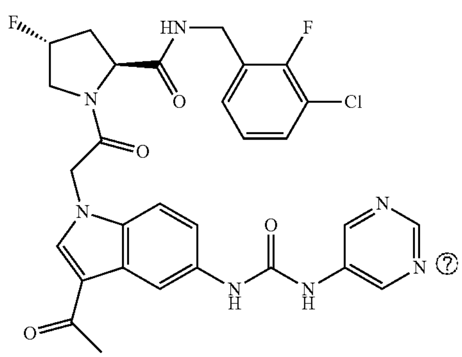 [SMILES: CC(=O)c1cn(CC(=O)N2C[C@H](F)C[C@H]2C(=O)NCc2cccc(Cl)c2F)c2ccc(NC(=O)Nc3cncnc3)cc12] | (2S,4R)-1-(2-(3-acetyl-5-(3-(pyrimidin-5-yl)ureido)-1H-indol-1-yl)acetyl)-N-(3-chloro-2-fluorobenzyl)-4-fluoropyrrolidine-2-carboxamide | *** | 1.4 | 610 |
| 209 | 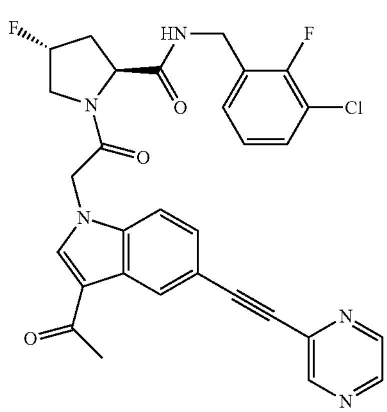 [SMILES: CC(=O)c1cn(CC(=O)N2C[C@H](F)C[C@H]2C(=O)NCc2cccc(Cl)c2F)c2ccc(C#Cc3cnccn3)cc12] | (2S,4R)-1-(2-(3-acetyl-5-(pyrazin-2-ylethynyl)-1H-indol-1-yl)acetyl)-N-(3-chloro-2-fluorobenzyl)-4-fluoropyrrolidine-2-carboxamide | *** | 1.86 | 576 |

| Cmp. No. | Structure | Name | IC$_{50}$ (μM) | RT min (Method 1 or 2) | M + 1 |
|---|---|---|---|---|---|
| 210 | 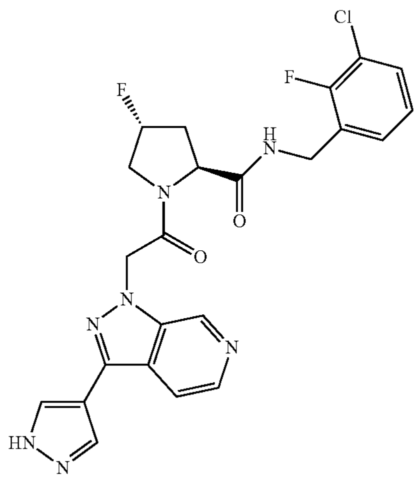 [SMILES: O=C(NCc1cccc(Cl)c1F)[C@@H]1C[C@@H](F)CN1C(=O)Cn1nc(-c2cn[nH]c2)c2ccncc21] | (2S,4R)-1-(2-(3-(1H-pyrazol-4-yl)-1H-pyrazolo[3,4-c]pyridin-1-yl)acetyl)-N-(3-chloro-2-fluorobenzyl)-4-fluoropyrrolidine-2-carboxamide | *** | 1.0 | 500 |
| 211 | 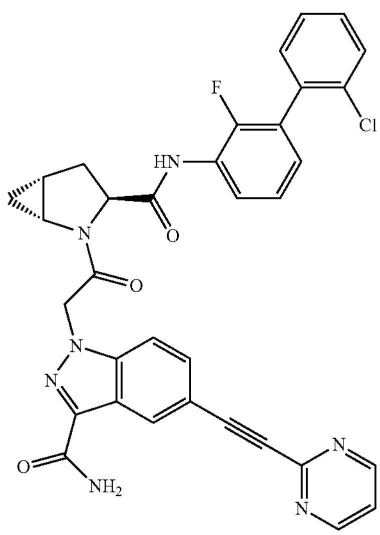 [SMILES: NC(=O)c1nn(CC(=O)N2[C@@H]3C[C@@H]3C[C@H]2C(=O)Nc2cccc(-c3ccccc3Cl)c2F)c2ccc(C#Cc3ncccn3)cc12] | 1-(2-((1R,3S,5R)-3-((2'-chloro-2-fluoro-[1,1'-biphenyl]-3-yl)carbamoyl)-2-azabicyclo[3.1.0]hexan-2-yl)-2-oxoethyl)-5-(pyrimidin-2-ylethynyl)-1H-indazole-3-carboxamide | *** | 2.1 | 634 |
| 212 | 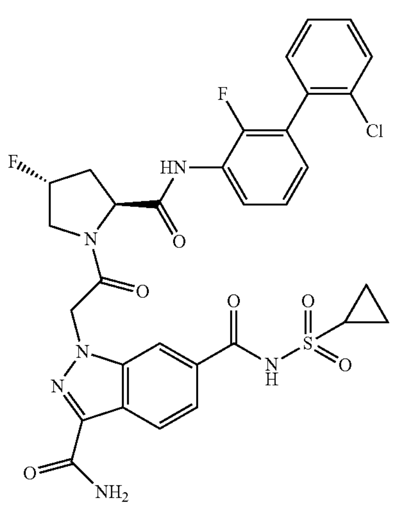 [SMILES: NC(=O)c1nn(CC(=O)N2C[C@H](F)C[C@H]2C(=O)Nc2cccc(-c3ccccc3Cl)c2F)c2cc(C(=O)NS(=O)(=O)C3CC3)ccc12] | 1-(2-((2S,4R)-2-((2'-chloro-2-fluoro-[1,1'-biphenyl]-3-yl)carbamoyl)-4-fluoropyrrolidin-1-yl)-2-oxoethyl)-N6-(cyclopropylsulfonyl)-1H-indazole-3,6-dicarboxamide | *** | 2.0 | 685 |

| Cmp. No. | Structure | Name | IC$_{50}$ (μM) | RT min (Method 1 or 2) | M + 1 |
|---|---|---|---|---|---|
| 213 | 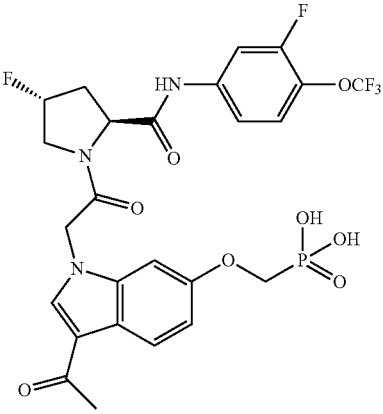 [SMILES: CC(=O)c1cn(CC(=O)N2C[C@H](F)C[C@H]2C(=O)Nc2ccc(OC(F)(F)F)c(F)c2)c2cc(OCP(=O)(O)O)ccc12] | (((3-acetyl-1-(2-((2S,4R)-4-fluoro-2-((3-fluoro-4-(trifluoromethoxy)phenyl)carbamoyl)pyrrolidin-1-yl)-2-oxoethyl)-1H-indol-6-yl)oxy)methyl)phosphonic acid | *** | 1.46 | 620 |
| 214 | 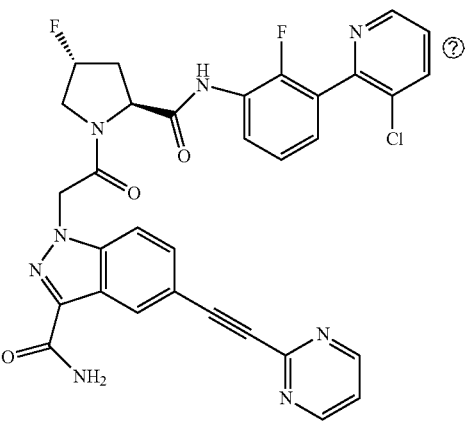 [SMILES: NC(=O)c1nn(CC(=O)N2C[C@H](F)C[C@H]2C(=O)Nc2cccc(-c3ncccc3Cl)c2F)c2ccc(C#Cc3ncccn3)cc12] | 1-(2-((2S,4R)-2-((3-(3-chloropyridin-2-yl)-2-fluorophenyl)carbamoyl)-4-fluoropyrrolidin-1-yl)-2-oxoethyl)-5-(pyrimidin-2-ylethynyl)-1H-indazole-3-carboxamide | *** | 1.54 | 641 |
| 215 | 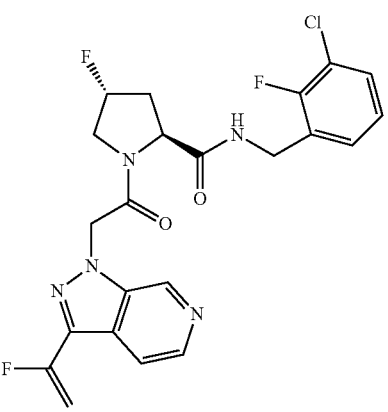 [SMILES: C=C(F)c1nn(CC(=O)N2C[C@H](F)C[C@H]2C(=O)NCc2cccc(Cl)c2F)c2cnccc12] | (2S,4R)-N-(3-chloro-2-fluorobenzyl)-4-fluoro-1-(2-(3-(1-fluorovinyl)-1H-pyrazolo[3,4-c]pyridin-1-yl)acetyl)pyrrolidine-2-carboxamide | *** | 1.61 | 478 |

-continued

| Cmp. No. | Structure | Name | IC$_{50}$ (μM) | RT min (Method 1 or 2) | M + 1 |
|---|---|---|---|---|---|
| 216 | 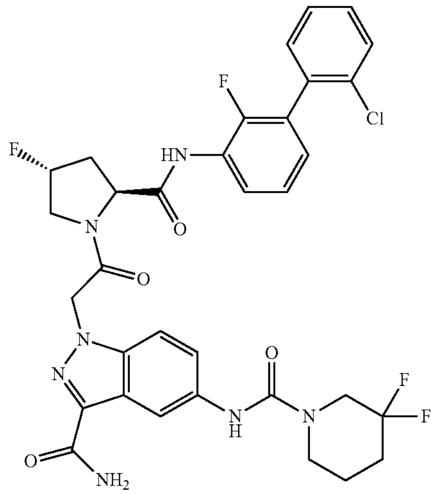 [SMILES: NC(=O)c1nn(CC(=O)N2C[C@H](F)C[C@H]2C(=O)Nc2cccc(-c3ccccc3Cl)c2F)c2ccc(NC(=O)N3CCCC(F)(F)C3)cc12] | 1-(2-((2S,4R)-2-((2'-chloro-2-fluoro-[1,1'-biphenyl]-3-yl)carbamoyl)-4-fluoropyrrolidin-1-yl)-2-oxoethyl)-5-(3,3-difluoropiperidine-1-carboxamido)-1H-indazole-3-carboxamide | *** | 2.09 | 700 |
| 217 | 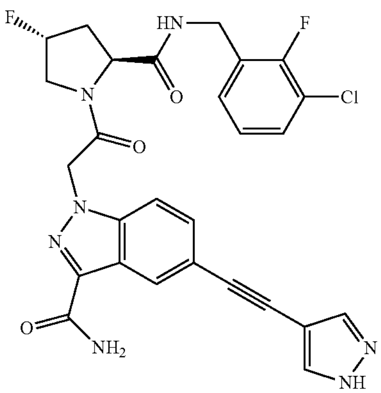 [SMILES: NC(=O)c1nn(CC(=O)N2C[C@H](F)C[C@H]2C(=O)NCc2cccc(Cl)c2F)c2ccc(C#Cc3cn[nH]c3)cc12] | 5-((1H-pyrazol-4-yl)ethynyl)-1-(2-((2S,4R)-2-((3-chloro-2-fluorobenzyl)carbamoyl)-4-fluoropyrrolidin-1-yl)-2-oxoethyl)-1H-indazole-3-carboxamide | *** | 1.49 | 566 |
| 218 | 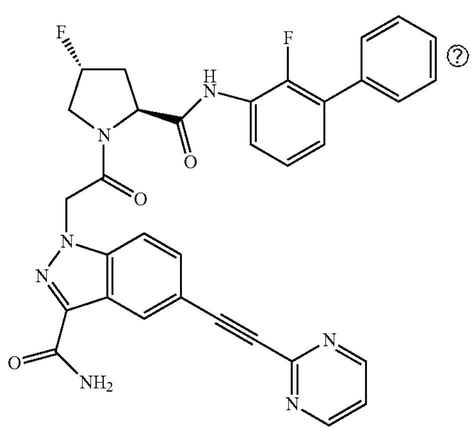 [SMILES: NC(=O)c1nn(CC(=O)N2C[C@H](F)C[C@H]2C(=O)Nc2cccc(-c3ccccc3)c2F)c2ccc(C#Cc3ncccn3)cc12] | 1-(2-((2S,4R)-2-((3'-chloro-2-fluoro-[1,1'-biphenyl]-3-yl)carbamoyl)-4-fluoropyrrolidin-1-yl)-2-oxoethyl)-5-(pyrimidin-2-ylethynyl)-1H-indazole-3-carboxamide | *** | 2.1 | 640 |

| Cmp. No. | Structure | Name | IC$_{50}$ (μM) | RT min (Method 1 or 2) | M + 1 |
|---|---|---|---|---|---|
| 219 | 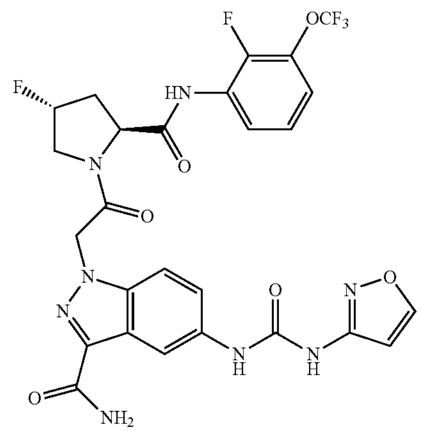 [SMILES: NC(=O)c1nn(CC(=O)N2C[C@H](F)C[C@H]2C(=O)Nc2cccc(OC(F)(F)F)c2F)c2ccc(NC(=O)Nc3ccon3)cc12] | 1-(2-((2S,4R)-4-fluoro-2-((2-fluoro-3-(trifluoromethoxy)phenyl)carbamoyl)pyrrolidin-1-yl)-2-oxoethyl)-5-(3-(isoxazol-3-yl)ureido)-1H-indazole-3-carboxamide | *** | 1.71 | 637 |
| 220 | 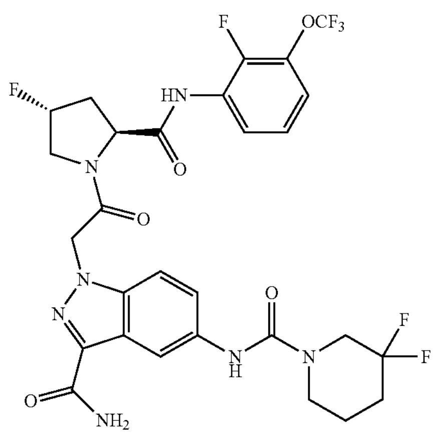 [SMILES: NC(=O)c1nn(CC(=O)N2C[C@H](F)C[C@H]2C(=O)Nc2cccc(OC(F)(F)F)c2F)c2ccc(NC(=O)N3CCCC(F)(F)C3)cc12] | 5-(3,3-difluoropiperidine-1-carboxamido)-1-(2-((2S,4R)-4-fluoro-2-((2-fluoro-3-(trifluoromethoxy)phenyl)carbamoyl)pyrrolidin-1-yl)-2-oxoethyl)-1H-indazole-3-carboxamide | *** | 1.90 | 674 |
| 221 | 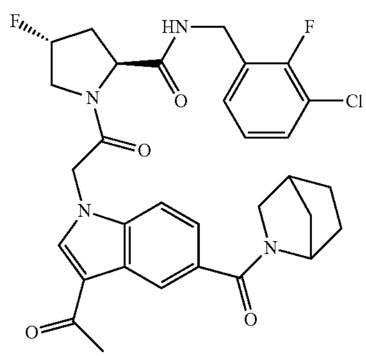 [SMILES: CC(=O)c1cn(CC(=O)N2C[C@H](F)C[C@H]2C(=O)NCc2cccc(Cl)c2F)c2ccc(C(=O)N3CC4CCC3C4)cc12] | (2S,4R)-1-(2-(3-acetyl-5-(2-azabicyclo[2.2.1]heptane-2-carbonyl)-1H-indol-1-yl)acetyl)-N-(3-chloro-2-fluorobenzyl)-4-fluoropyrrolidine-2-carboxamide | *** | 1.76 | 597 |
| 222 | 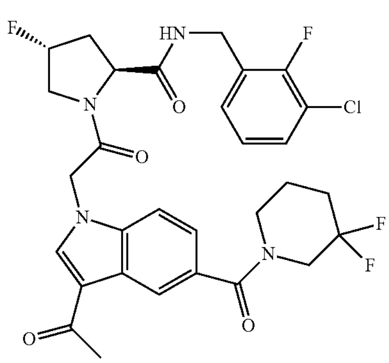 [SMILES: CC(=O)c1cn(CC(=O)N2C[C@H](F)C[C@H]2C(=O)NCc2cccc(Cl)c2F)c2ccc(C(=O)N3CCCC(F)(F)C3)cc12] | (2S,4R)-1-(2-(3-acetyl-5-(3,3-difluoropiperidine-1-carbonyl)-1H-indol-1-yl)acetyl)-N-(3-chloro-2-fluorobenzyl)-4-fluoropyrrolidine-2-carboxamide | *** | 1.83 | 621 |

| Cmp. No. | Structure | Name | IC$_{50}$ (μM) | RT min (Method 1 or 2) | M + 1 |
|---|---|---|---|---|---|
| 223 | 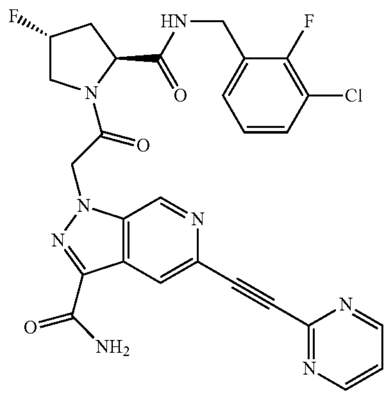 [SMILES: NC(=O)c1nn(CC(=O)N2C[C@H](F)C[C@H]2C(=O)NCc2cccc(Cl)c2F)c2cnc(C#Cc3ncccn3)cc12] | 1-(2-((2S,4R)-2-((3-chloro-2-fluorobenzyl)carbamoyl)-4-fluoropyrrolidin-1-yl)-2-oxoethyl)-5-(pyrimidin-2-ylethynyl)-1H-pyrazolo[3,4-c]pyridine-3-carboxamide | *** | 1.32 | 579 |
| 224 | 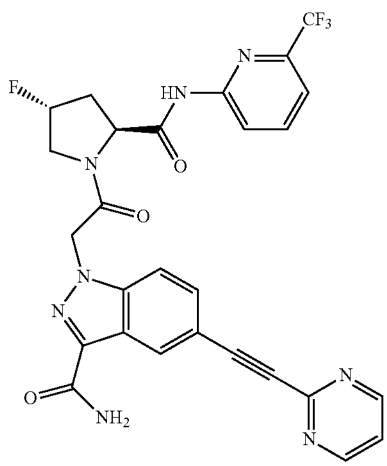 [SMILES: NC(=O)c1nn(CC(=O)N2C[C@H](F)C[C@H]2C(=O)Nc2cccc(C(F)(F)F)n2)c2ccc(C#Cc3ncccn3)cc12] | 1-(2-((2S,4R)-4-fluoro-2-((6-(trifluoromethyl)pyridin-2-yl)carbamoyl)pyrrolidin-1-yl)-2-oxoethyl)-5-(pyrimidin-2-ylethynyl)-1H-indazole-3-carboxamide | *** | 1.61 | 581 |
| 225 | 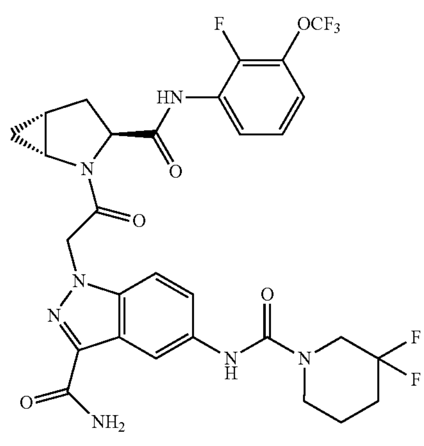 [SMILES: NC(=O)c1nn(CC(=O)N2[C@@H]3C[C@@H]3C[C@H]2C(=O)Nc2cccc(OC(F)(F)F)c2F)c2ccc(NC(=O)N3CCCC(F)(F)C3)cc12] | 5-(3,3-difluoropiperidine-1-carboxamido)-1-(2-((1R,3S,5R)-3-((2-fluoro-3-(trifluoromethoxy)phenyl)carbamoyl)-2-azabicyclo[3.1.0]hexan-2-yl)-2-oxoethyl)-1H-indazole-3-carboxamide | *** | 1.97 | 668 |

| Cmp. No. | Structure | Name | IC$_{50}$ (μM) | RT min (Method 1 or 2) | M + 1 |
|---|---|---|---|---|---|
| 226 | 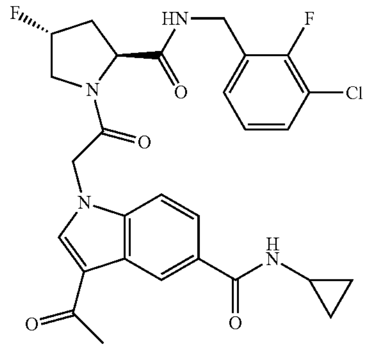 [SMILES: CC(=O)c1cn(CC(=O)N2C[C@H](F)C[C@H]2C(=O)NCc2cccc(Cl)c2F)c2ccc(C(=O)NC3CC3)cc12] | 3-acetyl-1-(2-((2S,4R)-2-((3-chloro-2-fluorobenzyl)carbamoyl)-4-fluoropyrrolidin-1-yl)-2-oxoethyl)-N-cyclopropyl-1H-indole-5-carboxamide | *** | 1.54 | 557 |
| 227 | 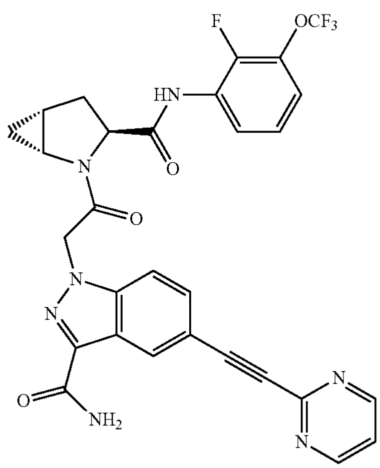 [SMILES: NC(=O)c1nn(CC(=O)N2[C@@H]3C[C@@H]3C[C@H]2C(=O)Nc2cccc(OC(F)(F)F)c2F)c2ccc(C#Cc3ncccn3)cc12] | 1-(2-((1R,3S,5R)-3-((2-fluoro-3-(trifluoromethoxy)phenyl)carbamoyl)-2-azabicyclo[3.1.0]hexan-2-yl)-2-oxoethyl)-5-(pyrimidin-2-ylethynyl)-1H-indazole-3-carboxamide | *** | 1.87 | 608 |
| 228 | 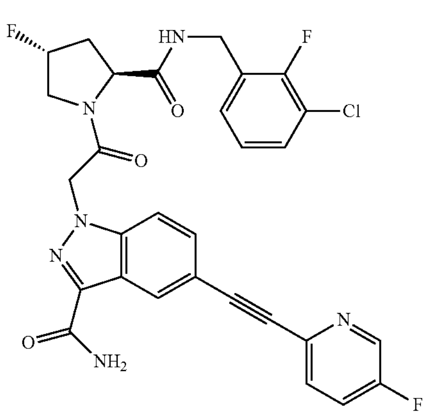 [SMILES: NC(=O)c1nn(CC(=O)N2C[C@H](F)C[C@H]2C(=O)NCc2cccc(Cl)c2F)c2ccc(C#Cc3ccc(F)cn3)cc12] | 1-(2-((2S,4R)-2-((3-chloro-2-fluorobenzyl)carbamoyl)-4-fluoropyrrodin-1-yl)-2-oxoethyl)-5-((5-fluoropyridin-2-yl)ethynyl)-1H-indazole-3-carboxamide | *** | 1.91 | 595 |

| Cmp. No. | Structure | Name | IC$_{50}$ (μM) | RT min (Method 1 or 2) | M + 1 |
|---|---|---|---|---|---|
| 229 | 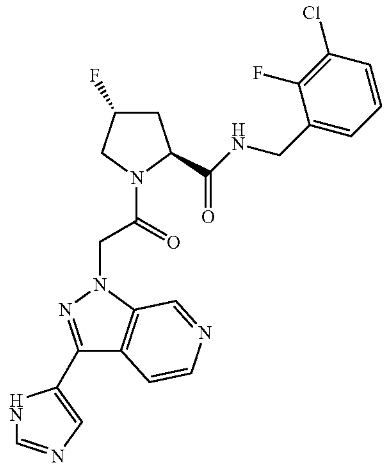 [SMILES: O=C(NCc1cccc(Cl)c1F)[C@@H]1C[C@@H](F)CN1C(=O)Cn1nc(-c2cnc[nH]2)c2ccncc21] | (2S,4R)-1-(2-(3-(1H-imidazol-5-yl)-1H-pyrazolo[3,4-c]pyridin-1-yl)acetyl)-N-(3-chloro-2-fluorobenzyl)-4-fluoropyrrolidine-2-carboxamide | *** | 0.86 | 500 |
| 230 | 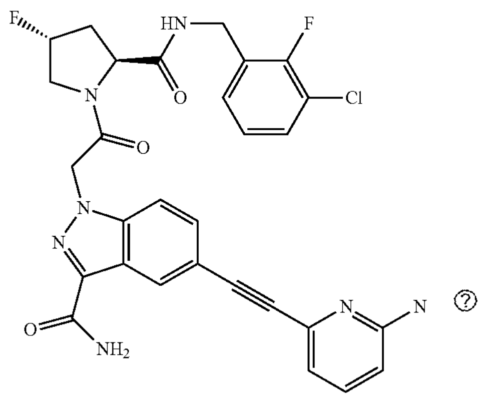 [SMILES: NC(=O)c1nn(CC(=O)N2C[C@H](F)C[C@H]2C(=O)NCc2cccc(Cl)c2F)c2ccc(C#Cc3cccc(N)n3)cc12] | 5-((6-aminopyridin-2-yl)ethynyl)-1-(2-((2S,4R)-2-((3-chloro-2-fluorobenzyl)carbamoyl)-4-fluoropyrrolidin-1-yl)-2-oxoethyl)-1H-indazole-3-carboxamide | *** | 1.27 | 592 |
| 231 | 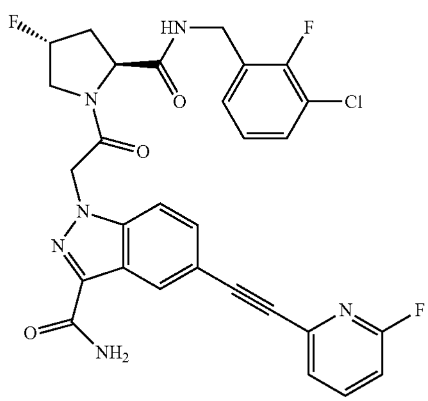 [SMILES: NC(=O)c1nn(CC(=O)N2C[C@H](F)C[C@H]2C(=O)NCc2cccc(Cl)c2F)c2ccc(C#Cc3cccc(F)n3)cc12] | 1-(2-((2S,4R)-2-((3-chloro-2-fluorobenzyl)carbamoyl)-4-fluoropyrrolidin-1-yl)-2-oxoethyl)-5-((6-fluoropyridin-2-yl)ethynyl)-1H-indazole-3-carboxamide | *** | 1.96 | 595 |

| Cmp. No. | Structure | Name | IC$_{50}$ (μM) | RT min (Method 1 or 2) | M + 1 |
|---|---|---|---|---|---|
| 232 | 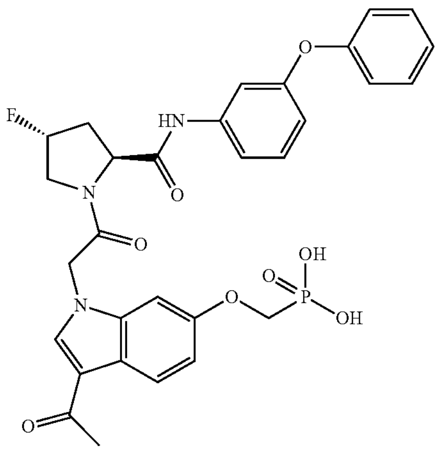 [SMILES: CC(=O)c1cn(CC(=O)N2C[C@H](F)C[C@H]2C(=O)Nc2cccc(Oc3ccccc3)c2)c2cc(OCP(=O)(O)O)ccc12] | (((3-acetyl-1-(2-((2S,4R)-4-fluoro-2-((3-phenoxyphenyl)carbamoyl)pyrrolidin-1-yl)-2-oxoethyl)-1H-indol-6-yl)oxy)methyl)phosphonic acid | ** | 1.51 | 610 |
| 233 | 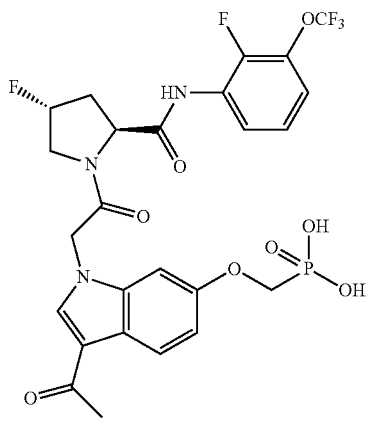 [SMILES: CC(=O)c1cn(CC(=O)N2C[C@H](F)C[C@H]2C(=O)Nc2cccc(OC(F)(F)F)c2F)c2cc(OCP(=O)(O)O)ccc12] | (((3-acetyl-1-(2-((2S,4R)-4-fluoro-2-((2-fluoro-3-(trifluoromethoxy)phenyl)carbamoyl)pyrrolidin-1-yl)-2-oxoethyl)-1H-indol-6-yl)oxy)methyl)phosphonic acid | *** | 1.34 | 620 |
| 234 | 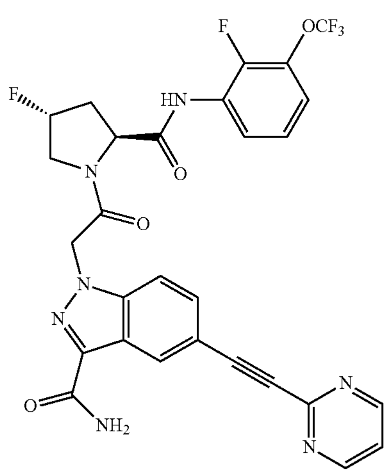 [SMILES: NC(=O)c1nn(CC(=O)N2C[C@H](F)C[C@H]2C(=O)Nc2cccc(OC(F)(F)F)c2F)c2ccc(C#Cc3ncccn3)cc12] | 1-(2-((2S,4R)-4-fluoro-2-((2-fluoro-3-(trifluoromethoxy)phenyl)carbamoyl)pyrrolidin-1-yl)-2-oxoethyl)-5-(pyrimidin-2-ylethynyl)-1H-indazole-3-carboxamide | *** | 1.77 | 614 |

| Cmp. No. | Structure | Name | IC$_{50}$ (μM) | RT min (Method 1 or 2) | M + 1 |
|---|---|---|---|---|---|
| 235 | 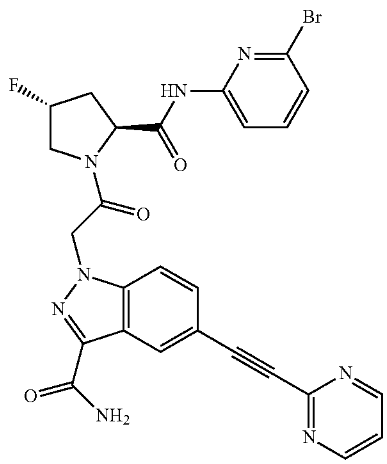 [SMILES: NC(=O)c1nn(CC(=O)N2C[C@H](F)C[C@H]2C(=O)Nc2cccc(Br)n2)c2ccc(C#Cc3ncccn3)cc12] | 1-(2-((2S,4R)-2-((6-bromopyridin-2-yl)carbamoyl)-4-fluoropyrrolidin-1-yl)-2-oxoethyl)-5-(pyrimidin-2-ylethynyl)-1H-indazole-3-carboxamide | *** | 1.48 | 591 |
| 236 | 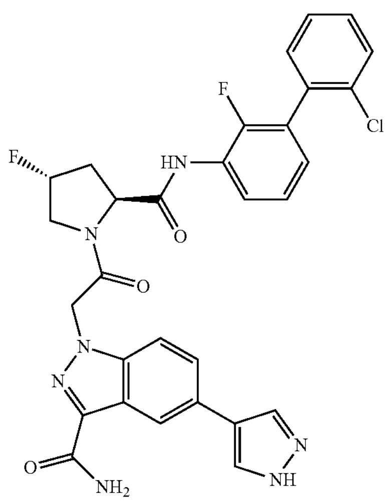 [SMILES: NC(=O)c1nn(CC(=O)N2C[C@H](F)C[C@H]2C(=O)Nc2cccc(-c3ccccc3Cl)c2F)c2ccc(-c3cn[nH]c3)cc12] | 1-(2-((2S,4R)-2-((2'-chloro-2-fluoro-[1,1'-biphenyl]-3-yl)carbamoyl)-4-fluoropyrrolidin-1-yl)-2-oxoethyl)-5-(1H-pyrazol-4-yl)-1H-indazole-3-carboxamide | *** | 1.79 | 604 |
| 237 | 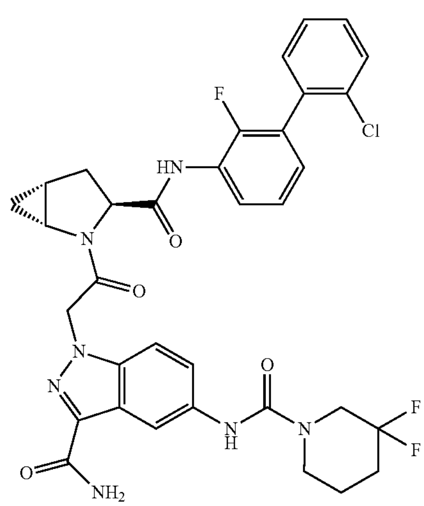 [SMILES: NC(=O)c1nn(CC(=O)N2[C@@H]3C[C@@H]3C[C@H]2C(=O)Nc2cccc(-c3ccccc3Cl)c2F)c2ccc(NC(=O)N3CCCC(F)(F)C3)cc12] | 1-(2-((1R,3S,5R)-3-((2'-chloro-2-fluoro-[1,1'-biphenyl]-3-yl)carbamoyl)-2-azabicyclo[3.1.0]hexan-2-yl)-2-oxoethyl)-5-(3,3-difluoropiperidine-1-carboxamido)-1H-indazole-3-carboxamide | *** | 2.17 | 694 |

| Cmp. No. | Structure | Name | IC$_{50}$ (μM) | RT min (Method 1 or 2) | M + 1 |
|---|---|---|---|---|---|
| 238 | 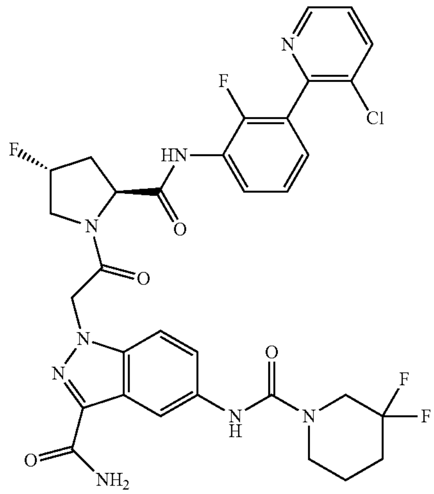 [SMILES: NC(=O)c1nn(CC(=O)N2C[C@H](F)C[C@H]2C(=O)Nc2cccc(-c3ncccc3Cl)c2F)c2ccc(NC(=O)N3CCCC(F)(F)C3)cc12] | 1-(2-((2S,4R)-2-((3-(3-chloropyridin-2-yl)-2-fluorophenyl)carbamoyl)-4-fluoropyrrolidin-1-yl)-2-oxoethyl)-5-(3,3-difluoropiperidine-1-carboxamido)-1H-indazole-3-carboxamide | *** | 1.65 | 701 |
| 239 | 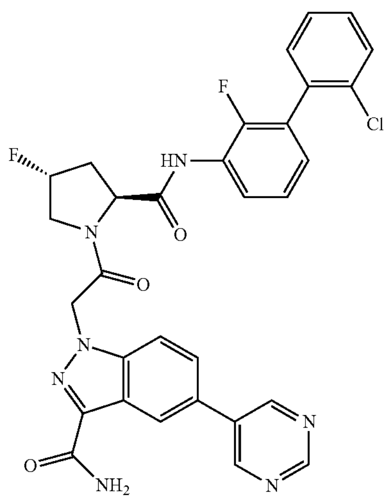 [SMILES: NC(=O)c1nn(CC(=O)N2C[C@H](F)C[C@H]2C(=O)Nc2cccc(-c3ccccc3Cl)c2F)c2ccc(-c3cncnc3)cc12] | 1-(2-((2S,4R)-2-((2'-chloro-2-fluoro-[1,1'-biphenyl]-3-yl)carbamoyl)-4-fluoropyrrolidin-1-yl)-2-oxoethyl)-5-(pyrimidin-5-yl)-1H-indazole-3-carboxamide | *** | 1.82 | 616 |
| 240 | 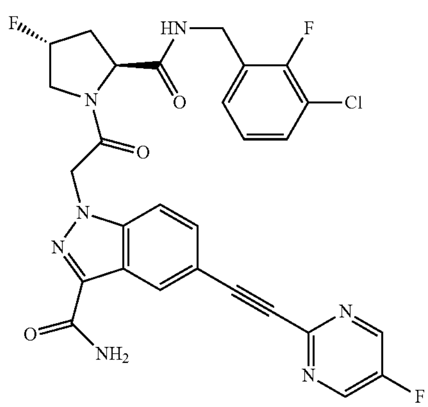 | 1-(2-((2S,4R)-2-((3-chloro-2-fluorobenzyl)carbamoyl)-4-fluoropyrrolidin-1-yl)-2-oxoethyl)-5-((5-fluoropyrimidin-2-yl)ethynyl)-1H-indazole-3-carboxamide | *** | 1.73 | 596 |

| Cmp. No. | Structure | Name | IC$_{50}$ (μM) | RT min (Method 1 or 2) | M + 1 |
|---|---|---|---|---|---|
| 241 | 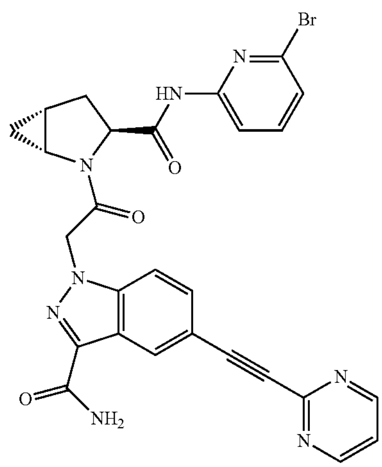 [SMILES: NC(=O)c1nn(CC(=O)N2[C@@H]3C[C@@H]3C[C@H]2C(=O)Nc2cccc(Br)n2)c2ccc(C#Cc3ncccn3)cc12] | 1-(2-((1R,3S,5R)-3-((6-bromopyridin-2-yl)carbamoyl)-2-azabicyclo[3.1.0]hexan-2-yl)-2-oxoethyl)-5-(pyrimidin-2-ylethynyl)-1H-indazole-3-carboxamide | *** | 1.6 | 585 |
| 242 | 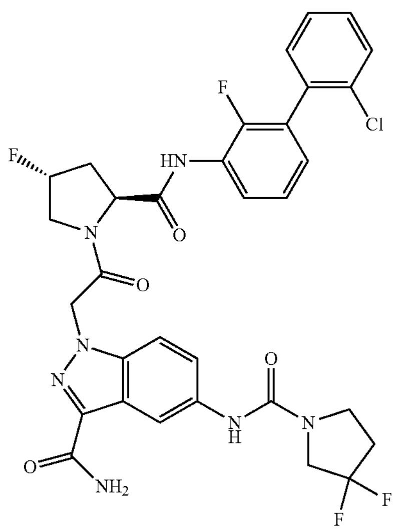 [SMILES: NC(=O)c1nn(CC(=O)N2C[C@H](F)C[C@H]2C(=O)Nc2cccc(-c3ccccc3Cl)c2F)c2ccc(NC(=O)N3CCC(F)(F)C3)cc12] | 1-(2-((2S,4R)-2-((2'-chloro-2-fluoro-[1,1'-biphenyl]-3-yl)carbamoyl)-4-fluoropyrrolidin-1-yl)-2-oxoethyl)-5-(3,3-difluoropyrrolidine-1-carboxamido)-1H-indazole-3-carboxamide | *** | 2.03 | 686 |
| 243 | 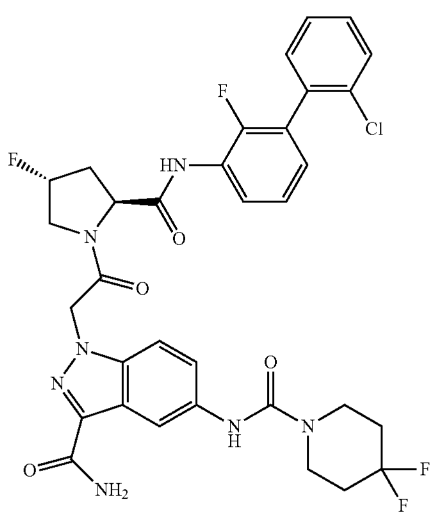 [SMILES: NC(=O)c1nn(CC(=O)N2C[C@H](F)C[C@H]2C(=O)Nc2cccc(-c3ccccc3Cl)c2F)c2ccc(NC(=O)N3CCC(F)(F)CC3)cc12] | 1-(2-((2S,4R)-2-((2'-chloro-2-fluoro-[1,1'-biphenyl]-3-yl)carbamoyl)-4-fluoropyrrolidin-1-yl)-2-oxoethyl)-5-(3,3-difluoropyrrolidine-1-carboxamido)-1H-indazole-3-carboxamide | *** | 2.11 | 700 |

-continued

| Cmp. No. | Structure | Name | IC$_{50}$ (μM) | RT min (Method 1 or 2) | M + 1 |
|---|---|---|---|---|---|
| 244 | 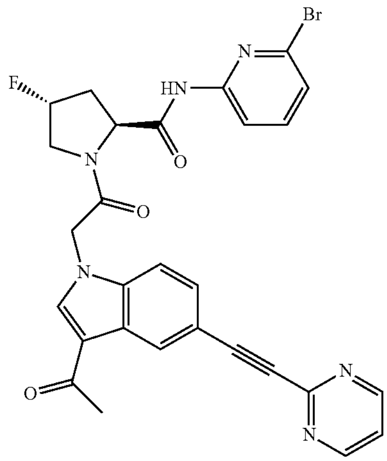 [SMILES: CC(=O)c1cn(CC(=O)N2C[C@H](F)C[C@H]2C(=O)Nc2cccc(Br)n2)c2ccc(C#Cc3ncccn3)cc12] | (2S,4R)-1-(2-(3-acetyl-5-(pyrimidin-2-ylethynyl)-1H-indol-1-yl)acetyl)-N-(6-bromopyridin-2-yl)-4-fluoropyrrolidine-2-carboxamide | *** | 1.70 | 589 |
| 245 | 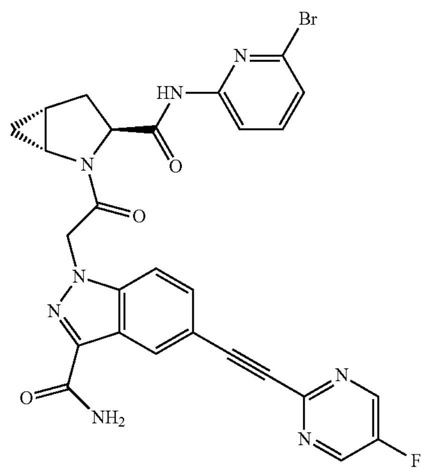 [SMILES: NC(=O)c1nn(CC(=O)N2[C@@H]3C[C@@H]3C[C@H]2C(=O)Nc2cccc(Br)n2)c2ccc(C#Cc3ncc(F)cn3)cc12] | 1-(2-((1R,3S,5R)-3-((6-bromopyridin-2-yl)carbamoyl)-2-azabicyclo[3.1.0]hexan-2-yl)-2-oxoethyl)-5((5-fluoropyrimidin-2-yl)ethynyl)-1H-indazole-3-carboxamide | *** | 1.81 | 603 |
| 246 | 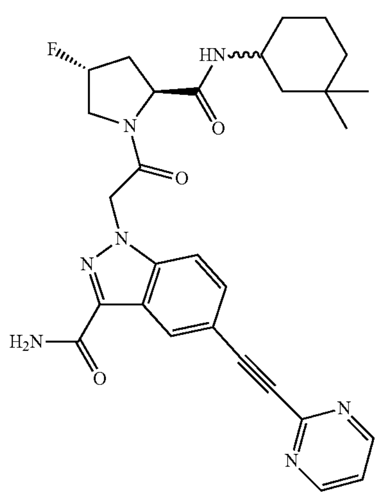 [SMILES: CC1(C)CCCC(NC(=O)[C@@H]2C[C@@H](F)CN2C(=O)Cn2nc(C(N)=O)c3cc(C#Cc4ncccn4)ccc32)C1] | 1-(2-((2S,4R)-2-((3,3-dimethylcyclohexyl)carbamoyl)-4-fluoropyrrolidin-1-yl)-2-oxoethyl)-5-(pyrimidin-2-ylethynyl)-1H-indazole-3-carboxamide | *** | 1.69 | 546 |

| Cmp. No. | Structure | Name | IC$_{50}$ (μM) | RT min (Method 1 or 2) | M + 1 |
|---|---|---|---|---|---|
| 247 | 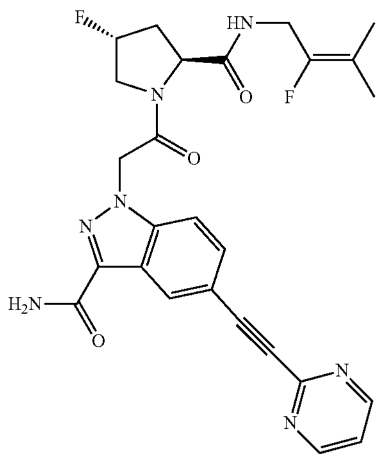 [SMILES: CC(C)=C(F)CNC(=O)[C@@H]1C[C@@H](F)CN1C(=O)Cn1nc(C(N)=O)c2cc(C#Cc3ncccn3)ccc21] | 1-(2-((2S,4R)-4-fluoro-2-((2-fluoro-3-methylbut-2-en-1-yl)carbamoyl)pyrrolidin-1-yl)-2-oxoethyl)-5-(pyrimidin-2-ylethynyl)-1H-indazole-3-carboxamide | *** | 1.31 | 522 |
| 248 | 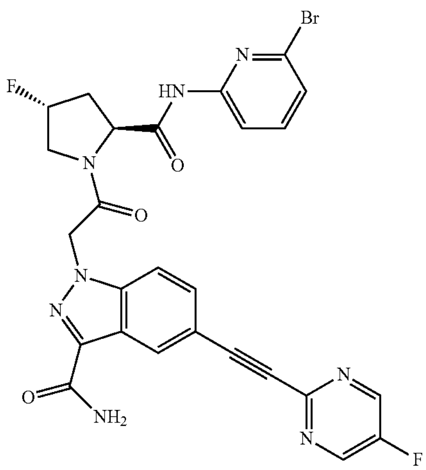 [SMILES: NC(=O)c1nn(CC(=O)N2C[C@H](F)C[C@H]2C(=O)Nc2cccc(Br)n2)c2ccc(C#Cc3ncc(F)cn3)cc12] | 1-(2-((2S,4R)-2-((6-bromopyridin-2-yl)carbamoyl)-4-fluoropyrrolidin-1-yl)-2-oxoethyl)-5-((5-fluoropyrimidin-2-yl)ethynyl)-1H-indazole-3-carboxamide | *** | 1.69 | 609 |
| 249 | 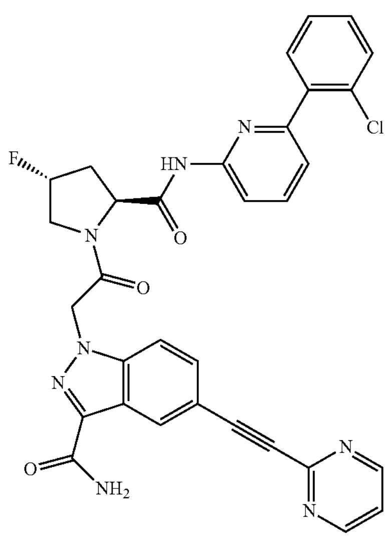 [SMILES: NC(=O)c1nn(CC(=O)N2C[C@H](F)C[C@H]2C(=O)Nc2cccc(-c3ccccc3Cl)n2)c2ccc(C#Cc3ncccn3)cc12] | 1-(2-((2S,4R)-2-((6-(2-chlorophenyl)pyridin-2-yl)carbamoyl)-4-fluoropyrrolidin-1-yl)-2-oxoethyl)-5-(pyrimidin-2-ylethynyl)-1H-indazole-3-carboxamide | *** | 1.91 | 623 |

-continued

| Cmp. No. | Structure | Name | IC$_{50}$ (µM) | RT min (Method 1 or 2) | M + 1 |
|---|---|---|---|---|---|
| 250 | 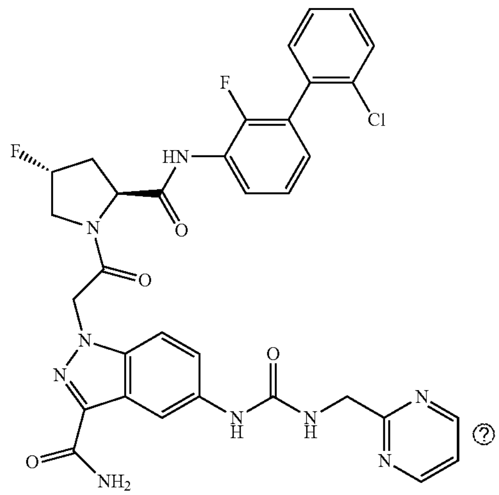 [SMILES: NC(=O)c1nn(CC(=O)N2C[C@H](F)C[C@H]2C(=O)Nc2cccc(-c3ccccc3Cl)c2F)c2ccc(NC(=O)NCc3ncccn3)cc12] | 1-(2-((2S,4R)-2-((2'-chloro-2-fluoro-[1,1'-biphenyl]-3-yl)carbamoyl)-4-fluoropyrrolidin-1-yl)-2-oxoethyl)-5-(3-(pyrimidin-2-ylmethyl)ureido)-1H-indazole-3-carboxamide | *** | 1.69 | 688 |
| 251 | 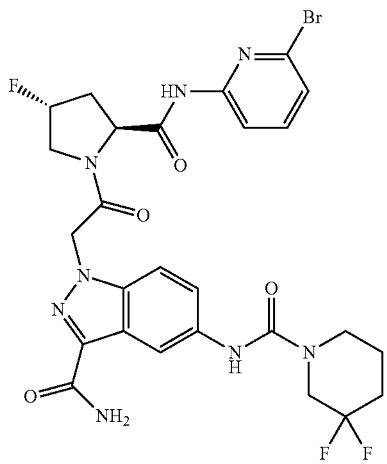 [SMILES: NC(=O)c1nn(CC(=O)N2C[C@H](F)C[C@H]2C(=O)Nc2cccc(Br)n2)c2ccc(NC(=O)N3CCCC(F)(F)C3)cc12] | 1-(2-((2S,4R)-2-((6-bromopyridin-2-yl)carbamoyl)-4-fluoropyrrolidin-1-yl)-2-oxoethyl)-5-(3,3-difluoropiperidine-1-carboxamido)-1H-indazole-3-carboxamide | *** | 1.59 | 651 |
| 252 | 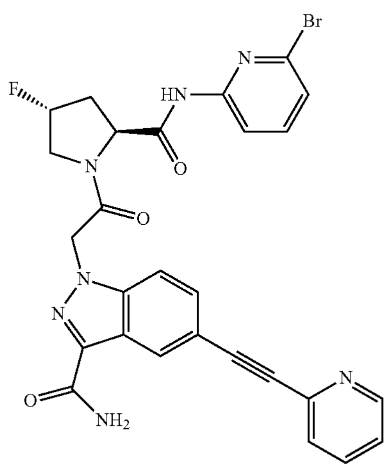 [SMILES: NC(=O)c1nn(CC(=O)N2C[C@H](F)C[C@H]2C(=O)Nc2cccc(Br)n2)c2ccc(C#Cc3ccccn3)cc12] | 1-(2-((2S,4R)-2-((6-bromopyridin-2-yl)carbamoyl)-4-fluoropyrrolidin-1-yl)-2-oxoethyl)-5-(pyridin-2-ylethynyl)-1H-indazole-3-carboxamide | *** | 1.60 | 590 |

-continued

| Cmp. No. | Structure | Name | IC$_{50}$ (μM) | RT min (Method 1 or 2) | M + 1 |
|---|---|---|---|---|---|
| 253 | 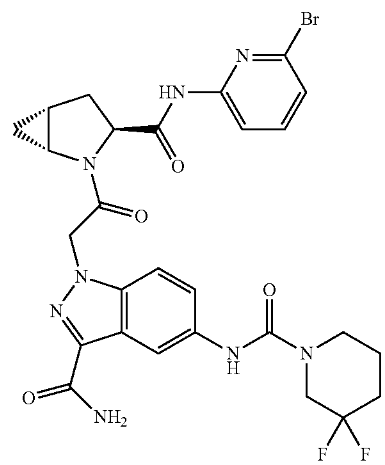 [SMILES: NC(=O)c1nn(CC(=O)N2[C@@H]3C[C@@H]3C[C@H]2C(=O)Nc2cccc(Br)n2)c2ccc(NC(=O)N3CCCC(F)(F)C3)cc12] | 1-(2-((1R,3S,5R)-3-((6-bromopyridin-2-yl)carbamoyl)-2-azabicyclo[3.1.0]hexan-2-yl)-2-oxoethyl)-5-(3,3-difluoropiperidine-1-carboxamido)-1H-indazole-3-carboxamide | *** | 1.75 | 645 |
| 254 | 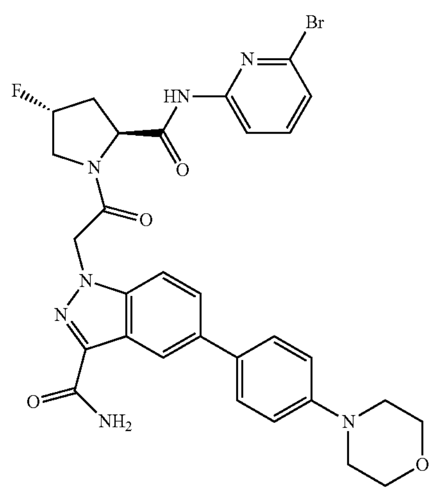 [SMILES: NC(=O)c1nn(CC(=O)N2C[C@H](F)C[C@H]2C(=O)Nc2cccc(Br)n2)c2ccc(-c3ccc(N4CCOCC4)cc3)cc12] | 1-(2-((2S,4R)-2-((6-bromopyridin-2-yl)carbamoyl)-4-fluoropyrrolidin-1-yl)-2-oxoethyl)-5-(4-morpholinophenyl)-1H-indazole-3-carboxamide | *** | 1.82 | 650 |
| 255 | 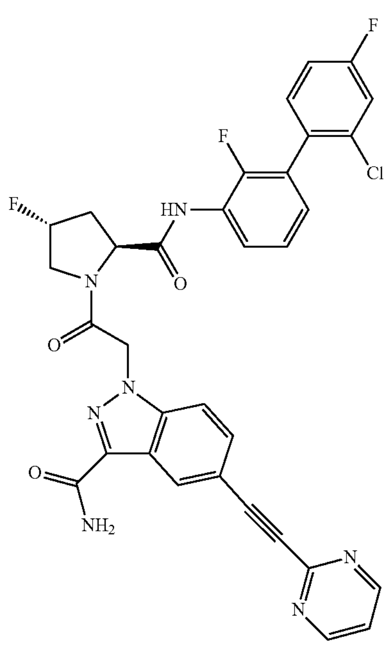 [SMILES: NC(=O)c1nn(CC(=O)N2C[C@H](F)C[C@H]2C(=O)Nc2cccc(-c3ccc(F)cc3Cl)c2F)c2ccc(C#Cc3ncccn3)cc12] | 1-(2-((2S,4R)-2-((2'-chloro-2,4'-difluoro-[1,1'-biphenyl]-3-yl)carbamoyl)-4-fluoropyrrolidin-1-yl)-2-oxoethyl)-5-(pyrimidin-2-ylethynyl)-1H-indazole-3-carboxamide | | 2.04 | 658 |

-continued

| Cmp. No. | Structure | Name | IC$_{50}$ (μM) | RT min (Method 1 or 2) | M + 1 |
|---|---|---|---|---|---|
| 256 | 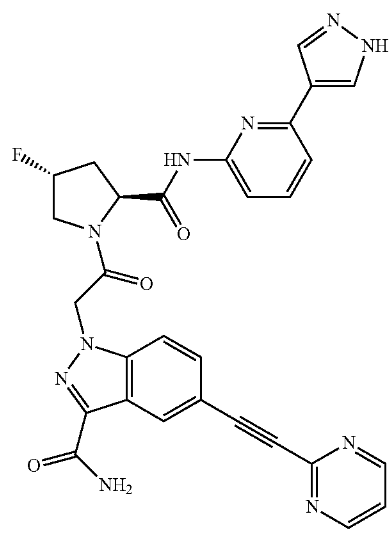 [SMILES: NC(=O)c1nn(CC(=O)N2C[C@H](F)C[C@H]2C(=O)Nc2cccc(-c3cn[nH]c3)n2)c2ccc(C#Cc3ncccn3)cc12] | 1-(2-((2S,4R)-2-((6-(1H-pyrazol-4-yl)pyridin-2-yl)carbamoyl)-4-fluoropyrrolidin-1-yl)-2-oxoethyl)-5-(pyrimidin-2-ylethynyl)-1H-indazole-3-carboxamide | 1.11 | | 579 |
| 257 | 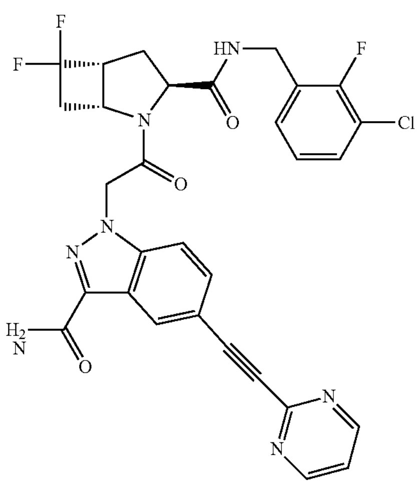 [SMILES: NC(=O)c1nn(CC(=O)N2[C@@H]3CC(F)(F)[C@@H]3C[C@H]2C(=O)NCc2cccc(Cl)c2F)c2ccc(C#Cc3ncccn3)cc12] | 1-(2-((1R,3S,5R)-3-((3-chloro-2-fluorobenzyl)carbamoyl)-6,6-difluoro-2-azabicyclo[3.2.0]heptan-2-yl)-2-oxoethyl)-5-(pyrimidin-2-ylethynyl)-1H-indazole-3-carboxamide | 1.79 | | 622 |
| 258 | 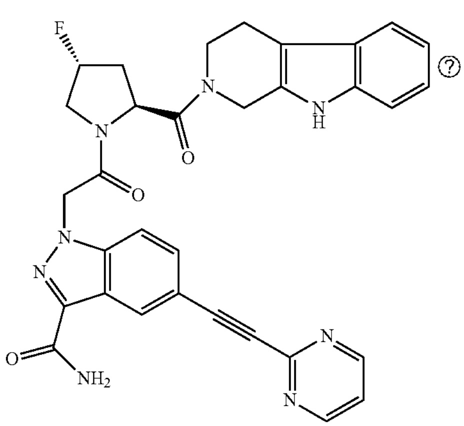 [SMILES: NC(=O)c1nn(CC(=O)N2C[C@H](F)C[C@H]2C(=O)N2CCc3c([nH]c4ccccc34)C2)c2ccc(C#Cc3ncccn3)cc12] | 1-(2-((2S,4R)-4-fluoro-2-(2,3,4,9-tetrahydro-1H-pyrido[3,4-b]indole-2-carbonyl)pyrrolidin-1-yl)-2-oxoethyl)-5-(pyrimidin-2-ylethynyl)-1H-indazole-3-carboxamide | * | 1.65 | |

Example 22

Human Factor D Assay

Human factor D (purified from human serum, Complement Technology, Inc.) at 80 nM final concentration is incubated with test compound at various concentrations for 5 minutes at room temperature in 50 mM Tris, 1M NaCl, pH 7.5. A synthetic substrate Z-L-Lys-SBzl and DTNB (Ellman's reagent) are added to final concentrations of 100 μM each. The increase in color is recorded at $OD_{405}$ nm in a microplate in kinetic mode over 30 minutes with 30 second time points in a spectrofluorimeter. $IC_{50}$ values are calculated by non-linear regression from the percentage of inhibition of complement factor D activity as a function of test compound concentration.

Example 23

Hemolysis Assay

The hemolysis assay was previously described by G. Ruiz-Gomez, et al., J. Med. Chem. (2009) 52: 6042-6052. In our assay red blood cells (RBC), rabbit erythrocyctes (purchased from Complement Technologies), are washed using GVB Buffer (0.1% gelatin, 5 mM Veronal, 145 mM NaCl, 0.025% $NaN_3$, pH 7.3) plus 10 mM final Mg-EGTA. Cells are used at a concentration of $1 \times 10^8$ cells/mL. Prior to the hemolysis assay, the optimum concentration of Normal Human Serum (NHS) needed to achieve 100% lysis of rabbit erythrocytes is determined by titration. NHS (Complement Technologies) is incubated with inhibitor for 15 min at 37° C., rabbit erythrocytes in buffer were added and incubated for an additional 30 min at 37° C. Positive control (100% lysis) consists of serum and RBC and negative control (0% lysis) of Mg-EGTA buffer and RBC only. Samples are centrifuged at 2000 g for 5 min, and supernatants collected. Optical density of the supernatant is monitored at 405 nm using a UV/visible spectrophotometer. Percentage lysis in each sample is calculated relative to positive control (100% lysis).

What is claimed is:
1. A compound of formula

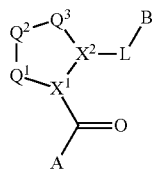

or a pharmaceutically acceptable salt thereof, wherein
$Q^1$ is $C(R^1R^{1'})$;
$Q^2$ is $C(R^2R^{2'})$;
$Q^3$ is $C(R^3R^{3'})$;
$X^1$ and $X^2$ are independently N or CH, or $X^1$ and $X^2$ together are C=C;
$R^1$, $R^{1'}$, $R^2$, $R^{2'}$, $R^3$, and $R^{3'}$ are independently chosen at each occurrence from (a) and (b):
(a) hydrogen, halogen, hydroxyl, nitro, cyano, amino, $C_1$-$C_6$alkyl, $C_2$-$C_6$alkenyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, $C_0$-$C_4$alkyl$NR^9R^{10}$, —C(O)$OR^9$, —OC(O)$R^9$, —$NR^9$C(O)$R^{10}$, —C(O)$NR^9R^{10}$, —OC(O)$NR^9R^{10}$, —$NR^9$C(O)$OR^{10}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, and ($C_3$-$C_7$cycloalkyl)$C_0$-$C_4$alkyl;
(b) —$C_0$-$C_4$alkyl($C_3$-$C_7$cycloalkyl) and —O—$C_0$-$C_4$alkyl($C_3$-$C_7$cycloalkyl);
Additionally any one of the following rings (c), (d), (e), (f), (g), or (h) may be present:
(c) $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S;
(d) $R^2$ and $R^{2'}$ may be taken together to form a 3- to 6-membered carbocyclic spiro ring;
(e) $R^2$ and $R^{2'}$ may be taken together to form a 3- to 6-membered heterocyclic spiro ring, each of which spiro rings (c), (d), and (e) is unsubstituted or substituted with one or more halogen or methyl substituents;
(f) $R^1$ and $R^2$ may be taken together to form a 3-membered carbocyclic ring;
(g) $R^1$ and $R^2$ may be taken together to form a 4- to 6-membered carbocyclic ring or a 4- to 6-membered heterocyclic ring containing 1 or 2 heteroatoms independently chosen from N, O, and S;
(h) $R^2$ and $R^3$, if bound to adjacent carbon atoms, may be taken together to form a 3- to 6-membered carbocyclic ring or a 3- to 6-membered heterocyclic ring; each of which ring (f), (g), and (h) may be unsubstituted or substituted with 1 or more substituents independently chosen from halogen, hydroxyl, cyano, —COOH, $C_1$-$C_4$alkyl, $C_2$-$C_4$alkenyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;
A is a heterocyclic group chosen from:

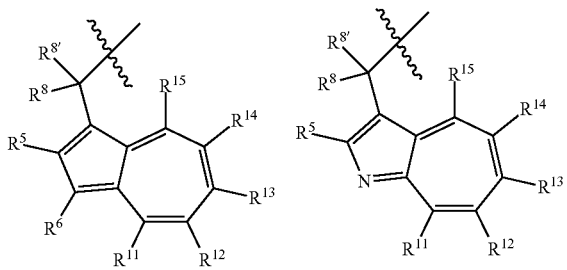

$R^5$ and $R^6$ are independently chosen from (i) and (j):
(i) —CHO, —C(O)$NH_2$, —C(O)NH($CH_3$), or $C_2$-$C_6$alkanoyl;
(j) hydrogen, hydroxyl, halogen, cyano, nitro, —COOH, —$SO_2NH_2$, vinyl, $C_1$-$C_6$alkyl, $C_2$-$C_6$alkenyl, $C_1$-$C_6$alkoxy, —$C_0$-$C_4$alkyl($C_3$-$C_7$cycloalkyl), —C(O)$C_0$-$C_4$alkyl($C_3$-$C_7$cycloalkyl), —P(O)(OR$^9$)$_2$, —OC(O)$R^9$, —C(O)$OR^9$, —C(O)N($CH_2CH_2R^9$)($R^{10}$), —$NR^9$C(O)$R^{10}$, phenyl, or 5- to 6-membered heteroaryl;
each $R^5$ and $R^6$ other than hydrogen, hydroxyl, cyano, and —COOH is unsubstituted or substituted with one or more substituents independently chosen from halogen, hydroxyl, amino, imino, cyano, cyanoimino, $C_1$-$C_2$alkyl, $C_1$-$C_4$alkoxy, —$C_0$-$C_2$alkyl(mono- and di-$C_1$-$C_4$alkylamino), $C_1$-$C_2$haloalkyl, and $C_1$-$C_2$haloalkoxy;

$R^{6'}$ is hydrogen, halogen, hydroxyl, $C_1$-$C_4$alkyl, or $C_1$-$C_4$alkoxy; or $R^6$ and $R^{6'}$ may be taken together to form an oxo, vinyl, or imino group;

$R^7$ is hydrogen, $C_1$-$C_6$alkyl, or —$C_0$-$C_4$alkyl($C_3$-$C_7$cycloalkyl);

$R^8$ and $R^{8'}$ are independently chosen from hydrogen, halogen, hydroxyl, $C_1$-$C_6$alkyl, $C_1$-$C_6$alkoxy, and ($C_1$-$C_4$alkylamino)$C_0$-$C_2$alkyl, or $R^8$ and $R^{8'}$ are taken together to form an oxo group;

$R^{11}$, $R^{14}$, and $R^{15}$ are independently chosen at each occurrence from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy;

$R^{12}$ and $R^{13}$ are independently chosen from (k), (l), and (m):

(k) hydrogen, halogen, hydroxyl, nitro, cyano, amino, —COOH, $C_1$-$C_2$haloalkyl, and $C_1$-$C_2$haloalkoxy, (l) $C_1$-$C_6$alkyl, $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$R$^{10}$, —SO$_2$NR$^9$R$^{10}$, —OC(O)R$^9$, and —C(NR$^9$)NR$^9$R$^{10}$, each of which (l) is unsubstituted or substituted with one or more substituents independently selected from halogen, hydroxyl, nitro, cyano, amino, —COOH, —CONH$_2$ $C_1$-$C_2$haloalkyl, and $C_1$-$C_2$haloalkoxy, and each of which ((l) is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_4$alkylester, —$C_0$-$C_4$alkyl)($C_3$-$C_7$cycloalkyl), $C_1$-$C_2$haloalkyl, and $C_1$-$C_2$haloalkoxy;

(m) —$C_2$-$C_6$alkynyl, —$C_2$-$C_6$alkynylR$^{23}$, $C_2$-$C_6$alkanoyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$NR$^{22}$-JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, —O(CH$_2$)$_{1-4}$SO$_2$NR$^{21}$R$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NS(O)$_2$R$^{22}$, -JOC(O)NR$^{21}$R$^{22}$, -JOC(O)NR$^{24}$R$^{25}$-JNR$^9$C(O)OR$^{10}$, -JNR$^9$C(O)OR$^{23}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^9$R$^{10}$, -JNR$^9$C(O)NR$^{10}$R$^{23}$, -JNR$^9$C(O)NR$^{24}$R$^{25}$, —CCR$^{21}$, —(CH$_2$)$_{1-4}$OC(O)R$^{21}$, -JC(O)OR$^{23}$, —$C_2$-$C_4$alkylR$^{23}$, —$C_2$-$C_4$alkenylR$^{23}$, —$C_2$-$C_4$alkynylR$^{23}$, and -Jparacyclophane;

where J is independently chosen at each occurrence from a covalent bond, $C_1$-$C_4$alkylene, —O$C_1$-$C_4$alkylene, $C_2$-$C_4$alkenylene, and $C_2$-$C_4$alkynylene;

$R^{21}$ and $R^{22}$ are independently chosen at each occurrence from hydroxyl, cyano, amino, $C_1$-$C_6$alkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)$C_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

$R^{23}$ is independently chosen at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings;

each of which (m) may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy; and L is either (n), (o), or (p) where (n) is a group of the formula

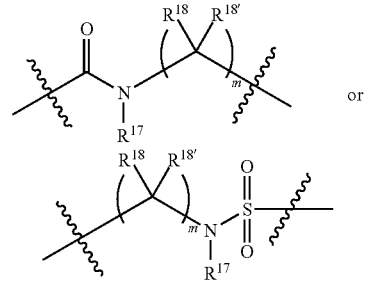

where $R^{17}$ is hydrogen or $C_1$-$C_6$alkyl and $R^{18}$ and $R^{18'}$ are independently chosen from hydrogen, halogen, and methyl; and m is 0, 1, 2, or 3;

(o) is a bond; and (p) or a group of the formula

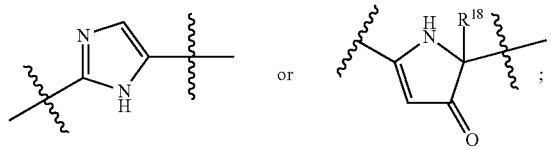

B is a monocyclic or bicyclic carbocyclic or carbocyclic-oxy group or a monocyclic, bicyclic, or tricyclic heterocyclic group having 1, 2, 3, or 4 heteroatoms independently selected from N, O, and S and from 4 to 7 ring atoms per ring, or B is a $C_2$-$C_6$alkenyl or $C_2$-$C_6$alkynyl group;

each of which B is unsubstituted or substituted with one or more substituents independently chosen from (q) and (r) and 0 or 1 substituents chosen from (s) and (t);
(q) halogen, hydroxyl, —COOH, cyano, $C_1$-$C_6$alkyl, $C_2$-$C_6$alkanoyl, $C_1$-$C_6$alkoxy, —$C_0$-$C_4$alkylN$R^9R^{10}$, —$SO_2R^9$, $C_1$-$C_2$haloalkyl, and $C_1$-$C_2$haloalkoxy;
(r) nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)N$R^9R^{23}$, -JOS$O_2$O$R^{21}$, —C(O)(C$H_2$)$_{1-4}$S(O)$R^{21}$, —O(C$H_2$)$_{1-4}$S(O)N$R^{21}R^{22}$, -JOP(O)(O$R^{21}$)(O$R^{22}$), -JP(O)(O$R^{21}$)(O$R^{22}$), -JOP(O)(O$R^{21}$)$R^{22}$, -JP(O)(O$R^{21}$)$R^{22}$, -JOP(O)$R^{21}R^{22}$, -JP(O)$R^{21}R^{22}$, -JSP(O)(O$R^{21}$)(O$R^{22}$), -JSP(O)(O$R^2$)($R^{22}$), -JSP(O)($R^{21}$)($R^{22}$), -JN$R^9$P(O)(NH$R^{21}$)(NH$R^{22}$), -JN$R^9$P(o)(O$R^{21}$)(NH$R^{22}$), -JN$R^9$P(O)(O$R^{21}$)(O$R^{22}$), -JC(S)$R^{21}$, -JN$R^{21}$S$O_2R^{22}$, -JN$R^9$S(O)$_n$N$R^{10}R^{22}$, -JS$O_2$N$R^9$CO$R^{22}$, -JS$O_2$N$R^9$CON$R^{21}R^{22}$, -JN$R^{21}$S$O_2R^{22}$, -JC(O)N$R^{21}$S$O_2R^{22}$, -JC(N$H_2$)N$R^{22}$, -JC(N$H_2$)NS(O)$_2R^{22}$, -JOC(O)N$R^{21}R^{22}$, -JN$R^{21}$C(O)O$R^{22}$, -JN$R^{21}$OC(O)$R^{22}$, —(C$H_2$)$_{1-4}$C(O)N$R^{21}R^{22}$, -JC(O)$R^{24}R^{25}$, -JN$R^9$C(O)$R^{21}$, -JC(O)$R^{21}$, -JN$R^9$C(O)N$R^{10}R^{22}$, —CC$R^{21}$, —(C$H_2$)$_{1-4}$OC(O)$R^{21}$, and -JC(O)O$R^{23}$;
each of which (r) may be unsubstituted or substituted with one or more substituents independently chosen from halogen, hydroxyl, nitro, cyano, amino, oxo, —B(OH)$_2$, —Si(C$H_3$)$_3$, —COOH, —CON$H_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;
(s) naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which (s) is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy; and
(t) tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which (t) is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —OSi(C$H_3$)$_2$C(C$H_3$)$_3$, $C_1$-$C_2$haloalkyl, and $C_1$-$C_2$haloalkoxy.

2. The compound of claim 1, wherein $R^{2'}$ and $R^2$ are hydrogen and fluorine respectively.

3. The compound of claim 1, wherein the formula is:

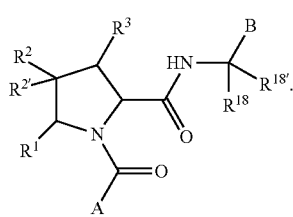

4. The compound of claim 1, wherein the formula is.

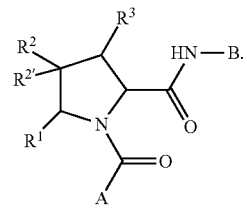

5. The compound of claim 1, wherein the formula is:

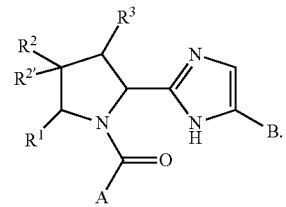

6. The compound of claim 1, wherein the formula is:

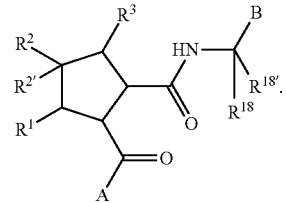

7. The compound of claim 1, wherein the formula is:

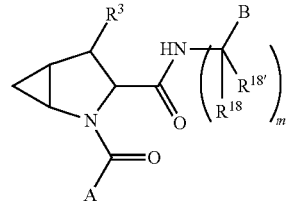

where m is 0 or 1.

8. The compound of claim 1, wherein the formula is:

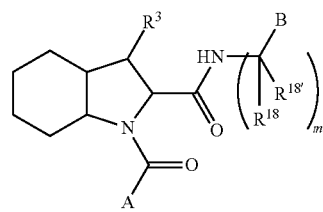

where m is 0 or 1.

9. The compound of claim 1, wherein the formula is:

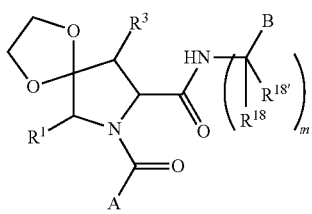

where m is 0 or 1.

10. The compound of claim 1, wherein the formula is:

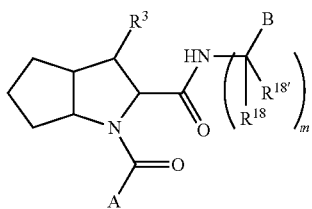

where m is 0 or 1.

11. A pharmaceutical composition comprising a compound of claim 1, together with a pharmaceutically acceptable carrier.

12. The compound of claim 1, wherein the formula is:

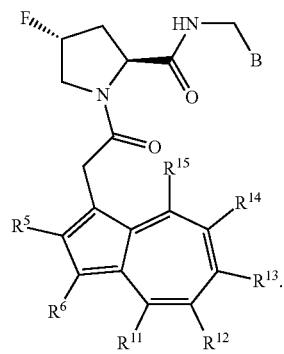

13. The compound of claim 12, wherein the compound is:

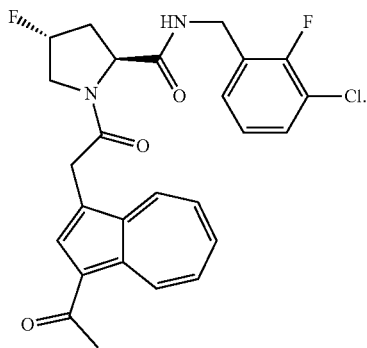 [SMILES: CC(=O)c1cc(CC(=O)N2C[C@H](F)C[C@H]2C(=O)NCc2cccc(Cl)c2F)c2cccccc1-2]

14. The compound of claim 12, wherein the compound is:

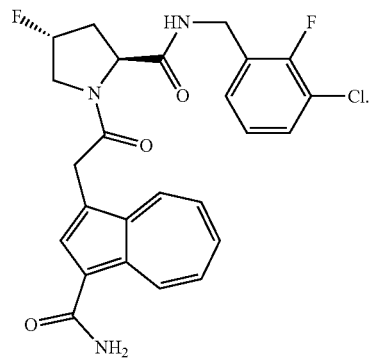 [SMILES: NC(=O)c1cc(CC(=O)N2C[C@H](F)C[C@H]2C(=O)NCc2cccc(Cl)c2F)c2cccccc1-2]

15. The compound of claim 12, wherein the compound is:

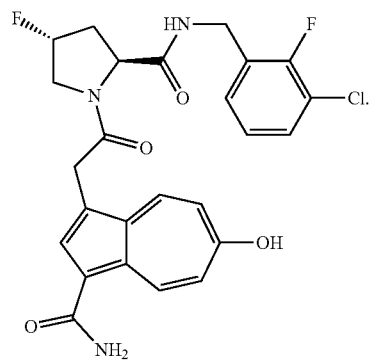 [SMILES: NC(=O)c1cc(CC(=O)N2C[C@H](F)C[C@H]2C(=O)NCc2cccc(Cl)c2F)c2ccc(O)ccc1-2]

16. The compound of claim 12, wherein the compound is:

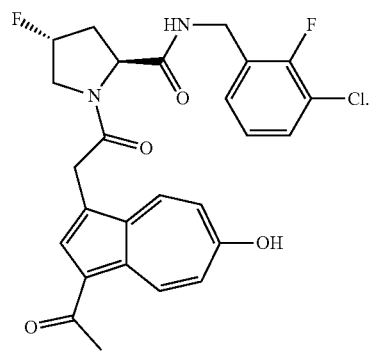 [SMILES: CC(=O)c1cc(CC(=O)N2C[C@H](F)C[C@H]2C(=O)NCc2cccc(Cl)c2F)c2ccc(O)ccc1-2]

17. The compound of claim 1, wherein:

$R^{12}$ and $R^{13}$ are selected from hydrogen, halogen, hydroxyl, nitro, cyano, amino, —COOH, $C_1$-$C_2$haloalkyl, and $C_1$-$C_2$haloalkoxy; and $R^{11}$, $R^{14}$, and $R^{15}$ are hydrogen.

18. The compound of claim 1, wherein:

$R^{12}$ and $R^{13}$ are selected from hydrogen $C_1$-$C_6$alkyl, $C_2$-$C_6$alkanoyl, $C_1$-$C_6$alkoxy, —C(O)OR$^9$, $C_1$-$C_6$thioalkyl, —C$_0$-$C_4$alkylNR$^9$R$^{10}$, —C(O)NR$^9$R$^{10}$, —SO$_2$R$^9$R$^{10}$, —SO$_2$NR$^9$R$^{10}$, and —OC(O)R$^9$; and $R^{11}$, $R^{14}$, and $R^{15}$ are hydrogen.

19. The compound of claim 1, wherein:
R$^{13}$ is selected from hydrogen, halogen, hydroxyl, nitro, cyano, amino, —COOH, C$_1$-C$_2$haloalkyl, and C$_1$-C$_2$haloalkoxy; and
R$^{11}$, R$^{12}$, R$^{14}$, and R$^{15}$ are hydrogen.

20. The compound of claim 1, wherein:
R$^{13}$ is selected from hydrogen C$_1$-C$_6$alkyl, C$_2$-C$_6$alkanoyl, C$_1$-C$_6$alkoxy, —C(O)OR$^9$, C$_1$-C$_6$thioalkyl, —C$_0$-C$_4$alkylNR$^9$R$^{10}$, —C(O)NR$^9$R$^{10}$, —SO$_2$R$^9$R$^{10}$, —SO$_2$NR$^9$R$^{10}$, and —OC(O)R$^9$; and
R$^{11}$, R$^{12}$, R$^{14}$, and R$^{15}$ are hydrogen.

21. The compound of claim 1, wherein

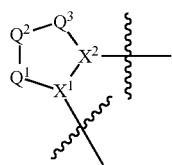 is 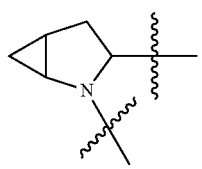.

22. The compound of claim 21, wherein

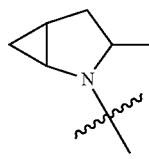 is 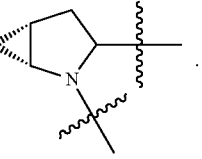.

23. The compound of claim 1, wherein Q is

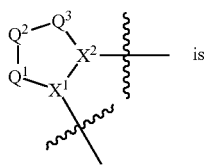 is 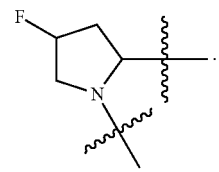.

24. The compound of claim 23, wherein

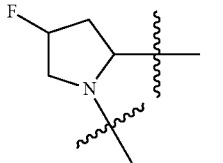 is 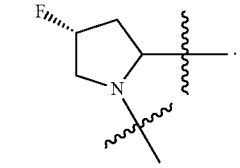.

* * * * *